United States Patent
Jafar-nejad

(10) Patent No.: US 12,129,466 B2
(45) Date of Patent: Oct. 29, 2024

(54) COMPOUNDS AND METHODS FOR MODULATING UBE3A-ATS

(71) Applicant: Ionis Pharmaceuticals, Inc., Carlsbad, CA (US)

(72) Inventor: Paymaan Jafar-nejad, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/576,245

(22) Filed: Jan. 14, 2022

(65) Prior Publication Data

US 2022/0411793 A1 Dec. 29, 2022

Related U.S. Application Data

(63) Continuation of application No. 17/236,671, filed on Apr. 21, 2021, now Pat. No. 11,261,446, which is a continuation of application No. PCT/US2020/025110, filed on Mar. 27, 2020.

(60) Provisional application No. 62/877,765, filed on Jul. 23, 2019, provisional application No. 62/826,521, filed on Mar. 29, 2019.

(51) Int. Cl.
  *C07H 21/04* (2006.01)
  *C12N 15/113* (2010.01)

(52) U.S. Cl.
  CPC ...... *C12N 15/113* (2013.01); *C12N 2310/111* (2013.01); *C12N 2310/113* (2013.01); *C12N 2310/315* (2013.01); *C12N 2310/321* (2013.01); *C12N 2310/323* (2013.01); *C12N 2310/3341* (2013.01); *C12N 2310/341* (2013.01)

(58) Field of Classification Search
  None
  See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lableu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |

(Continued)

FOREIGN PATENT DOCUMENTS

| | | |
|---|---|---|
| EP | 1764108 | 3/2008 |
| WO | WO 1998/39352 | 9/1998 |

(Continued)

OTHER PUBLICATIONS

Galiveti, Chenna R., et al. "Differential regulation of non-protein coding RNAs from Prader-Willi Syndrome locus." Scientific reports 4.1 (2014): 6445.*

(Continued)

*Primary Examiner* — Kimberly Chong

(74) *Attorney, Agent, or Firm* — McNeill PLLC

(57) ABSTRACT

Provided are compounds, methods, and pharmaceutical compositions for reducing the amount or activity of UBE3A-ATS, the endogenous antisense transcript of ubiquitin protein ligase E3A (UBE3A) in a cell or subject, and in certain instances increasing the expression of paternal UBE3A and the amount of UBE3A protein in a cell or subject. Such compounds, methods, and pharmaceutical compositions are useful to ameliorate at least one symptom or hallmark of a neurogenetic disorder. Such symptoms and hallmarks include developmental delays, ataxia, speech impairment, sleep problems, seizures, and EEG abnormalities. Such neurogenetic disorders include Angelman Syndrome.

19 Claims, No Drawings

Specification includes a Sequence Listing.

(56) References Cited

U.S. PATENT DOCUMENTS

| | | |
|---|---|---|
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,184,212 B1 | 2/2001 | Miraglia et al. |
| 6,268,490 B1 | 7/2001 | Imanishi et al. |
| 6,300,132 B1 | 10/2001 | Monia et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,617,162 B2 | 9/2003 | Dobie et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,015,315 B1 | 3/2006 | Cook et al. |
| 7,034,133 B2 | 4/2006 | Wengel et al. |
| 7,053,207 B2 | 5/2006 | Wengel |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,820,809 B2 | 10/2010 | Khvorova et al. |
| 7,875,733 B2 | 1/2011 | Bhat et al. |
| 7,888,497 B2 | 2/2011 | Bentwich et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 9,359,603 B2 | 6/2016 | Lutz et al. |
| 9,617,539 B2 | 4/2017 | Rigo et al. |
| 10,253,312 B2 | 4/2019 | Maeder et al. |
| 10,400,243 B2 | 9/2019 | Whipple et al. |
| 11,261,446 B2 | 3/2022 | Jafar-nejad |
| 2001/0053519 A1 | 12/2001 | Fodor et al. |
| 2003/0087855 A1 | 5/2003 | Ward et al. |
| 2003/0158403 A1 | 8/2003 | Manoharan et al. |
| 2003/0175906 A1 | 9/2003 | Manoharan et al. |

(56) References Cited

U.S. PATENT DOCUMENTS

| | | |
|---|---|---|
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2007/0111227 A1 | 5/2007 | Green et al. |
| 2008/0039618 A1 | 2/2008 | Allerson et al. |
| 2008/0108583 A1 | 5/2008 | Feinstein et al. |
| 2009/0012281 A1 | 1/2009 | Swayze et al. |
| 2010/0190837 A1 | 7/2010 | Migawa et al. |
| 2010/0197762 A1 | 8/2010 | Swayze et al. |
| 2013/0130378 A1 | 5/2013 | Manoharan et al. |
| 2013/0225659 A1 | 8/2013 | Bennett et al. |
| 2014/0107330 A1 | 4/2014 | Freier et al. |
| 2014/0315992 A1 | 10/2014 | Hakonarson et al. |
| 2015/0018540 A1 | 1/2015 | Prakash et al. |
| 2015/0141320 A1 | 5/2015 | Kreig et al. |
| 2015/0184153 A1 | 7/2015 | Freier et al. |
| 2015/0191723 A1 | 7/2015 | Rigo et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2017/0191064 A1 | 7/2017 | Costa et al. |
| 2017/0362592 A1 | 12/2017 | Whipple et al. |
| 2019/0048337 A1 | 2/2019 | Hsu et al. |
| 2021/0277397 A1 | 9/2021 | Freier et al. |

FOREIGN PATENT DOCUMENTS

| | | |
|---|---|---|
| WO | WO 1999/014226 | 3/1999 |
| WO | WO 2000/063364 | 10/2000 |
| WO | WO 2001/049687 | 7/2001 |
| WO | WO 2001/092582 | 12/2001 |
| WO | WO 2003/004602 | 1/2003 |
| WO | WO 2004/035765 | 10/2003 |
| WO | WO 2004/016754 | 2/2004 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/087113 | 8/2007 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 2/2011 |
| WO | WO 2011/079261 | 6/2011 |
| WO | WO 2011/109398 | 9/2011 |
| WO | WO 2011/139702 | 11/2011 |
| WO | WO 2012/009402 | 1/2012 |
| WO | WO 2012/012467 | 1/2012 |
| WO | WO 2012/064806 | 5/2012 |
| WO | WO 2013/033230 | 7/2013 |
| WO | WO 2013/173637 | 11/2013 |
| WO | WO 2014/004572 | 1/2014 |
| WO | WO 2014/036525 | 3/2014 |
| WO | WO 2016/086104 | 6/2016 |
| WO | WO 2017/081223 | 5/2017 |
| WO | WO 2017/081250 | 5/2017 |
| WO | WO 2019/084050 | 5/2019 |
| WO | WO 2019/109001 | 6/2019 |
| WO | WO 2020/205463 | 10/2020 |

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Allshire, "Molecular biology. RNAi and heterochromatin—a hushed-up affair" Science (2002) 297(5588):1818-1819.

Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.

Altmann et al., "Second Generation of Antisense Oligonucleotides: From Nuclease Resistance to Biological Efficacy in Animals" Chimia. (1996) 50(4):168-176.

Altmann et al., "Second-generation antisense oligonucleotides: structure—activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Beaudet et al., "Angelman syndrome: Drugs to awaken a paternal gene," Nature (2012) 481: 150-152.

Braasch et al., "Locked nucleic acid (LNA): fine-tuning the recognition of DNA and RNA" Chem. Biol. (2001) 8:1-7.

Braasch et al., "Novel antisense and peptide nucleic acid strategies for controlling gene expression" Biochemistry (2002) 41(14):4503-4510.

Branch et al., "A good antisense molecule is hard to find," TIBS (1998) 23:45-50.

Buiting et al., "Angelman syndrome—insights into a rare neurogenetic disorder" Nat Rev Neurol (2016) 12:584-593.

Cattanach et al., "A candidate model for Angelman syndrome in the mouse" Mamm. Genome (1997) 8(7):472-478.

Chamberlain et al., "Angelman Syndrome, a Genomic Imprinting Disorder of the Brain" J Neorosc (2010) 30: 9958-9963.

Chamberlain et al., "Induced pluripotent stem cell models of the genomic imprinting disorders Angelman and Prader-Willi syndromes" PNAS (2010) 107: 17668-17673.

Chen et al., "Motor coordination deficits in Alpkl mutant mice with the inserted piggyBac transposon" BMC Neruosci. (2011) 12:1.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chung et al., "Prader-Willi syndrome: reflections on seminal studies and future therapies" Open Biol (2020) 10:200195.

Church et al., "Lineage-specific biology revealed by a finished genome assembly of the mouse" PLoS Biol. (2009) 7: e1000112.

Clark et al., "Purkinje cell expression of a mutant allele of SCA1 in transgenic mice leads to disparate effects on motor behaviors, followed by a progressive cerebellar dysfunction and histological alterations" J. Neurosci. (1997) 17(19):7385-7395.

Crooke et al., "Basic Principles of Antisense Therapeutics" Antisense Research and Application (1998) Chapter 1:1-50.

Crooke et al., "Pharmacokinetic Properties of Several Novel Oligonucleotide Analogs in mice" J. Pharmacol. Exp. Ther. (1996) 277(2):923-937.

Crooke, St., et al., "Antisense Drug Technology" Second Edition, CRC Press (2008) Chapters 1-28.

Crooke et al., "Basic Principles of Antisense Technology" Antisense Drug Technology: Principles, Strategies and Applications (2001) p. 1-18.

Danckwardt et al., "Focus Quality Control 3' end mRNA processing: molecular mechanisms and implications for health and disease" EMBO J (2008) 27: 482-498.

Dindot et al., "The Angelman syndrome ubiquitin ligase localizes to the synapse and nucleus, and maternal deficiency results in abnormal dendritic spine morphology" Hum. Mol. Genet. (2008) 17(1):111-118.

(56) References Cited

OTHER PUBLICATIONS

Efthymiou et al., "Functional Screening Assays with Neurons Generated from Pluripotent Stem Cell-Derived Neural Stem Cells" J Biomol Screen (2014) 19: 32-43.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Elayadi et al., "Application of PNA and LNA oligomers to chemotherapy" Curr. Opinion Invens. Drugs (2001) 2:558-561.
Faghihi et al., "RNAi screen indicates widespread biological function for human natural antisense transcripts" PLoS One (2010) 5(10):e13177.
Faghihi et al., "Regulatory roles of natural antisense transcripts" Nat Rev Mol Cell Biol (2009) 10: 637-643.
Fink et al., "Disrupted neuronal maturation in Angelman syndrome-derived induced pluripotent stem cells." Nat. Commun. (2017) 8:1-14.
Freier et al., "The ups and downs of nucleic acid duplex stability: structure-stability studies on chemically-modified DNA:RNA duplexes" Nucleic Acids Research (1997) 25(22):4429-4443.
Freier et al., "Methods of Selecting Sites in RNA for Antisense Targeting" Antisense Drug Technology: Principles, Strategies and Application (2001) p. 107-118.
Frieden et al., "Expanding the design horizon of antisense oligonucleotides with alpha-L-LNA" Nucleic Acids Research (2003) 31(21):6365-6372.
Gautschi et al., "Activity of a novel bcl-2/bcl-xL bispecific antisense oligonucleotide against tumors of diverse histologic origins" J. Natl. Cancer Inst. (2001) 93:463-471.
Germain, "Developing Novel Therapeutic Approaches for Angelman Syndrome Using Human iPSCs" ASF Scientific Meeting (2019).
Gu et al., "Base pairing properties of D- and L-cyclohexene nucleic acids (CeNA)" Oligonucleotides (2003) 13(6):479-489.
Gu et al., "Enzymatic resolution and base pairing properties of D- and L-cyclohexenyl nucleic acids (CeNA)" Nucleosides Nucleotides Nucleic Acids (2005) 24(5-7):993-998.
Gu et al., "Synthesis of enantiomeric-pure cyclohexenyl nucleoside building blocks for oligonucleotide synthesis" Tetrahedron (2004) 60(9):2111-2123.
Hagedorn et al., "Locked nucleic acid: modality, diversity, and drug discovery" Drug Discovery Today (2018) 23: 101-114.
Hall et al., "Establishment and maintenance of a heterochromatin domain" Science (2002) 297(5590):2232-2237.
Hawkins et al., "Transcriptional regulation of Oct4 by a long non-coding RNA antisense to Oct4-pseudogene 5" Transcription (2010) 1(3):165-175.
Horvath et al., "Stereoselective synthesis of (-)-ara-cyclohexenyl-adenine" Tetrahedron Letters (2007) 48:3621-3623.
Huang et al., "Topoisomerase inhibitors unsilence the dormant allele of Ube3a in neurons" Nature (2012) 481(3780): 185-189.
Jenuwein, "Molecular biology. An RNA-guided pathway for the epigenome" Science (2002) 297(5590):2215-2218.
Jiang et al., "Mutation of the Angelman ubiquitin ligase in mice causes increased cytoplasmic p53 and deficits of contextual learning and long-term potentiation" Neruon (1998) 21(4):799-811.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.
King et al., "Topoisomerases facilitate transcription of long genes linked to autism" Nature (2013) 501: 58-62.
Koch et al., "Quantum Mechanical Studies of DNA and LNA" Nucl Acid Therap (2014) 24: 139-148.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kumar et al., "The first analogues of LNA (locked nucleic acids): phosphorothioate-LNA and 2'-thio-LNA" Bioorg Med Chem Lett. (1998) 8:2219-2222.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Luo et al., "A Ribonucleolytic Rat Torpedoes RNA Polymerase II" Cell (2004) 119: 911-914.
Maher et al., "Comparative hybrid arrest by tandem antisense oligodeoxyribonucleotides or oligodeoxyribonucleoside methylphosphonates in a cell-free system" Nucl. Acid. Res. (1988) 16(8):3341-3358.
Manoharan et al., "Chemical Modifications to Improve Uptake and Bioavailability of Antisense Oligonucleotides" Ann. N.Y. Acad. Sci. (1992) 660: 306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "Oligonucleotide Conjugates: Alteration of the Pharmacokinetic Properties of Antisense Agents" Nucleosides & Nucleotides (1995) 14(3-5):969-973.
Martin, "New acces to 2'-O-alkylated ribonucleosides and properties of 2'-O-alkylated oligoribonucleotides" Helv. Chim. Acta. (1995) 78:486-504.
Meng et al., "Ube3a-ATS is an atypical RNA polymerase II transcript that represses the paternal expression of Ube3a" Hum. Mol. Genet. (2012) 21(13):3001-3012.
Meng et al., "Towards a therapy for Angelman Syndrome by Targeting a long-coding RNA" Nature (2015) 518:409-412.
Meng et al., "Truncation of Ube3a-ATS Unsilences Paternal UBE3a and Ameliorates Behavioral Defects in the Angelman Syndrome Mouse Model" PLOS Genetics (2013) 9:e1004039.
Miller et al., "Phenotypic characterization of a genetically diverse panel of mice for behavioral despair and anxiety" PLoS One (2010) 5(12):e14458.
Mishra et al., "Improved leishmanicidal effect of phosphorotioate antisense oligonucleotides by LDL-mediated delivery" Biochim. Biophys. Acta (1995) 1264:229-237.
Modarresi et al., "Inhibition of natural antisense transcripts in vivo results in gene-specific transcriptional upregulation" Nat. Biotechnol. (2012) 30(5):453-459.
Modarresi et al., "Inhibition of natural antisense transcripts in vivo results in gene-specific transcriptional upregulation" Nat. Biotechnol. (2012) 30(5) Supporting Materials.
Morris et al., "Bidirectional transcription directs both transcriptional gene activation and suppression in human cells" PLoS Genet. (2008) 4(11):e1000258.
Nauwelaerts et al., "Cyclohexenyl nucleic acids: conformationally flexible oligonucleotides" Nucleic Acids Res. (2005) 33(8):2452-2463.
Nauwelaerts et al., "Structural characterization and biological evaluation of small interfering RNAs containing cyclohexenyl nucleosides" J. Am. Chem. Soc. (2007) 129(30):9340-9348.
New England Biolabs 1998/99 Catalog (cover page and pp. 121 and 284).
Njung'e et al., "Evaluation of marble-burying behavior as a model of anxiety" Pharmacol. Biochem. Behav. (1991) 38(1):63-67.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.

(56) References Cited

OTHER PUBLICATIONS

Pal-Bhadra et al., "Heterochromatic silencing and HP1 localization in *Drosophila* are dependent on the RNAi machinery" Science (2004) 303(5658):669-672.
Papargyri et al., "Chemical Diversity of Locked Nucleic Acid-Modified Antisense Oligonucleotides Allows Optimization of Pharmaceutical Properties" Mol Ther Nuclic Acids (2020) 19: 706-717.
Plagge "Non-Coding RNAs at the Gnas and Snrpn-Ube3a Imprinted Gene Loci and Their Involvement in Hereditary Disorders" Front Genet. (2012) 3: 1-6.
Philpot et al., "Angelman syndrome: advancing the research frontier of neurodevelopment disorders" J Neurodevelop Disord (2011) 3: 50-56.
Powell et al., "R-loop formation at Snord116 mediates topotecan inhibition of Ube3a-antisense and allele-specific chromatin decondensation" Proc Natl Acad Sci (2013) 110: 13938-43.
Reynolds et al., "Rational siRNA design for RNA interference" Nature Biotechnology (2004) 22(3):326-330.
Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.
Robeyns et al., "Structure of the fully modified left-handed cyclohexene nucleic acid sequence GTGTACAC" J. Am. Chem. Soc. (2008) 130(6):1979-1984.
Rougeulle et al. "An imprinted antisense RNA overlaps UBE3A and a second maternally expressed transcript" Nature Genet (1998) 19: 15-16.
Rougeulle et al., "The Angelman syndrome candidate gene, UBE3A/E6-AP, is imprinted in brain" Nature Generics (1997) 17: 14-15.
Runte et al., "The IC-SNURF-SNRPN Transcript serves as a Host for Multiple Small Nucleolar RNA Species and as an Antisense RNA for UBE3A" Human Molecular Genetics (2001) 10: 2687-2700.
Sahoo et al., "Prader-Willi phenotype caused by paternal deficiency for the HBII-85 C/D box small nucleolar RNA cluster" Nat. Genet. (2008) 40(6):719-721.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Heterocyclic Base Modifications in Nucleic Acids and Their Applications in Antisense Oligonucleotides" Antisense Research and Applications (1993) pp. 273-288.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Shea et al., "Synthesis, hybridization properties and antiviral activity of lipid-oligodeoxynucleotide conjugates" Nucl. Acids Res. (1990) 18(13):3777-3783.
Shi et al., "In situ entry of oligonucleotides into brain cells can occur through a nucleic acid channel" Oligonucleotides (2007) 17: 122-133.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Smith et al., "Comparison of biosequences" Adv. Appl. Math. (1981) 2(4):482-489.
Smith et al., "Transcription is Required to Establish Maternal Imprinting at the Prader-Willi Syndrome and Angelman Syndrome Locus" PLoS Genetics (2011) 7: 1-10.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Tsai et al., "Paternal deletion from Snrpn to Ube3a in the mouse causes hypotonia, growth retardation and partial lethality and provides evidence for a gene contributing to Prader-Willi syndrome" Hum. Mol. Genet. (1999) 8(8):1357-1364.
Verbeure et al., "RNase H mediated cleavage of RNA by cyclohexene nucleic acid (CeNA)" Nucleic Acids Res. (2001) 29(24):4941-4947.
Verdel et al., "RNAi-mediated targeting of heterochromatin by the RITS complex" Science (2004) 303(5668):672-676.
Volpe et al., "Regulation of heterochromatic silencing and histone H3 lysine-9 methylation by RNAi" Science (2002) 297(5588):1833:1837.
Wahlestedt et al., "Potent and nontoxic antisense oligonucleotide containing locked nucleic acids" Proc. Natl. Acad. Sci. USA (2000) 97: 5633-5638.
Wahlestedt et al., "Natural antisense and noncoding RNA transcripts as potential drug targets" Drug Discovery Today (2006) 11: 503-508.
Wahlestedt et al., "Regulatory Natural Antisense Transcripts" Keystone Symposium on MicroRNAs and Human Disease: Banff, Alberta CA (Feb. 11-16, 2011).
Wahlestedt et al., "Regulatory Natural Antisense Transcripts" Keystone Symposium Programme: Banff, Alberta CA (Feb. 11-16, 2011).
Wang et al., "A straightforward stereoselective synthesis of D- and L-5-hydroxy-4-hydroxymethyl-2-cyclohexenylguanine" J. Org. Chem. (2001) 66(25):8478-8482.
Wang et al., "Cyclohexene nucleic acids (CeNA) form stable duplexes with RNA and induce RNase H activity" Nucleosides Nucleotides Nucleic Acids (2001) 20(4-7):785-788.
Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.
Wang et al., "Stereocontrolled synthesis of ara-type cyclohexenyl nucleosides" J. Org. Chem. (2003) 68(11):4499-4505.
Williams et al., "Clinical and genetic aspects of Angelman syndrome" Genet. Med. (2010) 12(7):385-395.
Woolf et al., "Specificity of antisense oligonucleotides in vivo" Proc. Natl. Acad. Sci. (1992) 89(16):7305-7309.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search report for application EP 2864479 dated May 10, 2016.
International Search Report for application PCT/US2013/47701 dated Feb. 14, 2014.
International Search Report for application PCT/US2015/062622 dated Jan. 15, 2016.
International Search Report for application PCT/US20/025110 dated Aug. 19, 2020.
Extended EP Search Report for 20784141.2 dated Aug. 21, 2023.
GenBank Accession NC_000015.10, uploaded Mar. 2018, 2 pages.
GenBank Accession NM_130838.1, uploaded Jul. 2017, 7 pages.

* cited by examiner

COMPOUNDS AND METHODS FOR MODULATING UBE3A-ATS

SEQUENCE LISTING

The present application is being filed along with a Sequence Listing in electronic format. The Sequence Listing is provided as a file entitled BIOL0349WOSEQ_ST25.tst, created on Mar. 16, 2020, which is 1.87 MB in size. The information in the electronic format of the sequence listing is incorporated herein by reference in its entirety.

FIELD

Provided are compounds, methods, and pharmaceutical compositions for reducing the amount or activity of UBE3A-ATS, the endogenous antisense transcript of ubiquitin protein ligase E3A (UBE3A) in a cell or subject, and in certain instances increasing the expression of paternal UBE3A and the amount of UBE3A protein in a cell or subject. Such compounds, methods, and pharmaceutical compositions are useful to ameliorate at least one symptom or hallmark of a neurogenetic disorder. Such symptoms and hallmarks include developmental delays, ataxia, speech impairment, sleep problems, seizures, and EEG abnormalities. Such neurogenetic disorders include Angelman Syndrome.

BACKGROUND

Angelman Syndrome (AS) is a developmental disorder that affects ~1/15,000 live births and is caused by a deficiency of ubiquitin protein ligase E3A (UBE3A). Of the two copies of the UBE3A gene in neurons, the maternal gene is typically expressed, while the paternal gene is subject to genetic imprinting and silencing. Angelman Syndrome is caused when a functional copy of the UBE3A gene is not inherited from the mother, either because of a mutation, a deletion, paternal uniparental disomy of chromosome 15, or an imprinting defect. See, Buiting, et al., "Angelman Syndrome—insights into a rare neurogenetic disorder", *Nature Rev. Neuro.*, 2016, 12:584-593.

Angelman Syndrome patients experience developmental delays and speech impairment, and commonly experience sleep problems, seizures, and EEG abnormalities. The disorder is usually diagnosed in the first few years of life and the diagnosis can be confirmed by genetic testing. However, therapies for Angelman Syndrome remain limited and focus mainly on symptomatic management. See, Williams, C. A. et al., Genet. Med., 12: 385-395, 2010.

Recently, topoisomerase inhibitors currently used in cancer treatment were found to "unsilence" paternal UBE3A expression in both a neuronal culture system and mice. See, Huang, H. S. et al., Nature, 481: 185-189, 2012. However, the exact mechanism of unsilencing paternal UBE3A expression remains unknown and topoisomerase inhibitors are fraught with safety concerns because they are known to be non-specific and capable of inducing DNA damage, such as single and double-strand breaks.

Currently there is a lack of acceptable options for treating neurogenetic disorders such as AS. It is therefore an object herein to provide compounds, methods, and pharmaceutical compositions for the treatment of such diseases.

SUMMARY OF THE INVENTION

Provided herein are compounds, methods and pharmaceutical compositions for reducing the amount or activity of UBE3A-ATS RNA, and in certain embodiments increasing the expression of paternal UBE3A RNA or protein in a cell or subject. In certain embodiments, the subject has a neurogenetic disorder. In certain embodiments, the subject has Angelman Syndrome (AS). In certain embodiments, compounds useful for reducing expression of UBE3A-ATS RNA, or a portion thereof, are oligomeric compounds. In certain embodiments, compounds useful for reducing expression of UBE3A-ATS RNA, or a portion thereof, are modified oligonucleotides. In certain embodiments, compounds useful for increasing expression of paternal UBE3A RNA or protein are oligomeric compounds. In certain embodiments, compounds useful for increasing expression of paternal UBE3A RNA or protein are modified oligonucleotides.

Also provided are methods useful for ameliorating at least one symptom or hallmark of a neurogenetic disorder. In certain embodiments, the neurogenetic disorder is Angelman Syndrome. In certain embodiments, the symptom or hallmark includes developmental delays, ataxia, speech impairment, sleep problems, seizures, and/or EEG abnormalities.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyribosyl sugar moiety. In certain embodiments, a 2'-deoxynucleoside is a 2'-β-D-deoxynucleoside and comprises a 2'-β-D-deoxyribosyl sugar moiety, which has the β-D configuration as found in naturally occurring deoxyribonucleic acids (DNA). In certain embodiments, a 2'-deoxynucleoside may comprise a modified nucleobase or may comprise an RNA nucleobase (uracil).

As used herein, "2'-MOE" or "2'-MOE sugar moiety" means a 2'-OCH$_2$CH$_2$OCH$_3$ group in place of the 2'—OH group of a ribosyl sugar moiety. "MOE" means methoxyethyl. Unless otherwise indicated, a 2'-MOE has the β-D stereochemical configuration.

As used herein, "2'-MOE nucleoside" means a nucleoside comprising a 2'-MOE sugar moiety.

As used herein, "2'-OMe" or "2'-O-methyl sugar moiety" means a 2'-OCH$_3$ group in place of the 2'—OH group of a ribosyl sugar moiety. Unless otherwise indicated, a 2'-OMe has the β-D stereochemical configuration.

As used herein, "2'-OMe nucleoside" means a nucleoside comprising a 2'-OMe sugar moiety.

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to a subject.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom or hallmark is developmental delays, ataxia, speech impairment, sleep problems, seizures, and EEG abnormalities.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cleavable moiety" means a bond or group of atoms that is cleaved under physiological conditions, for example, inside a cell, a subject, or a human.

As used herein, "complementary" in reference to an oligonucleotide means that at least 70% of the nucleobases of the oligonucleotide or one or more portions thereof and the nucleobases of a target nucleic acid or one or more portions thereof are capable of hydrogen bonding with one another when the nucleobase sequence of the oligonucleotide and the other nucleic acid are aligned in opposing directions. As used herein, complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or target nucleic acids need not have nucleobase complementarity at each nucleoside. Rather, some mismatches are tolerated. As used herein, "fully complementary" or "100% complementary" in reference to an oligonucleotide, or portion thereof, means that the oligonucleotide, or portion thereof, is complementary to another oligonucleotide or target nucleic acid at each nucleobase of the shorter of the two oligonucleotides, or at each nucleoside if the oligonucleotides are the same length.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "constrained ethyl" or "cEt" or "cEt modified sugar moiety" means β-D ribosyl bicyclic sugar moiety wherein the second ring of the bicyclic sugar is formed via a bridge connecting the 4'-carbon and the 2'-carbon of the β-D ribosyl sugar moiety, wherein the bridge has the formula 4'-CH(CH$_3$)—O-2', and wherein the methyl group of the bridge is in the S configuration.

As used herein, "cEt nucleoside" means a nucleoside comprising a cEt modified sugar moiety.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moiety of each nucleoside of the gap is a 2'-β-D-deoxyribosyl sugar moiety. Thus, the term "MOE gapmer" indicates a gapmer having a gap comprising 2'-β-D-deoxynucleosides and wings comprising 2'-MOE nucleosides. Unless otherwise indicated, a MOE gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid that is amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "internucleoside linkage" means the covalent linkage between contiguous nucleosides in an oligonucleotide. As used herein, "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "motif" means the pattern of unmodified and/or modified sugar moieties, nucleobases, and/or internucleoside linkages, in an oligonucleotide.

As used herein, "neurogenetic disorder" means a condition of the nervous system caused by a heritable genetic factor, including, but not limited to, a mutation, a deletion, uniparental disomy, or an imprinting defect.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a target nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to a subject. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein, "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein, "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "prodrug" means a therapeutic agent in a form outside the body that is converted to a different form within a subject or cells thereof. Typically, conversion of a prodrug within the subject is facilitated by the action of an enzymes (e.g., endogenous or viral enzyme) or chemicals present in cells or tissues and/or by physiologic conditions.

As used herein, "reducing or inhibiting the amount or activity", "reducing the amount or activity", or "inhibiting the amount or activity" refers to a reduction or blockade of the transcriptional expression or activity relative to the transcriptional expression or activity in an untreated or control sample and does not necessarily indicate a total elimination of transcriptional expression or activity.

As used herein, "RNA" means any RNA transcript, including endogenous antisense transcripts that do not encode a protein (e.g., UBE3A-ATS), and also includes pre-mRNA and mature mRNA unless otherwise specified.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard cell assay" means the assay described in Example 1 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "subject" means a human or non-human animal.

As used herein, "sugar moiety" means an unmodified sugar moiety or a modified sugar moiety. As used herein, "unmodified sugar moiety" means a 2'-OH(H) β-D-ribosyl moiety, as found in RNA (an "unmodified RNA sugar moiety"), or a 2'-H(H) β-D-deoxyribosyl sugar moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "symptom or hallmark" means any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to a subject. For example, a therapeutically effective amount improves a symptom or hallmark of a disease.

Certain Embodiments

The present disclosure provides the following non-limiting numbered embodiments:

Embodiment 1. An oligomeric compound comprising a modified oligonucleotide consisting of 12 to 30 linked nucleosides wherein the nucleobase sequence of the modified oligonucleotide is at least 90% complementary to an equal length portion of a UBE3A-ATS RNA, and wherein the modified oligonucleotide comprises at least one modification selected from a modified sugar moiety and a modified internucleoside linkage.

Embodiment 2. An oligomeric compound comprising a modified oligonucleotide consisting of 12 to 30 linked nucleosides and having a nucleobase sequence comprising at least 12, 13, 14, 15, 16, 17, 18, 19, or 20 contiguous nucleobases of any of SEQ ID NOs: 17-2762, 2786-2863, 2872-2904.

Embodiment 3. An oligomeric compound comprising a modified oligonucleotide consisting of 12 to 30 linked nucleosides and having a nucleobase sequence comprising at least 12, 13, 14, 15, 16, 17, or 18 contiguous nucleobases of any of SEQ ID NOs: 2763-2785 or 2864-2871.

Embodiment 4. An oligomeric compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 contiguous nucleobases complementary to:
  an equal length portion of nucleobases 461,413-461,487 of SEQ ID NO: 1;
  an equal length portion of nucleobases 468,968-469,013 of SEQ ID NO: 1; or an equal length portion of nucleobases 483,965-484,003 of SEQ ID NO: 1

Embodiment 5. An oligomeric compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, or at least 18 contiguous nucleobases of a sequence selected from:
  SEQ ID Nos:1053, 1329, 1501, 1576, 1873, 1949, 2025, 2096, 2245, 2512, 2591, 2680-2682, and 2844;
  SEQ ID Nos: 376, 377, 2751-2756, 2773-2776, 2872, 2873, 2876-2878; or
  SEQ ID Nos: 172, 764-770, 995, 1445, 1668, 1743, 2255, 2595, 2762-2767.

Embodiment 6. The oligomeric compound of any of embodiments 1-5, wherein the modified oligonucleotide has a nucleobase sequence that is at least 80%, 85%, 90%, 95%, or 100% complementary to the nucleobase sequence of SEQ ID NO: 1, SEQ ID NO: 2915, or SEQ ID NO: 2916 when measured across the entire nucleobase sequence of the modified oligonucleotide.

Embodiment 7. The oligomeric compound of any of embodiments 1-6, wherein the modified oligonucleotide comprises at least one modified nucleoside.

Embodiment 8. The oligomeric compound of embodiment 7, wherein the modified oligonucleotide comprises at least one modified nucleoside comprising a modified sugar moiety.

Embodiment 9. The oligomeric compound of embodiment 8, wherein the modified oligonucleotide comprises at least one modified nucleoside comprising a bicyclic sugar moiety.

Embodiment 10. The oligomeric compound of embodiment 9, wherein the modified oligonucleotide comprises at least one modified nucleoside comprising a bicyclic sugar moiety having a 2'-4' bridge, wherein the 2'-4' bridge is selected from —O—$CH_2$—; and —O—$CH(CH_3)$—.

Embodiment 11. The oligomeric compound of any of embodiments 7-10, wherein the modified oligonucleotide comprises at least one modified nucleoside comprising a non-bicyclic modified sugar moiety.

Embodiment 12. The oligomeric compound of embodiment 11, wherein the non-bicyclic modified sugar moiety is a 2'-MOE modified sugar moiety or 2'-OMe modified sugar moiety.

Embodiment 13. The oligomeric compound of any of embodiments 7-8, wherein the modified oligonucleotide comprises at least one modified nucleoside comprising a sugar surrogate.

Embodiment 14. The oligomeric compound of embodiment 13, wherein the modified oligonucleotide comprises at least one modified nucleoside comprising a sugar surrogate selected from morpholino and PNA.

Embodiment 15. The oligomeric compound of any of embodiments 1-8 or 11-14, wherein the modified oligonucleotide does not comprise a bicyclic sugar moiety.

Embodiment 16. The oligomeric compound of any of embodiments 1-15, wherein the modified oligonucleotide is a gapmer.

Embodiment 17. The oligomeric compound of any of embodiments 1-16, wherein the modified oligonucleotide has a sugar motif comprising:
a 5'-region consisting of 1-6 linked 5'-region nucleosides;
a central region consisting of 6-10 linked central region nucleosides; and
a 3'-region consisting of 1-6 linked 3'-region nucleosides; wherein
each of the 5'-region nucleosides and each of the 3'-region nucleosides comprises a modified sugar moiety
and each of the central region nucleosides comprises a 2'-β-D-deoxyribosyl sugar moiety.

Embodiment 18. The oligomeric compound of embodiment 17, wherein the modified oligonucleotide has
a 5'-region consisting of 5 linked 5'-region nucleosides;
a central region consisting of 10 linked central region nucleosides; and
a 3'-region consisting of 5 linked 3'-region nucleosides; wherein
each of the 5'-region nucleosides and each of the 3'-region nucleosides comprises a 2'-MOE modified sugar moiety, and each of the central region nucleosides comprises a 2'-β-D-deoxyribosyl sugar moiety.

Embodiment 19. The oligomeric compound of embodiment 17, wherein the modified oligonucleotide has
a 5'-region consisting of 4 linked 5'-region nucleosides;
a central region consisting of 10 linked central region nucleosides; and
a 3'-region consisting of 6 linked 3'-region nucleosides; wherein
each of the 5'-region nucleosides and each of the 3'-region nucleosides a 2'-MOE modified sugar moiety,
and each of the central region nucleosides comprises a 2'-β-D-deoxyribosyl sugar moiety.

Embodiment 20. The oligomeric compound of embodiment 17, wherein the modified oligonucleotide has
a 5'-region consisting of 6 linked 5'-region nucleosides;
a central region consisting of 10 linked central region nucleosides; and
a 3'-region consisting of 4 linked 3'-region nucleosides; wherein
each of the 5'-region nucleosides and each of the 3'-region nucleosides a 2'-MOE modified sugar moiety,
and each of the central region nucleosides comprises a 2'-β-D-deoxyribosyl sugar moiety.

Embodiment 21. The oligomeric compound of embodiment 17, wherein the modified oligonucleotide has
a 5'-region consisting of 5 linked 5'-region nucleosides;
a central region consisting of 8 linked central region nucleosides; and
a 3'-region consisting of 5 linked 3'-region nucleosides; wherein
each of the 5'-region nucleosides and each of the 3'-region nucleosides a 2'-MOE modified sugar moiety,
and each of the central region nucleosides comprises a 2'-β-D-deoxyribosyl sugar moiety.

Embodiment 22. The oligomeric compound of embodiment 17, wherein the modified oligonucleotide has
a 5'-region consisting of 4 linked 5'-region nucleosides;
a central region consisting of 8 linked central region nucleosides; and
a 3'-region consisting of 6 linked 3'-region nucleosides; wherein
each of the 5'-region nucleosides and each of the 3'-region nucleosides a 2'-MOE modified sugar moiety,
and each of the central region nucleosides comprises a 2'-β-D-deoxyribosyl sugar moiety.

Embodiment 23. The oligomeric compound of embodiment 17, wherein the modified oligonucleotide has
a 5'-region consisting of 4 linked 5'-region nucleosides;
a central region consisting of 8 linked central region nucleosides; and
a 3'-region consisting of 6 linked 3'-region nucleosides; wherein
each of the 5'-region nucleosides and each of the 3'-region nucleosides a 2'-MOE modified sugar moiety,
and each of the central region nucleosides comprises a 2'-β-D-deoxyribosyl sugar moiety.

Embodiment 24. The oligomeric compound of any of embodiments 1-23, wherein the modified oligonucleotide comprises at least one modified internucleoside linkage.

Embodiment 25. The oligomeric compound of embodiment 24, wherein each internucleoside linkage of the modified oligonucleotide is a modified internucleoside linkage.

Embodiment 26. The oligomeric compound of embodiment 24 or 25 wherein the modified internucleoside linkage is a phosphorothioate internucleoside linkage.

Embodiment 27. The oligomeric compound of embodiment 24 or 26 wherein the modified oligonucleotide comprises at least one phosphodiester internucleoside linkage.

Embodiment 28. The oligomeric compound of any of embodiments 24, 26, or 27, wherein each internucleoside linkage is independently selected from a phosphodiester internucleoside linkage or a phosphorothioate internucleoside linkage.

Embodiment 29. The oligomeric compound of embodiments 1-24 or 27-28, wherein the modified oligonucleotide has an internucleoside linkage motif selected from among: sooooossssssssssooss, sooooossssssssssoss, sooooosssssssss-soss, sooosssssssssooss, sooosssssssssooooss, or soossssssssssooooss; wherein, s=a phosphorothioate internucleoside linkage and o=a phosphodiester internucleoside linkage.

Embodiment 30. The oligomeric compound of any of embodiments 1-29, wherein the modified oligonucleotide comprises a modified nucleobase.

Embodiment 31. The oligomeric compound of embodiment 30, wherein the modified nucleobase is a 5-methyl cytosine.

Embodiment 32. The oligomeric compound of any of embodiments 1-31, wherein the modified oligonucleotide consists of 12-30, 12-22, 12-20, 14-18, 14-20, 15-17, 15-25, 16-20, 18-22 or 18-20 linked nucleosides.

Embodiment 33. The oligomeric compound of any of embodiments 1-32, wherein the modified oligonucleotide consists of 18 linked nucleosides.

Embodiment 34. The oligomeric compound of any of embodiments 1-2, 4, or 6-32, wherein the modified oligonucleotide consists of 20 linked nucleosides.

Embodiment 35. The oligomeric compound of any of embodiments 1-34, consisting of the modified oligonucleotide.

Embodiment 36. The oligomeric compound of any of embodiments 1-34, comprising a conjugate group comprising a conjugate moiety and a conjugate linker.

Embodiment 37. The oligomeric compound of embodiment 36, wherein the conjugate linker consists of a single bond.

Embodiment 38. The oligomeric compound of embodiment 36, wherein the conjugate linker is cleavable.

Embodiment 39. The oligomeric compound of embodiment 36, wherein the conjugate linker comprises 1-3 linker-nucleosides.

Embodiment 40. The oligomeric compound of any of embodiments 36-39, wherein the conjugate group is attached to the modified oligonucleotide at the 5'-end of the modified oligonucleotide.

Embodiment 41. The oligomeric compound of any of embodiments 36-39, wherein the conjugate group is attached to the modified oligonucleotide at the 3'-end of the modified oligonucleotide.

Embodiment 42. The oligomeric compound of any of embodiments 1-34 or 36-41, comprising a terminal group.

Embodiment 43. The oligomeric compound of any of embodiments 1-42 wherein the oligomeric compound is a singled-stranded oligomeric compound.

Embodiment 44. The oligomeric compound of any of embodiments 1-38 or 40-43, wherein the oligomeric compound does not comprise linker-nucleosides.

Embodiment 45. An oligomeric duplex comprising an oligomeric compound of any of embodiments 1-42 or 44.

Embodiment 46. An antisense compound comprising or consisting of an oligomeric compound of any of embodiments 1-44 or an oligomeric duplex of embodiment 45.

Embodiment 47. A pharmaceutical composition comprising an oligomeric compound of any of embodiments 1-44 or an oligomeric duplex of embodiment 45 and a pharmaceutically acceptable carrier or diluent.

Embodiment 48. The pharmaceutical composition of embodiment 47, wherein the pharmaceutically acceptable diluent is artificial cerebral spinal fluid.

Embodiment 49. The pharmaceutical composition of embodiment 48, wherein the pharmaceutical composition consists essentially of the modified oligonucleotide and phosphate buffered saline.

Embodiment 50. A method comprising administering to a subject a pharmaceutical composition of any of embodiments 47-50.

Embodiment 51. A method of treating a disease associated with UBE3A-ATS comprising administering to an individual having or at risk for developing a disease associated with UBE3A-ATS a therapeutically effective amount of a pharmaceutical composition according to any of embodiments 47-49; and thereby treating the disease associated with UBE3A-ATS.

Embodiment 52. The method of embodiment 51, wherein the UBE3A-ATS-associated disease is Angelman Syndrome.

Embodiment 53. The method of any of embodiments 50-52, wherein at least one symptom or hallmark of the UBE3A-ATS-associated disease is ameliorated.

Embodiment 54. The method of embodiment 53, wherein the symptom or hallmark is developmental delays, ataxia, speech impairment, sleep problems, seizures, or EEG abnormalities.

Embodiment 55. A modified oligonucleotide according to the following chemical structure:

(SEQ ID NO: 1949)

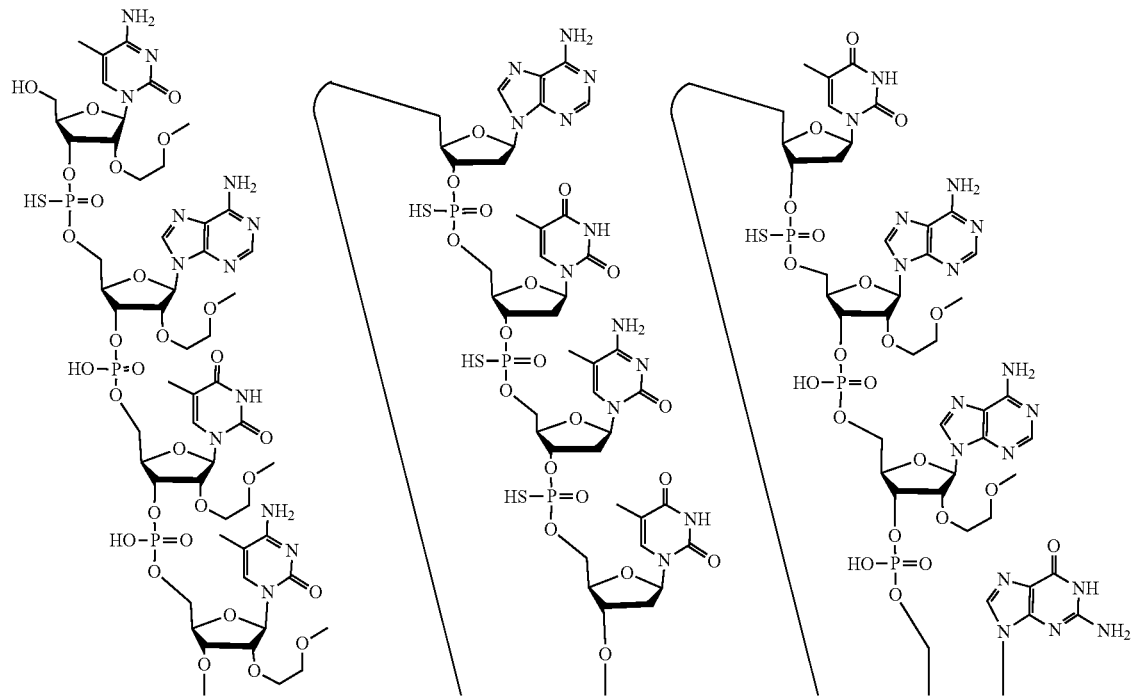

-continued
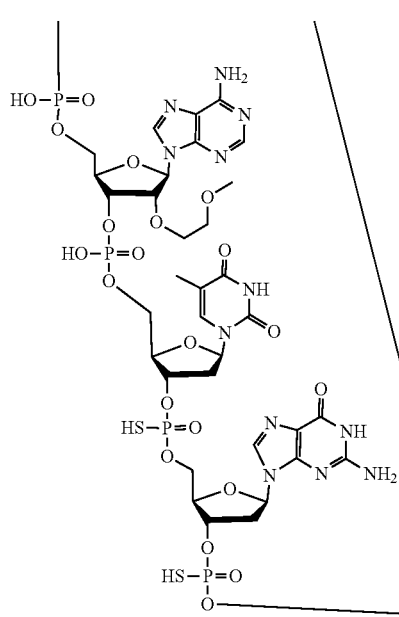
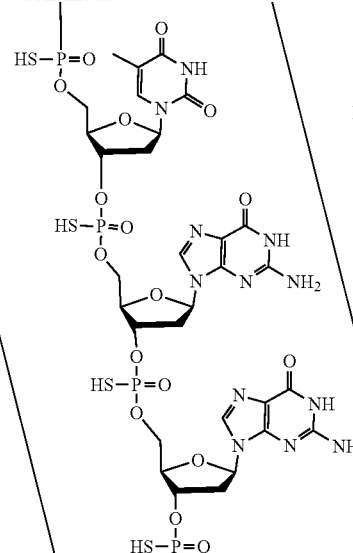
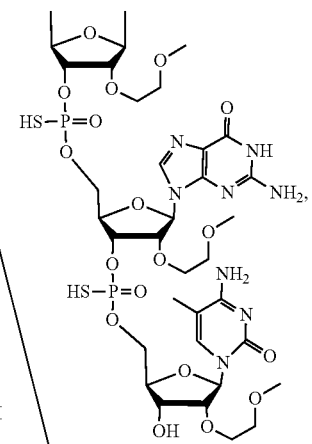
or a salt thereof.
Embodiment 56. A modified oligonucleotide according to the following chemical structure:
(SEQ ID NO: 1949)
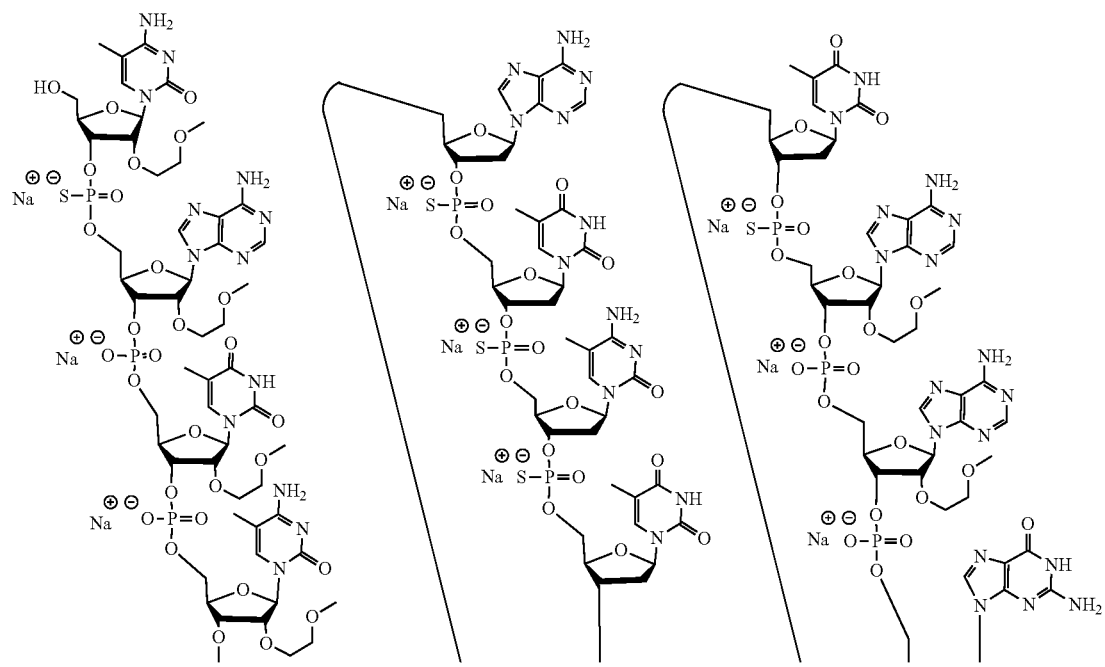

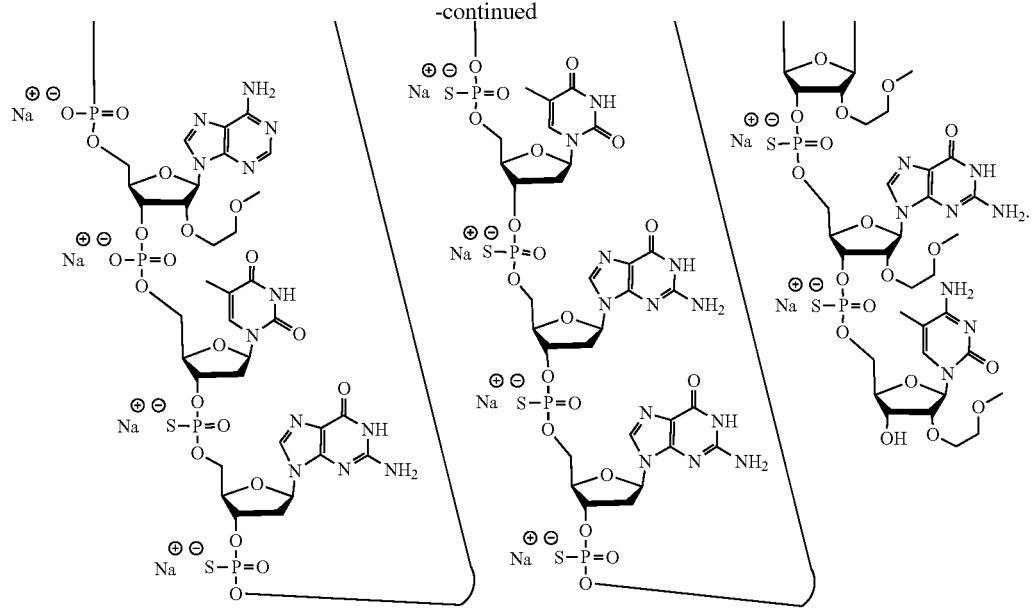
Embodiment 57. A modified oligonucleotide according to the following chemical structure:
(SEQ ID NO: 2751)
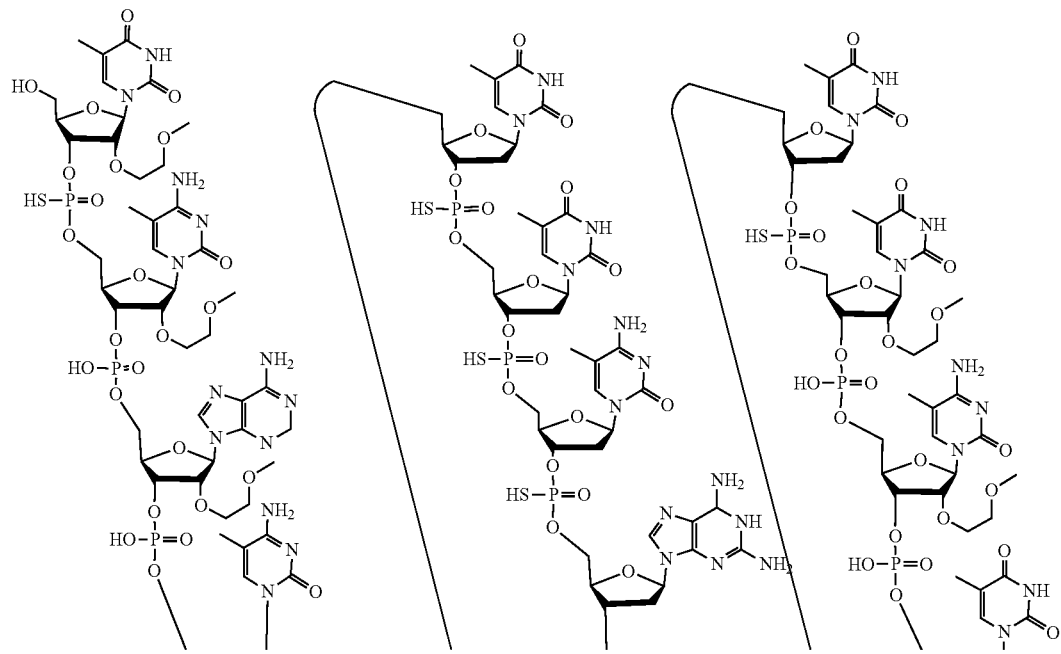

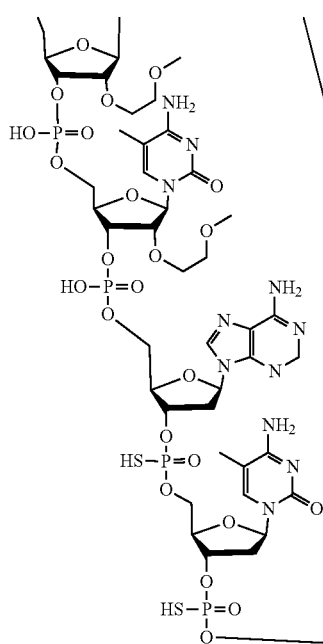
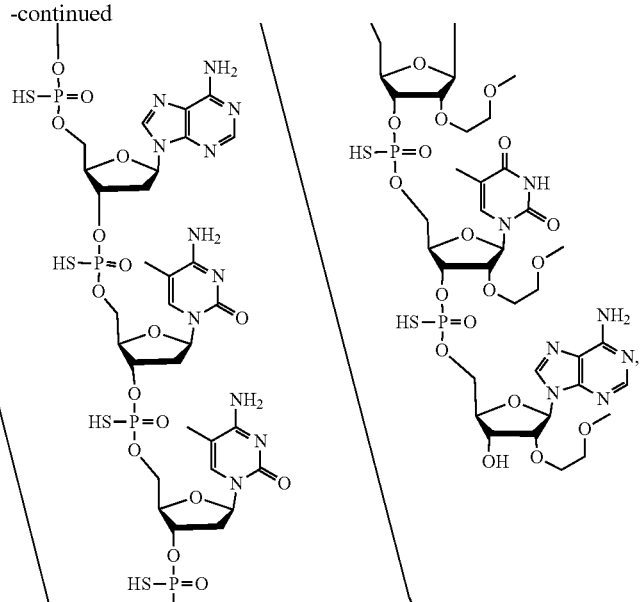
or a salt thereof.
Embodiment 58. A modified oligonucleotide according to the following chemical structure:
(SEQ ID NO: 2751)
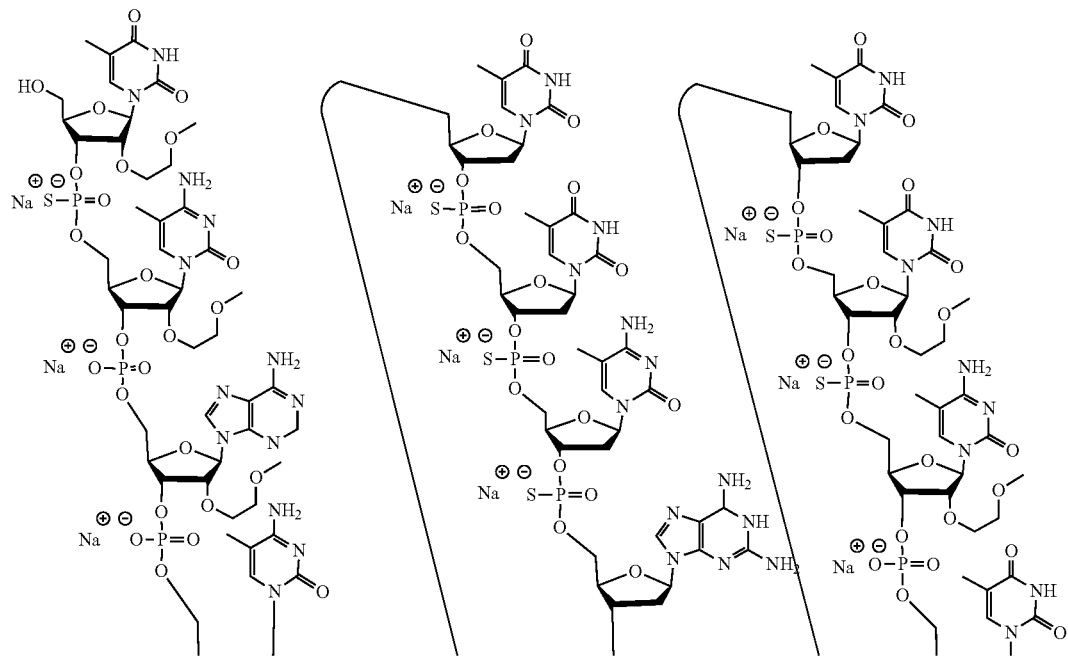

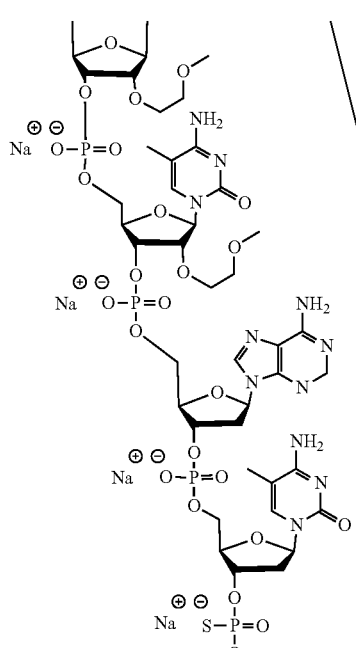
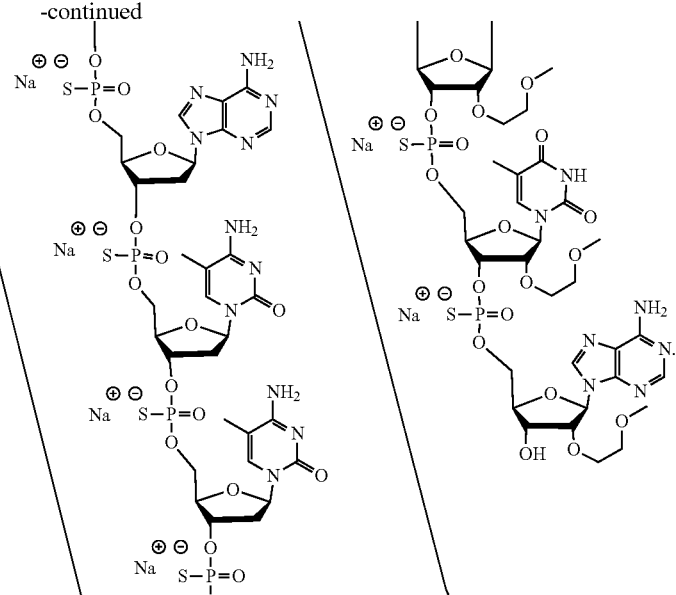
Embodiment 59. A modified oligonucleotide according to the following chemical structure:
(SEQ ID NO: 2752)
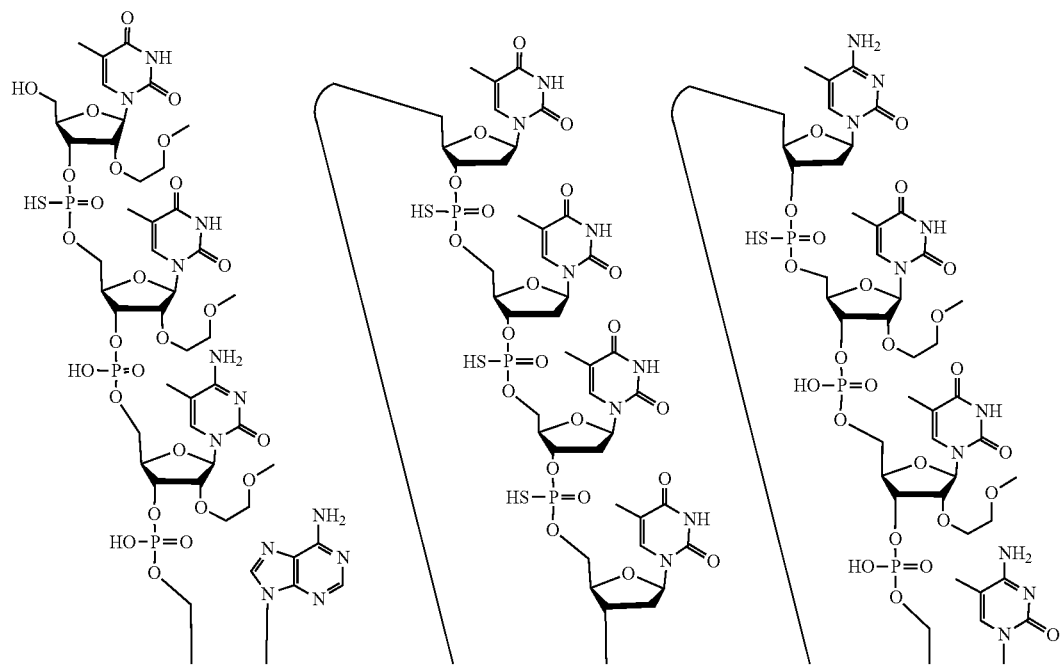

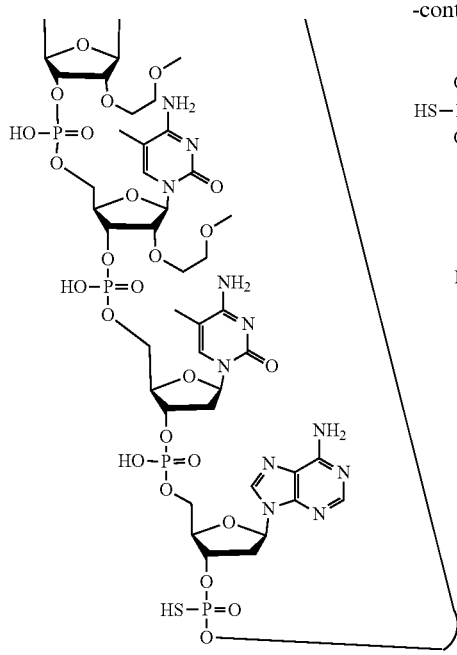
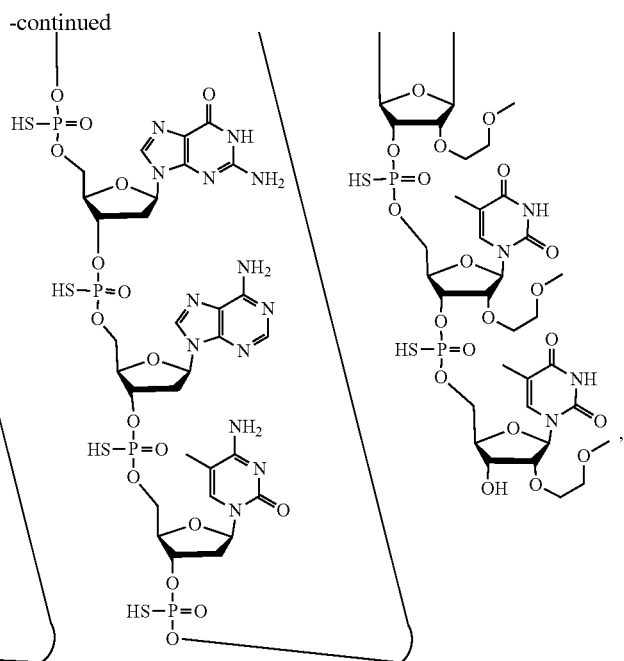
or a salt thereof.
Embodiment 60. A modified oligonucleotide corresponding to the following chemical structure:
(SEQ ID NO: 2752)
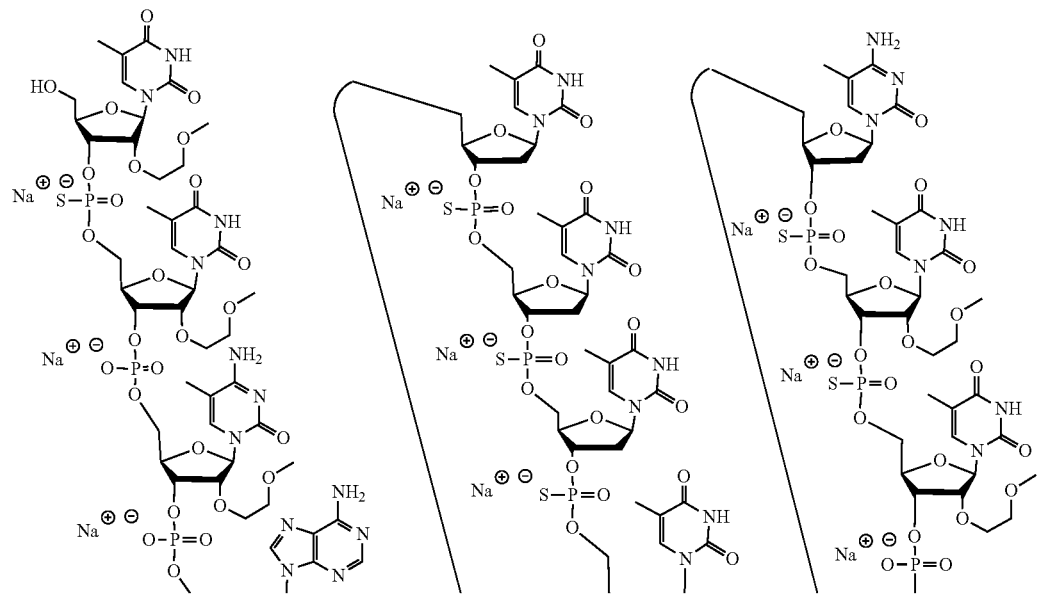

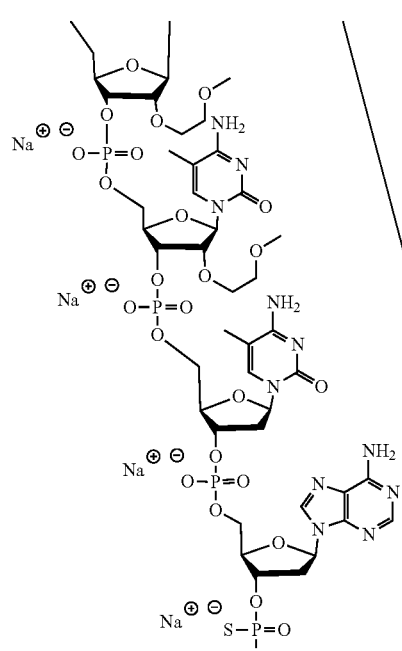
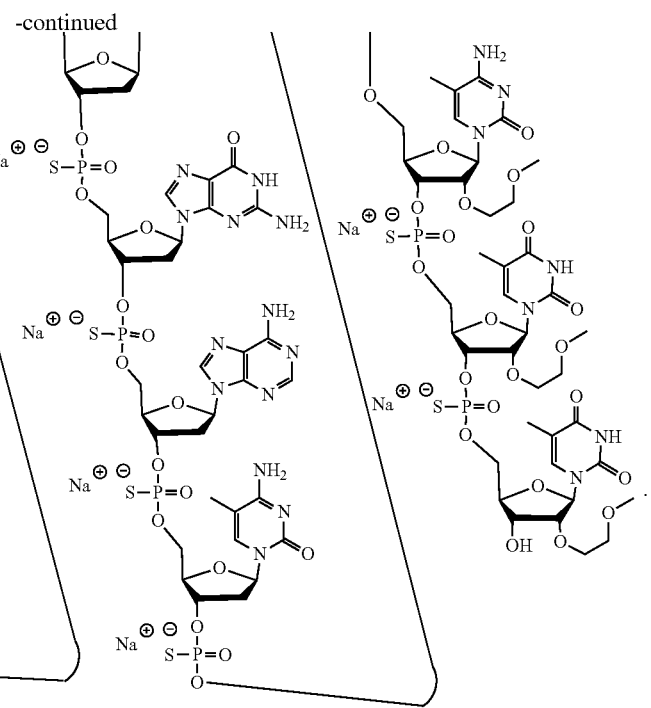
Embodiment 61. A modified oligonucleotide according to the following chemical structure:
(SEQ ID NO: 765)
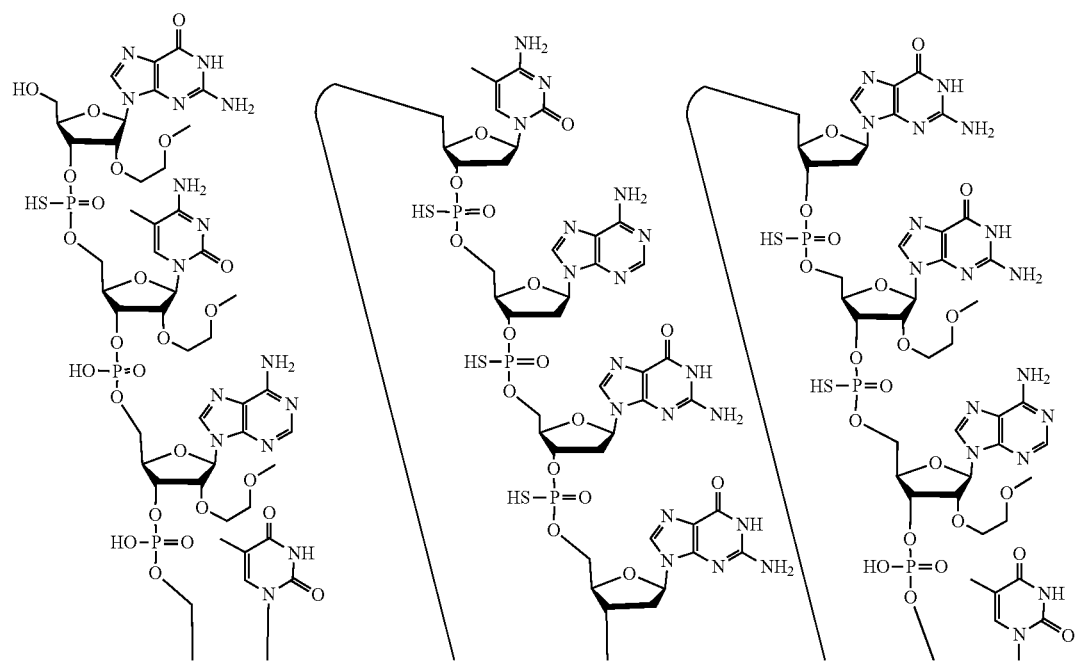

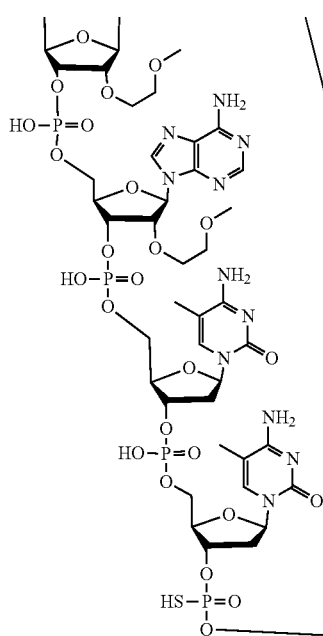
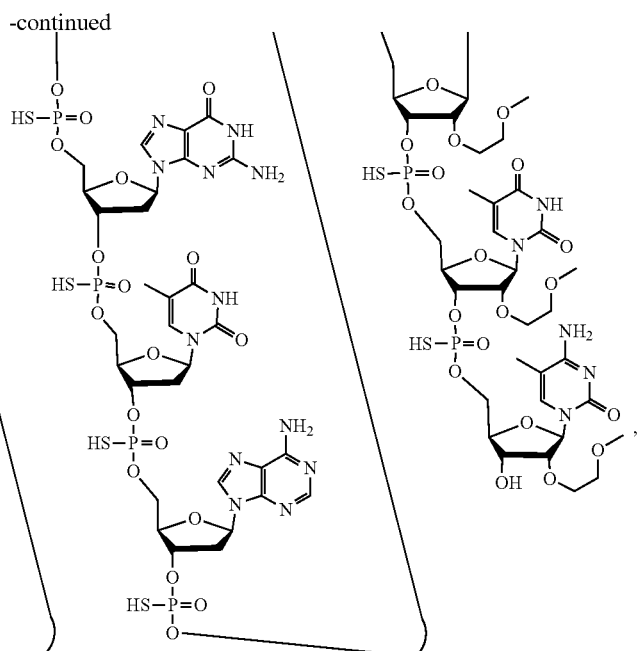
or a salt thereof.
Embodiment 62. A modified oligonucleotide according to the following chemical structure:
(SEQ ID NO: 765)
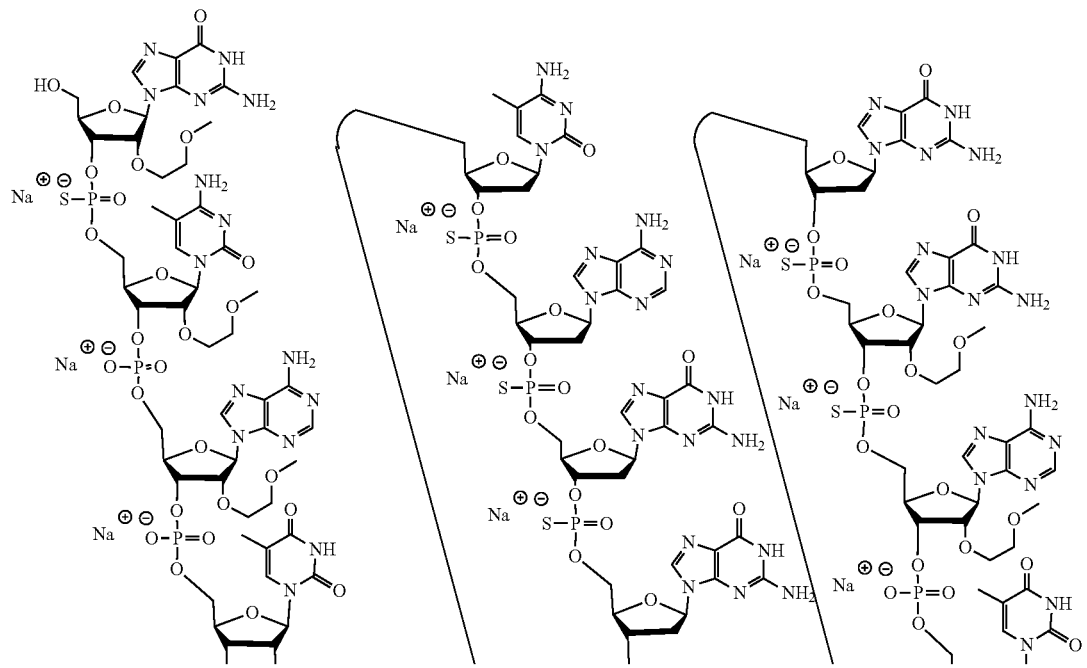

27 28
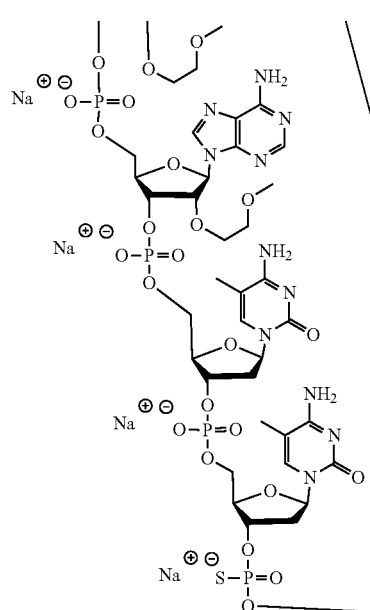
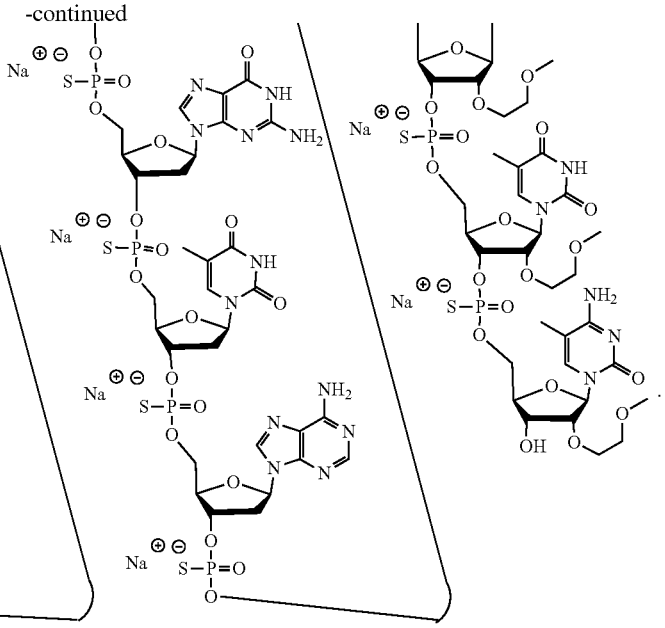
-continued
Embodiment 63. A modified oligonucleotide according to the following chemical structure:
(SEQ ID NO: 2866)
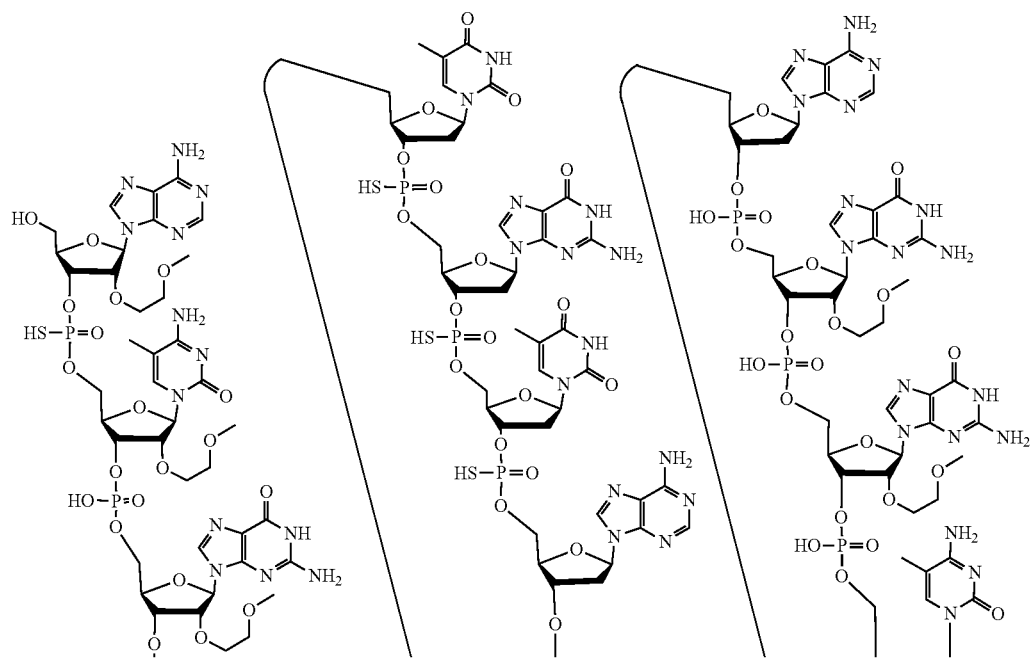

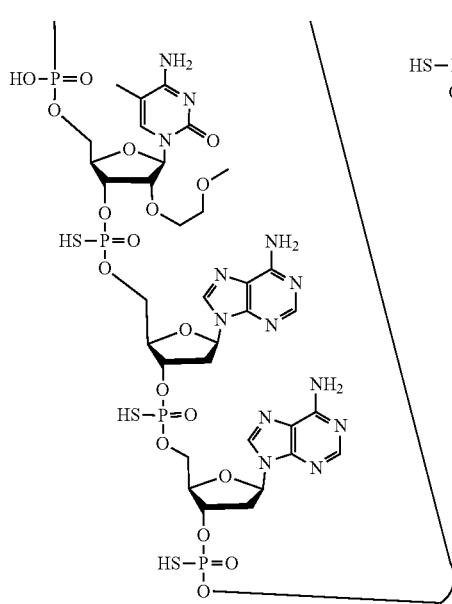
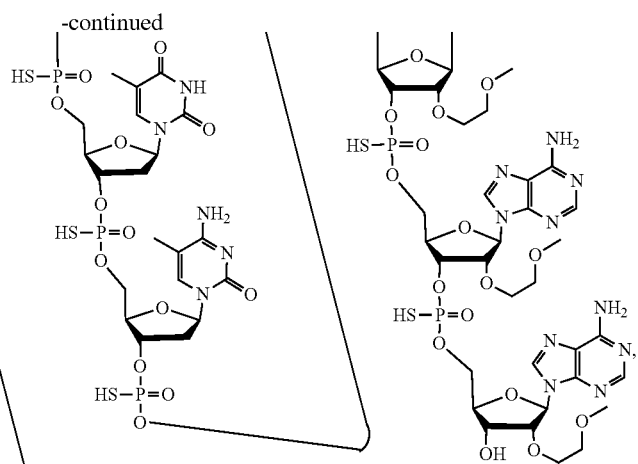
or a salt thereof.
Embodiment 64. A modified oligonucleotide according to the following chemical structure:
(SEQ ID NO: 2866)
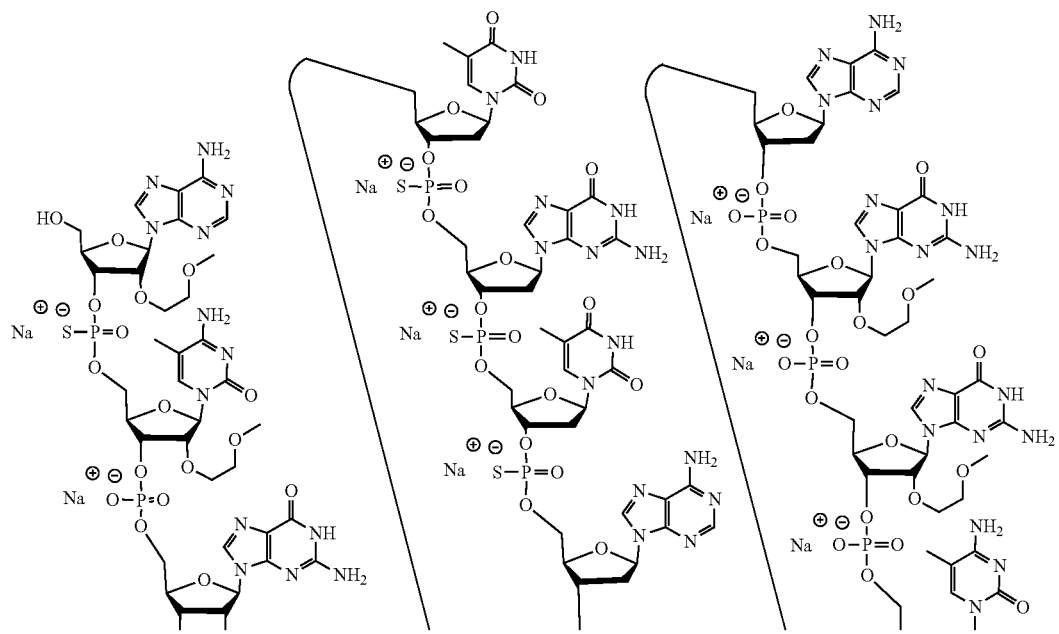

31
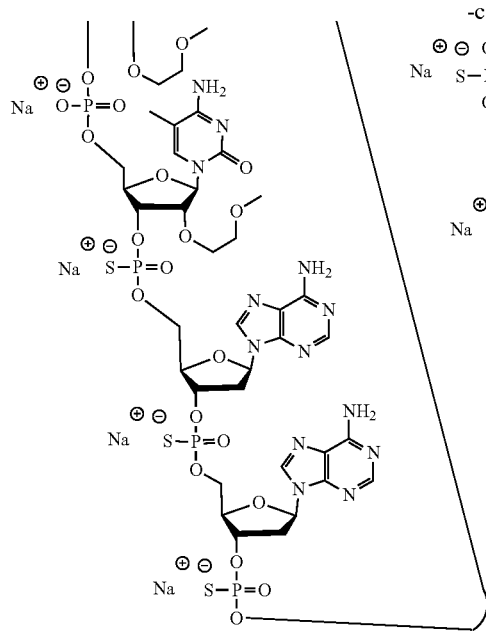
32
-continued
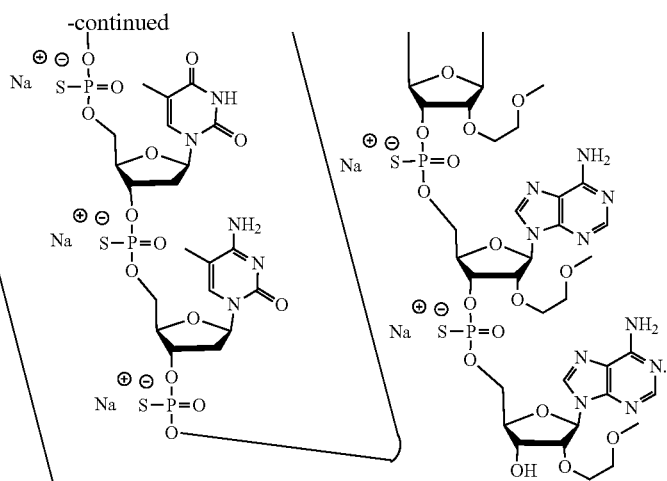
Embodiment 65. A modified oligonucleotide according to the following chemical structure:
(SEQ ID NO: 2873)
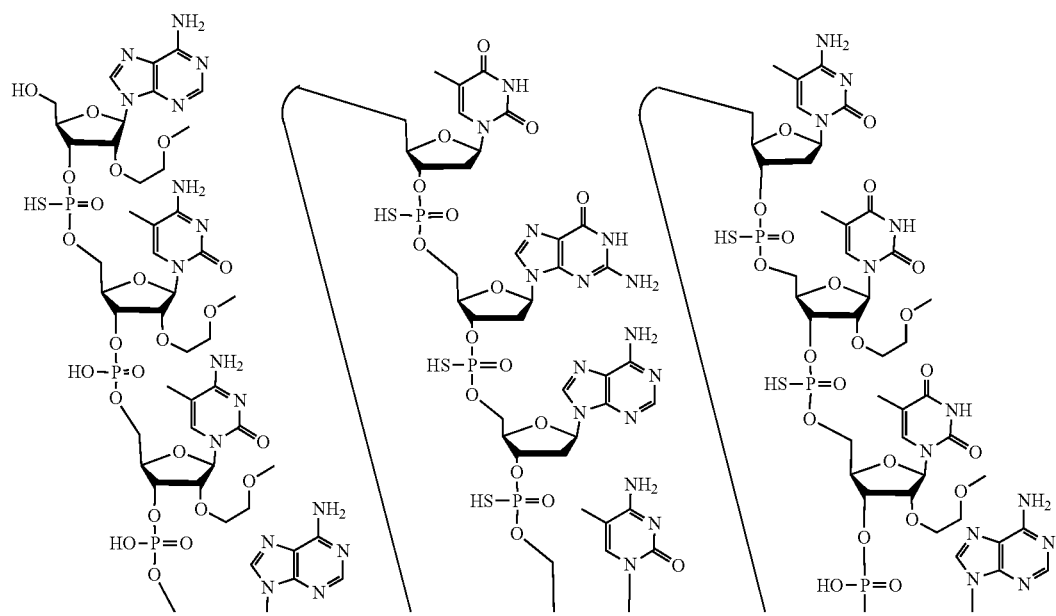

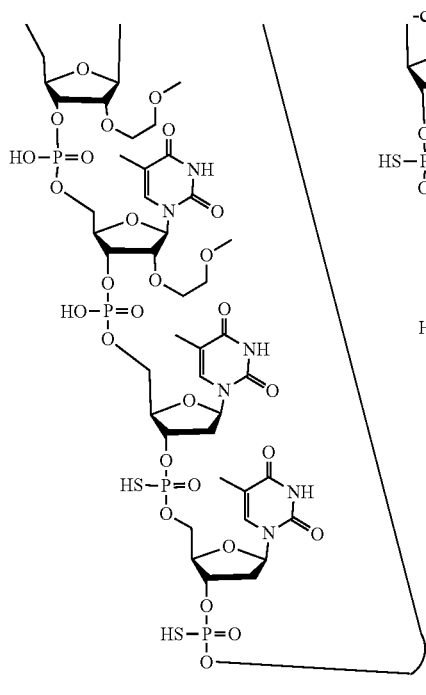
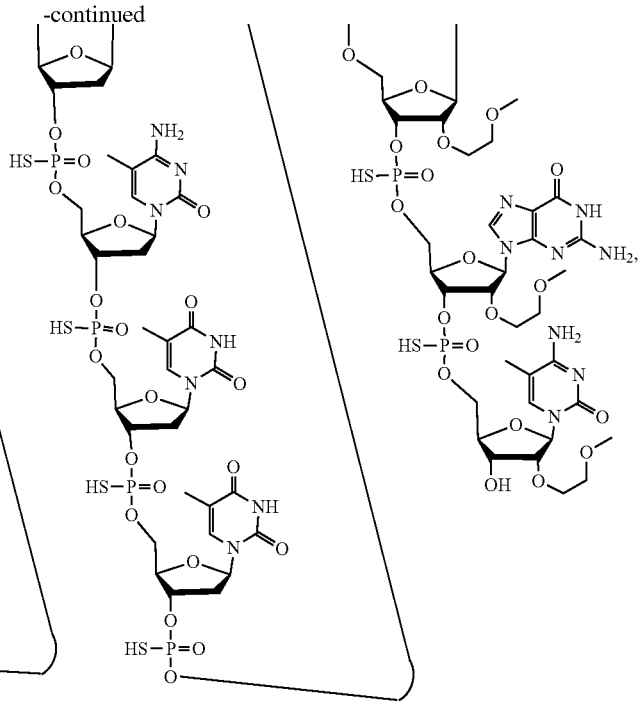
or a salt thereof.
Embodiment 66. A modified oligonucleotide according to the following chemical structure:
(SEQ ID NO: 2873)
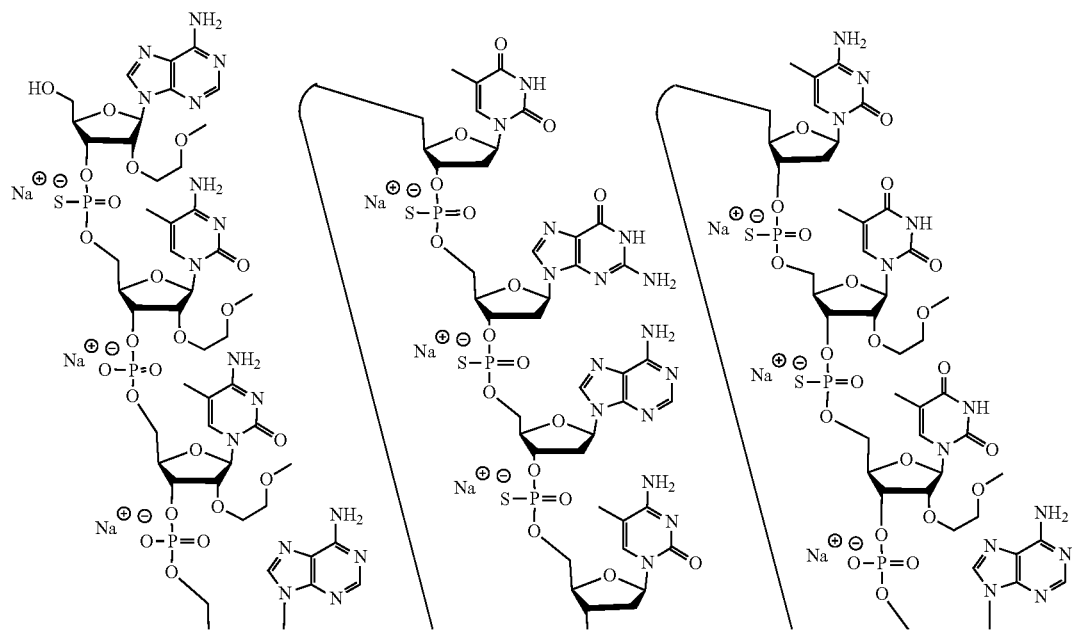

-continued

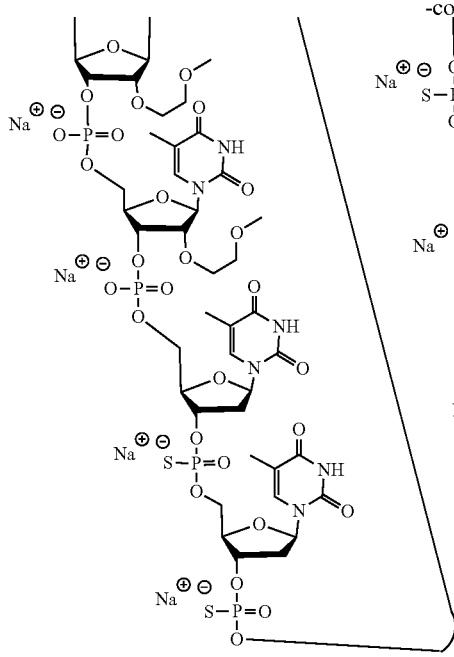
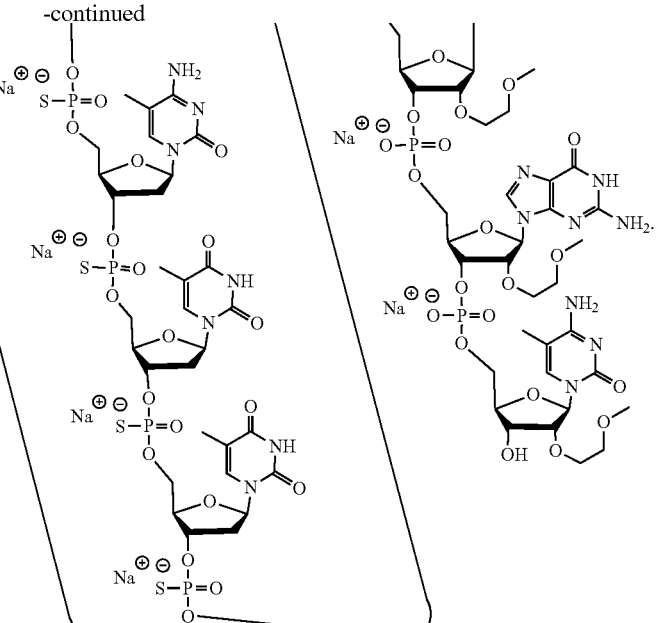

Embodiment 67. The modified oligonucleotide of any of embodiments 55, 57, 59, 61, 63, or 65, which is a sodium salt of the chemical structure.

Embodiment 68. A pharmaceutical composition comprising the modified oligonucleotide of any of embodiments 55-67 and a pharmaceutically acceptable carrier or diluent.

Embodiment 69. The pharmaceutical composition of embodiment 68, wherein the pharmaceutically acceptable diluent is artificial cerebrospinal fluid.

Embodiment 70. The pharmaceutical composition of embodiment 69, wherein the pharmaceutical composition consists essentially of the modified oligonucleotide and artificial cerebrospinal fluid.

Embodiment 71. A compound comprising a modified oligonucleotide according to the following chemical notation: $^{m}C_{es}A_{eo}T_{eo}{}^{m}C_{eo}A_{eo}T_{ds}G_{ds}A_{ds}T_{ds}{}^{m}C_{ds}T_{ds}T_{ds}G_{ds}G_{ds}T_{ds}A_{eo}A_{eo}G_{es}G_{es}{}^{m}C_{e}$ (SEQ ID NO: 1949), wherein:
A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

Embodiment 72. A compound comprising a modified oligonucleotide according to the following chemical notation: $T_{es}{}^{m}C_{eo}A_{eo}{}^{m}C_{eo}{}^{m}C_{eo}A_{eo}T_{ds}T_{ds}T_{ds}T_{ds}G_{ds}A_{ds}{}^{m}C_{ds}{}^{m}C_{ds}T_{ds}T_{ds}{}^{m}C_{eo}T_{es}T_{es}A_{e}$ (SEQ ID NO: 2751), wherein:
A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

Embodiment 73. A compound comprising a modified oligonucleotide according to the following chemical notation: $T_{es}T_{eo}{}^{m}C_{eo}A_{eo}{}^{m}C_{eo}{}^{m}C_{eo}A_{ds}T_{ds}T_{ds}T_{ds}T_{ds}G_{ds}A_{ds}{}^{m}C_{ds}{}^{m}C_{ds}T_{ds}T_{eo}{}^{m}C_{es}T_{es}T_{e}$ (SEQ ID NO: 2752), wherein:
A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

Embodiment 74. A compound comprising a modified oligonucleotide according to the following chemical notation: $G_{es}{}^{m}C_{eo}A_{eo}T_{eo}A_{eo}{}^{m}C_{eo}{}^{m}C_{ds}{}^{m}C_{ds}A_{ds}G_{ds}G_{ds}G_{ds}T_{ds}A_{ds}G_{ds}G_{ds}A_{eo}T_{es}T_{es}{}^{m}C_{e}$ (SEQ ID NO: 765), wherein:
A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

Embodiment 75. A compound comprising a modified oligonucleotide according to the following chemical notation: $A_{es}{}^{m}C_{eo}G_{eo}{}^{m}C_{es}A_{ds}A_{ds}T_{ds}G_{ds}T_{ds}A_{ds}T_{ds}{}^{m}C_{ds}A_{eo}G_{eo}G_{eo}{}^{m}C_{es}A_{es}A_{e}$ (SEQ ID NO: 2866), wherein:
A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

Embodiment 76. A compound comprising a modified oligonucleotide according to the following chemical notation: $A_{es}{}^{m}C_{eo}{}^{m}C_{eo}A_{eo}T_{eo}T_{ds}T_{ds}T_{ds}G_{ds}A_{ds}{}^{m}C_{ds}{}^{m}C_{ds}T_{ds}T_{ds}{}^{m}C_{ds}T_{eo}T_{e}A_{es}G_{es}{}^{m}C_{e}$ (SEQ ID NO: 2873), wherein:

A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

Embodiment 77. The compound of any of embodiments 71-76, comprising the modified oligonucleotide covalently linked to a conjugate group.

Embodiment 78. A pharmaceutical composition of any of embodiments 71-77, and a pharmaceutically acceptable diluent or carrier.

Embodiment 79. The pharmaceutical composition of embodiment 78, wherein the pharmaceutically acceptable diluent is artificial cerebrospinal fluid.

Embodiment 80. The pharmaceutical composition of embodiment 79, wherein the pharmaceutical composition consists essentially of the modified oligonucleotide and artificial cerebrospinal fluid.

Embodiment 81. A chirally enriched population of modified oligonucleotides of any of embodiments 55-67, wherein the population is enriched for modified oligonucleotides comprising at least one particular phosphorothioate internucleoside linkage having a particular setereochemical configuration.

Embodiment 82. The chirally enriched population of embodiment 81, wherein the population is enriched for modified oligonucleotides comprising at least one particular phorphorothioate internucleoside linkage having the (Sp) configuration.

Embodiment 83. The chirally enriched population of embodiment 81, wherein the population is enriched for modified oligonucleotides comprising at least one particular phorphorothioate internucleoside linkage having the (Rp) configuration.

Embodiment 84. The chirally enriched population of embodiment 81, wherein the population is enriched for modified oligonucleotides having a particular, independently selected stereochemical configuration at each phosphorothioate internucleoside linkage Embodiment 85. The chirally enriched population of embodiment 84, wherein the population is enriched for modified oligonucleotides having the (Sp) configuration at each phosphorothioate internucleoside linkage.

Embodiment 86. The chirally enriched population of embodiment 84, wherein the population is enriched for modified oligonucleotides having the (Rp) configuration at each phosphorothioate internucleoside linkage.

Embodiment 87. The chirally enriched population of embodiment 84, wherein the population is enriched for modified oligonucleotides having the (Rp) configuration at one particular phosphorothioate internucleoside linkage and the (Sp) configuration at each of the remaining phosphorothioate internucleoside linkages.

Embodiment 88. The chirally enriched population of embodiment 81 or embodiment 84 wherein the population is enriched for modified oligonucleotides having at least 3 contiguous phosphorothioate internucleoside linkages in the Sp, Sp, and Rp configurations, in the 5' to 3' direction.

Embodiment 89. A chirally enriched population of modified oligonucleotides of any of embodiments 55-67, wherein all of the phosphorothioate internucleoside linkages of the modified oligonucleotide are stereorandom.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'—(CH$_2$)$_2$-2', 4'—(CH$_2$)$_3$-2', 4'-CH$_2$—O-2' ("LNA"), 4'—(CH$_2$)$_2$—O-2' ("ENA"), 4'-CH(CH$_3$)—O-2' (referred to as "constrained ethyl" or "cEt"), 4'-CH$_2$—O—CH$_2$-2', 4'-CH$_2$—N(R)-2', 4'—CH(CH$_2$OCH$_3$)—O- 2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'—C(R$_a$R$_b$)—O—NR)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$J$_1$), or sulfoxyl (S(=O)-J$_1$); and
each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., J. Org. Chem., 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

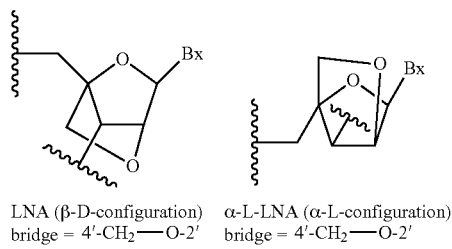

LNA (β-D-configuration)    α-L-LNA (α-L-configuration)
bridge = 4'-CH$_2$—O-2'    bridge = 4'-CH$_2$—O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

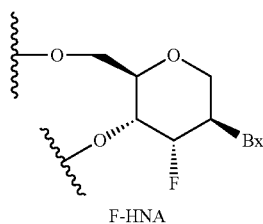

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

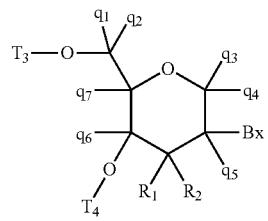

wherein, independently, for each of said modified THP nucleoside:
Bx is a nucleobase moiety;
$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;
$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and
each of $R_1$ and $R_2$ is independently selected from among:
hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q2$, $q3$, $q4$, $q5$, $q6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

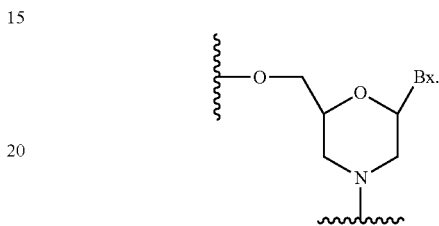

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleosides comprising an unmodified nucleobase. In certain embodiments, modified oligonucleotides comprise one or more nucleosides comprising a modified nucleobase. In certain embodiments, modified oligonucleotides comprise one or more nucleosides that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—$CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, sizeexpanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp) Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphodiesters, which contain a phosphodiester bond ("P(O$_2$)=O") (also referred to as unmodified or naturally occurring linkages), phosphotriesters, methylphosphonates, phosphoramidates, and phosphorothioates ("P(O$_2$)=S"), and phosphorodithioates ("HS—P=5"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

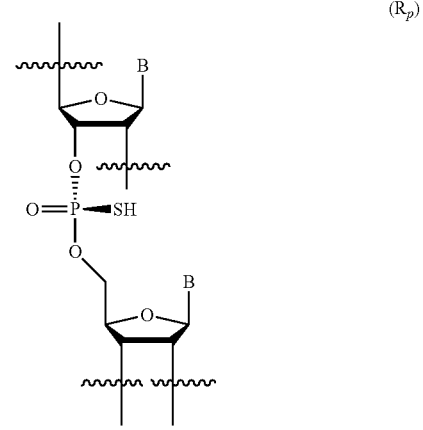

(R$_p$)

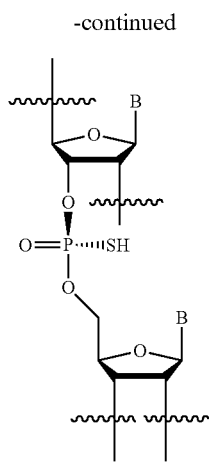

(S$_p$)

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal methoxypropyl (MOP), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or portion thereof in a defined pattern or sugar motif. In certain instances, such sugar motifs include but are not limited to any of the sugar modifications discussed herein.

In certain embodiments, modified oligonucleotides have a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one nucleoside of each wing of a gapmer comprises a modified sugar moiety. In certain embodiments, at least two nucleosides of each wing of a gapmer comprises a modified sugar moiety. In certain embodiments, at least three nucleosides of each wing of a gapmer comprises a modified sugar moiety. In certain embodiments, at least four nucleosides of each wing of a gapmer comprises a modified sugar moiety. In certain embodiments, at least five nucleosides of each wing of a gapmer comprises a modified sugar moiety.

In certain embodiments, the gap of a gapmer comprises 7-12 nucleosides. In certain embodiments, each nucleoside of the gap of a gapmer comprises a 2'-β-D-deoxyribosyl sugar moiety. In certain embodiments, at least one nucleoside of the gap of a gapmer comprises a modified sugar moiety.

In certain embodiments, the gapmer is a deoxy gapmer. In certain embodiments, the nucleosides on the gap side of each wing/gap junction comprise 2'-deoxyribosyl sugar moieties and the nucleosides on the wing sides of each wing/gap junction comprise modified sugar moieties. In certain embodiments, each nucleoside of the gap comprises a 2'-β-D-deoxyribosyl sugar moiety. In certain embodiments, each nucleoside of each wing of a gapmer comprises a modified sugar moiety. In certain embodiments, exactly one nucleoside of the gap comprises a modified sugar moiety and each remaining nucleoside of the gap comprises a 2'-β-D-deoxyribosyl sugar moiety.

In certain embodiments, modified oligonucleotides comprise or consist of a portion having a fully modified sugar motif. In such embodiments, each nucleoside of the fully modified portion of the modified oligonucleotide comprises a modified sugar moiety. In certain embodiments, each nucleoside of the entire modified oligonucleotide comprises a modified sugar moiety. In certain embodiments, modified oligonucleotides comprise or consist of a portion having a fully modified sugar motif, wherein each nucleoside within the fully modified portion comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 3-10-3 gapmer consists of 3 linked nucleosides in each wing and 10 linked nucleosides in the gap. Where such nomenclature is followed by a specific modification, that modification is the modification in each sugar moiety of each wing and the gap nucleosides comprise 2'-β-D-deoxyribosyl sugar moieties. Thus, a 5-10-5 MOE gapmer consists of 5 linked 2'-MOE nucleosides in the 5'-wing, 10 linked 2'-β-D-deoxynucleosides in the gap, and 5 linked 2'-MOE nucleosides in the 3'-wing. A 3-10-3 cEt gapmer consists of 3 linked cEt nucleosides in the 5'-wing, 10 linked 2'-β-D-deoxynucleosides in the gap, and 3 linked cEt nucleosides in the 3'-wing. A 5-8-5 gapmer consists of 5 linked nucleosides comprising a modified sugar moiety in the 5'-wing, 8 linked 2'-β-D-deoxynucleosides in the gap, and 5 linked nucleosides comprising a modified sugar moiety in the 3'-wing. A 5-8-5 mixed gapmer has at least two different modified sugar moieties in the 5'- and/or the 3'-wing.

In certain embodiments, modified oligonucleotides are 5-10-5 MOE gapmers. In certain embodiments, modified oligonucleotides are 4-10-6 MOE gapmers. In certain embodiments, modified oligonucleotides are 6-10-4 MOE gapmers. In certain embodiments, modified oligonucleotides are 5-8-5 MOE gapmers. In certain embodiments, modified oligonucleotides are 6-8-4 MOE gapmers. In certain embodiments, modified oligonucleotides are 4-8-6 MOE gapmers. In certain embodiments, modified oligonucleotides are X—Y—Z MOE gapmers, wherein X and Z are independently selected from 1, 2, 3, 4, 5, or 6 and Y is 7, 8, 9, 10, or 11.

2. Certain Nucleobase Motifs

In certain embodiments, oligonucleotides comprise modified and/or unmodified nucleobases arranged along the oligonucleotide or portion thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-β-D-deoxyribosyl sugar moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or portion thereof in a defined pattern or motif. In certain embodiments, each internucleoside linking group is a phosphodiester internucleoside linkage ($P(O_2)=O$). In certain embodiments, each internucleoside linking group of a modified oligonucleotide is a phosphorothioate internucleoside linkage ($P(O_2)=S$). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

In certain embodiments, modified nucleotides have an internucleoside linkage motif of soooosssssssssssoooss, wherein each "s" represents a phosphorothioate internucleoside linkage and each "o" represents a phosphodiester internucleoside linkage. In certain embodiments, modified nucleotides have an internucleoside linkage motif of sooooossssssssssssoss, wherein each "s" represents a phosphorothioate internucleoside linkage and each "o" represents a phosphodiester internucleoside linkage. In certain embodiments, modified nucleotides have an internucleoside linkage motif of soooosssssssssssoss, wherein each "s" represents a phosphorothioate internucleoside linkage and each "o" represents a phosphodiester internucleoside linkage. In certain embodiments, modified nucleotides have an internucleoside linkage motif of soooossssssssssoooss, wherein each "s" represents a phosphorothioate internucleoside linkage and each "o" represents a phosphodiester internucleoside linkage. In certain embodiments, modified nucleotides have an internucleoside linkage motif of sooosssssssssssoooss, wherein each "s" represents a phosphorothioate internucleoside linkage and each "o" represents a phosphodiester internucleoside linkage. In certain embodiments, modified nucleotides have an internucleoside linkage motif of soosssssssssoooss, wherein each "s" represents a phosphorothioate internucleoside linkage and each "o" represents a phosphodiester internucleoside linkage.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides β-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target RNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

D. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another.

Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a portion of an oligonucleotide has a nucleobase sequence that is complementary to a second oligonucleotide or an identified reference nucleic acid, such as a target nucleic acid. In certain embodiments, the nucleobase sequence of a portion or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-cathonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

In certain embodiments, conjugate groups may be selected from any of a C22 alkyl, C20 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, C5 alkyl, C22 alkenyl, C20 alkenyl, C16 alkenyl, C10 alkenyl, C21 alkenyl, C19 alkenyl, C18 alkenyl, C15 alkenyl, C14 alkenyl, C13 alkenyl, C12 alkenyl, C11 alkenyl, C9 alkenyl, C8 alkenyl, C7 alkenyl, C6 alkenyl, or C5 alkenyl.

In certain embodiments, conjugate groups may be selected from any of C22 alkyl, C20 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, and C5 alkyl, where the alkyl chain has one or more unsaturated bonds.

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-calboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphodiester internucleoside linkage and covalently attached to the remainder of the conjugate linker or conjugate moiety by a phosphate or phosphorothioate linkage. In certain such embodiments, the cleavable moiety is 2'-deoxyadenosine.

3. Cell-Targeting Moieties

In certain embodiments, a conjugate group comprises a cell-targeting moiety. In certain embodiments, a conjugate group has the general formula:

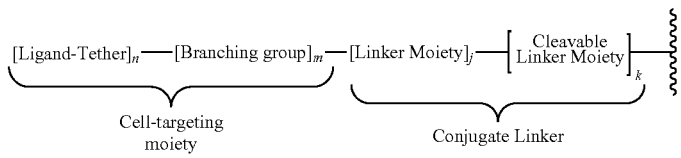

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a portion complementary to a target nucleic acid and a second oligomeric compound having a portion complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or subject.

V. Certain Target Nucleic Acids

In certain embodiments, oligomeric compounds comprise or consist of an oligonucleotide comprising a portion that is complementary to a target nucleic acid. In certain embodiments, the target nucleic acid is an endogenous RNA molecule. In certain embodiments, the target nucleic acid encodes a protein. In certain embodiments, the target nucleic acid is selected from: an endogenous antisense transcript that does not encode a protein (e.g., UBE3A-ATS), a mature mRNA, and a pre-mRNA, including intronic, exonic and untranslated regions. In certain embodiments, the target RNA is an antisense transcript. In certain embodiments, the target RNA is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a portion that is 100% or fully complementary to a target nucleic acid. In certain embodiments, the portion of full complementarity is 6, 7, 8, 9, 10, 11, 12, 13, 14, 15, 16, 17, 18, 19, 20, 21, 22, 23, or 24 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. UBE3A-ATS

In certain embodiments, oligomeric compounds comprise or consist of an oligonucleotide, or portion thereof, that is complementary to a target nucleic acid, wherein the target nucleic acid is UBE3A-ATS. In certain embodiments, UBE3A-ATS nucleic acid has the sequence set forth in SEQ ID NO: 1 (GENBANK Accession No: NC_000015.10_TRUNC_24821647_25441028), SEQ ID NO: 2915 (Ensemble Gene ID ENSG00000224078), or SEQ ID NO: 2916 (the cDNA of Ensemble transcript ENST00000554726.1).

In certain embodiments, an oligomeric compound complementary to SEQ ID NO: 1, SEQ ID NO: 2915, or SEQ ID NO: 2916 is capable of reducing UBE3A-ATS in a cell. In certain embodiments, an oligomeric compound complementary to SEQ ID NO: 1 is capable of increasing UBE3A RNA or protein in a cell. In certain embodiments, an oligomeric compound complementary to SEQ ID NO: 1, SEQ ID NO: 2915, or SEQ ID NO: 2916 is capable of increasing paternal UBE3A RNA or protein in a cell. In certain embodiments, the cell is in vitro. In certain embodiments, the cell is in a subject. In certain embodiments, the oligomeric compound consists of a modified oligonucleotide. In certain embodiments, an oligomeric compound complementary to SEQ ID NO: 1, SEQ ID NO: 2915, or SEQ ID NO: 2916 is capable of ameliorating one or more symptom or hallmark of a neurogenetic disorder when administered to a subject. In certain embodiments, the neurogenetic disorder is AS. In certain embodiments, the symptoms or hallmarks are selected from developmental delays, ataxia, speech impairment, sleep problems, seizures, and EEG abnormalities.

In certain embodiments, an oligomeric compound complementary to SEQ ID NO: 1, SEQ ID NO: 2915, or SEQ ID NO: 2916 is capable of reducing the detectable amount of UBE3A-ATS RNA in vitro by at least 10%, at least 20%, at least 30%, at least 40%, at least 50%, at least 60%, at least 70%, at least 80%, or at least 90%. In certain embodiments, an oligomeric compound complementary to SEQ ID NO: 1, SEQ ID NO: 2915, or SEQ ID NO: 2916 is capable of increasing the detectable amount of UBE3A protein in vitro by at least 10%, at least 20%, at least 30%, at least 40%, at least 50%, at least 60%, at least 70%, at least 80%, or at least 90%. In certain embodiments, an oligomeric compound complementary to SEQ ID NO: 1, SEQ ID NO: 2915, or SEQ ID NO: 2916 is capable of reducing the detectable amount of UBE3A-ATS RNA in the CSF of a subject by at least 10%, at least 20%, at least 30%, at least 40%, at least 50%, at least 60%, at least 70%, at least 80%, or at least 90%. In certain embodiments, an oligomeric compound complementary to SEQ ID NO: 1, SEQ ID NO: 2915, or SEQ ID NO: 2916 is capable of increasing the detectable amount of UBE3A protein in the CSF of a subject by at least 10%, at least 20%, at least 30%, at least 40%, at least 50%, at least 60%, at least 70%, at least 80%, or at least 90%.

C. Certain Target Nucleic Acids in Certain Tissues

In certain embodiments, oligomeric compounds comprise or consist of an oligonucleotide comprising a portion that is complementary to a target nucleic acid, wherein the target nucleic acid is expressed in a pharmacologically relevant tissue. In certain embodiments, the pharmacologically relevant tissues are the cells and tissues that comprise the central nervous system. Such tissues include the cortex, hippocampus, and spinal cord.

VI. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to a subject, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphate linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or a salt thereof" expressly includes all such forms that may be fully or partially protonated/de-protonated/in association with a cation. In certain instances, one or more specific cation is identified.

In certain embodiments, modified oligonucleotides or oligomeric compounds are in aqueous solution with sodium. In certain embodiments, modified oligonucleotides or oligomeric compounds are in aqueous solution with potassium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of a modified oligonucleotide or an oligomeric compound in milligrams indicates the mass of the free acid form of the modified oligonucleotide or oligomeric compound. As described above, in aqueous solution, the free acid is in equilibrium with anionic and salt forms. However, for the purpose of calculating dose, it is assumed that the modified oligonucleotide or oligomeric compound exists as a solvent-free, sodium-acetate free, anhydrous, free acid. For example, where a modified oligonucleotide or an oligomeric compound is in solution comprising sodium (e.g., saline), the modified oligonucleotide or oligomeric compound may be partially or fully de-protonated and in association with Na+ ions. However, the mass of the protons is nevertheless counted toward the weight of the dose, and the mass of the Na+ ions are not counted toward the weight of the dose. Thus, for example, a dose, or dosage unit, of 100 mg of Compound No. 1263518 equals the number of fully protonated molecules that weighs 100 mg. This would be equivalent to 106 mg of solvent-free, sodium-acetate free, anhydrous sodiated Compound No. 1263518. When an oligomeric compound comprises a conjugate group, the mass of the conjugate group is included in calculating the dose of such oligomeric compound. If the conjugate group also has an acid, the conjugate group is likewise assumed to be fully protonated for the purpose of calculating dose.

VII. Certain Compositions

1. Compound No. 1065645

In certain embodiments, Compound No. 1065645 is characterized as a 5-10-5 MOE gapmer having a sequence (from 5' to 3') of CATCATGATCTTGGTAAGGC (SEQ ID NO: 1949), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages and the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

In certain embodiments, Compound No. 1065645 is represented by the following chemical notation: $^mC_{es}A_{eo}T_{eo}^m$-$C_{eo}A_{eo}T_{ds}G_{ds}A_{ds}T_{ds}^mC_{ds}T_{ds}T_{ds}G_{ds}G_{ds}T_{ds}A_{eo}A_{eo}$ $G_{es}G_{es}^mC_e$ (SEQ ID NO: 1949), wherein:

A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1065645 is represented by the following chemical structure:

Structure 1. Compound No. 1065645

(SEQ ID NO: 1949)

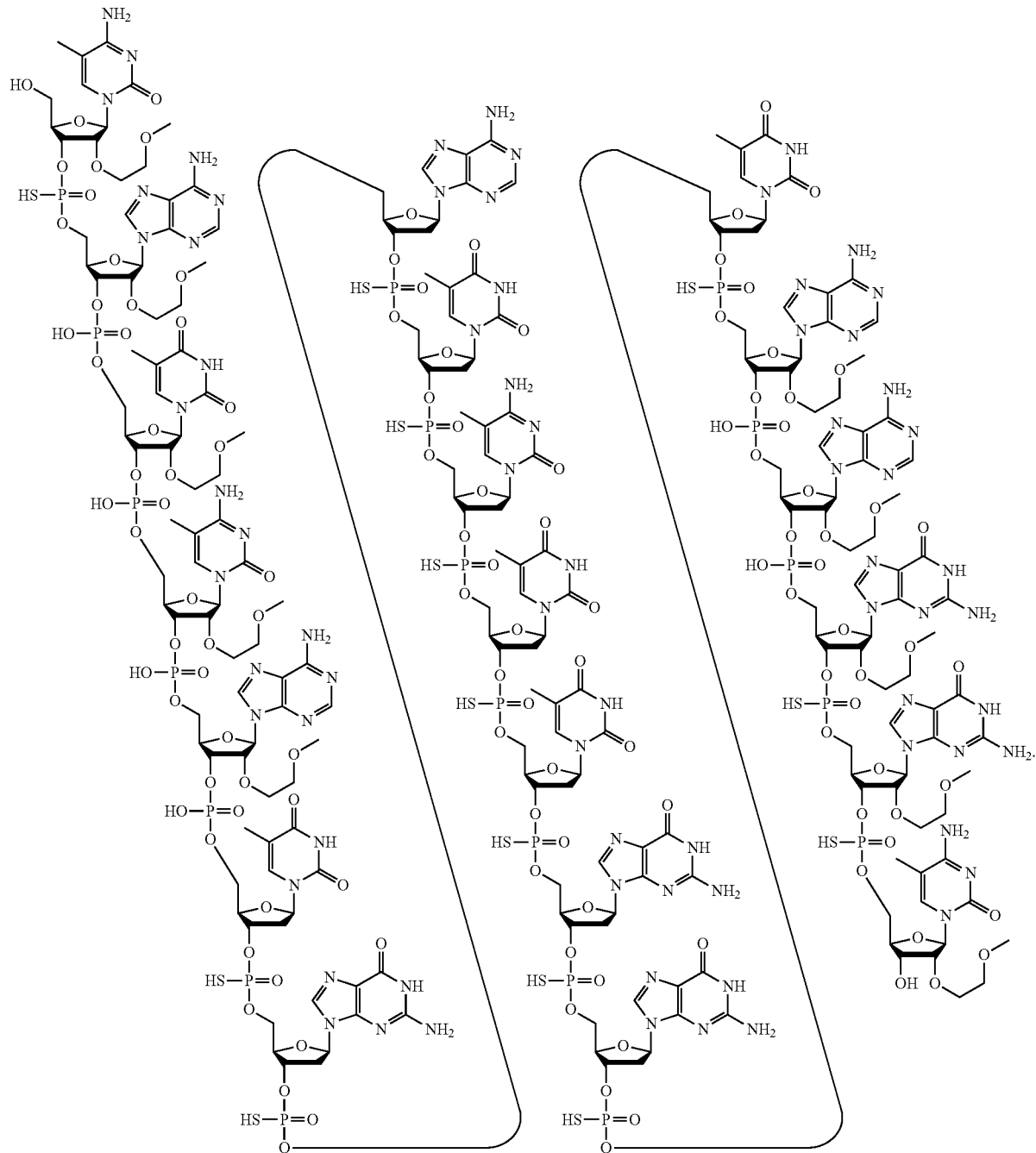

In certain embodiments, the sodium salt of Compound No. 1065645 is represented by the following chemical structure:

Structure 2. The sodium salt of Compound No. 1065645

(SEQ ID NO: 1949)

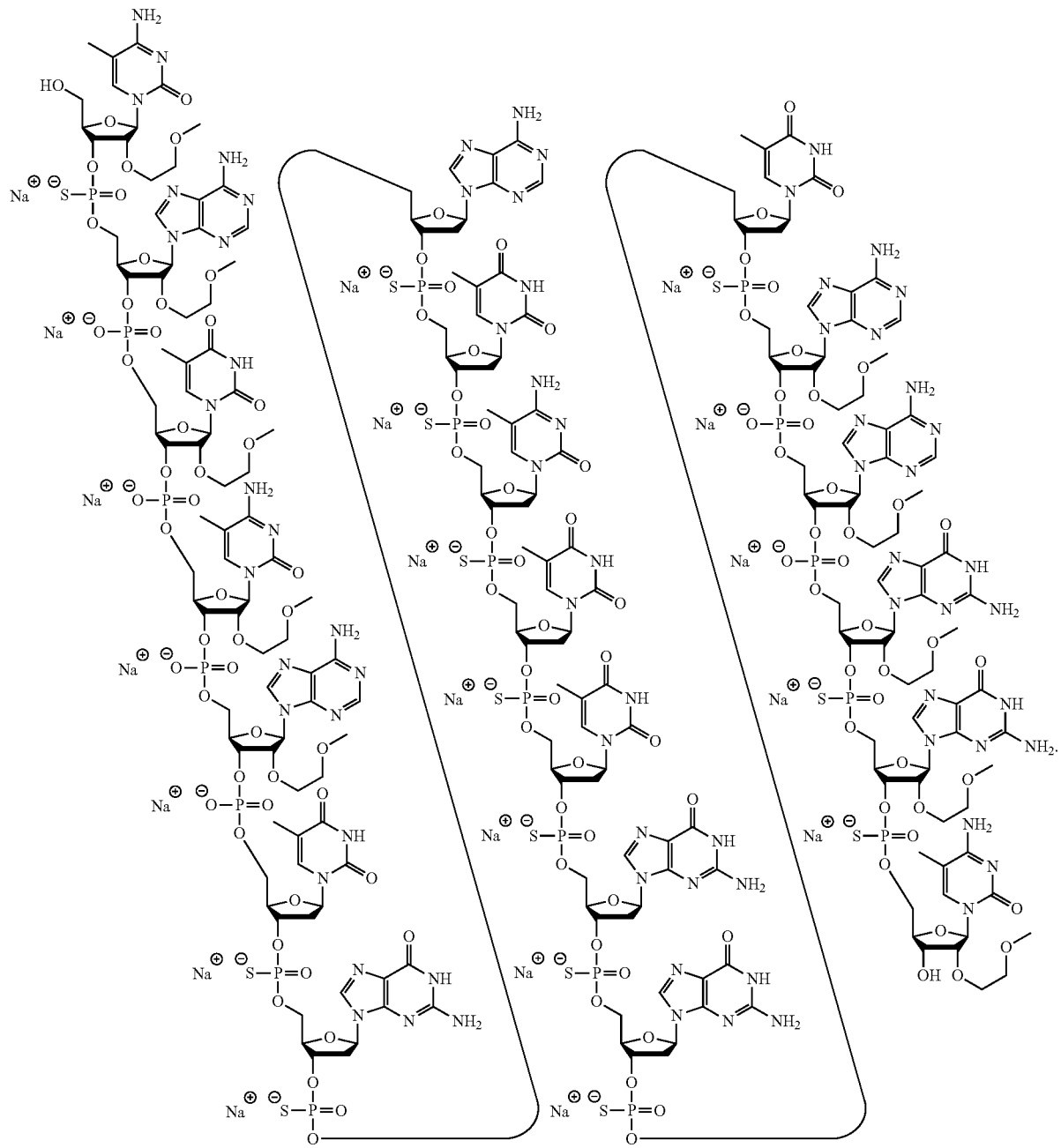

2. Compound No. 1263517

In certain embodiments, Compound No. 1263517 is characterized as a 6-10-4 MOE gapmer having a sequence (from 5' to 3') of TCACCATTTTGACCTTCTTA (SEQ ID NO: 2751), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1263517 is represented by the following chemical notation: $T^{es\,m}C_{eo}A_{eo}{}^{m}$-$C_{eo}{}^{m}C_{eo}A_{eo}T_{ds}T_{ds}T_{ds}T_{ds}G_{ds}A_{ds}{}^{m}C_{ds}{}^{m}C_{ds}T_{ds}T_{ds}{}^{m}C_{eo}T_{es}$ $T_{es}A_{e}$ (SEQ ID NO: 2751), wherein:

A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1263517 is represented by the following chemical structure:

Structure 3. Compound No. 1263517

(SEQ ID NO: 2751)

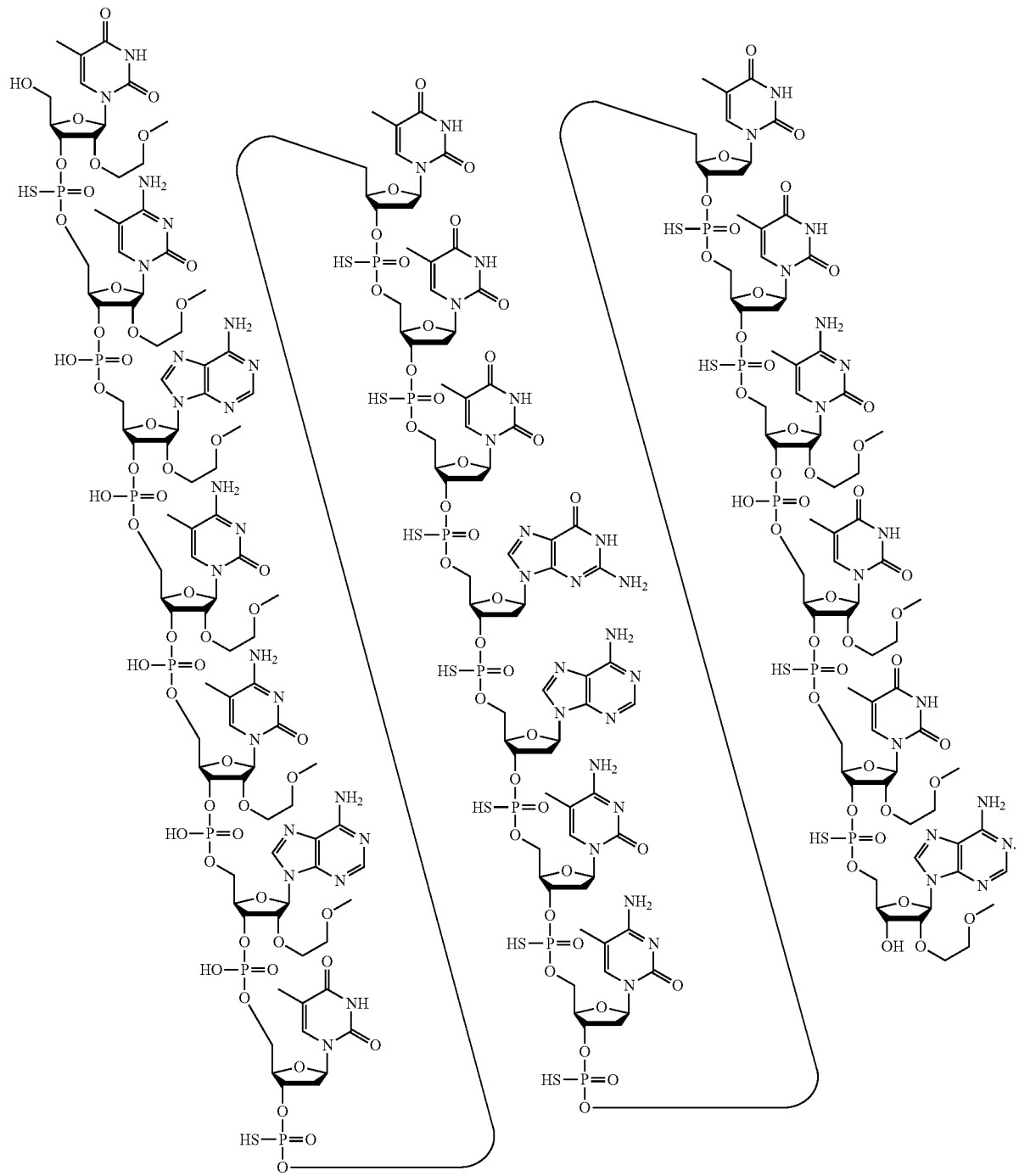

In certain embodiments, the sodium salt of Compound No. 1263517 is represented by the following chemical structure:

Structure 4. The sodium salt of Compound No. 1263517

(SEQ ID NO: 2751)

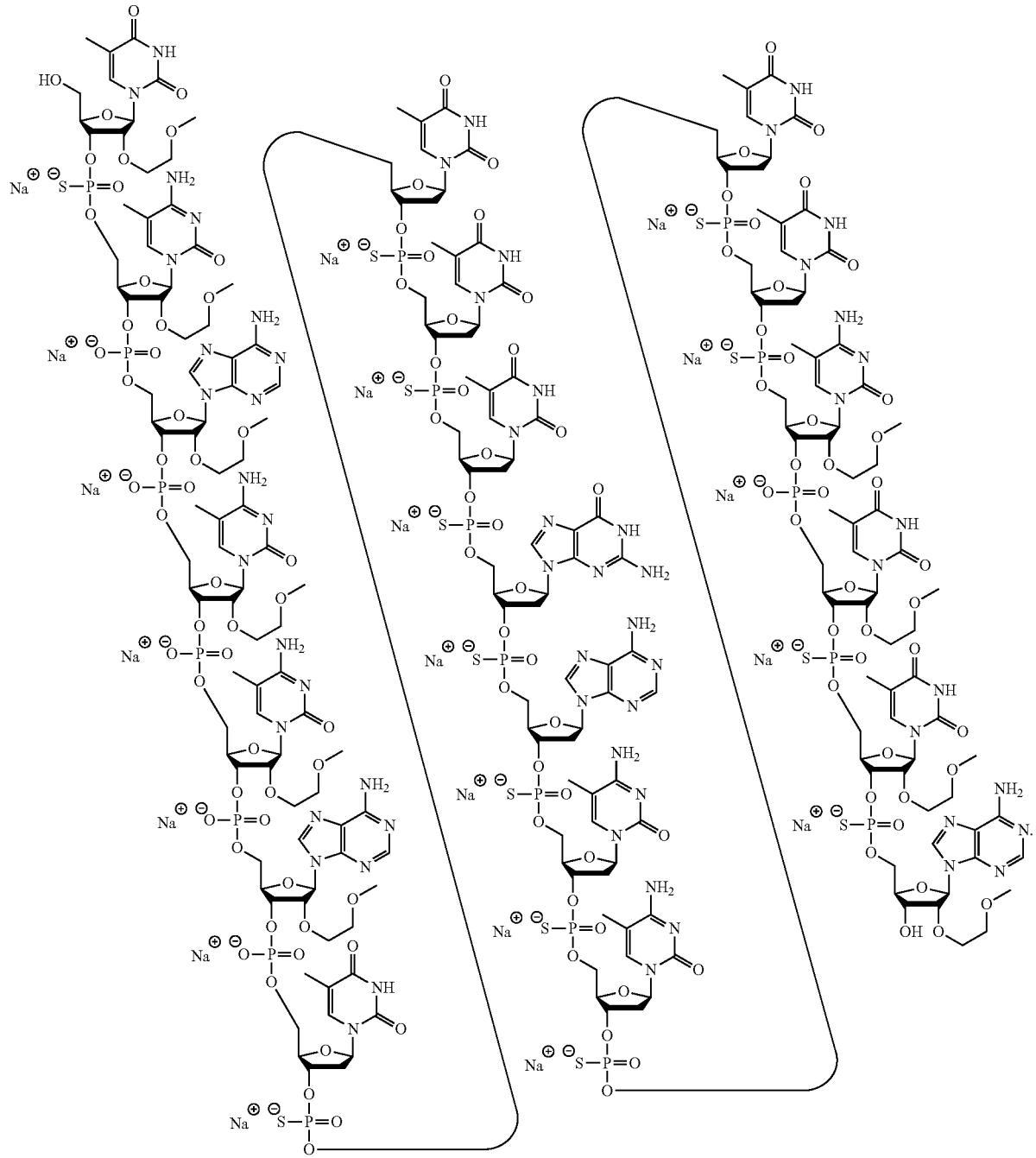

3. Compound No. 1263518

In certain embodiments, Compound No. 1263518 is characterized as a 6-10-4 MOE gapmer having a sequence (from 5' to 3') of TTCACCATTTTGACCTTCTT (SEQ ID NO: 2752), wherein each of nucleosides 1-6 and 17-20 (from 5' to 3') are 2'-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1263518 is represented by the following chemical notation: $T_{es}T_{eo}{}^mC_{eo}A_{eo}{}^mC_{eo}{}^mC_{eo}A_{ds}T_{ds}T_{ds}T_{ds}T_{ds}G_{as}A_{ds}{}^mC_{ds}{}^mC_{ds}T_{ds}T_{eo}{}^mC_{es}T_{es}T_{e}$ (SEQ ID NO: 2752), wherein:

A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1263518 is represented by the following chemical structure:

Structure 5. Compound No. 1263518

(SEQ ID NO: 2752)

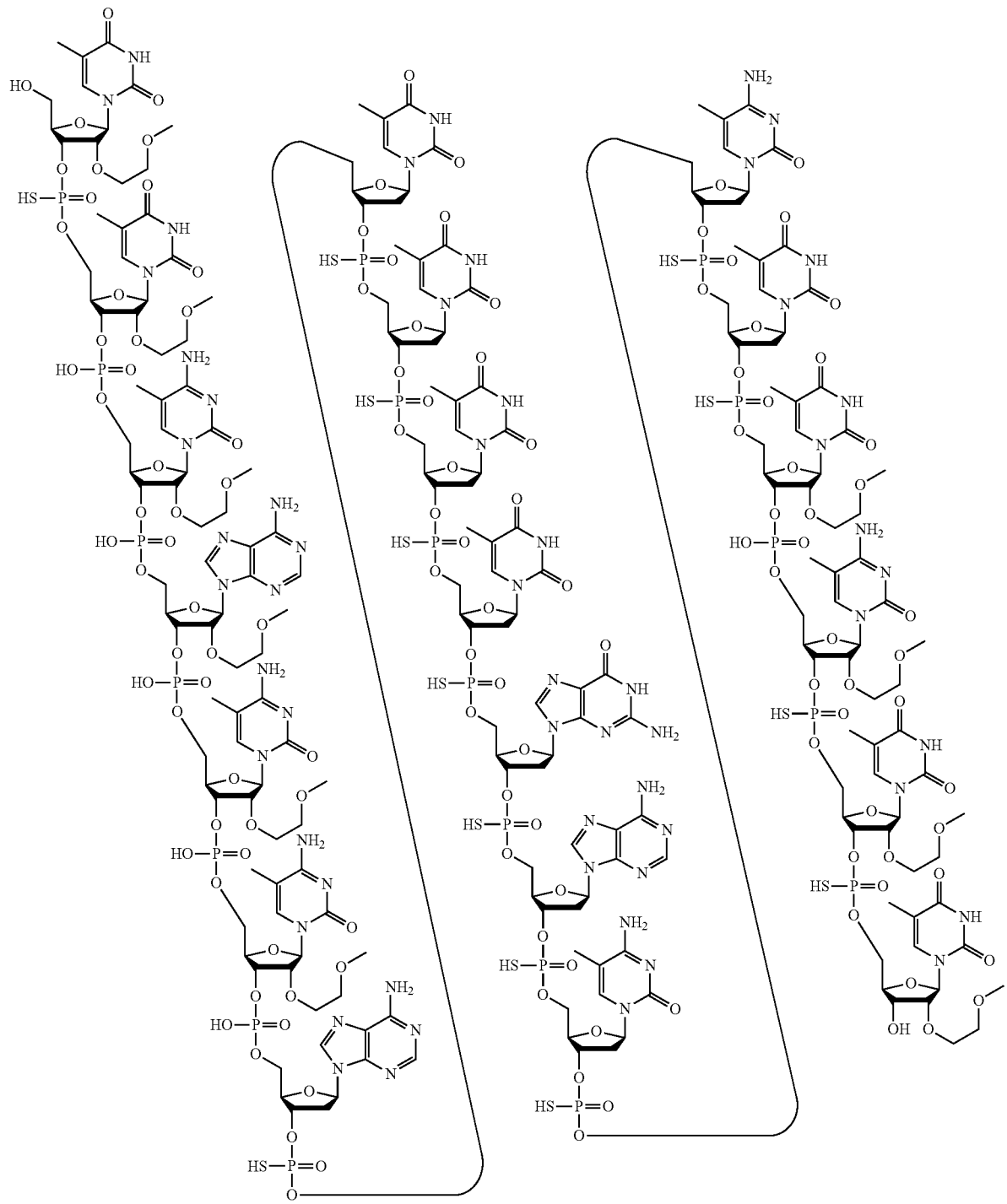

In certain embodiments, the sodium salt of Compound No. 1263518 is represented by the following chemical structure:

3') are 2'-MOE nucleosides and each of nucleosides 7-16 are 2'-β-D-deoxynucleosides, wherein the internucleoside link- Structure 6. The sodium salt of Compound No. 1263518

(SEQ ID NO: 2752)

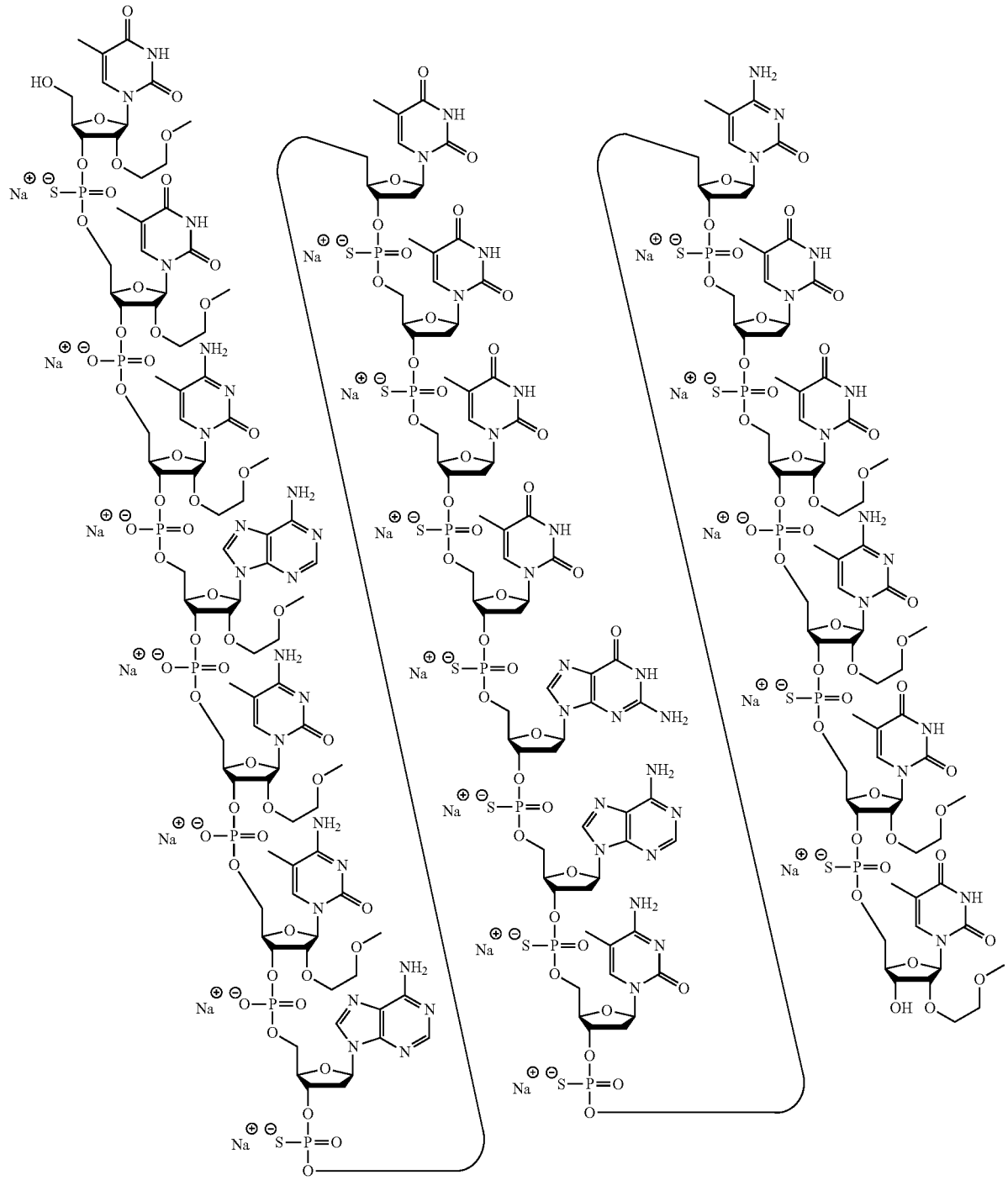

4. Compound No. 1263533

In certain embodiments, Compound No. 1263533 is characterized as a 6-10-4 MOE gapmer having a sequence (from 5' to 3') of GCATACCCAGGGTAGGATTC (SEQ ID NO: 765), wherein each of nucleosides 1-6 and 17-20 (from 5' to ages between nucleosides 2 to 3, 3 to 4, 4 to 5, 5 to 6, 6 to 7, and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

In certain embodiments, Compound No. 1263533 is represented by the following chemical notation: $G_{es}{}^mC_{eo}A_{eo}T_{eo}A_{eo}{}^mC_{eo}{}^mC_{ds}{}^mC_{ds}A_{ds}G_{ds}G_{ds}G_{ds}T_{ds}A_{ds}G_{ds}G_{ds}A_{e^-o}T_{es}T_{es}{}^mC_e$ (SEQ ID NO: 765), wherein:
- A=an adenine nucleobase,
- mC=a 5-methyl cytosine nucleobase,
- G=a guanine nucleobase,
- T=a thymine nucleobase,
- e=a 2'-MOE sugar moiety,
- d=a 2'-β-D-deoxyribosyl sugar moiety,
- s=a phosphorothioate internucleoside linkage, and
- o=a phosphodiester internucleoside linkage.

In certain embodiments, Compound No. 1263533 is represented by the following chemical structure:

Structure 7. Compound No. 1263533

(SEQ ID NO: 765)

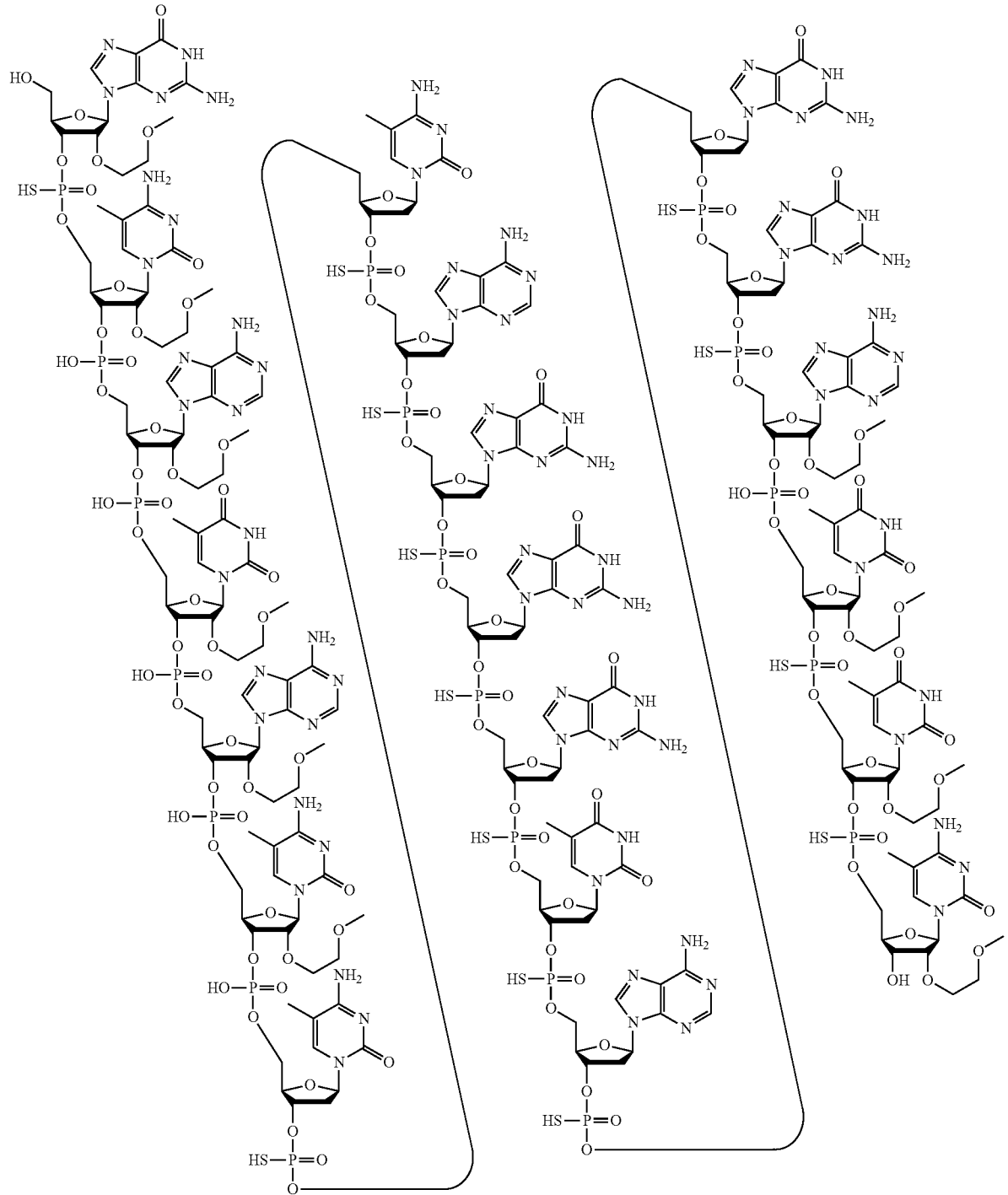

In certain embodiments, the sodium salt of Compound No. 1263533 is represented by the chemical structure:

are 2'-β-D-deoxynucleosides, wherein the internucleoside linkages between nucleosides 2 to 3, 3 to 4, 13 to 14, 14 to Structure 8. The sodium salt of Compound No. 1263533

(SEQ ID NO: 765)

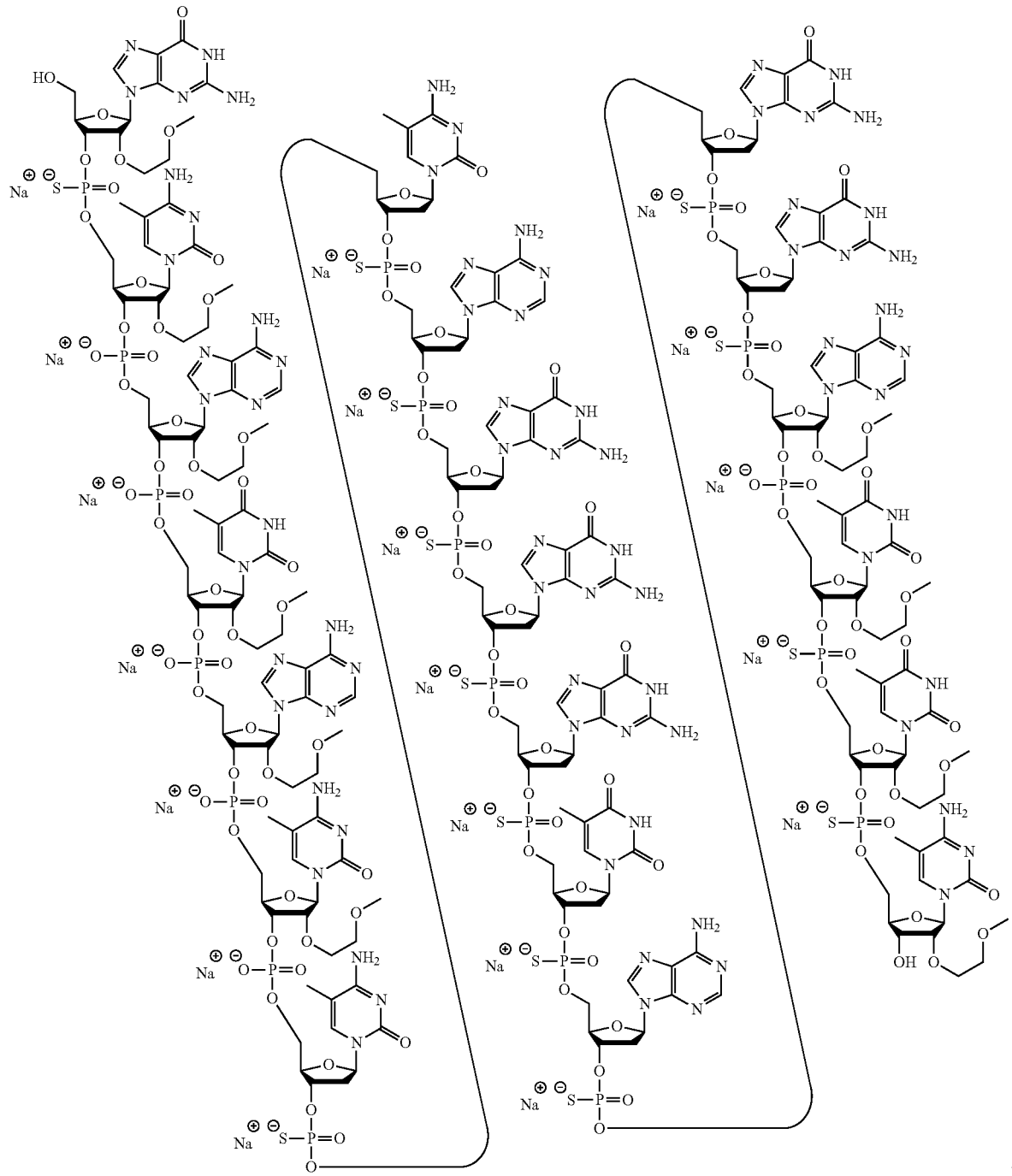

5. Compound No. 1273039

In certain embodiments, Compound No. 1273039 is characterized as a 4-8-6 MOE gapmer having a sequence (from 5' to 3') of ACGCAATGTATCAGGCAA (SEQ ID NO: 2866), wherein each of nucleosides 1-4 and 13-18 (from 5' to 3') are 2'-MOE nucleosides and each of nucleosides 5-12 are 2'-β-D-deoxynucleosides, wherein the internucleoside linkages between nucleosides 2 to 3, 3 to 4, 13 to 14, 14 to 15, and 15 to 16 are phosphodiester internucleoside linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 16 to 17, and 17 to 18 are phosphorothioate internucleoside linkages, and wherein each cytosine is a 5-methyl cytosine.

In certain embodiments, Compound No. 1273039 is represented by the following chemical notation: $A_{es}{}^{m}C_{eo}G_{eo}{}^{m}C_{es}A_{ds}A_{ds}T_{ds}G_{ds}T_{ds}A_{ds}T_{ds}{}^{m}C_{ds}A_{eo}G_{eo}G_{eo}{}^{m}C_{es}A_{es}A_{e}$ (SEQ ID NO: 2866), wherein:

A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1273039 is represented by the following chemical structure:

Structure 9. Compound No. 1273039

(SEQ ID NO: 2866)

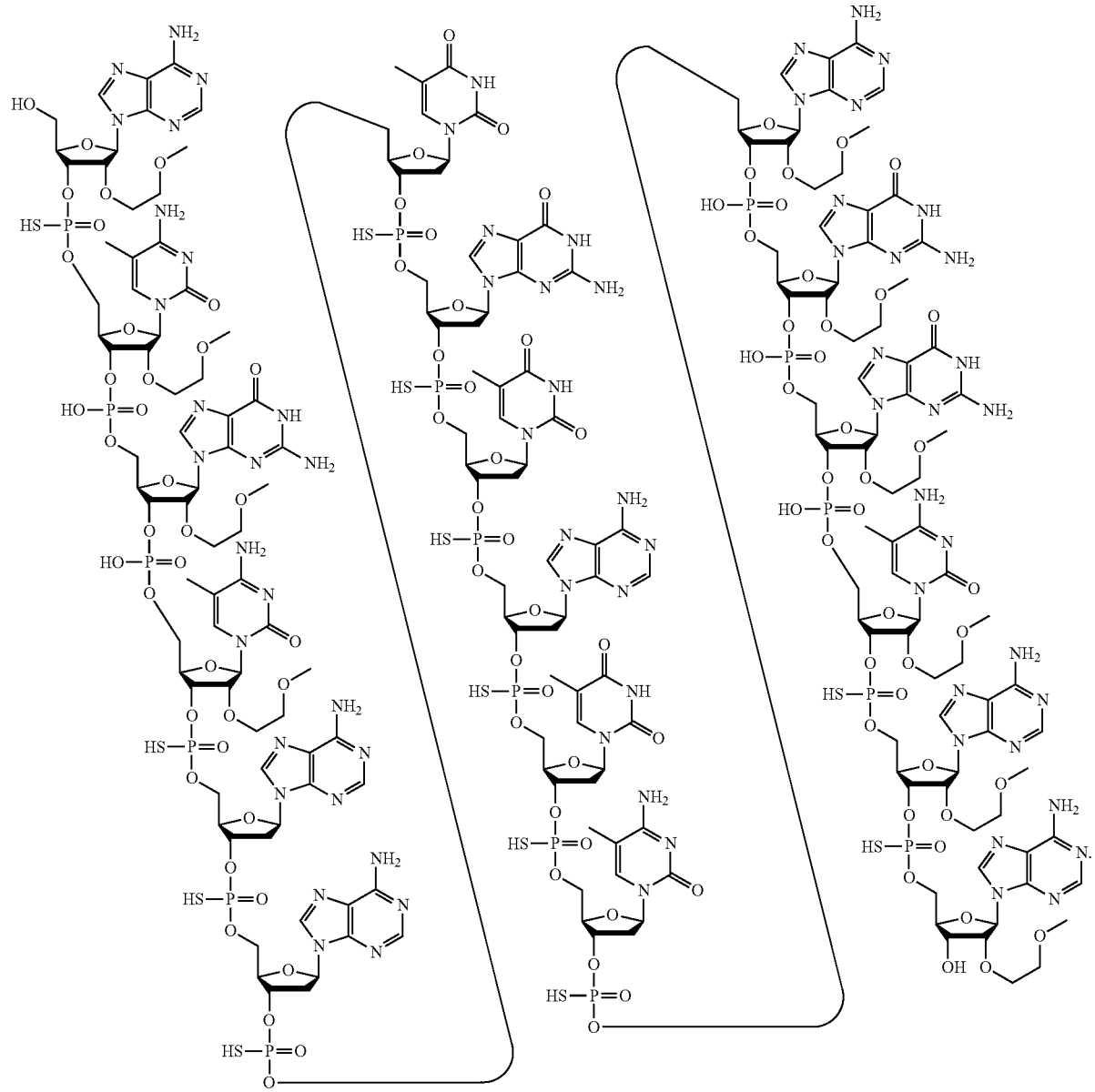

In certain embodiments, the sodium salt of Compound No. 1273039 is represented by the following chemical structure:

Structure 10. The sodium salt of Compound No. 1273039

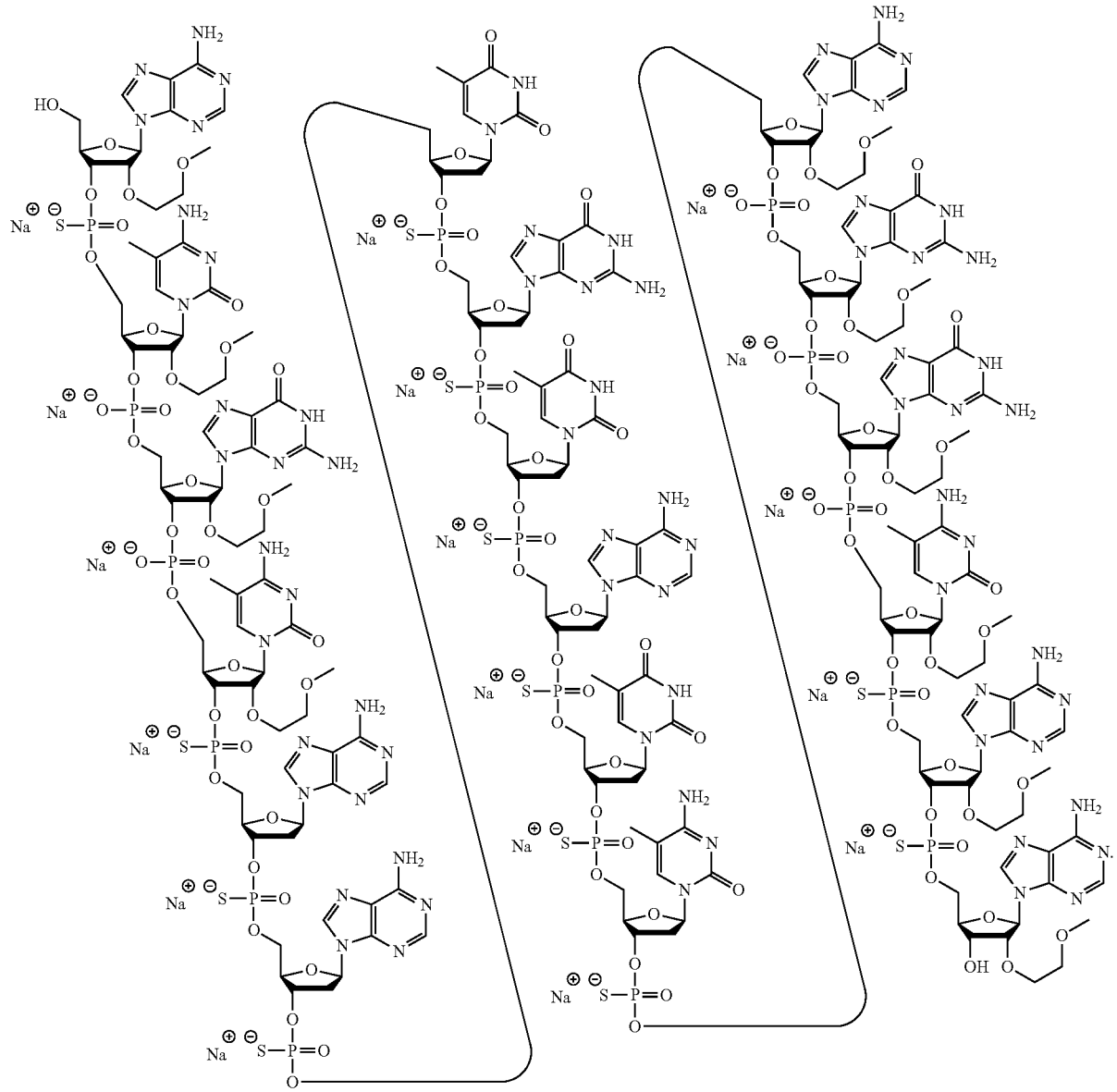

In certain embodiments, Compound No. 1273062 is represented by the following chemical notation: $A_{es}{}^m C_{eo}{}^m$-

(SEQ ID NO: 2866)

6. Compound No. 1273062

In certain embodiments, Compound No. 1273062 is characterized as a 5-10-5 MOE gapmer having a sequence (from 5' to 3') of ACCATTTTGACCTTCTTAGC (SEQ ID NO: 2873), wherein each of nucleosides 1-5 and 16-20 (from 5' to 3') are 2'-MOE nucleosides and each of nucleosides 6-15 are 2'-β-D-deoxynucleosides, wherein the internucleoside linkages between nucleosides 2 to 3, 3 to 4, 4 to 5, 5 to 6, 16 to 17, and 17 to 18 are phosphodiester internucleoside linkages and the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

$C_{eo} A_{eo} T_{eo} T_{ds} T_{ds} T_{ds} G_{ds} A_{ds} {}^m C_{ds} {}^m C_{ds} T_{ds} T_{ds} {}^m C_{ds} T_{eo}$-
$T_{eo} A_{es} G_{es} {}^m C_e$ (SEQ ID NO: 2873), wherein:

A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1273062 is represented by the following chemical structure:

Structure 11. Compound No. 1273062
(SEQ ID NO: 2873)
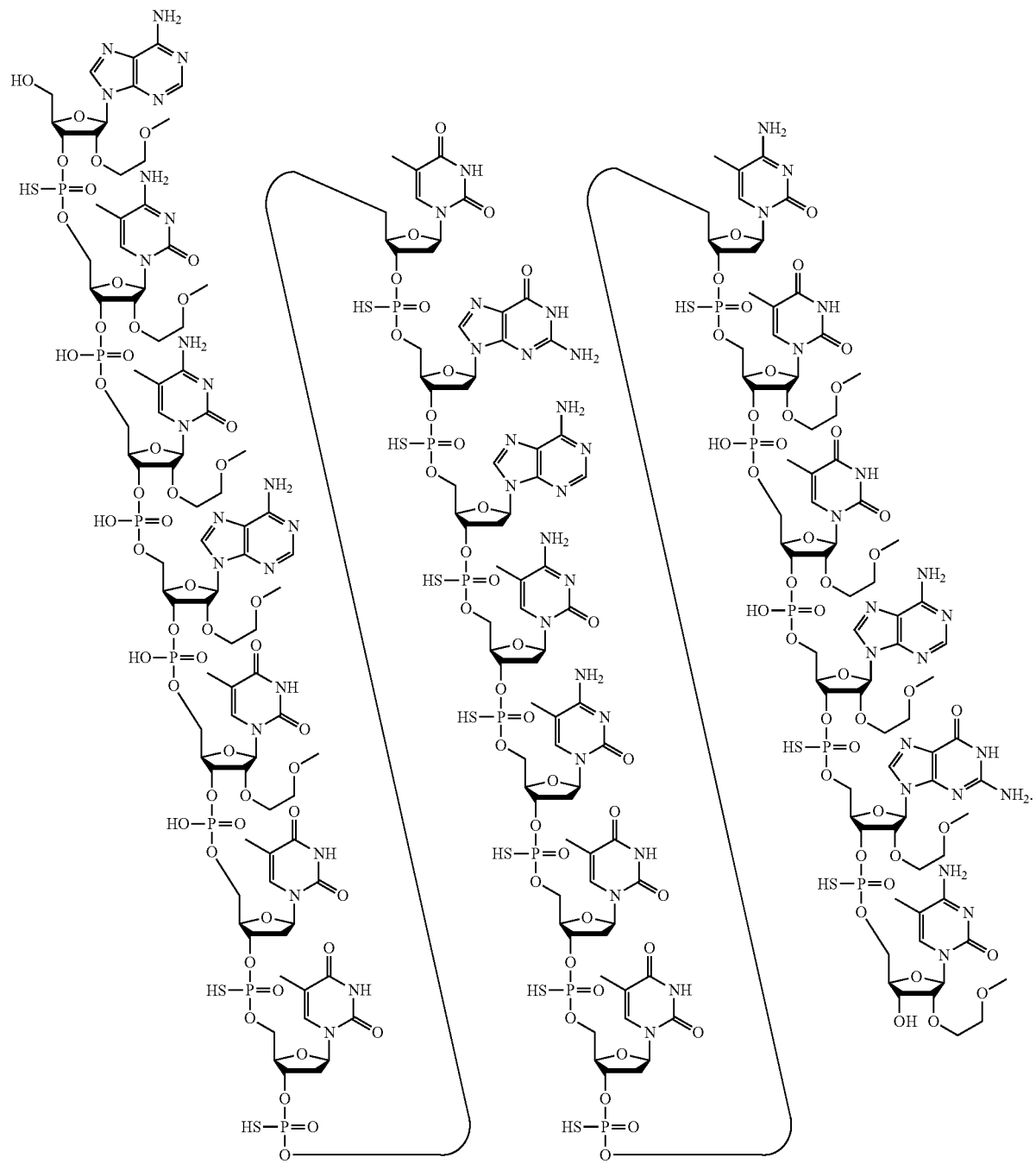

In certain embodiments, the sodium salt of Compound No. 1273062 is represented by the following chemical structure:

Structure 12. The sodium salt of Compound No. 1273062

(SEQ ID NO: 2873)

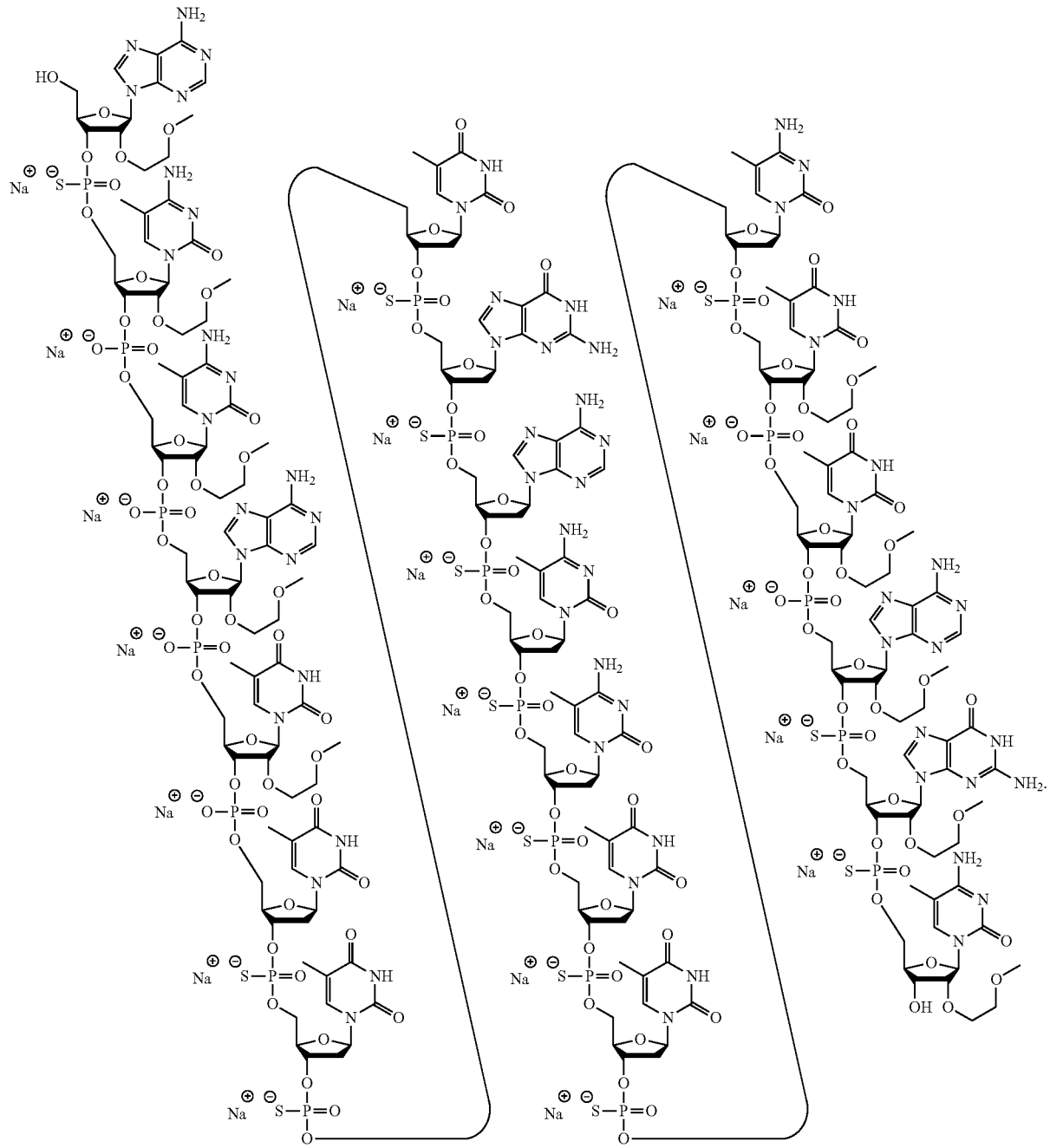

2'-β-D-deoxyribosyl sugar moiety; having a sequence of (from 5' to 3') AAATTATTTATACACCATCA (SEQ ID NO: 2905), wherein each "C" is a 5-methyl cytosine; and wherein each internucleoside linkage is a phosphorothioate internucleoside linkage. Compound #586_9 has cytosines at positions 13, 15, and 16 whereas Compound No. 1219022 5-methyl cytosines at those positions. According to Wan and Seth, "[i]ntroduction of the 5-methyl group on cytosine reduces the immunostimulatory profile of certain DNA VIII. Certain Comparator Compounds In certain embodiments, Compound No. 1219022, a surrogate of which (Compound #586_9) is provided in WO2017/081223 (incorporated herein by reference), was used as a comparator compound. Compound No. 1219022 is a mixed LNA/DNA oligonucleotide having a sugar motif of (from 5' to 3') llddldlddddddddddllll, wherein each "1" represents an LNA sugar moiety and each "d" represents a oligonucleotides and also enhances nuclease stability" (J. Med. Chem. 2016, 59, 9645-9667).

In certain embodiments, Compound No. 1219023, a surrogate of which (Compound #572_7) is provided in WO2017/081223 (incorporated herein by reference), was used as a comparator compound. Compound No. 1219023 is a mixed LNA/DNA oligonucleotide having a sugar motif of (from 5' to 3') llldddlddddddddddlll, wherein each "l" represents an LNA sugar moiety and each "d" represents a 2'-ß-D-deoxyribosyl sugar moiety; having a sequence of (from 5' to 3') TTTATCAATATCTTCTCA (SEQ ID NO: 2906), wherein each "C" is a 5-methyl cytosine; and wherein each internucleoside linkage is a phosphorothioate internucleoside linkage. Compound #572_7 has cytosines at positions 12 and 15 whereas Compound No. 1219023 has 5-methyl cytosines at those positions.

In certain embodiments, Compound No. 1219024, a surrogate of which (Compound #591_1) is provided in WO2017/081223 (incorporated herein by reference), was used as a comparator compound. Compound No. 1219024 is a mixed LNA/DNA oligonucleotide having a sugar motif of (from 5' to 3') ldldldddddddddddddll, wherein each "l" represents an LNA sugar moiety and each "d" represents a 2'-ß-D-deoxyribosyl sugar moiety; having a sequence of (from 5' to 3') GCACATTCTTTCTATACCT (SEQ ID NO: 2907), wherein each "C" is a 5-methyl cytosine; and wherein each internucleoside linkage is a phosphorothioate internucleoside linkage. Compound #591_1 has cytosines at positions 2, 4, 8, 12 and 17 whereas Compound No. 1219024 has 5-methyl cytosines at those positions.

In certain embodiments, Compound No. 1219025, a surrogate of which (Compound #169_52) is provided in WO2017/081223 (incorporated herein by reference), was used as a comparator compound. Compound No. 1219025 is a mixed LNA/DNA oligonucleotide having a sugar motif of (from 5' to 3') lldlldddddddddddll, wherein each "l" represents an LNA sugar moiety and each "d" represents a 2'-ß-D-deoxyribosyl sugar moiety; having a sequence of (from 5' to 3') TTATAGCCATTCTATCT (SEQ ID NO: 2908), wherein each "C" is a 5-methyl cytosine; and wherein each internucleoside linkage is a phosphorothioate internucleoside linkage. Compound #169_52 has cytosines at positions 7, 8, and 12 whereas Compound No. 1219025 has 5-methyl cytosines at those positions.

In certain embodiments, Compound No. 1219026, a surrogate of which (Compound #624_5) is provided in WO2017/081223 (incorporated herein by reference), was used as a comparator compound. Compound No. 1219026 is a mixed LNA/DNA oligonucleotide having a sugar motif of (from 5' to 3') ldlllddddddddllll, wherein each "l" represents an LNA sugar moiety and each "d" represents a 2'-ß-D-deoxyribosyl sugar moiety; having a sequence of (from 5' to 3') CTCAAAGATCATTCTCA (SEQ ID NO: 2909), wherein each "C" is a 5-methyl cytosine; and wherein each internucleoside linkage is a phosphorothioate internucleoside linkage. Compound #624_5 has a cytosine at position 10 whereas Compound No. 1219026 has a 5-methyl cytosine at that position.

In certain embodiments, Compound No. 1219027, a surrogate of which (Compound #626_8) is provided in WO2017/081223 (incorporated herein by reference), was used as a comparator compound. Compound No. 1219027 is a mixed LNA/DNA oligonucleotide having a sugar motif of (from 5' to 3') ldldldldddddddddldll, wherein each "l" represents an LNA sugar moiety and each "d" represents a 2'-ß-D-deoxyribosyl sugar moiety; having a sequence of (from 5' to 3') TTACACTTAATTATACTTCC (SEQ ID NO: 2910), wherein each "C" is a 5-methyl cytosine; and wherein each internucleoside linkage is a phosphorothioate internucleoside linkage. Compound #626_8 has cytosines at positions 4, 6, and 16 whereas Compound No. 1219027 has 5-methyl cytosines at those positions.

In certain embodiments, Compound No. 1219028, a surrogate of which (Compound #639_5) is provided in WO2017/081223 (incorporated herein by reference), was used as a comparator compound. Compound No. 1219028 is a mixed LNA/DNA oligonucleotide having a sugar motif of (from 5' to 3') ldddddddddddlldlll, wherein each "l" represents an LNA sugar moiety and each "d" represents a 2'-ß-D-deoxyribosyl sugar moiety; having a sequence of (from 5' to 3') GTTTCCATCTACTATTAA (SEQ ID NO: 2911), wherein each "C" is a 5-methyl cytosine; and wherein each internucleoside linkage is a phosphorothioate internucleoside linkage. Compound #639_5 has cytosines at positions 5, 6, 9 and 12 whereas Compound No. 1219028 has 5-methyl cytosines at those positions.

In certain embodiments, Compound No. 1219029, a surrogate of which (Compound #642_12) is provided in WO2017/081223 (incorporated herein by reference), was used as a comparator compound. Compound No. 1219029 is a mixed LNA/DNA oligonucleotide having a sugar motif of (from 5' to 3') llddlddddddddddddll, wherein each "l" represents an LNA sugar moiety and each "d" represents a 2'-ß-D-deoxyribosyl sugar moiety; having a sequence of (from 5' to 3') CTGTATACACCATCCCA (SEQ ID NO: 2912), wherein each "C" is a 5-methyl cytosine; and wherein each internucleoside linkage is a phosphorothioate internucleoside linkage. Compound #642_12 has cytosines at positions 8, 10, 11, 14 and 15 whereas Compound No. 1219029 has 5-methyl cytosines at those positions.

In certain embodiments, Compound No. 1219030, a surrogate of which (Compound #304_6) is provided in WO2017/081223 (incorporated herein by reference), was used as a comparator compound. Compound No. 1219030 is a mixed LNA/DNA oligonucleotide having a sugar motif of (from 5' to 3') lddllddddddddllll, wherein each "l" represents an LNA sugar moiety and each "d" represents a 2'-ß-D-deoxyribosyl sugar moiety, having a sequence of (from 5' to 3') AGTTCTACTATACTTTC (SEQ ID NO: 2913), wherein each "C" is a 5-methyl cytosine; and wherein each internucleoside linkage is a phosphorothioate internucleoside linkage. Compound #304_6 has cytosines at positions 8 and 13 whereas Compound No. 1219030 has 5-methyl cytosines at those positions.

In certain embodiments, Compound No. 1219031, a surrogate of which (Compound #573_8) is provided in WO2017/081223 (incorporated herein by reference), was used as a comparator compound. Compound No. 1219031 is a mixed LNA/DNA oligonucleotide having a sugar motif of (from 5' to 3') llddldlddddddddddll, wherein each "l" represents an LNA sugar moiety and each "d" represents a 2'-ß-D-deoxyribosyl sugar moiety; having a sequence of (from 5' to 3') TATACCTTTCTTTAACCCTT (SEQ ID NO: 2914), wherein each "C" is a 5-methyl cytosine; and wherein each internucleoside linkage is a phosphorothioate internucleoside linkage. Compound #573_8 has cytosines at positions 6, 10, 16, 17, and 18 whereas Compound No. 1219031 has cytosines at those positions.

Compound Nos. 1219022-1219031 (relating to Compound Nos. #586_9, #572_7, #591_1, #169_52, #624_5, #626_8, #639_5 #642_12, #304_6, #573_8, respectively) were selected as comparator compounds from Example 7 of WO2017/081223, which provides a subset of active compounds "selected for potency and efficacy testing."

In certain embodiments, compounds described herein are superior relative to compounds described in WO2017/081223 because they demonstrate one or more improved properties, such as in vivo tolerability.

For example, as described herein, certain compounds Compound No. 1263517, Compound No. 1263518, Compound No. 1263533, Compound No. 1273039, and Compound No. 1273062 achieved 3-hour FOB scores in mice of 1.0 (Table 88), 0.0 (Table 88), 1.0 (Table 88), 1.0 (Table 96), and 0.0 (Table 96), respectively, whereas each of comparator compounds Compound No. 1219022, Compound No. 1219024, Compound No. 1219025, Compound No. 1219028, Compound No. 1219029, Compound No. 1219030, and Compound No. 1219031 achieved 3-hour FOB scores in mice of 7.0, 5.3, 4.0, 6.0, 6.3, 5.0, and 5.3 (Table 119), respectively. Therefore, certain compounds described herein are more tolerable than comparator compounds Compound No. 1219022, Compound No. 1219024, Compound No. 1219025, Compound No. 1219028, Compound No. 1219029, Compound No. 1219030, and Compound No. 1219031 in this assay.

For example, as described herein, certain compounds Compound No. 1065645, Compound No. 1263517, Compound No. 1263518, Compound No. 1263533, Compound No. 1273039, and Compound No. 1273062 each achieved 2-week FOB scores in mice of 0.0 (Example 12, Table 112), whereas Compound No. 1219023, Compound No. 1219024, Compound No. 1219025, Compound No. 1219026, Compound No. 1219028, Compound No. 1219029, Compound No. 1219030, and Compound No. 1219031 achieved 2-week delayed FOB scores in mice of 3.5, 6.5, 6.0, 6.0, 6.0, 6.0, 6.0, 5.0, and 6.0, respectively (Table 119). Therefore, certain compounds described herein are more tolerable than comparator compounds Compound No. 1219023 and Compound No. 1219026 in this assay.

For example, as described herein, certain compounds Compound No. 1065645, Compound No. 1263517, Compound No. 1263518, Compound No. 1263533, Compound No. 1273039, and Compound No. 1273062 do not cause a significant difference in body weight as compared to PBS-treated rats in an 8-week study, whereas treatment with Compound No. 1219027 leads to a greater than 10% weight loss compared to PBS-treated rats (p-value<0.05, Table 120). Therefore, certain compounds described herein are more tolerable than comparator Compound No. 1219027 in this assay.

IX. Certain Hotspot Regions

In certain embodiments, nucleobases in the ranges specified below comprise a hotspot region of UBE3A-ATS. In certain embodiments, modified oligonucleotides that are complementary to a hotspot region of UBE3A-ATS achieve an average of more than 50% reduction of UBE3A-ATS RNA in vitro in the standard cell assay.

1. Nucleobases 461,413-461,487 of SEQ ID NO: 1

In certain embodiments, nucleobases 461,413-461,487 of SEQ ID NO: 1 comprise a hotspot region. In certain embodiments, modified oligonucleotides are complementary to a portion of nucleobases 461,413-461,487 of SEQ ID NO: 1. In certain embodiments, modified oligonucleotides are 20 nucleobases in length. In certain embodiments, modified oligonucleotides are 18 nucleobases in length. In certain embodiments, modified oligonucleotides are gapmers. In certain embodiments, the gapmers are MOE gapmers. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': sooooossssssssssooss, sooooossssssssss-soss, sooooosssssssssoss, sooosssssssssooss, sooossssssssss-soooss, or soosssssssssoooss.

The nucleobase sequences of SEQ ID Nos: 1053, 1329, 1501, 1576, 1873, 1949, 2025, 2096, 2245, 2512, 2591, 2680-2682, and 2844 are complementary to a portion of nucleobases 461,413-461,487 of SEQ ID NO: 1. The nucleobase sequence of Compound Nos: 749901-749904, 1065641-1065646, 1165562-1165563, 1165857-1165858, and 1273001 are complementary to a portion of nucleobases 461,413-461,487 of SEQ ID NO: 1.

In certain embodiments, modified oligonucleotides complementary to a portion of nucleobases 461,413-461,487 of SEQ ID NO: 1 achieve at least 36% reduction of UBE3A-ATS RNA in vitro in the standard cell assay. In certain embodiments, modified oligonucleotides complementary to a portion of nucleobases 461,413-461,487 of SEQ ID NO: 1 achieve an average of 60% reduction of UBE3A-ATS RNA in vitro in the standard cell assay.

2. Nucleobases 468,968-469,013 of SEQ ID NO: 1

In certain embodiments, nucleobases 468,968-469,013 of SEQ ID NO: 1 comprise a hotspot region. In certain embodiments, modified oligonucleotides are complementary to a portion of nucleobases 468,968-469,013 of SEQ ID NO: 1. In certain embodiments, modified oligonucleotides are 20 nucleobases in length. In certain embodiments, modified oligonucleotides are 18 nucleobases in length. In certain embodiments, modified oligonucleotides are gapmers. In certain embodiments, the gapmers are MOE gapmers. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': sooooossssssssssooss, sooooossssssssss-soss, sooooosssssssssoss, sooosssssssssooss, sooossssssssss-soooss, or soosssssssssoooss.

The nucleobase sequences of SEQ ID Nos: 376, 377, 2751-2756, 2773-2776, 2872, 2873, 2876-2878 are complementary to a portion of nucleobases 468,968-469,013 of SEQ ID NO: 1.

The nucleobase sequence of Compound Nos: 750031-750032, 1263408-1263411, 1263426, 1263441, 1263460-1263465, 1263486-1263492, 1263517-1263523, 1273061, 1273062, and 1273065-1273067 are complementary to a portion of nucleobases 468,968-469,013 of SEQ ID NO: 1.

In certain embodiments, modified oligonucleotides complementary to a portion of nucleobases 468,968-469,013 of SEQ ID NO: 1 achieve at least 75% reduction of UBE3A-ATS RNA in vitro in the standard cell assay. In certain embodiments, modified oligonucleotides complementary to a portion of nucleobases 468,968-469,013 of SEQ ID NO: 1 achieve an average of 78% reduction of UBE3A-ATS RNA in vitro in the standard cell assay. In certain embodiments, modified oligonucleotides complementary to a portion of nucleobases 468,968-469,013 of SEQ ID NO: 1 achieve an average of 410% upregulation of UBE3A-ATS RNA in vitro at 6.7 µM in cell culture.

3. Nucleobases 483,965-484,003 of SEQ ID NO: 1

In certain embodiments, nucleobases 483,965-484,003 of SEQ ID NO: 1 comprise a hotspot region. In certain embodiments, modified oligonucleotides are complementary to a portion of 483,965-484,003 of SEQ ID NO: 1. In certain embodiments, modified oligonucleotides are 20 nucleobases in length. In certain embodiments, modified oligonucleotides are 18 nucleobases in length. In certain embodiments, modified oligonucleotides are gapmers. In certain embodiments, the gapmers are MOE gapmers. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': soooossssssssssooss, sooooosssssssssssoss, soooossssssssssoss, sooossssssssssooss, sooossssssssssooss, or soosssssssssooss.

The nucleobase sequences of SEQ ID Nos: 172, 764-770, 995, 1445, 1668, 1743, 2255, 2595, 2762-2767 are complementary to a portion of nucleobases 483,965-484,003 of SEQ ID NO: 1.

The nucleobase sequence of Compound Nos: 617557, 699781, 750138-750144, 1065918-1065921, 1165621, 1165878, and 1263532-1263557 are complementary to a portion of nucleobases 483,965-484,003 of SEQ ID NO: 1.

In certain embodiments, modified oligonucleotides complementary to a portion of nucleobases 483,965-484, 003 of SEQ ID NO: 1 achieve at least 24% reduction of UBE3A-ATS RNA in vitro in the standard cell assay. In certain embodiments, modified oligonucleotides complementary to nucleobases 483,965-484,003 of SEQ ID NO: 1 achieve an average of 65% reduction of UBE3A-ATS RNA in vitro in the standard cell assay. In certain embodiments, modified oligonucleotides complementary to a portion of nucleobases 468,968-469,013 of SEQ ID NO: 1 achieve an average of 330% upregulation of UBE3A-ATS RNA in vitro at 6.7 µM in cell culture.

4. Additional Hotspot Regions

In certain embodiments, the ranges described in the Table below comprise hotspot regions. Each hotspot region begins with the nucleobase of SEQ ID NO: 1 identified in the "Start Site SEQ ID NO: 1" column and ends with the nucleobase of SEQ ID NO: 1 identified in the "Stop Site SEQ ID NO: 1" column. In certain embodiments, modified oligonucleotides are complementary within any of the hotspot regions 1-61, as defined in the table below. In certain embodiments, modified oligonucleotides are 18 nucleobases in length. In certain embodiments, modified oligonucleotides are 20 nucleobases in length. In certain embodiments, modified oligonucleotides are gapmers. In certain embodiments, modified oligonucleotides are 4-8-6, 6-8-4, 5-8-5, 4-10-6, 6-10-4, or 5-10-5 MOE gapmers.

The nucleobase sequence of compounds listed in the "Compound ID in range" column in the table below are complementary to SEQ ID NO: 1 within the specified hotspot region. The nucleobase sequence of the oligonucleotides listed in the "SEQ ID NO: in range" column in the table below are complementary to the target sequence, SEQ ID NO: 1, within the specified hotspot region.

In certain embodiments, modified oligonucleotides complementary to nucleobases within the hotspot region achieve at least "Min.% Red" (minimum % reduction, relative to untreated control cells) of UBE3A-ATS RNA in vitro in the standard cell assay, as indicated in the table below. In certain embodiments, modified oligonucleotides complementary to nucleobases within the hotspot region achieve an average of "Avg.% Red." (average % reduction, relative to untreated control cells) of UBE3A-ATS RNA in vitro in the standard cell assay, as indicated in the table below. In certain embodiments, modified oligonucleotides complementary to nucleobases within the hotspot region achieve a maximum of "Max. % Red." (maximum % reduction, relative to untreated control cells) of UBE3A-ATS RNA in vitro in the standard cell assay, as indicated in the table below.

TABLE 1

UBE3A-ATS Hotspots

| Hotspot ID | Start Site SEQ ID NO: 1 | Stop Site SEQ ID NO: 1 | Min. % Red. | Max. % Red. | Avg. % Red. | Compound ID in range | SEQ ID NO: in range |
|---|---|---|---|---|---|---|---|
| 1 | 461413 | 461487 | 36 | 89 | 60 | 749901-749904, 1065641-1065646, 1165562-1165563, 1165857-1165858, 1273001 | 1053, 1329, 1501, 1576, 1873, 1949, 2025, 2096, 2245, 2512, 2591, 2680-2682, 2844 |
| 2 | 468968 | 469013 | 75 | 81 | 78 | 750031-750032, 1263408-1263411, 1263426, 1263441, 1263460-1263465, 1263486-1263492, 1263517-1263523, 1273061, 1273062, 1273065-1273067 | 376, 377, 2751-2756, 2773-2776, 2872, 2873, 2876-2878 |
| 3 | 483965 | 484003 | 24 | 91 | 65 | 617557, 699781, 750138-750144, 1065918-1065921, 1165621, 1165878, 1263532-1263557 | 172, 764-770, 995, 1445, 1668, 1743, 2255, 2595, 2762-2767 |
| 4 | 349103# | 349150# | 35 | 82 | 56 | 750519-750533 | 181-195 |
| 5 | 457354 | 457405 | 37 | 85 | 66 | 749848, 1065574-1065576, 1165519-1165521, 1179839-1179840 | 552, 973, 1273, 1795, 2162, 2237, 2370, 2537, 2671 |
| 6 | 457899 | 457936 | 49 | 77 | 59 | 749852, 1065581-1065582 | 556, 1497, 1945 |
| 7 | 457969 | 458013 | 36 | 78 | 61 | 749853, 1065583-1065586, 1165523-1165525 | 557, 1124, 1199, 1647, 2021, 2089, 2464, 2538 |
| 8 | 458523 | 458558 | 64 | 77 | 71 | 749861-749862, 1065595 | 565, 566, 1050 |
| 9 | 458560 | 458627 | 45 | 81 | 64 | 749863-749867, 1065596-1065600, 1272999 | 567-571, 1125, 1498, 1573, 1946, 2022, 2842 |

TABLE 1-continued

UBE3A-ATS Hotspots

| Hotspot ID | Start Site SEQ ID NO: 1 | Stop Site SEQ ID NO: 1 | Min. % Red. | Max. % Red. | Avg. % Red. | Compound ID in range | SEQ ID NO: in range |
|---|---|---|---|---|---|---|---|
| 10 | 458935 | 458976 | 30 | 85 | 60 | 1065602-1065605, 1165530-1165540, 1165853 | 901, 1425, 1648, 1724, 2091, 2092, 2164, 2165, 2239, 2240, 2392-2393, 2465, 2511, 2539, 2540 |
| 11 | 460105 | 460137 | 43 | 82 | 60 | 749882, 1065615-1065619, 1165547-1165549 | 586, 1126, 1201, 1649, 1725, 2023, 2093, 2467, 2542 |
| 12 | 460348 | 460381 | 36 | 77 | 58 | 1065621-1065622, 1165550-1165551 | 902, 976, 2167, 2242 |
| 13 | 460641 | 460686 | 50 | 67 | 57 | 617531, 1065629-1065631 | 107, 1500, 1948, 2024 |
| 14 | 460974 | 461021 | 75 | 91 | 82 | 749893-749894, 1165855, 1263451-1263455, 1263473-1263478, 1263504-1263509 | 597, 598, 2219, 2745-2749 |
| 15 | 461597 | 461627 | 50 | 85 | 68 | 1065651-1065655 | 904, 978, 1278, 1428, 1800 |
| 16 | 463502 | 463531 | 60 | 71 | 66 | 749931, 1065674-1065675 | 1503, 1578, 2708 |
| 17 | 463826 | 463872 | 50 | 71 | 62 | 749938, 749939, 1065680 | 1728, 2714, 2715 |
| 18 | 464377 | 464428 | 32 | 77 | 58 | 749951, 1065684-1065687, 1165572-1165577, 1273006-1273008 | 1280, 1356, 1802, 1876, 2097, 2172, 2247, 2398, 2471, 2546, 2727, 2849-2851 |
| 19 | 464522 | 464575 | 47 | 77 | 62 | 749952-749954, 1065690, 1165578, 1263412-1263416, 1263427-1263431, 1263442-1263446, 1263466-1263469, 1263494-1263499, 1263524-1263530, 1273068-1273070 | 1504, 2098, 2728-2730, 2757-2760, 2777-2781, 2879-2881 |
| 20 | 464994 | 465032 | 27 | 76 | 52 | 617457, 749957-749964, 1065698-1065702, 1165866 | 33, 907, 981, 1281, 1357, 1877, 2136, 2733-2739 |
| 21 | 465231 | 465266 | 23 | 83 | 63 | 749969, 1065706-1065713, 1165583-1165587, 1263403-1263407, 1263421-1263425, 1263436-1263440, 1263456, 1263479-1263485, 1263510-1263516, 1273063, 1273064 | 318, 908, 1132, 1207, 1432, 1655, 1730, 1953, 2028, 2174, 2248, 2400, 2473, 2548, 2750, 2768-2772, 2875 |
| 22 | 465372 | 465413 | 33 | 73 | 54 | 749972, 1065717-1065719, 1165588-1165592, 1165867-1165869 | 321, 1058, 1358, 1878, 2099, 2137, 2175, 2249, 2401, 2475, 2514, 2593 |
| 23 | 465600 | 465631 | 65 | 68 | 67 | 749975, 1065727-1065728, 1272944-1272947 | 324, 1433, 1731, 2787-2790 |
| 24 | 466244 | 466282 | 38 | 68 | 54 | 1065742-1065744, 1165595-1165598 | 1434, 1657, 1732, 2176, 2251, 2403, 2549 |
| 25 | 466529 | 466570 | 31 | 80 | 57 | 617460, 749989-749998, 1065760-1065762 | 36, 338-346, 911, 985, 1435 |
| 26 | 466979 | 467014 | 51 | 75 | 65 | 617461, 750000-750005, 1065764 | 37, 347-351, 1806 |
| 27 | 467043 | 467095 | 44 | 93 | 69 | 617539, 750006, 1065765-1065767, 1272943, 1272960, 1273005 | 115, 352, 1061, 1361, 1881, 2786, 2803, 2848 |
| 28 | 468335 | 468372 | 42 | 68 | 56 | 1065781-1065783, 1165609, 1165875 | 1062, 1362, 1882, 2139, 2405 |
| 29 | 475827 | 475877 | 39 | 71 | 57 | 617470, 1065830-1065834 | 46, 1065, 1365, 1513, 1588, 1961 |
| 30 | 482148 | 482181 | 49 | 70 | 68 | 750122, 1065889-1065890, 1165612 | 748, 919, 993, 2406 |
| 31 | 487589 | 487629 | 73 | 79 | 76 | 750172, 1065953-1065955, 1272973, 1272974 | 798, 997, 1297, 1818, 2816, 2817 |
| 32 | 487772 | 487826 | 44 | 73 | 62 | 750175-750177, 1065957 | 801-803, 1373 |
| 33 | 489873 | 489927 | 52 | 73 | 59 | 750195-750196, 1065989 | 398, 399, 1375 |
| 34 | 493831 | 493860 | 44 | 63 | 56 | 750202-750204 | 405-407 |
| 35 | 499081 | 499119 | 47 | 70 | 55 | 1066036-1066038 | 1078, 1378, 1898 |

TABLE 1-continued

UBE3A-ATS Hotspots

| Hotspot ID | Start Site SEQ ID NO: 1 | Stop Site SEQ ID NO: 1 | Min. % Red. | Max. % Red. | Avg. % Red. | Compound ID in range | SEQ ID NO: in range |
|---|---|---|---|---|---|---|---|
| 36 | 500605 | 500658 | 36 | 66 | 58 | 750265-750266, 1066064-1066065 | 683, 684, 929, 1004 |
| 37 | 500846 | 500905 | 30 | 86 | 55 | 750269-750270, 1066073-1066077, 1165670 | 687-688, 1155, 1230, 1678, 1976, 2051, 2562 |
| 38 | 501335 | 501375 | 42 | 67 | 56 | 1066091-1066094, 1272975-1272977 | 1156, 1231, 1679, 1753, 2818-2820 |
| 39 | 502125 | 502157 | 65 | 79 | 72 | 750291, 1066119-1066121 | 708, 1531, 1606, 1979 |
| 40 | 502194 | 502228 | 51 | 88 | 65 | 750292, 1066124-1066125 | 709, 1233, 1681 |
| 41 | 502416 | 502452 | 49 | 59 | 54 | 1066130-1066132 | 1308, 1829, 1904 |
| 42 | 502580 | 502618 | 57 | 59 | 58 | 750295, 1066140-1066142 | 712, 1234, 1682, 1756 |
| 43 | 503427 | 503461 | 36 | 73 | 61 | 750301, 1066185, 1165724 | 718, 1983, 2197 |
| 44 | 503636 | 503675 | 55 | 72 | 62 | 750307-750308, 1066190 | 724, 725, 1759 |
| 45 | 503973 | 504034 | 20 | 81 | 56 | 617503-617505, 617581-617582, 750313-750324, 750383, 1066202 | 79-81, 155-157, 302, 731-736, 2059 |
| 46 | 504088 | 504122 | 45 | 85 | 65 | 750325-750327, 1066206 | 245, 246, 737, 1760 |
| 47 | 504431 | 504460 | 49 | 70 | 57 | 1066218-1066219, 1165736-1165740 | 1164, 2060, 2119, 2276, 2427, 2495, 2574 |
| 48 | 506031 | 506071 | 33 | 66 | 52 | 750356, 750357, 1066274-1066276 | 275, 276, 1317, 1838, 1913 |
| 49 | 508739 | 508780 | 20 | 83 | 56 | 617503-617504, 617580-617582, 750313-750323, 750383, 1066202 | 79, 80, 155-157, 302, 730-735, 2059 |
| 50 | 509208 | 509271 | 46 | 68 | 63 | 750394-750395, 1066377-1066378 | 313-314, 1995, 2070 |
| 51 | 510203 | 510247 | 36 | 77 | 60 | 750400-750401, 1066394-1066395, 1165828 | 810, 811, 1175, 2071, 2440 |
| 52 | 510832 | 510872 | 44 | 70 | 55 | 1066418-1066421 | 1326, 1402, 1847, 1922 |
| 53 | 513442 | 513486 | 66 | 81 | 72 | 750436-750439 | 846-849 |

The oligonucleotides described in this section are complementary to this hotspot region at multiple sites. These sites are described in detail in Table 4b herein below (Example 1).

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein mC indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effect of 5-10-5 MOE Gapmer Modified Oligonucleotides on Human UBE3A-ATS RNA In Vitro, Single Dose Modified oligonucleotides complementary to human UBE3A-ATS nucleic acid were tested for their effect on UBE3A-ATS RNA levels in vitro.

The modified oligonucleotides in the tables below are 5-10-5 MOE gapmers. The gapmers are 20 nucleosides in length, wherein the central gap segment consists of ten 2'-O-D-deoxynucleosides and the 5' and 3' wing segments each consists of five 2'-MOE nucleosides. The sugar motif for the gampers is (from 5' to 3'): eeeeedddddddddddeeeee; wherein 'd' represents a 2'-β-D-deoxyribosyl sugar moiety, and 'e' represents a 2'-MOE sugar moiety. Each internucleoside linkage of Compound IDs 617441-617596 (in Tables 2 and 3) is a phosphorothioate internucleoside linkage. All other compounds (Tables 4-33) have an internucleoside linkage motif of (from 5' to 3'): soooosssssssssooss, wherein each "s" represents a phosphorothioate internucleoside linkage and each "o" represents a phosphodiester internucleoside linkage.

All cytosine residues are 5-methylcytosines.

"Start site" indicates the 5'-most nucleoside to which the modified oligonucleotide is complementary in the human gene sequence. "Stop site" indicates the 3'-most nucleoside to which the modified oligonucleotide is complementary in the target nucleic acid sequence. Each modified oligonucleotide listed in the Tables below is 100% complementary to SEQ ID NO: 1 (GENBANK Accession No NC_000015.10 truncated from nucleotides 24821647 to 25441028). Selected compounds in the table below are complementary to the target nucleic acid sequence at more than three specific sites. For these compounds, the "start site" and "stop site" values in the Tables below are indicated with a hashtag (#) and indicate only the first site to which the compound is complementary. Additional sites to which these compounds are complementary are indicated in Table 4b below.

Human IPSC cell derived iCell GABANeurons (Cellular Dynamics) were cultured per manufacturer instructions at 20,000-60,000 cells per well (as indicated in the table heading) and were treated with 5,000-10,000 nM of modified oligonucleotide (as indicated in the table heading) by free uptake. After a treatment period of approximately 6 days, total RNA was isolated from the cells and UBE3A-ATS RNA levels were measured by quantitative real-time RTPCR. Human UBE3A-ATS primer probe set RTS4796 (forward sequence CTCCCCCAGTTCTGGAATGA, designated herein as SEQ ID NO: 2; reverse sequence TACACAGGGATTTGAGCCTGCTA, designated herein as SEQ ID NO: 3; probe sequence CCCACAGATCAAGCATTCCCCAAAGA, designated herein as SEQ ID NO: 4) was used to measure RNA levels. UBE3A-ATS RNA levels were normalized to total RNA content, as measured by RIBOGREEN®. Reduction of UBE3A-ATS RNA is presented in the tables below as percent UBE3A-ATS RNA amount relative to untreated control (UTC) cells. Each table represents results from an individual assay plate. The values marked with an asterisk (*) indicate that the modified oligonucleotide is complementary to the amplicon region of the primer probe set. Additional assays may be used to measure the potency and efficacy of the modified oligonucleotides complementary to the amplicon region. "N.D." indicates that a value was not determined in this experiment due to experimental error. However, activities of selected modified oligonucleotides, including those that are not defined in Example 1, are successfully demonstrated in dose-response studies herein below.

TABLE 2

Reduction of UBE3A-ATS RNA by 7,000 nM 5-10-5 MOE gapmers with PS internucleoside linkages in vitro (60,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617441 | 449466 | 449485 | ATGTTGCTTGCACTCCATCA | 85 | 17 |
| 617442 | 449945 | 449964 | ACAACATAAGGTCTTATTGT | 87 | 18 |
| 617443 | 450581 | 450600 | TTTTCAACTCCAGAATTTTC | 87 | 19 |
| 617444 | 451644 | 451663 | TTCAGTCTTATACAGAAATG | 94 | 20 |
| 617445 | 452473 | 452492 | GGACTGACACAGAAAACTGG | 115 | 21 |
| 617446 | 454843 | 454862 | AGGGTAGAAGACTAGCATAC | 111 | 22 |
| 617447 | 455272 | 455291 | GGCCATTCATTCAGCCACAC | 95 | 23 |
| 617448 | 455405 | 455424 | TAAAGATTTTATGAAAATAC | 104 | 24 |

TABLE 2-continued

Reduction of UBE3A-ATS RNA by 7,000 nM 5-10-5 MOE gapmers with PS internucleoside linkages in vitro (60,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617449 | 456040 | 456059 | TTTAGAACATGTGAATTTCA | 109 | 25 |
| 617450 | 457025 | 457044 | AGACATATCACAGTTGCTTG | 89 | 26 |
| 617451 | 457601 | 457620 | AATATAATGTAGTATGACCA | 59 | 27 |
| 617452 | 458989 | 459008 | GAGGACACTGGCACATCTAT | 59 | 28 |
| 617453 | 459376 459401 | 459395 459420 | TTAAATAATAAAATATATTT | 108 | 29 |
| 617454 | 461190 | 461209 | ATTGGAGCAAAAAGGGATCA | 45 | 30 |
| 617455 | 462327 | 462346 | AATTATTCCCTATATCCTGT | 45 | 31 |
| 617456 | 463905 | 463924 | CAACTGTTACCAAGACTTCA | 24 | 32 |
| 617457 | 465003 | 465022 | ATCTGCGAATAGAGGCCCTC | 44 | 33 |
| 617458 | 465460 | 465479 | AAGGTTTTTATTTCATCACT | 68 | 34 |
| 617459 | 465872 | 465891 | GCCCATGGATGGTTGTCAAA | 34 | 35 |
| 617460 | 466539 | 466558 | TAGGTTGCATAAAGCCAGGC | 23 | 36 |
| 617461 | 466981 | 467000 | CACACATCTTGTTCCCTCAA | 23 | 37 |
| 617462 | 467508 | 467527 | TTTTTTTAATCCTCTGATGA | 123 | 38 |
| 617463 | 467914 | 467933 | AGTCTCTTTTCTTTCGGTGC | 34 | 39 |
| 617464 | 468085 | 468104 | GGAAAGTTCTTCTCTCTCCT | 69 | 40 |
| 617465 | 469204 | 469223 | ATTTGGTCTAAAGTGAAGTT | 91 | 41 |
| 617466 | 470003 | 470022 | TTTTGTGAGATTTTTGAATA | 101 | 42 |
| 617467 | 471815 | 471834 | TGTTAAATGCTTTTCTAAAT | 80 | 43 |
| 617468 | 472985 | 473004 | CTGATGATTGATTGTTTCCT | 71 | 44 |
| 617469 | 474868 | 474887 | TATGATAATGTGTAGTTTTT | 110 | 45 |
| 617470 | 475850 | 475869 | AAGGGTAATACGGACCTCAT | 29 | 46 |
| 617471 | 476475 | 476494 | CTATTTTTGCTTCCCTTAT | 56 | 47 |
| 617472 | 479448 | 479467 | GAATTCTTAGAAAGTTAATT | 118 | 48 |
| 617473 | 479585 | 479604 | TGCCATCTTCAAGACTAAGG | 33 | 49 |
| 617474 | 480527 | 480546 | AATGGAAAAGATGTATCACG | 92 | 50 |
| 617475 | 481063 | 481082 | AACTTTGGCAGCTATTCAAT | 88 | 51 |
| 617476 | 481522 | 481541 | GACACTAGGTTTTGCAAAAG | 63 | 52 |
| 617477 | 481663 | 481682 | TATGAATTTTCAATTCAATG | 155 | 53 |
| 617478 | 483415 | 483434 | CACTTAAGGGAACTTTCAGA | 84 | 54 |
| 617479 | 483933 | 483952 | GAGATGATGTTAAGCTTTCA | 75 | 55 |
| 617480 | 484344 | 484363 | TAAGACAAGTGGCCATGAAG | 92 | 56 |
| 617481 | 484760 | 484779 | CTCTGTTCTGTCTCAAAACA | 47 | 57 |
| 617482 | 485496 | 485515 | TATAAGAAAGAAGATTACAG | 132 | 58 |
| 617483 | 486358 | 486377 | AAATGTTAATAGACTGCGAT | 93 | 59 |
| 617484 | 486941 | 486960 | TTAAACTCCCCAGTCAAAAG | 108 | 60 |

TABLE 2-continued

Reduction of UBE3A-ATS RNA by 7,000 nM 5-10-5 MOE gapmers with PS internucleoside linkages in vitro (60,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617485 | 488180 | 488199 | ATTTACTTCAAACAGGAGCT | 42 | 61 |
| 617486 | 489476 | 489495 | TCAGGAAATTAAAGCATTCA | 81 | 62 |
| 617487 | 489630 | 489649 | CCTAACCTGGATCTCAGATA | 57 | 63 |
| 617488 | 493552 | 493571 | TACAGCAACCCTAGAAAACT | 121 | 64 |
| 617489 | 493893 | 493912 | ATCTTTGGCAGATGTAACCT | 63 | 65 |
| 617490 | 495750 | 495769 | GAGTATTATCCAAAAGAACA | 83 | 66 |
| 617491 | 497275 | 497294 | AAAGCCCAGGATTAGGCAGC | 63 | 67 |
| 617492 | 497366 | 497385 | CTACAAAGAGTGAATCATGA | 130 | 68 |
| 617493 | 498003 | 498022 | TAATCTTAAGTTTAAGTGGA | 68 | 69 |
| 617494 | 498883 | 498902 | AAAAAGACATAGAATGACAG | 100 | 70 |
| 617495 | 499237 | 499256 | AGATACAAATTTAAAAAAGT | 119 | 71 |
| 617496 | 499672 | 499691 | GGTAGCCCCAATACAGATTC | 62 | 72 |
| 617497 | 500044 | 500063 | CTTCAACAGCAGACTTGATC | 65 | 73 |
| 617498 | 501513 | 501532 | GGTCCACACAGAGTTCAAAT | 73 | 74 |
| 617499 | 501703 | 501722 | CTTTGGGACATCCCAAAGTT | 113 | 75 |
| 617500 | 502388 | 502407 | TACACATCTTGTATACAAGG | 60 | 76 |
| 617501 | 503258 | 503277 | TAATACTTTCTTGAGTAATA | 124 | 77 |
| 617502 | 503904 | 503923 | GGGTGGTTGGATTGCTTTAT | 47 | 78 |
| 617503 | 503977 508743 | 503996 508762 | CTGCACACTGTACAGGAGGG | 80 | 79 |
| 617504 | 503985 508751 | 504004 508770 | TTGATTCACTGCACACTGTA | 67 | 80 |
| 617505 | 504015 | 504034 | GTGCAGGAAGGAGGTTTTGT | 55 | 81 |
| 617506 | 504943 | 504962 | ATACAGTATATACATCATCC | 42 | 82 |
| 617507 | 505266 | 505285 | AAGTTTAAAACAAAAAAGG | 119 | 83 |
| 617508 | 507068 | 507087 | AATGTCTGTTCTTTGTGGTA | 91 | 84 |
| 617509 | 507897 | 507916 | ATACCTGCTTTTGTGACAAT | 75 | 85 |
| 617510 | 508556 | 508575 | GAGTGTAGCTCATTTCAGAA | 74 | 86 |
| 617511 | 509785 | 509804 | TTTCTCAATGTCAACTCTCA | 68 | 87 |
| 617512 | 510721 | 510740 | CAAGCCGAATCTTGACATAC | 73 | 88 |
| 617513 | 511227 | 511246 | GACCAGAAAAGCTACATAGC | 87 | 89 |
| 617514 | 512575 | 512594 | ATTTTGTATATTGTAGCTTT | 105 | 90 |
| 617515 | 513295 | 513314 | CCATCTTTCTGTTATCTTGT | 51 | 91 |
| 617516 | 513982 | 514001 | CTTTGTTTCTTTTTAAGAAA | 108 | 92 |
| 617517 | 514259 | 514278 | ACCTTGACAACACCCTAGCT | 89 | 93 |
| 617518 | 515123 | 515142 | AAAAAGGAACCATAAACTAA | 117 | 94 |

TABLE 3

Reduction of UBE3A-ATS RNA by 7,000 nM 5-10-5 MOE gapmers with PS internucleoside linkages in vitro (60,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617461 | 466981 | 467000 | CACACATCTTGTTCCCTCAA | 29 | 37 |
| 617519 | 449812 | 449831 | GGTGTGTCAGCTGTGCTGGT | 62 | 95 |
| 617520 | 450498 | 450517 | ATCATACCTTCACTTTTTTT | 101 | 96 |
| 617521 | 450896 | 450915 | TTCATTGAGCTTCCTGGATA | 100 | 97 |
| 617522 | 451804 | 451823 | TTACTTCTTTTTCATTAAGT | 86 | 98 |
| 617523 | 454628 | 454647 | AGTAAACACTCCAACAAAAA | 126 | 99 |
| 617524 | 455049 | 455068 | GGTCTAAGCAAAATGTGAAG | 137 | 100 |
| 617525 | 455323 | 455342 | CAGTTAGGCCTGCTCCGAAT | 102 | 101 |
| 617526 | 455499 | 455518 | ACTCTGAAAATAGCCAATTT | 134 | 102 |
| 617527 | 456944 | 456963 | AGTATCTATCTACAATTAAA | 112 | 103 |
| 617528 | 457237 | 457256 | AATGGCTTAGCTACTCACCC | 72 | 104 |
| 617529 | 458254 | 458273 | CCTCTCTGCAAAACAAGAGA | 74 | 105 |
| 617530 | 459153 | 459172 | ATTACTCATTCTGGGAATGC | 35 | 106 |
| 617531 | 460667 | 460686 | GTTTTCAGCATGATTCTAAC | 46 | 107 |
| 617532 | 461259 | 461278 | CATATATAAAAATTAGAATG | 122 | 108 |
| 617533 | 463621 | 463640 | AATGCCACAAAGCTGGCTGT | 97 | 109 |
| 617534 | 464514 | 464533 | GTGCACAGATAATGACTAGA | 69 | 110 |
| 617535 | 465402 | 465421 | CAGTGAGAAGTCAATTGTCA | 67 | 111 |
| 617536 | 465580 | 465599 | TCCTTTAGCATTTCTATTAG | 28 | 112 |
| 617537 | 466423 | 466442 | AACATGTGCTTGCAAGCCAT | 46 | 113 |
| 617538 | 466701 | 466720 | AAATAACTGGATCTCATAAC | 55 | 114 |
| 617539 | 467064 | 467083 | CTTAGGAGAGAAACACTTTC | 56 | 115 |
| 617540 | 467546 | 467565 | TACATCCTGTAGGCTTTCTT | 55 | 116 |
| 617541 | 467961 | 467980 | ACTGAGAAATCTCTTGAATG | 92 | 117 |
| 617542 | 468624 | 468643 | TTGCTCTTTTACTTTGTTC | 37 | 118 |
| 617543 | 469731 | 469750 | ACTCTAAGTTTTATTAATAG | 105 | 119 |
| 617544 | 470091 | 470110 | TTTGGAAGAGCTTAATAAAG | 110 | 120 |
| 617545 | 472023 | 472042 | TAGCTAGAATTTCAACTACT | 63 | 121 |
| 617546 | 474443 | 474462 | ATGTAGTATTTATTTCATTT | 120 | 122 |
| 617547 | 474957 | 474976 | GCCTAATATGTGTCATCCTG | 28 | 123 |
| 617548 | 475998 | 476017 | CCTCAATTCTATGGTTAGTT | 52 | 124 |
| 617549 | 479376 | 479395 | TCTTGGAGATGACTTCTCTG | 75 | 125 |
| 617550 | 479580 | 479599 | TCTTCAAGACTAAGGTAGGG | 54 | 126 |
| 617551 | 479654 | 479673 | AGTAAGGTCTGTTATTCTCC | 35 | 127 |
| 617552 | 480998 | 481017 | GCTATACAACAAAAGAATT | 123 | 128 |
| 617553 | 481073 | 481092 | ACTGTGGAAAACTTTGGCA | 54 | 129 |
| 617554 | 481582 | 481601 | ATAATCTACATGTATAGACC | 85 | 130 |

TABLE 3-continued

Reduction of UBE3A-ATS RNA by 7,000 nM 5-10-5 MOE gapmers with PS internucleoside linkages in vitro (60,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617555 | 481984 | 482003 | AAAAGCCAATTCTGAAATTC | 44 | 131 |
| 617556 | 483689 | 483708 | ATTCTCCTACCTCTCAGCCT | 107 | 132 |
| 617558 | 484654 | 484673 | AACTGTAGCAAATATACTAC | 110 | 133 |
| 617559 | 485236 | 485255 | AAATTACTGCTCTGTAAAAG | 93 | 134 |
| 617560 | 485886 | 485905 | GATTCAATGAAATAAAAAAT | 144 | 135 |
| 617561 | 486894 | 486913 | AATGACATAGCTTATGCTGT | 104 | 136 |
| 617562 | 488162 | 488181 | CTAGAAATTAAGACATCCCT | 63 | 137 |
| 617563 | 488563 | 488582 | GCCACACCATCAAAAGAACC | 77 | 138 |
| 617564 | 489518 | 489537 | TGGACCACCTAAGACCTCAA | 62 | 139 |
| 617565 | 489731 | 489750 | ACCGGTTCCCAATTTTCTCC | 82 | 140 |
| 617566 | 493655 | 493674 | GAGAGAATACGGCCCTGATG | 77 | 141 |
| 617567 | 494790 | 494809 | AACTTCAATCAGAGTAATAT | 117 | 142 |
| 617568 | 496045 | 496064 | GGCAAAGGAATGAAGAGACC | 69 | 143 |
| 617569 | 497328 | 497347 | GCCAATAACAAGAAAAGAGA | 96 | 144 |
| 617570 | 497416 | 497435 | ATCAAATTGGATGACCTAAA | 122 | 145 |
| 617571 | 498140 | 498159 | CAATGGATTTCAATTACACT | 54 | 146 |
| 617572 | 498893 | 498912 | ATTCTCCAACAAAAAGACAT | 93 | 147 |
| 617573 | 499276 | 499295 | GTAGCTACAAGAAGTAATTG | 117 | 148 |
| 617574 | 499958 | 499977 | AAAGAATGCCTATAAGAATT | 118 | 149 |
| 617575 | 500578 | 500597 | CTACTGGCATCAGTCAAAAC | 60 | 150 |
| 617576 | 501578 | 501597 | AAAAGGCAAGGCTAAGGAGT | 69 | 151 |
| 617577 | 502305 | 502324 | CCCACACAGGTCATTCATTC | 52 | 152 |
| 617578 | 503150 | 503169 | TGTATACACCATCCCAGAAA | 93 | 153 |
| 617579 | 503795 | 503814 | AAAATGCCAGTTTGTTGTAC | 60 | 154 |
| 617580 | 503973<br>508739 | 503992<br>508758 | ACACTGTACAGGAGGGTGTC | 69 | 155 |
| 617581 | 503981<br>508747 | 504000<br>508766 | TTCACTGCACACTGTACAGG | 70 | 156 |
| 617582 | 503993<br>508759 | 504012<br>508778 | AAATGATGTTGATTCACTGC | 36 | 157 |
| 617583 | 504551 | 504570 | AGAGTTTTCATGAATTCAGG | 46 | 158 |
| 617584 | 505011 | 505030 | GGTTTCTTTCATTAAATAGC | 63 | 159 |
| 617585 | 506396 | 506415 | GAGGCAACTCCTGAGAGCTG | 64 | 160 |
| 617586 | 507650 | 507669 | TTAAATGTCAGGAGGTCCCC | 57 | 161 |
| 617587 | 508201 | 508220 | TGTCATCTGATCTCACACAT | 86 | 162 |
| 617588 | 508772 | 508791 | CAAAGTCCAAGGGAAATGAT | 71 | 163 |
| 617589 | 510010 | 510029 | CACAGTAGAGGCAAATGAGA | 79 | 164 |
| 617590 | 511058 | 511077 | GACATTTAGGATGATGATAT | 72 | 165 |

TABLE 3-continued

Reduction of UBE3A-ATS RNA by 7,000 nM 5-10-5 MOE gapmers with PS internucleoside linkages in vitro (60,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617591 | 512158 | 512177 | GTTGTATTAATGGACTTTTG | 65 | 166 |
| 617592 | 513203 | 513222 | ATTTTTTGCATAAGTGCATT | 86 | 167 |
| 617593 | 513508 | 513527 | ACATTTCTTAGTTGAACAGT | 29 | 168 |
| 617594 | 514104 | 514123 | AGATTCTTCCCCAATCCCAT | 81 | 169 |
| 617595 | 514524 | 514543 | CTCACTTGTCTCCTTTTACC | 73 | 170 |
| 617596 | 515282 | 515301 | ACAATAAGGAAGAGCAAAAC | 104 | 171 |

TABLE 4

Reduction of UBE3A-ATS RNA by 5,000 nM 5-10-5 MOE gapmers with mixed PO/PS internucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617456 | 463905 | 463924 | CAACTGTTACCAAGACTTCA | 22 | 32 |
| 617457 | 465003 | 465022 | ATCTGCGAATAGAGGCCCTC | 22 | 33 |
| 617460 | 466539 | 466558 | TAGGTTGCATAAAGCCAGGC | 35 | 36 |
| 617461 | 466981 | 467000 | CACACATCTTGTTCCCTCAA | 36 | 37 |
| 617557 | 483977 | 483996 | ATCATGTGCATACCCAGGGT | 9 | 172 |
| 705110 | 229870[#] | 229889[#] | TCACTCATTTTGTTCAGCTT | 33 | 173 |
| 705112 | 232607[#] | 232626[#] | GTTTTCACTCATTTGTTCA | 61 | 174 |
| 750513 | 220331 456700 | 220350 456719 | ACAATTATTCTCATCATCGA | 113 | 175 |
| 750514 | 220346 456715 | 220365 456734 | CCTCAGCATCCTCAGACAAT | 80 | 176 |
| 750515 | 220359 456728 | 220378 456747 | TCTGGAATGAGTCCCTCAGC | 73 | 177 |
| 750516 | 220371 456740 | 220390 456759 | CTCAGATTGACATCTGGAAT | 123 | 178 |
| 750517 | 229869[#] | 229888[#] | CACTCATTTTGTTCAGCTTT | 15 | 179 |
| 750518 | 232608[#] | 232627[#] | AGTTTTCACTCATTTTGTTC | 67 | 180 |
| 750519 | 349103[#] | 349122[#] | GTCATCACCTCTCTTCAGGA | 22 | 181 |
| 750520 | 349105[#] | 349124[#] | AAGTCATCACCTCTCTTCAG | 35 | 182 |
| 750521 | 349107[#] | 349126[#] | TTAAGTCATCACCTCTCTTC | 55 | 183 |
| 750522 | 349109[#] | 349128[#] | TTTTAAGTCATCACCTCTCT | 37 | 184 |
| 750523 | 349111[#] | 349130[#] | ATTTTAAGTCATCACCTCT | 45 | 185 |
| 750524 | 349113[#] | 349132[#] | TGATTTTAAGTCATCACCT | 25 | 186 |
| 750525 | 349115[#] | 349134[#] | CATGATTTTAAGTCATCAC | 55 | 187 |
| 750526 | 349117[#] | 349136[#] | AGCATGATTTTAAGTCATC | 65 | 188 |
| 750527 | 349119[#] | 349138[#] | TGAGCATGATTTTAAGTCA | 46 | 189 |

TABLE 4-continued

Reduction of UBE3A-ATS RNA by 5,000 nM 5-10-5 MOE gapmers with mixed PO/PS intemucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750528 | 349121# | 349140# | ATTGAGCATGATTTTTAAGT | 56 | 190 |
| 750529 | 349123# | 349142# | CTATTGAGCATGATTTTTAA | 60 | 191 |
| 750530 | 349125# | 349144# | TCCTATTGAGCATGATTTT | 56 | 192 |
| 750531 | 349127# | 349146# | AATCCTATTGAGCATGATTT | 41 | 193 |
| 750532 | 349129# | 349148# | GTAATCCTATTGAGCATGAT | 26 | 194 |
| 750533 | 349131# | 349150# | GCGTAATCCTATTGAGCATG | 34 | 195 |
| 750534 | 349133# | 349152# | CAGCGTAATCCTATTGAGCA | 63 | 196 |
| 750535 | 349135# | 349154# | CTCAGCGTAATCCTATTGAG | 50 | 197 |
| 750536 | 349137# | 349156# | GCCTCAGCGTAATCCTATTG | 71 | 198 |
| 750537 | 349139# | 349158# | GGGCCTCAGCGTAATCCTAT | 48 | 199 |
| 750538 | 349141# | 349160# | CTGGGCCTCAGCGTAATCCT | 28 | 200 |
| 750539 | 349143# | 349162# | GGCTGGGCCTCAGCGTAATC | 75 | 201 |
| 750540 | 355254# | 355273# | TAGGCTGGGCCTCAGCGTAA | 32 | 202 |
| 750541 | 349147# | 349166# | CCTAGGCTGGGCCTCAGCGT | 98 | 203 |
| 750542 | 349149# | 349168# | CACCTAGGCTGGGCCTCAGC | 21 | 204 |
| 750543 | 349151# | 349170# | CTCACCTAGGCTGGGCCTCA | 55 | 205 |
| 750544 | 349153# | 349172# | TTCTCACCTAGGCTGGGCCT | 24 | 206 |
| 750545 | 349155# | 349174# | AATTCTCACCTAGGCTGGGC | 53 | 207 |
| 750546 | 349157# | 349176# | AAAATTCTCACCTAGGCTGG | 39 | 208 |
| 750547 | 349159# | 349178# | CCAAAATTCTCACCTAGGCT | 46 | 209 |
| 750548 | 349162# | 349181# | CTTCCAAAATTCTCACCTAG | 95 | 210 |
| 750549 | 349165# | 349184# | CCTCTTCCAAAATTCTCACC | 17 | 211 |
| 750550 | 349168# | 349187# | CATCCTCTTCCAAAATTCTC | 75 | 212 |
| 750551 | 349171# | 349190# | CAGCATCCTCTTCCAAAATT | 50 | 213 |
| 750552 | 349174# | 349193# | TCCCAGCATCCTCTTCCAAA | 70 | 214 |
| 750553 | 349177# | 349196# | GGATCCCAGCATCCTCTTCC | 53 | 215 |
| 750554 | 349346 409462 | 349365 409481 | GCCACCCACATGCCCTGCCC | 25 | 216 |
| 750555 | 349390# | 349409# | AGAGCTCACTGAAAGACACA | 63 | 217 |
| 750556 | 349392# | 349411# | GAAGAGCTCACTGAAAGACA | 85 | 218 |
| 750557 | 349442# | 349461# | GCAGGATCCACTCACCTATG | 27 | 219 |
| 750558 | 349957# | 349976# | CAGAGCTCAGCCTTGACCCA | 45 | 220 |
| 750559 | 350910# | 350929# | AGCTCAGTGCAGGAGACCAG | 56 | 221 |
| 750560 | 350914# | 350933# | CCACAGCTCAGTGCAGGAGA | 72 | 222 |
| 750561 | 350924# | 350943# | GATGTGCTCACCACAGCTCA | 115 | 223 |
| 750562 | 351544# | 351563# | GGAACCCTTTCCTGCCTGGA | 56 | 224 |
| 750563 | 353287# | 353306# | CAATATAAGGTTCTCATCAT | 42 | 225 |

TABLE 4-continued

Reduction of UBE3A-ATS RNA by 5,000 nM 5-10-5 MOE gapmers with mixed PO/PS intemucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750564 | 353293# | 353312# | TCAGGACAATATAAGGTTCT | 115 | 226 |
| 750565 | 353305# | 353324# | CATCACCTCTCTTCAGGACA | 37 | 227 |
| 750566 | 353356 407396 | 353375 407415 | TCTCACCTAGGCTAGGCCTC | 44 | 228 |
| 750567 | 353579# | 353598# | AGCTCACTGAAAGACACAAG | 49 | 229 |
| 750568 | 358746# | 358765# | AGGAAGGGCCTGAGCTTCAG | 34 | 230 |
| 750569 | 363914 384545 | 363933 384564 | CTCACCACACCTCAGTGCAG | 93 | 231 |
| 750570 | 364549# | 364568# | CTTTCCTGCCTGGACCACCA | 68 | 232 |
| 750571 | 366064 373449 | 366083 373468 | TTGGGCACCCTCCAGATGCC | 63 | 233 |
| 750572 | 366247 370104 386794 | 366266 370123 386813 | CACTCACCTATGCTGGTCAA | 72 | 234 |
| 750573 | 366487 407918 | 366506 407937 | TCAGCTGGGTGCTGCCCTGC | 117 | 235 |
| 750574 | 366668 374053 | 366687 374072 | CCATTCAGGGCCATGGGTTT | 67 | 236 |
| 750575 | 391964 393859 403520 | 391983 393878 403539 | TCCCTGCACATGCATCCAGC | 97 | 237 |
| 750576 | 395822 420812 | 395841 420831 | ACTCCAGGGACCAAGAGCTC | 49 | 238 |
| 750577 | 397780 415262 | 397799 415281 | GAGACCCACTGAGATGGCCC | 26 | 239 |
| 750578 | 402885 410060 | 402904 410079 | ACCCCATGACCCTGGAGGTG | 63 | 240 |
| 750579 | 403932 424209 | 403951 424228 | ATGACCCAGCAGGATGCAC | 57 | 241 |
| 750580 | 422678 426410 | 422697 426429 | TCACCCACCACTGTCCAGAG | 95 | 242 |
| 750581 | 422778 426510 | 422797 426529 | GTACCACTGAGATGGCCCAT | 68 | 243 |
| 750582 | 423273 430180 | 423292 430199 | AATGCAGACCTGGCAGTCGC | 50 | 244 |

TABLE 4b

SEQ ID NO: 1 start sites for modified oligonucleotides complementary to repeat regions

| Compound Number | # of comp. sites within SEQ ID NO: 1 | SEQ ID NO: 1 start sites | SEQ ID NO: |
|---|---|---|---|
| 705110 | 20 | 229870, 232603, 235253, 237932, 240726, 243420, 246181, 248825, 251500, 258532, 259677, 261158, 261978, 263775, 264917, 266052, 267194, 268313, 270176, 272427 | 173 |
| 705112 | 16 | 232607, 237936, 243424, 252518, 254323, 258536, 259681, 261162, 261982, 263779, 264921, 266056, 267198, 268317, 270180, 272431 | 174 |
| 750517 | 21 | 229869, 232602, 235252, 237931, 240725, 243419, 246180, 248824, 251499, 257447, 258531, 259676, 261157, 261977, 263774, 264916, 266051, 267193, 268312, 270175, 272426 | 179 |

TABLE 4b-continued

SEQ ID NO: 1 start sites for modified oligonucleotides complementary to repeat regions

| Compound Number | # of comp. sites within SEQ ID NO: 1 | SEQ ID NO: 1 start sites | SEQ ID NO: |
|---|---|---|---|
| 750518 | 16 | 232608, 237937, 243425, 252519, 254324, 258537, 259682, 261163, 261983, 263780, 264922, 266057, 267199, 268318, 270181, 272432 | 180 |
| 750519 | 20 | 349103, 353307, 357118, 364011, 367794, 369796, 371701, 377828, 379703, 381607, 382737, 384642, 388298, 393921, 396997, 401626, 414465, 420126, 421994, 423858, 427578 | 181 |
| 750520 | 30 | 349105, 353309, 355214, 357120, 358879, 364013, 365917, 367796, 369798, 371703, 373302, 375957, 377830, 379705, 381609, 382739, 384644, 386464, 388300, 393923, 396999, 400729, 401628, 410769, 414467, 420128, 421996, 423860, 425727, 427580 | 182 |
| 750521 | 33 | 349107, 351019, 353311, 355216, 357122, 358881, 364015, 365919, 367798, 369800, 371705, 373304, 375959, 377832, 379707, 381611, 382741, 384646, 386466, 388302, 390180, 393925, 397001, 400731, 401630, 410771, 412631, 414469, 420130, 421998, 423862, 425729, 427582 | 183 |
| 750522 | 33 | 349109, 351021, 353313, 355218, 357124, 358883, 364017, 365921, 367800, 369802, 371707, 373306, 375961, 377834, 379709, 381613, 382743, 384648, 386468, 388304, 390182, 393927, 397003, 400733, 401632, 410773, 412633, 414471, 420132, 422000, 423864, 425731, 427584 | 184 |
| 750523 | 31 | 349111, 351023, 353315, 355220, 357126, 358885, 364019, 365923, 367802, 369804, 371709, 373308, 375963, 377836, 379711, 381615, 382745, 384650, 386470, 388306, 393929, 397005, 401634, 410775, 412635, 414473, 420134, 422002, 423866, 425733, 427586 | 185 |
| 750524 | 32 | 349113, 351025, 353317, 355222, 357128, 358887, 364021, 365925, 367804, 369806, 371711, 373310, 375965, 377838, 379713, 381617, 382747, 384652, 386472, 388308, 393931, 397007, 401636, 405499, 410777, 412637, 414475, 420136, 422004, 423868, 425735, 427588 | 186 |
| 750525 | 30 | 349115, 351027, 353319, 355224, 357130, 358889, 364023, 365927, 367806, 369808, 371713, 373312, 375967, 377840, 384654, 386474, 388310, 393933, 397009, 401638, 405501, 410779, 412639, 414477, 420138, 422006, 423870, 425737, 427590, 429251 | 187 |
| 750526 | 31 | 349117, 351029, 353321, 355226, 357132, 358891, 362700, 364025, 365929, 367808, 369810, 371715, 373314, 375969, 377842, 384656, 386476, 388312, 397011, 401640, 405503, 410781, 412641, 414479, 418232, 420140, 422008, 423872, 425739, 427592, 429253 | 188 |
| 750527 | 31 | 349119, 351031, 355228, 357134, 358893, 362702, 364027, 365931, 367810, 369812, 371717, 373316, 375971, 377844, 384658, 386478, 388314, 392044, 397013, 401642, 405505, 410783, 412643, 414481, 418234, 420142, 422010, 423874, 425741, 427594, 429255 | 189 |
| 750528 | 32 | 349121, 351033, 355230, 357136, 358895, 360780, 362704, 364029, 365933, 367812, 369814, 371719, 373318, 375973, 377846, 384660, 386480, 388316, 392046, 397015, 401644, 405507, 410785, 412645, 414483, 418236, 420144, 422012, 423876, 425743, 427596, 429257 | 190 |
| 750529 | 32 | 349123, 351035, 355232, 357138, 358897, 362706, 364031, 365935, 367814, 369816, 371721, 373320, 375975, 377848, 384662, 386482, 388318, 392048, 397017, 401646, 403603, 405509, 410787, 412647, 414485, 418238, 420146, 422014, 423878, 425745, 427598, 429259 | 191 |
| 750530 | 33 | 349125, 349125, 351037, 355234, 357140, 358899, 362708, 364033, 365937, 367816, 369818, 371723, 373322, 375977, 377850, 384664, 386484, 388320, 392050, 397019, 401648, 403605, 405511, 410789, 412649, 414487, 418240, 420148, 422016, 423880, 425747, 427600, 429261 | 192 |
| 750531 | 32 | 349127, 351039, 355236, 357142, 358901, 362710, 364035, 365939, 367818, 369820, 371725, 373324, 375979, 377852, 384666, 386486, 388322, 392052, 397021, 401650, 403607, 405513, 410791, 412651, 414489, 418242, 420150, 422018, 423882, 425749, 427602, 429263 | 193 |
| 750532 | 31 | 349129, 355238, 357144, 358903, 362712, 364037, 365941, 367820, 369822, 371727, 373326, 375981, 377854, 386488, 388324, 392054, 397023, 398903, 401652, 403609, 405515, 410793, 412653, 414491, 418244, 420152, 422020, 423884, 425751, 427604, 429265 | 194 |
| 750533 | 28 | 349131, 355240, 357146, 358905, 362714, 364039, 365943, 367822, 369824, 371729, 373328, 375983, 377856, 386490, 388326, 392056, 397025, 401654, 403611, 410795, 414493, 418246, 420154, 422022, 423886, 425753, 427606, 429267 | 195 |
| 750534 | 29 | 349133, 355242, 357148, 358907, 362716, 364041, 365945, 367824, 369826, 371731, 373330, 375985, 377858, 386492, 388328, 392058, 397027, 401656, 403613, 409248, 410797, 414495, 418248, 420156, 422024, 423888, 425755, 427608, 429269 | 196 |
| 750535 | 29 | 349135, 355244, 357150, 358909, 362718, 364043, 365947, 367826, 369828, 371733, 373332, 375987, 377860, 386494, 388330, 392060, 397029, 401658, 403615, 409250, 410799, 414497, 418250, 420158, 422026, 423890, 425757, 427610, 429271 | 197 |
| 750536 | 30 | 349137, 355246, 357152, 358911, 362720, 364045, 365949, 367828, 369830, 371735, 373334, 375989, 377862, 386496, 392062, 393955, 397031, 401660, 403617, 407381, 409252, 410801, 414499, 418252, 420160, 422028, 423892, 425759, 427612, 429273 | 198 |

TABLE 4b-continued

SEQ ID NO: 1 start sites for modified oligonucleotides complementary to repeat regions

| Compound Number | # of comp. sites within SEQ ID NO: 1 | SEQ ID NO: 1 start sites | SEQ ID NO: |
|---|---|---|---|
| 750537 | 30 | 349139, 355248, 357154, 358913, 360801, 362722, 364047, 365951, 367830, 369832, 371737, 373336, 375991, 377864, 386498, 392064, 393957, 397033, 401662, 403619, 409254, 410803, 414501, 418254, 420162, 422030, 423894, 425761, 427614, 429275 | 199 |
| 750538 | 25 | 349141, 355250, 357156, 358915, 360803, 362724, 365953, 367832, 369834, 371739, 373338, 375993, 377866, 392066, 393959, 397035, 401664, 403621, 410805, 418256, 420164, 422032, 425763, 427616, 429277 | 200 |
| 750539 | 22 | 349143, 355252, 357158, 358917, 362726, 365955, 369836, 373340, 375995, 377868, 392068, 393961, 397037, 401666, 403623, 410807, 418258, 420166, 422034, 425765, 429279, 448197 | 201 |
| 750540 | 20 | 349145, 355254, 358919, 362728, 365957, 369838, 373342, 375997, 377870, 392070, 393963, 401668, 403625, 410809, 418260, 420168, 422036, 425767, 429281, 448199 | 202 |
| 750541 | 18 | 349147, 355256, 358921, 362730, 365959, 369840, 373344, 375999, 377872, 393965, 401670, 410811, 418262, 420170, 422038, 425769, 429283, 448201 | 203 |
| 750542 | 17 | 349149, 351061, 355258, 358923, 362732, 365961, 369842, 373346, 376001, 377874, 393967, 410813, 418264, 420172, 422040, 425771, 429285 | 204 |
| 750543 | 16 | 349151, 351063, 355260, 358925, 362734, 365963, 369844, 373348, 376003, 377876, 393969, 418266, 420174, 422042, 425773, 429287 | 205 |
| 750544 | 15 | 349153, 351065, 355262, 358927, 362736, 365965, 369846, 373350, 376005, 377878, 418268, 420176, 422044, 425775, 429289 | 206 |
| 750545 | 14 | 349155, 351067, 355264, 358929, 362738, 365967, 369848, 373352, 376007, 377880, 418270, 420178, 425777, 429291 | 207 |
| 750546 | 13 | 349157, 351069, 355266, 358931, 362740, 365969, 369850, 373354, 376009, 418272, 420180, 425779, 429293 | 208 |
| 750547 | 14 | 349159, 351071, 355268, 358933, 362742, 365971, 369852, 373356, 376011, 407403, 418274, 420182, 425781, 429295 | 209 |
| 750548 | 17 | 349162, 351074, 355271, 358936, 362745, 365974, 369855, 373359, 376014, 407406, 412686, 416425, 418277, 420185, 425784, 427637, 429298 | 210 |
| 750549 | 12 | 349165, 351077, 357180, 358939, 362748, 365977, 373362, 376017, 412689, 418280, 425787, 429301 | 211 |
| 750550 | 9 | 349168, 351080, 357183, 358942, 365980, 373365, 376020, 412692, 425790 | 212 |
| 750551 | 11 | 349171, 351083, 357186, 358945, 365983, 373368, 376023, 381675, 405557, 412695, 425793 | 213 |
| 750552 | 14 | 349174, 351086, 358948, 360836, 365986, 371772, 373371, 376026, 377898, 381678, 393992, 412698, 422065, 425796 | 214 |
| 750553 | 10 | 349177, 351089, 358951, 371775, 377901, 381681, 384716, 412701, 422068, 425799 | 215 |
| 750555 | 23 | 349390, 351292, 353581, 355499, 361054, 364302, 368083, 370059, 371989, 373589, 378120, 379994, 383026, 388586, 390466, 401917, 403871, 409508, 411053, 412917, 414751, 420414, 429518 | 217 |
| 750556 | 24 | 349392, 351294, 353583, 355501, 361056, 364304, 368085, 370061, 371991, 373591, 376253, 378122, 383028, 388588, 390468, 401919, 403873, 409510, 411055, 412919, 420416, 422284, 426016, 429520 | 218 |
| 750557 | 13 | 349442, 353633, 366255, 373640, 378173, 390519, 397322, 401968, 407684, 409560, 414803, 420466, 429569 | 219 |
| 750558 | 7 | 349957, 359696, 374917, 376821, 383615, 389153, 411626 | 220 |
| 750559 | 12 | 350910, 358772, 365811, 373197, 375845, 403478, 407243, 410663, 423753, 425620, 427479, 429146 | 221 |
| 750560 | 12 | 350914, 358776, 365815, 373201, 375849, 390074, 403482, 410667, 423757, 425624, 427483, 429150 | 222 |
| 750561 | 10 | 350924, 358786, 360674, 365825, 375859, 390084, 401536, 409127, 425634, 427493 | 223 |
| 750562 | 10 | 351544, 353840, 361305, 363233, 397528, 399421, 413175, 415009, 418768, 424402 | 224 |
| 750563 | 20 | 353287, 357098, 358857, 363991, 365896, 367774, 369776, 379683, 381587, 382717, 384622, 388278, 398857, 401606, 403563, 414445, 416346, 425705, 427558, 429219 | 225 |
| 750564 | 20 | 353293, 357104, 360748, 363997, 367780, 369782, 379689, 381593, 382723, 384628, 388284, 393907, 396983, 398863, 401612, 405475, 414451, 416352, 427564, 429225 | 226 |
| 750565 | 17 | 353305, 357116, 364009, 367792, 369794, 379701, 381605, 382735, 384640, 388296, 393919, 396995, 401624, 414463, 420124, 423856, 427576 | 227 |
| 750567 | 12 | 353579, 361052, 370057, 378118, 388584, 390464, 401915, 409506, 412915, 414749, 420412, 429516 | 229 |
| 750568 | 11 | 358746, 362555, 365785, 369656, 375819, 381477, 382607, 386333, 390044, 416238, 421864 | 230 |
| 750570 | 11 | 364549, 385176, 392568, 397522, 399415, 404124, 407883, 413169, 415003, 418762, 428112 | 232 |

TABLE 5

Reduction of UBE3A-ATS RNA by 7,000 nM 5-10-5 MOE gapmers with mixed PO/PS intemucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617456 | 463905 | 463924 | CAACTGTTACCAAGACTTCA | 40 | 32 |
| 617457 | 465003 | 465022 | ATCTGCGAATAGAGGCCCTC | 30 | 33 |
| 617460 | 466539 | 466558 | TAGGTTGCATAAAGCCAGGC | 40 | 36 |
| 617461 | 466981 | 467000 | CACACATCTTGTTCCCTCAA | 41 | 37 |
| 617557 | 483977 | 483996 | ATCATGTGCATACCCAGGGT | 26 | 172 |
| 750326 | 504100 | 504119 | CTTCAACTAACAGTATCTTA | 20 | 245 |
| 750327 | 504103 | 504122 | AGTCTTCAACTAACAGTATC | 51 | 246 |
| 750328 | 504126 | 504145 | CTATTTCATTAAGTCACCCC | 53 | 247 |
| 750329 | 504179 | 504198 | GGACAGCTGTGTGGAGGGAT | 26 | 248 |
| 750330 | 504218 | 504237 | ACCACCAGGGAGACCAGCCT | 68 | 249 |
| 750331 | 504228 | 504247 | CAGCCTTTCTACCACCAGGG | 55 | 250 |
| 750332 | 504229 | 504248 | TCAGCCTTTCTACCACCAGG | 32 | 251 |
| 750333 | 504334 | 504353 | ACAGAGTGTTTACTGTGAGC | 29 | 252 |
| 750334 | 504503 | 504522 | TCCATGGAATGGCTGTCATG | 39 | 253 |
| 750335 | 504731 | 504750 | TTCCTTCAGAGTTATTTCTT | 73 | 254 |
| 750336 | 504740 | 504759 | TTATTCTCCTTCCTTCAGAG | 70 | 255 |
| 750337 | 504741 | 504760 | GTTATTCTCCTTCCTTCAGA | 41 | 256 |
| 750338 | 504817 | 504836 | GAAGTAGTCCTGCCCTTTCC | 60 | 257 |
| 750339 | 504923 | 504942 | ATATCCTTTCCTCTCCTACT | 78 | 258 |
| 750340 | 504958 | 504977 | GACTGATGGTTACCCATACA | 40 | 259 |
| 750341 | 504987 | 505006 | CATTTAACAACTATTATCTT | 27 | 260 |
| 750342 | 505003 | 505022 | TCATTAAATAGCTAACCATT | 91 | 261 |
| 750343 | 505043 | 505062 | CCACTTTGCAACTCAAGATT | 31 | 262 |
| 750344 | 505046 | 505065 | CAGCCACTTTGCAACTCAAG | 20 | 263 |
| 750345 | 505051 | 505070 | GACTCCAGCCACTTTGCAAC | 62 | 264 |
| 750346 | 505073 | 505092 | CCAGAAATTTAGTCTGTTGT | 59 | 265 |
| 750347 | 505096 | 505115 | CATAAGCTGCTGGATTTGTT | 51 | 266 |
| 750348 | 505241 | 505260 | GAAGAGAACGAGGATATAAA | 35 | 267 |
| 750349 | 505306 | 505325 | GTGATATATTAGAACTGTAT | 28 | 268 |
| 750350 | 505443 | 505462 | AGAGGATTTAGAGTTAAAAT | 22 | 269 |
| 750351 | 505569 | 505588 | ACTGAAAGGTCTGTATGTTT | 73 | 270 |
| 750352 | 505656 | 505675 | CAGGCCTAGCTTCCACCTAA | 108 | 271 |
| 750353 | 505837 | 505856 | TCTGTCAAAGACCTGTGAGG | 56 | 272 |
| 750354 | 505922 | 505941 | TCTGCTTGTGGTTCTTCCCT | 71 | 273 |
| 750355 | 505985 | 506004 | CAAATATGGAATAGCACTTG | 54 | 274 |
| 750356 | 506040 | 506059 | GTTGAGAACGGTATTGAGTA | 56 | 275 |
| 750357 | 506052 | 506071 | CTCTTGTTTTCAGTTGAGAA | 42 | 276 |

TABLE 5-continued

Reduction of UBE3A-ATS RNA by 7,000 nM 5-10-5 MOE gapmers with mixed PO/PS intemucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750358 | 506097 | 506116 | ATTTCTCCATGGACTCCAGA | 47 | 277 |
| 750359 | 506109 | 506128 | CATTGGCTTCATATTTCTCC | 11 | 278 |
| 750360 | 506306 | 506325 | TATTGCCTTCACTGCTGCCT | 9 | 279 |
| 750361 | 506518 | 506537 | ACTGACTTGCTCTGCCTACT | 71 | 280 |
| 750362 | 506617 | 506636 | GAGAAGTCTCTCATGGCACC | 40 | 281 |
| 750363 | 506731 | 506750 | GGAGTGCTCCACACTTCTGT | 27 | 282 |
| 750364 | 506776 | 506795 | CTCCAGGTTGTGGAGGTTGT | 75 | 283 |
| 750365 | 506783 | 506802 | GTATATACTCCAGGTTGTGG | 23 | 284 |
| 750366 | 506881 | 506900 | ACTTCTCATTCTCTCCACCA | 17 | 285 |
| 750367 | 507189 | 507208 | AAAGCATTTTCTACCAGAGC | 45 | 286 |
| 750368 | 507198 | 507217 | TAGACAAGGAAAGCATTTTC | 54 | 287 |
| 750369 | 507312 | 507331 | CACCTGCCCTGCTTTTGCTT | 41 | 288 |
| 750370 | 507324 | 507343 | TGGTCCTAGCTTCACCTGCC | 89 | 289 |
| 750371 | 507357 | 507376 | AGATCCAACCTGTGTGGAAA | 61 | 290 |
| 750372 | 507534 | 507553 | AGAAATTAGAGCCAGGTTCC | 36 | 291 |
| 750373 | 507635 | 507654 | TCCCCCCAGAAGGCTTGACT | 71 | 292 |
| 750374 | 507755 | 507774 | TCGCTGGCCATTTCATATAT | 44 | 293 |
| 750375 | 507978 | 507997 | AAAACATGTTAACTGTTATC | 40 | 294 |
| 750376 | 508159 | 508178 | TTAGCCATGTGCTTTGTGAC | 68 | 295 |
| 750377 | 508208 | 508227 | TCCCTTCTGTCATCTGATCT | 59 | 296 |
| 750378 | 508218 | 508237 | AAGGTAGTTCTCCCTTCTGT | 93 | 297 |
| 750379 | 508426 | 508445 | TTCCATTGCACTCCTTTCTA | 113 | 298 |
| 750380 | 508530 | 508549 | TAAAAGGAAAACCCACTTGT | 72 | 299 |
| 750381 | 508700 | 508719 | TACAGAAATTACCAGTAAAG | 38 | 300 |
| 750382 | 508710 | 508729 | TCCAGATTTCTACAGAAATT | 102 | 301 |
| 750383 | 503980 508746 | 503999 508765 | TCACTGCACACTGTACAGGA | 78 | 302 |
| 750384 | 508890 | 508909 | TGCCTAGTTCCCTCCTGAAA | 98 | 303 |
| 750385 | 508908 | 508927 | TTATGTTTACTTCATGACTG | 91 | 304 |
| 750386 | 508945 | 508964 | CTTCATTATTCTCTAGTGCC | 14 | 305 |
| 750387 | 509013 | 509032 | CTATTCCCCTTCAACATGTG | 44 | 306 |
| 750388 | 509060 | 509079 | CATACCCAACATGCTTGCAT | 44 | 307 |
| 750389 | 509079 | 509098 | AATGCATTACCCTACAATGC | 105 | 308 |
| 750390 | 509127 | 509146 | CTCATCACAACTGGGTGGTA | 76 | 309 |
| 750391 | 509134 | 509153 | ATCCCAGCTCATCACAACTG | 88 | 310 |
| 750392 | 509167 | 509186 | TCCAAGTGCTTCAAGCTGAG | 100 | 311 |
| 750393 | 509189 | 509208 | CACCCACAGCAGGCAGATAA | 58 | 312 |

TABLE 5-continued

Reduction of UBE3A-ATS RNA by 7,000 nM 5-10-5 MOE gapmers with mixed PO/PS internucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750394 | 509208 | 509227 | TACCTTGCTCCAAAATAATC | 37 | 313 |
| 750395 | 509230 | 509249 | CTGTTTCTTGAGGCAAATGA | 54 | 314 |
| 750396 | 509787 | 509806 | CTTTTCTCAATGTCAACTCT | 48 | 315 |
| 750397 | 510028 | 510047 | AGAGTTATACACGGAACCCA | 71 | 316 |

TABLE 6

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617456 | 463905 | 463924 | CAACTGTTACCAAGACTTCA | 26 | 32 |
| 617457 | 465003 | 465022 | ATCTGCGAATAGAGGCCCTC | 46 | 33 |
| 617460 | 466539 | 466558 | TAGGTTGCATAAAGCCAGGC | 8 | 36 |
| 617461 | 466981 | 467000 | CACACATCTTGTTCCCTCAA | 21 | 37 |
| 617557 | 483977 | 483996 | ATCATGTGCATACCCAGGGT | 23 | 172 |
| 749968 | 465163 | 465182 | TTCTAGGGCTCCAGTTTATG | 86 | 317 |
| 749969 | 465238 | 465257 | TGGTCATCTCGGGTATATAA | 20 | 318 |
| 749970 | 465341 | 465360 | CTTACTATCTTCAAGAATTC | 68 | 319 |
| 749971 | 465346 | 465365 | TTTTTCTTACTATCTTCAAG | 56 | 320 |
| 749972 | 465394 | 465413 | AGTCAATTGTCAGACTTATT | 37 | 321 |
| 749973 | 465587 | 465606 | AAGGAGTTCCTTTAGCATTT | 27 | 322 |
| 749974 | 465594 | 465613 | CAGACCGAAGGAGTTCCTTT | 50 | 323 |
| 749975 | 465612 | 465631 | TCCAGTGCCTTTCTATTTCA | 33 | 324 |
| 749976 | 465686 | 465705 | ACTTTGTTTTAAACTTACAC | 46 | 325 |
| 749977 | 465765 | 465784 | CATCAACACAAGTTTATAAT | 47 | 326 |
| 749978 | 465892 | 465911 | AACTCCCACAAGGTACTCTT | 32 | 327 |
| 749979 | 465906 | 465925 | ACTGTCAACTCCTGAACTCC | 54 | 328 |
| 749980 | 465956 | 465975 | CAATGAATCTATTCTTAGAT | 122 | 329 |
| 749981 | 465978 | 465997 | GTGAAACTGTTTATACCCTT | 25 | 330 |
| 749982 | 465996 | 466015 | GTTGGTGATGCAGGTAAAGT | 24 | 331 |
| 749983 | 466024 | 466043 | TTGTTACTGAGCTGTGCCAC | 48 | 332 |
| 749984 | 466119 | 466138 | AAGTGGATCTCTTGGGCAGG | 22 | 333 |
| 749985 | 466182 | 466201 | TTTACCCTCTCCCAACCACT | 51 | 334 |
| 749986 | 466217 | 466236 | GGCTGCTGTTTGAGTCCCCA | 40 | 335 |
| 749987 | 466220 | 466239 | ATGGGCTGCTGTTTGAGTCC | 58 | 336 |
| 749988 | 466221 | 466240 | TATGGGCTGCTGTTTGAGTC | 55 | 337 |

TABLE 6-continued

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 749989 | 466529 | 466548 | AAAGCCAGGCCAGGTGCTGA | 64 | 338 |
| 749990 | 466532 | 466551 | CATAAAGCCAGGCCAGGTGC | 30 | 339 |
| 749991 | 466534 | 466553 | TGCATAAAGCCAGGCCAGGT | 20 | 340 |
| 749992 | 466537 | 466556 | GGTTGCATAAAGCCAGGCCA | 36 | 341 |
| 749993 | 466539 | 466558 | TAGGTTGCATAAAGCCAGGC | 46 | 36 |
| 749994 | 466541 | 466560 | TCTAGGTTGCATAAAGCCAG | 52 | 342 |
| 749995 | 466544 | 466563 | TTCTCTAGGTTGCATAAAGC | 33 | 343 |
| 749996 | 466546 | 466565 | CCTTCTCTAGGTTGCATAAA | 28 | 344 |
| 749997 | 466549 | 466568 | TCACCTTCTCTAGGTTGCAT | 34 | 345 |
| 749998 | 466551 | 466570 | TATCACCTTCTCTAGGTTGC | 44 | 346 |
| 749999 | 466701 | 466720 | AAATAACTGGATCTCATAAC | 55 | 114 |
| 750000 | 466979 | 466998 | CACATCTTGTTCCCTCAAGG | 26 | 347 |
| 750001 | 466981 | 467000 | CACACATCTTGTTCCCTCAA | 26 | 37 |
| 750002 | 466983 | 467002 | TTCACACATCTTGTTCCCTC | 26 | 348 |
| 750003 | 466986 | 467005 | TGCTTCACACATCTTGTTCC | 43 | 349 |
| 750004 | 466988 | 467007 | CCTGCTTCACACATCTTGTT | 49 | 350 |
| 750005 | 466991 | 467010 | GAACCTGCTTCACACATCTT | 36 | 351 |
| 750006 | 467049 | 467068 | CTTTCATCAGTTAGTCAGGT | 23 | 352 |
| 750007 | 467200 | 467219 | GGAGTTGGTTATTGGAAAAT | 48 | 353 |
| 750008 | 467289 | 467308 | TCTATTGGTGTTCCTTTTAG | 48 | 354 |
| 750009 | 467296 | 467315 | AGAGTAGTCTATTGGTGTTC | 22 | 355 |
| 750010 | 467363 | 467382 | CTTTTAAGATAATTTTTCTC | 90 | 356 |
| 750011 | 467417 | 467436 | TACGCTCCTTCATTTCATGC | 55 | 357 |
| 750012 | 467506 | 467525 | TTTTTAATCCTCTGATGAAT | 102 | 358 |
| 750013 | 467508 | 467527 | TTTTTTTAATCCTCTGATGA | 62 | 38 |
| 750014 | 467604 | 467623 | CTCTCTTCTCCTTTATGACT | 41 | 359 |
| 750015 | 467628 | 467647 | CTTAAATAAGTTTTCTACCC | 42 | 360 |
| 750016 | 467639 | 467658 | AGCCATTATTCTTAAATAA | 56 | 361 |
| 750017 | 467669 | 467688 | CATATCTTTTCCTAGATTTG | 110 | 362 |
| 750018 | 467813 | 467832 | AGAATCCTGTCTCCCTCTTA | 34 | 363 |
| 750019 | 467916 | 467935 | TGAGTCTCTTTTCTTTCGGT | 41 | 364 |
| 750020 | 467919 | 467938 | TGATGAGTCTCTTTTCTTTC | 35 | 365 |
| 750021 | 467921 | 467940 | TGTGATGAGTCTCTTTTCTT | 30 | 366 |
| 750022 | 467962 | 467981 | TACTGAGAAATCTCTTGAAT | 77 | 367 |
| 750023 | 468277 | 468296 | TAAAATTATTTATACACCAT | 73 | 368 |
| 750024 | 468359 | 468378 | TTTATACTGTAGTATGCATT | 53 | 369 |

TABLE 6-continued

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750025 | 468410 | 468429 | TTACTTCCCTACCCTTGCAT | 75 | 370 |
| 750026 | 468413 | 468432 | CTTTTACTTCCCTACCCTTG | 67 | 371 |
| 750027 | 468464 | 468483 | ATTTATTTTAAGCTGATAAC | 52 | 372 |
| 750028 | 468733 | 468752 | AAATCCATTTGTCCAGTCTG | 14 | 373 |
| 750029 | 468888 | 468907 | TATCTGCATGCAATATCTTT | 70 | 374 |
| 750030 | 468924 | 468943 | CTGTAAGTATAGATGCCTCT | 15 | 375 |
| 750031 | 468968 | 468987 | TTAGCCTTTTGATATAGTTT | 25 | 376 |
| 750032 | 468988 | 469007 | GCTTCACCATTTTGACCTTC | 19 | 377 |
| 750033 | 469140 | 469159 | TTTTGAAAGGGAGGCACTGA | 27 | 378 |
| 750034 | 469604 | 469623 | TGAGGTGTAATGTTGTTTAT | 32 | 379 |
| 750035 | 469717 | 469736 | TAATAGTCTCTATTGTTTTT | 50 | 380 |
| 750036 | 469884 | 469903 | CAAGTTAACTAATATGTTGG | 71 | 381 |
| 750037 | 469985 | 470004 | TATTGATTCAATTCCCTTAT | 23 | 382 |
| 750038 | 469988 | 470007 | GAATATTGATTCAATTCCCT | 37 | 383 |
| 750039 | 470062 | 470081 | AATTTTTTAAATGGTTGGC | 51 | 384 |

TABLE 7

Reduction of UBE3A-ATS RNA by 8,000 nM 5-10-5 MOE gapmers with mixed PO/PS internucleoside linkages vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617456 | 463905 | 463924 | CAACTGTTACCAAGACTTCA | 18 | 32 |
| 617457 | 465003 | 465022 | ATCTGCGAATAGAGGCCCTC | 36 | 33 |
| 617460 | 466539 | 466558 | TAGGTTGCATAAAGCCAGGC | 12 | 36 |
| 617461 | 466981 | 467000 | CACACATCTTGTTCCCTCAA | 16 | 37 |
| 617557 | 483977 | 483996 | ATCATGTGCATACCCAGGGT | 27 | 172 |
| 750182 | 488205 | 488224 | AACAGAGAATTGTATATCCA | 43 | 385 |
| 750183 | 488322 | 488341 | ACATGAGATCTTTAATAAGA | 73 | 386 |
| 750184 | 488343 | 488362 | CAAGAGAGAAGCCACTCATG | 64 | 387 |
| 750185 | 488685 | 488704 | AGCAGATTTGAGCTGGAAGA | 42 | 388 |
| 750186 | 488928 | 488947 | AACTGGCAGAAAATATCTCT | 36 | 389 |
| 750187 | 488941 | 488960 | AAAGAAGAACATAAACTGGC | 70 | 390 |
| 750188 | 489021 | 489040 | GTTGGCTCTATTTTCAAATG | 33 | 391 |
| 750189 | 489449 | 489468 | CTGTTTAGGCTGGACACTGT | 90 | 392 |
| 750190 | 489478 | 489497 | ATTCAGGAAATTAAAGCATT | 60 | 393 |

TABLE 7-continued

Reduction of UBE3A-ATS RNA by 8,000 nM 5-10-5 MOE gapmers with mixed PO/PS internucleoside linkages vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750191 | 489698 | 489717 | AGCAGAACAGACCTTATTTG | 41 | 394 |
| 750192 | 489712 | 489731 | CCTTCAACCAGAGGAGCAGA | 44 | 395 |
| 750193 | 489756 | 489775 | GATCTTGGTTTGTAGAAGGT | 35 | 396 |
| 750194 | 489824 | 489843 | TTCAAAATGGTAGAAAATTG | 64 | 397 |
| 750195 | 489873 | 489892 | TGAAAGGCCTACAGCAACCA | 46 | 398 |
| 750196 | 489893 | 489912 | ATGGGAGCTCTGGAAAACAG | 27 | 399 |
| 750197 | 490070 | 490089 | TTCTGAGTATATGTGAAACA | 39 | 400 |
| 750198 | 492874 | 492893 | ATAAGGAGATTAATTTAAGA | 86 | 401 |
| 750199 | 493278 | 493297 | GAATCAAAGAAAGAAGGAAT | 47 | 402 |
| 750200 | 493440 | 493459 | GCTGTAATAATAATCATATT | 41 | 403 |
| 750201 | 493678 | 493697 | AGAATTCTTCCCTACAGGTT | 51 | 404 |
| 750202 | 493831 | 493850 | CAGTAATTAATGTTCTTATA | 37 | 405 |
| 750203 | 493839 | 493858 | CCCCAATTCAGTAATTAATG | 39 | 406 |
| 750204 | 493841 | 493860 | GGCCCCAATTCAGTAATTAA | 56 | 407 |
| 750205 | 493882 | 493901 | ATGTAACCTATTCAAGATGA | 47 | 408 |
| 750206 | 493908 | 493927 | TTATTTGGAAGAAGAATCTT | 98 | 409 |
| 750207 | 494002 | 494021 | TATAAAATACTTTTTATGGG | 101 | 410 |
| 750208 | 494398 | 494417 | GACTGTGATAAAGATGTATA | 84 | 411 |
| 750209 | 494443 | 494462 | TAAGGGTCATGTACTATACA | 33 | 412 |
| 750210 | 494494 | 494513 | GTGTGTGCAATAGCCTAAAT | 27 | 413 |
| 750211 | 494554 | 494573 | CAGAAGCAAAAGATAGCAGC | 53 | 414 |
| 750212 | 494873 | 494892 | TATTAATGTACTTGAAGATG | 52 | 415 |
| 750213 | 495043 | 495062 | ATCAGTGTGTGCAGATTCTG | 45 | 416 |
| 750214 | 495050 | 495069 | TCCCATCATCAGTGTGTGCA | 27 | 417 |
| 750215 | 495201 | 495220 | TATGAAAATTAATGTTCAAG | 80 | 418 |
| 750216 | 495233 | 495252 | AAAAAATTTTAAACCCCTAG | 76 | 419 |
| 750217 | 495441 | 495460 | TCATGAAAGTAGAGAGTAAG | 68 | 420 |
| 750218 | 495659 | 495678 | TGAAACAATTTAAGTGCCCA | 64 | 421 |
| 750219 | 495718 | 495737 | TTGAAGGGATATCTTCATTC | 106 | 422 |
| 750220 | 495795 | 495814 | TCTGAAAAAATAGAACAAC | 64 | 423 |
| 750221 | 496202 | 496221 | AATAAAAGACCTGCACAGCA | 66 | 424 |
| 750222 | 496205 | 496224 | CAAAATAAAGACCTGCACA | 48 | 425 |
| 750223 | 496379 | 496398 | AGACCCTTATTTACACCATA | 65 | 426 |
| 750224 | 496557 | 496576 | CTATTAATGAGCTATCTGAA | 37 | 427 |
| 750225 | 496561 | 496580 | TCTACTATTAATGAGCTATC | 45 | 428 |
| 750226 | 496567 | 496586 | TTTCCATCTACTATTAATGA | 39 | 429 |

TABLE 7-continued

Reduction of UBE3A-ATS RNA by 8,000 nM 5-10-5 MOE gapmers with mixed PO/PS internucleoside linkages vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750227 | 496661 | 496680 | GTCTCCACCAGAACAAAACT | 69 | 430 |
| 750228 | 496691 | 496710 | ATGACATAACCATATACAAA | 35 | 431 |
| 750229 | 496697 | 496716 | TTACTGATGACATAACCATA | 71 | 432 |
| 750230 | 496869 | 496888 | CAAAATTCAACCTGGTTTCA | 39 | 433 |
| 750231 | 496927 | 496946 | ATGGAGGGTGTAAATCAAAT | 36 | 434 |
| 750232 | 497148 | 497167 | TGTTACACTGTTATTAAAGC | 28 | 435 |
| 750233 | 497197 | 497216 | AAAACAATGAAGCAGAGGGA | 37 | 436 |
| 750234 | 497299 | 497318 | TAATAAAAGTATCCCACCA | 72 | 437 |
| 750235 | 497429 | 497448 | GAAGTTATGCACCATCAAAT | 46 | 438 |
| 750236 | 497477 | 497496 | TTTACTACTGATATCACCAA | 41 | 439 |
| 750237 | 497680 | 497699 | AGAACAGACTAAGCCCGAAA | 40 | 440 |
| 750238 | 497917 | 497936 | AATTCTGGTGGAAAATACAG | 71 | 441 |
| 750239 | 497984 | 498003 | ACAGAAATCATATCAAATCC | 69 | 442 |
| 750240 | 498096 | 498115 | ATATATGAAACATTCCATCC | 39 | 443 |
| 750241 | 498127 | 498146 | TTACACTTTAGACCAAACGG | 37 | 444 |
| 750242 | 498179 | 498198 | GGGCAGATTGATCACCTAGA | 25 | 445 |
| 750243 | 498208 | 498227 | CGGGACCTCAATACTCTACT | 37 | 446 |
| 750244 | 498432 | 498451 | TAAATGGAAATTGAGAGCAG | 61 | 447 |
| 750245 | 498842 | 498861 | AAGTCACAACCACATACTGC | 57 | 448 |
| 750246 | 498894 | 498913 | GATTCTCCAACAAAAGACA | 50 | 449 |
| 750247 | 498942 | 498961 | GACACTAGCAGTTTCTTACC | 30 | 450 |
| 750248 | 499132 | 499151 | GCTTAAAGTAGCCTAAGGAT | 32 | 451 |
| 750249 | 499286 | 499305 | ACAATAAGTTGTAGCTACAA | 61 | 452 |
| 750250 | 499304 | 499323 | TTAAAAACAACTGTAGCTAC | 62 | 453 |
| 750251 | 499335 | 499354 | TTCCTATTAGGAGGTTTAAA | 43 | 454 |
| 750252 | 499395 | 499414 | ATAAGTAATTCATAGTCAGA | 44 | 455 |
| 750253 | 499452 | 499471 | GGCTTAAATAAAAGACTGCT | 63 | 456 |

TABLE 8

Reduction of UBE3A-ATS RNA by 8,000 nM 5-10-5 MOE gapmers with mixed PO/PS internucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617456 | 463905 | 463924 | CAACTGTTACCAAGACTTCA | 34 | 32 |
| 617457 | 465003 | 465022 | ATCTGCGAATAGAGGCCCTC | 44 | 33 |
| 617460 | 466539 | 466558 | TAGGTTGCATAAAGCCAGGC | 45 | 36 |

TABLE 8-continued

Reduction of UBE3A-ATS RNA by 8,000 nM 5-10-5 MOE gapmers with mixed PO/PS internucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617461 | 466981 | 467000 | CACACATCTTGTTCCCTCAA | 19 | 37 |
| 617557 | 483977 | 483996 | ATCATGTGCATACCCAGGGT | 37 | 172 |
| 749753 | 448285 | 448304 | TAAGATTCCATTGCCAGAAT | 115 | 457 |
| 749754 | 448296 | 448315 | AAGTTTCGCAATAAGATTCC | 103 | 458 |
| 749755 | 448500 | 448519 | TTTCAGTCAGCAAAGGCAGC | 80 | 459 |
| 749756 | 448681 | 448700 | TCTCAACCCTGAAAACAATC | 87 | 460 |
| 749757 | 448989 | 449008 | CATTGGCATTATTCACAGCA | 103 | 461 |
| 749758 | 449031 | 449050 | CTGACTGTCATTCATATAAG | 69 | 462 |
| 749759 | 449067 | 449086 | TGCATAACGATAATCATGTG | 161 | 463 |
| 749760 | 449112 | 449131 | TTGTAGATCCTGGCAAGTAT | 132 | 464 |
| 749761 | 449130 | 449149 | AAAAATAAAGTTTCCCTCTT | 64 | 465 |
| 749762 | 449167 | 449186 | CAAAACTTGTCAACATTATA | 129 | 466 |
| 749763 | 449218 | 449237 | CTATATTTAGACCAAATGAG | 91 | 467 |
| 749764 | 449254 | 449273 | CTGACATATATAAATTAGAA | 104 | 468 |
| 749765 | 449263 | 449282 | CATAGCAACCTGACATATAT | 109 | 469 |
| 749766 | 449279 | 449298 | ACAAACATTGTAAAAACATA | 92 | 470 |
| 749767 | 449337 | 449356 | TTAGAACATGTAGCCATAAT | 69 | 471 |
| 749768 | 449382 | 449401 | AATTGTATTTAATTTAATGA | 102 | 472 |
| 749769 | 449439 | 449458 | ATCATACTGGAGCCAGGTGA | 85 | 473 |
| 749770 | 449545 | 449564 | AATGCAGAAATAAGACCTTC | 88 | 474 |
| 749771 | 449765 | 449784 | CAGTCATCCTTATCTAAGGG | 63 | 475 |
| 749772 | 449786 | 449805 | AAGCCAAAGAGTACTCTTCC | 83 | 476 |
| 749773 | 449820 | 449839 | GATATCTGGGTGTGTCAGCT | 67 | 477 |
| 749774 | 449944 | 449963 | CAACATAAGGTCTTATTGTT | 74 | 478 |
| 749775 | 450083 | 450102 | GGTCTTCTAGAAGCTAATAG | 77 | 479 |
| 749776 | 450092 | 450111 | TTGATAAGTGGTCTTCTAGA | 64 | 480 |
| 749777 | 450204 | 450223 | CAATTCTTTTGAGTGTGTAC | 66 | 481 |
| 749778 | 450205 | 450224 | TCAATTCTTTTGAGTGTGTA | 70 | 482 |
| 749779 | 450511 | 450530 | GTGTGACATTGTCATCATAC | 87 | 483 |
| 749780 | 450710 | 450729 | CTTTATGCTTTCTGTTCTTT | 76 | 484 |
| 749781 | 450733 | 450752 | GAGACTCTCTTTGTTTCTTT | 96 | 485 |
| 749782 | 450906 | 450925 | TTCATTGGAATTCATTGAGC | 94 | 486 |
| 749783 | 450978 | 450997 | CAAGACTTTCTTCTTGTTTT | 115 | 487 |
| 749784 | 451042 | 451061 | AGTCAGCTGTTAATCTTCCT | 85 | 488 |
| 749785 | 451104 | 451123 | TTTTTCTTTGAGCATTTTTA | 104 | 489 |
| 749786 | 451250 | 451269 | TTTAAGTATTTAGAGAACTC | 122 | 490 |

TABLE 8-continued

Reduction of UBE3A-ATS RNA by 8,000 nM 5-10-5 MOE gapmers with mixed PO/PS internucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 749787 | 451286 | 451305 | TACCTAGGCTCACTTGCTTT | 91 | 491 |
| 749788 | 451306 | 451325 | TAGTTGTTGATTTGAATAAC | 87 | 492 |
| 749789 | 451308 | 451327 | TGTAGTTGTTGATTTGAATA | 93 | 493 |
| 749790 | 451389 | 451408 | TTATTTTAAAATCACTTCAG | 96 | 494 |
| 749791 | 451466 | 451485 | TCTTCTTTGGCAAATATATT | 126 | 495 |
| 749792 | 451604 | 451623 | TCCCTTTTTGCCATCTTTTG | 58 | 496 |
| 749793 | 451673 | 451692 | AATAAGTTTCTAATTTACAC | 113 | 497 |
| 749794 | 451834 | 451853 | TCTCATGTGTTTTTGTTCCT | 49 | 498 |
| 749795 | 451954 | 451973 | TAAACCTGGAGATTTTATCC | 128 | 499 |
| 749796 | 452167 | 452186 | GGGAACACACCATTCAGCAG | 38 | 500 |
| 749797 | 452222 | 452241 | AATCTTGTTGACTAAAAGTA | 114 | 501 |
| 749798 | 452255 | 452274 | GTCTCACGCTGTGTGAATCA | 104 | 502 |
| 749799 | 452257 | 452276 | AGGTCTCACGCTGTGTGAAT | 89 | 503 |
| 749800 | 452285 | 452304 | TGCTCCTATTTCAATATGAG | 100 | 504 |
| 749801 | 452324 | 452343 | ATAAGGTTCAAAAGCCGGTG | 182 | 505 |
| 749802 | 452459 | 452478 | AACTGGTAACATAAATGCAG | 99 | 506 |
| 749803 | 452485 | 452504 | TCAGAGCAAAATGGACTGAC | 142 | 507 |
| 749804 | 452517 | 452536 | TACAAATACCCAGTCTGCAG | 65 | 508 |
| 749805 | 452590 | 452609 | AAGGCCCTTATCATATGCCA | 96 | 509 |
| 749806 | 452661 | 452680 | TCCTATAAAAGAAGATATTT | 65 | 510 |
| 749807 | 452715 | 452734 | CTGTGAGAGCTCTGCCCTCA | 93 | 511 |
| 749808 | 453217 | 453236 | GTTAATAGTGTTCTTACATC | 106 | 512 |
| 749809 | 453233 | 453252 | CAGTGGAGTCAAGTTGGTTA | 135 | 513 |
| 749810 | 453350 | 453369 | TCTACTAGCTAACTTTATCA | 109 | 514 |
| 749811 | 453453 | 453472 | AGGATCAAAGCAGAAATTAA | 102 | 515 |
| 749812 | 453814 | 453833 | AAAAACATAGACTTTACTAA | 139 | 516 |
| 749813 | 453899 | 453918 | CACAAAAAACTGATTATATA | 92 | 517 |
| 749814 | 453933 | 453952 | GATCTGTGTTGTTCTTAAGT | 73 | 518 |
| 749815 | 453978 | 453997 | AAGGTAGATTTTATGGCTAC | 68 | 519 |
| 749816 | 454002 | 454021 | GGGCAAAAATAGCAACATAA | 47 | 520 |
| 749817 | 454067 | 454086 | AAGACATAGATGATCCCATA | 89 | 521 |
| 749818 | 454085 | 454104 | TATGAGATGTAAGGAGACAA | 86 | 522 |
| 749819 | 454303 | 454322 | GATAGGAGTAATCTTTTTTT | 86 | 523 |
| 749820 | 454611 | 454630 | AAACAAAAACTCTCCTAAGT | 77 | 524 |
| 749821 | 454657 | 454676 | AGAACTAACAGAATTAAGAG | 89 | 525 |
| 749822 | 454658 | 454677 | CAGAACTAACAGAATTAAGA | 111 | 526 |

TABLE 8-continued

Reduction of UBE3A-ATS RNA by 8,000 nM 5-10-5 MOE gapmers with mixed PO/PS internucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 749823 | 454661 | 454680 | ACACAGAACTAACAGAATTA | 71 | 527 |
| 749824 | 454759 | 454778 | AAAAAGAGGAAAACCGAAAG | 88 | 528 |

TABLE 9

Reduction of UBE3A-ATS RNA by 8,000 nM 5-10-5 MOE gapmers with a mixed PO/PS internucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617456 | 463905 | 463924 | CAACTGTTACCAAGACTTCA | 40 | 32 |
| 617457 | 465003 | 465022 | ATCTGCGAATAGAGGCCCTC | 49 | 33 |
| 617460 | 466539 | 466558 | TAGGTTGCATAAAGCCAGGC | 28 | 36 |
| 617461 | 466981 | 467000 | CACACATCTTGTTCCCTCAA | 33 | 37 |
| 617557 | 483977 | 483996 | ATCATGTGCATACCCAGGGT | 42 | 172 |
| 749825 | 454828 | 454847 | CATACAAATGTCACTAATAT | 114 | 529 |
| 749826 | 454836 | 454855 | AAGACTAGCATACAAATGTC | 85 | 530 |
| 749827 | 454864 | 454883 | ACAGGTGTATATTCCCTATC | 84 | 531 |
| 749828 | 454998 | 455017 | ATATATCTACTGAATATGAT | 108 | 532 |
| 749829 | 455062 | 455081 | CTCAGAACCCTTTGGTCTAA | 66 | 533 |
| 749830 | 455110 | 455129 | CTGACTTGACTTTAATGAAA | 68 | 534 |
| 749831 | 455148 | 455167 | GCATTCAGCTTATAGCAGAA | 58 | 535 |
| 749832 | 455150 | 455169 | CTGCATTCAGCTTATAGCAG | 84 | 536 |
| 749833 | 455193 | 455212 | AAACATTCCTCATACCACAC | 73 | 537 |
| 749834 | 455230 | 455249 | CTTATCCTTGATCCAGACAA | 78 | 538 |
| 749835 | 455436 | 455455 | AATGGGAAATGCTAAAGTTG | 72 | 539 |
| 749836 | 455459 | 455478 | AGTGACACAGTAGTTGTATC | 70 | 540 |
| 749837 | 455485 | 455504 | CAATTTCCTCTCTACCAAGC | 71 | 541 |
| 749838 | 455542 | 455561 | CTTTGTCATTTCATTTATAA | 70 | 542 |
| 749839 | 455603 | 455622 | ATACAGGCATCTCAGCCCTC | 61 | 543 |
| 749840 | 455767 | 455786 | AAAGTACCAAAGTGGCTGCT | 71 | 544 |
| 749841 | 455768 | 455787 | AAAAGTACCAAAGTGGCTGC | 68 | 545 |
| 749842 | 455829 | 455848 | GAAATAATGAACTCACAGTC | 70 | 546 |
| 749843 | 455960 | 455979 | CACAGTTGTTTAGGTCATCT | 119 | 547 |
| 749844 | 457070 | 457089 | GCATGCCATATTTCCTTCTT | 91 | 548 |
| 749845 | 457076 | 457095 | ATAGAGGCATGCCATATTTC | 86 | 549 |
| 749846 | 457151 | 457170 | AGCAAAATAATCTTAGAAA | 91 | 550 |

TABLE 9-continued

Reduction of UBE3A-ATS RNA by 8,000 nM 5-10-5 MOE gapmers with a mixed
PO/PS internucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 749847 | 457194 | 457213 | GATTCCAGGCCTTCTATCTC | 80 | 551 |
| 749848 | 457354 | 457373 | GGTCTCAATGAGGAAAAGGA | 34 | 552 |
| 749849 | 457424 | 457443 | ATAAAAGCAAAAGAGAGTTA | 84 | 553 |
| 749850 | 457556 | 457575 | TCTATTCTGAAACCCCAATA | 45 | 554 |
| 749851 | 457705 | 457724 | GACATGCCATCAAGAGAAGA | 59 | 555 |
| 749852 | 457917 | 457936 | ATGTATTAACCAATATTTTG | 51 | 556 |
| 749853 | 457993 | 458012 | AGAACCCACTTGATCTATTA | 53 | 557 |
| 749854 | 458199 | 458218 | TAAAGAATTGAGTACCAAAA | 64 | 558 |
| 749855 | 458268 | 458287 | TATCACATTAATTCCCTCTC | 37 | 559 |
| 749856 | 458289 | 458308 | TAGAATAGAAAAGCATGAAG | 71 | 560 |
| 749857 | 458328 | 458347 | AACAACTATATTTGCTTGTA | 39 | 561 |
| 749858 | 458346 | 458365 | ATAATCACACTAAATCTTAA | 70 | 562 |
| 749859 | 458391 | 458410 | CCTCTATTAAGATCTATGAG | 75 | 563 |
| 749860 | 458438 | 458457 | ACTTCATCAATATTTCCCCA | 31 | 564 |
| 749861 | 458537 | 458556 | GCACTTAAATTTATCAGTTG | 28 | 565 |
| 749862 | 458539 | 458558 | AAGCACTTAAATTTATCAGT | 36 | 566 |
| 749863 | 458567 | 458586 | TTAGTATGTCGAGAACTCAA | 24 | 567 |
| 749864 | 458588 | 458607 | AAGTTGAAACACATTTTAGC | 32 | 568 |
| 749865 | 458596 | 458615 | AGGATTAAAAGTTGAAACAC | 30 | 569 |
| 749866 | 458597 | 458616 | CAGGATTAAAAGTTGAAACA | 49 | 570 |
| 749867 | 458608 | 458627 | AATCAGGGAAGCAGGATTAA | 55 | 571 |
| 749868 | 458668 | 458687 | TGATTACTCTTGGCAGTAAT | 58 | 572 |
| 749869 | 458823 | 458842 | TGATAGATACTTGTATTAGC | 14 | 573 |
| 749870 | 458896 | 458915 | CAAATCTAAAGCTCATTTAC | 72 | 574 |
| 749871 | 458908 | 458927 | CTACCAAAATGTCAAATCTA | 56 | 575 |
| 749872 | 459220 | 459239 | GTAACCTGAATATTTCATGA | 37 | 576 |
| 749873 | 459228 | 459247 | AAATAATGGTAACCTGAATA | 56 | 577 |
| 749874 | 459240 | 459259 | AATACATTACTGAAATAATG | 86 | 578 |
| 749875 | 459256 | 459275 | TTTACCTTGACATTCTAATA | 40 | 579 |
| 749876 | 459450 | 459469 | TTAACCTATTTTAATAATAT | 89 | 580 |
| 749877 | 459567 | 459586 | TTAAGTGATTGGAAATAAAA | 82 | 581 |
| 749878 | 459580 | 459599 | CAATTAGGAATATTTAAGTG | 97 | 582 |
| 749879 | 459633 | 459652 | CCAGGCAATGGCTCTTTCAA | 66 | 583 |
| 749880 | 459645 | 459664 | TGTATAGTTTACCCAGGCAA | 37 | 584 |
| 749881 | 460066 | 460085 | CTTTATCAATCTAATCAATT | 65 | 585 |
| 749882 | 460115 | 460134 | ACTTTATAGTGTGGATGGTA | 22 | 586 |

TABLE 9-continued

Reduction of UBE3A-ATS RNA by 8,000 nM 5-10-5 MOE gapmers with a mixed PO/PS internucleoside linkages in vitro (35,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 749883 | 460146 | 460165 | TTTTAGGGAATTGTCCTGAT | 39 | 587 |
| 749884 | 460211 | 460230 | AAGGAAACACACATAATACC | 46 | 588 |
| 749885 | 460213 | 460232 | GGAAGGAAACACACATAATA | 26 | 589 |
| 749886 | 460272 | 460291 | CACTAAGGACAAAGATATGG | 75 | 590 |
| 749887 | 460303 | 460322 | TATTTGTTCATTCTCAAGAA | 56 | 591 |
| 749888 | 460545 | 460564 | CAACCTGGGCTCTCATCTAA | 41 | 592 |
| 749889 | 460709 | 460728 | AATGCTTGATCTGTGGGCTC | 32* | 593 |
| 749890 | 460749 | 460768 | ATTGTGTACACAGGGATTTG | 22* | 594 |
| 749891 | 460792 | 460811 | AACTGTATACTTTGAAAGTA | 68 | 595 |
| 749892 | 460870 | 460889 | GAAGCAAGTAAGTAAATAAT | 81 | 596 |
| 749893 | 460981 | 461000 | CTTAGATGTGTTTATCCAAA | 25 | 597 |
| 749894 | 460999 | 461018 | GTGTTTTTCCATTTTTCTCT | 9 | 598 |
| 749895 | 461027 | 461046 | TGGCTCTATCAAGGCTTCCC | 39 | 599 |
| 749896 | 461039 | 461058 | AATCCTATATTTTGGCTCTA | 34 | 600 |

TABLE 10

Reduction of UBE3A-ATS RNA by 10,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617456 | 463905 | 463924 | CAACTGTTACCAAGACTTCA | 47 | 32 |
| 617457 | 465003 | 465022 | ATCTGCGAATAGAGGCCCTC | 70 | 33 |
| 617460 | 466539 | 466558 | TAGGTTGCATAAAGCCAGGC | 51 | 36 |
| 617461 | 466981 | 467000 | CACACATCTTGTTCCCTCAA | 45 | 37 |
| 617557 | 483977 | 483996 | ATCATGTGCATACCCAGGGT | 29 | 172 |
| 699780 | 479654 | 479673 | AGTAAGGTCTGTTATTCTCC | 122 | 127 |
| 750040 | 470321 | 470340 | GAACTATCCTGCATCCGAGG | 41 | 601 |
| 750041 | 470398 | 470417 | CAACCATCGAGATGATCATA | 70 | 602 |
| 750042 | 471812 | 471831 | TAAATGCTTTTCTAAATCTA | 100 | 603 |
| 750043 | 471892 | 471911 | GCTTTTATAGTGTTGAGGCA | 81 | 604 |
| 750044 | 472153 | 472172 | TTAAGCTCTAATTAAAACAG | 113 | 605 |
| 750045 | 473241 | 473260 | TATTTCACTGGAGCTTTGAT | 107 | 606 |
| 750046 | 473564 | 473583 | AATCATCTACTGATGAACAC | 99 | 607 |
| 750047 | 473573 | 473592 | TCTTTATCTAATCATCTACT | 90 | 608 |
| 750048 | 473576 | 473595 | TTCTCTTTATCTAATCATCT | 111 | 609 |
| 750049 | 473697 | 473716 | AGTTCCTGGAAACCGCCATT | 63 | 610 |

TABLE 10-continued

Reduction of UBE3A-ATS RNA by 10,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750050 | 473789 | 473808 | ATGCTGTTGTACACTAGATC | 82 | 611 |
| 750051 | 473955 | 473974 | GTACACTATTGTTTTGATAT | 44 | 612 |
| 750052 | 474053 | 474072 | CACCCCTAATTTATATTACT | 56 | 613 |
| 750053 | 474069 | 474088 | CATAGGTCAATTCCTTCACC | 47 | 614 |
| 750054 | 474103 | 474122 | TTAATTTAAATAGTTTACAA | 100 | 615 |
| 750055 | 474123 | 474142 | CTAGCTTGAATGGATACCAA | 71 | 616 |
| 750056 | 474169 | 474188 | TAGTGGTTGCCTTAGTATTA | 52 | 617 |
| 750057 | 474198 | 474217 | CAAGTGCTATATTTTTTAA | 95 | 618 |
| 750058 | 474230 | 474249 | TATATATAATTGAGGGCCAC | 116 | 619 |
| 750059 | 474414 | 474433 | ATAATTATAAGATAGGGTTT | 127 | 620 |
| 750060 | 474618 | 474637 | ATTAGTATTGCTGCTCTAGC | 91 | 621 |
| 750061 | 474786 | 474805 | CCAACTGTAATCATTGATTT | 79 | 622 |
| 750062 | 474865 | 474884 | GATAATGTGTAGTTTTTTAT | 82 | 623 |
| 750063 | 474878 | 474897 | TAAGGTGTTGTATGATAATG | 78 | 624 |
| 750064 | 474953 | 474972 | AATATGTGTCATCCTGAAGA | 93 | 625 |
| 750065 | 475066 | 475085 | TCATTGTGAATTTCCCACAT | 81 | 626 |
| 750066 | 475233 | 475252 | TTAGGGATATACTGTTATAC | 72 | 627 |
| 750067 | 475268 | 475287 | AAAATTAGGTTATTGGATTG | 103 | 628 |
| 750068 | 475293 | 475312 | CTTTCACTCTCATTTCTTAA | 91 | 629 |
| 750069 | 475397 | 475416 | ACTTTCAAGTTTATTAATTT | 115 | 630 |
| 750070 | 475495 | 475514 | TACTTTCATTTATGTCTAGT | 78 | 631 |
| 750071 | 475503 | 475522 | GATATCTATACTTTCATTTA | 125 | 632 |
| 750072 | 475628 | 475647 | CATGTTTTTACACCAGCTGT | 87 | 633 |
| 750073 | 475693 | 475712 | TTACTTACTCAATTTCTTCT | 97 | 634 |
| 750074 | 476072 | 476091 | GTTTCAGCAGTTTCTGCTCC | 85 | 635 |
| 750075 | 476164 | 476183 | GGGCACTTAGGAGTTCCTAA | 80 | 636 |
| 750076 | 476337 | 476356 | CTCTGAGAGTGTTTAGAAAT | 55 | 637 |
| 750077 | 476350 | 476369 | GTGAAAGAAAATGCTCTGAG | 62 | 638 |
| 750078 | 476405 | 476424 | TACATCAGACAAGGCTCAGG | 91 | 639 |
| 750079 | 476845 | 476864 | TTCTATAATCTTATGGTTAA | 77 | 640 |
| 750080 | 476851 | 476870 | GAAGTGTTCTATAATCTTAT | 74 | 641 |
| 750081 | 477296 | 477315 | GTGAAAATTTTGTAGGTTGC | 110 | 642 |
| 750082 | 478347 | 478366 | TACAATCAGTGTCTTTCACC | 78 | 643 |
| 750083 | 478472 | 478491 | ATGGTTAGGGCTATGTTATG | 96 | 644 |
| 750084 | 478542 | 478561 | GAAATAAAACGCAATGTATC | 118 | 645 |
| 750085 | 478710 | 478729 | CTTGCATGTTGCCTTTTTCT | 129 | 646 |

TABLE 10-continued

Reduction of UBE3A-ATS RNA by 10,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
| --- | --- | --- | --- | --- | --- |
| 750086 | 479037 | 479056 | AACTCTCTGCCATTATTACT | 81 | 647 |
| 750087 | 479330 | 479349 | TAATCTCACTGGATACAGAA | 107 | 648 |
| 750088 | 479468 | 479487 | AAACATTTTACCATTTTATA | 133 | 649 |
| 750089 | 479644 | 479663 | GTTATTCTCCCTCTTGAACC | 82 | 650 |
| 750090 | 479647 | 479666 | TCTGTTATTCTCCCTCTTGA | 86 | 651 |
| 750091 | 479649 | 479668 | GGTCTGTTATTCTCCCTCTT | 51 | 652 |
| 750092 | 479652 | 479671 | TAAGGTCTGTTATTCTCCCT | 52 | 653 |
| 750093 | 479656 | 479675 | AAAGTAAGGTCTGTTATTCT | 92 | 654 |
| 750094 | 479659 | 479678 | CTAAAAGTAAGGTCTGTTAT | 74 | 655 |
| 750095 | 479661 | 479680 | GACTAAAAGTAAGGTCTGTT | 70 | 656 |
| 750096 | 479664 | 479683 | AATGACTAAAAGTAAGGTCT | 133 | 657 |
| 750097 | 480219 | 480238 | AAAGATATAGAACTGAAAAG | 128 | 658 |
| 750098 | 480286 | 480305 | GTTGGAGACTTCAATTTCCT | 89 | 659 |
| 750099 | 480361 | 480380 | AAACAACAGAGCCTCAAATA | 114 | 660 |
| 750100 | 480441 | 480460 | AAAATACCACAAAGATAGGC | 38 | 661 |
| 750101 | 480530 | 480549 | AAGAATGGAAAAGATGTATC | 57 | 662 |
| 750102 | 480533 | 480552 | TAAAAGAATGGAAAAGATGT | 99 | 663 |
| 750103 | 480648 | 480667 | AATTTTACCTCAGTATAAAA | 106 | 664 |
| 750104 | 480698 | 480717 | ATTACCAAATGCCACTGTAT | 59 | 665 |
| 750105 | 480714 | 480733 | GTTGCATAACATGTGTATTA | 65 | 666 |
| 750106 | 480787 | 480806 | AATTAACTGCTTAATGAGTA | 145 | 667 |
| 750107 | 480898 | 480917 | ATAAAGGTCACTTATTGTAT | 89 | 668 |
| 750108 | 480968 | 480987 | AATAAAACTGATACATACTA | 101 | 669 |
| 750109 | 481010 | 481029 | AATCAACTTTTAGCTATACA | 119 | 670 |
| 750110 | 481027 | 481046 | TATCATTATGACCTAGGAAT | 69 | 671 |

TABLE 11

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
| --- | --- | --- | --- | --- | --- |
| 617456 | 463905 | 463924 | CAACTGTTACCAAGACTTCA | 16 | 32 |
| 617457 | 465003 | 465022 | ATCTGCGAATAGAGGCCCTC | 21 | 33 |
| 617460 | 466539 | 466558 | TAGGTTGCATAAAGCCAGGC | 24 | 36 |
| 617461 | 466981 | 467000 | CACACATCTTGTTCCCTCAA | 15 | 37 |

TABLE 11-continued

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617557 | 483977 | 483996 | ATCATGTGCATACCCAGGGT | 12 | 172 |
| 750254 | 499480 | 499499 | ACTGGAATTACTAAAAGGGA | 62 | 672 |
| 750255 | 499621 | 499640 | AGTAGAGAGTGGGATGGTAT | 53 | 673 |
| 750256 | 499691 | 499710 | TAAGAAACATCACATTCAAG | 67 | 674 |
| 750257 | 500139 | 500158 | TGAACAGAATGAGAAGTTTA | 82 | 675 |
| 750258 | 500141 | 500160 | TCTGAACAGAATGAGAAGTT | 69 | 676 |
| 750259 | 500285 | 500304 | TGGTGTACATTGGATATGAA | 24 | 677 |
| 750260 | 500319 | 500338 | TTTCTAACATTTACTGTGGA | 83 | 678 |
| 750261 | 500367 | 500386 | TTCTAACATACTAATTAGCA | 41 | 679 |
| 750262 | 500384 | 500403 | CACCAATGCAAGCCAGCTTC | 28 | 680 |
| 750263 | 500526 | 500545 | TGTTTAGAGGTCAAGCCCTG | 75 | 681 |
| 750264 | 500570 | 500589 | ATCAGTCAAAACATGTTCTG | 56 | 682 |
| 750265 | 500629 | 500648 | TATTACACAAGGTATTGGTA | 35 | 683 |
| 750266 | 500639 | 500658 | ATGAAAGGTTTATTACACAA | 34 | 684 |
| 750267 | 500760 | 500779 | AATCAATTTGTGCCACAGGC | 34 | 685 |
| 750268 | 500786 | 500805 | GCAGCTTATAAAGAGAGCCA | 78 | 686 |
| 750269 | 500860 | 500879 | TTTGGTAGGTAACTACGGGT | 35 | 687 |
| 750270 | 500882 | 500901 | TCGGATATAGCTTTTACATA | 14 | 688 |
| 750271 | 501004 | 501023 | AAACTAAGCACATCCGATAG | 60 | 689 |
| 750272 | 501060 | 501079 | ATCATCTTTGATTTGACTTT | 37 | 690 |
| 750273 | 501091 | 501110 | TTCTTTATGAATCTTTGAAA | 51 | 691 |
| 750274 | 501151 | 501170 | GTAAAGAGCCACCTAAGGGA | 40 | 692 |
| 750275 | 501165 | 501184 | ATGAGATGGGCACAGTAAAG | 33 | 693 |
| 750276 | 501391 | 501410 | TCCCCAGATAATGCATAGAT | 49 | 694 |
| 750277 | 501437 | 501456 | GGTGGCATAGAAGGCAGCAC | 74 | 695 |
| 750278 | 501549 | 501568 | GGATGCAGCAGGAGAAGAAA | 42 | 696 |
| 750279 | 501576 | 501595 | AAGGCAAGGCTAAGGAGTGC | 27 | 697 |
| 750280 | 501679 | 501698 | AGAGAGCTAGAGCTAGGACT | 17 | 698 |
| 750281 | 501694 | 501713 | ATCCCAAAGTTACACAGAGA | 58 | 699 |
| 750282 | 501703 | 501722 | CTTTGGGACATCCCAAAGTT | 73 | 75 |
| 750283 | 501752 | 501771 | CACCTGTATCCAAAATTCAA | 47 | 700 |
| 750284 | 501788 | 501807 | CATATCTGAAGCACAGAGAG | 39 | 701 |
| 750285 | 501860 | 501879 | CAGTCTGCTCTGCTGCTCTG | 66 | 702 |
| 750286 | 501862 | 501881 | TCCAGTCTGCTCTGCTGCTC | 67 | 703 |
| 750287 | 501882 | 501901 | AGCTCAGAGGCAGCAGGAGC | 47 | 704 |
| 750288 | 502030 | 502049 | CTAAGCTCCATATTTAAATC | 69 | 705 |

TABLE 11-continued

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750289 | 502049 | 502068 | TTCAGGCTTCCTTCACAGCC | 69 | 706 |
| 750290 | 502052 | 502071 | TTCTTCAGGCTTCCTTCACA | 44 | 707 |
| 750291 | 502138 | 502157 | GGAATCAGTGCTACCCATTA | 23 | 708 |
| 750292 | 502194 | 502213 | TTAGCCATCATTTTATTCTC | 12 | 709 |
| 750293 | 502341 | 502360 | GGCCCATTTTTTCAATCTCA | 43 | 710 |
| 750294 | 502404 | 502423 | CATGGTCTTCCTTGACTACA | 40 | 711 |
| 750295 | 502580 | 502599 | AAGCCAATGCGCAAGAAAAG | 42 | 712 |
| 750296 | 503121 | 503140 | CATCCAGTTAATCTCTGACA | 31 | 713 |
| 750297 | 503125 | 503144 | CTCGCATCCAGTTAATCTCT | 38 | 714 |
| 750298 | 503145 | 503164 | ACACCATCCCAGAAATGGTC | 75 | 715 |
| 750299 | 503180 | 503199 | TTTCTGACTCCCTATCCAGT | 44 | 716 |
| 750300 | 503376 | 503395 | TTCCCCAGGGTCATAGGAGT | 71 | 717 |
| 750301 | 503442 | 503461 | GCACTGTCCCAGTTGGATTA | 27 | 718 |
| 750302 | 503490 | 503509 | ACCCAGCAAAATGTGGGTCT | 119 | 719 |
| 750303 | 503504 | 503523 | TTGGTTGTGGTGAAACCCAG | 79 | 720 |
| 750304 | 503533 | 503552 | TGTTAAAAGAGAAAAGAATC | 77 | 721 |
| 750305 | 503550 | 503569 | TTGCAGTGATGTACTGATGT | 26 | 722 |
| 750306 | 503599 | 503618 | TTGTTTTATAAGCAATTAG | 59 | 723 |
| 750307 | 503645 | 503664 | TATAAATATGCCCATATGCT | 28 | 724 |
| 750308 | 503656 | 503675 | CTGCCTGCAACTATAAATAT | 45 | 725 |
| 750309 | 503825 | 503844 | GTATCTCCTAGCCCAGTGCC | 32 | 726 |
| 750310 | 503828 | 503847 | ACTGTATCTCCTAGCCCAGT | 64 | 727 |
| 750311 | 503895 | 503914 | GATTGCTTTATTGCAACTAA | 63 | 728 |
| 750312 | 503936 | 503955 | CTTAAATAGTAGGAAAGCCA | 14 | 729 |
| 750313 | 503973<br>508739 | 503992<br>508758 | ACACTGTACAGGAGGGTGTC | 25 | 155 |
| 750314 | 503975<br>508741 | 503994<br>508760 | GCACACTGTACAGGAGGGTG | 30 | 730 |
| 750315 | 503977<br>508743 | 503996<br>508762 | CTGCACACTGTACAGGAGGG | 17 | 79 |
| 750316 | 503979<br>508745 | 503998<br>508764 | CACTGCACACTGTACAGGAG | 41 | 731 |
| 750317 | 503981<br>508747 | 504000<br>508766 | TTCACTGCACACTGTACAGG | 33 | 156 |
| 750318 | 503983<br>508749 | 504002<br>508768 | GATTCACTGCACACTGTACA | 34 | 732 |
| 750319 | 503985<br>508751 | 504004<br>508770 | TTGATTCACTGCACACTGTA | 19 | 80 |
| 750320 | 503987<br>508753 | 504006<br>508772 | TGTTGATTCACTGCACACTG | 28 | 733 |

TABLE 11-continued

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750321 | 503991 | 504010 | ATGATGTTGATTCACTGCAC | 19 | 734 |
|  | 508757 | 508776 |  |  |  |
| 750322 | 503993 | 504012 | AAATGATGTTGATTCACTGC | 43 | 157 |
|  | 508759 | 508778 |  |  |  |
| 750323 | 503995 | 504014 | GGAAATGATGTTGATTCACT | 29 | 735 |
|  | 508761 | 508780 |  |  |  |
| 750324 | 503998 | 504017 | TGTGGAAATGATGTTGATTC | 50 | 736 |
| 750325 | 504090 | 504109 | CAGTATCTTAACTGGTGAAC | 15 | 737 |

TABLE 12

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617456 | 463905 | 463924 | CAACTGTTACCAAGACTTCA | 25 | 32 |
| 617457 | 465003 | 465022 | ATCTGCGAATAGAGGCCCTC | 27 | 33 |
| 617460 | 466539 | 466558 | TAGGTTGCATAAAGCCAGGC | 25 | 36 |
| 617461 | 466981 | 467000 | CACACATCTTGTTCCCTCAA | 17 | 37 |
| 617557 | 483977 | 483996 | ATCATGTGCATACCCAGGGT | 13 | 172 |
| 699781 | 483977 | 483996 | ATCATGTGCATACCCAGGGT | 20 | 172 |
| 750111 | 481036 | 481055 | ACATAGAATTATCATTATGA | 49 | 738 |
| 750112 | 481073 | 481092 | ACTGTGGAAAAACTTTGGCA | 38 | 129 |
| 750113 | 481398 | 481417 | ATGGGTTAAAATACTTATAA | 79 | 739 |
| 750114 | 481451 | 481470 | TAAAACCTTTGTGCATAATG | 32 | 740 |
| 750115 | 481487 | 481506 | CAACAACAAAGCGGATAAA | 50 | 741 |
| 750116 | 481524 | 481543 | ATGACACTAGGTTTTGCAAA | 34 | 742 |
| 750117 | 481529 | 481548 | ACCTCATGACACTAGGTTTT | 26 | 743 |
| 750118 | 481571 | 481590 | GTATAGACCCAAACTATAAA | 35 | 744 |
| 750119 | 481573 | 481592 | ATGTATAGACCCAAACTATA | 55 | 745 |
| 750120 | 481725 | 481744 | TGATCTCTTCAACAAATTGT | 82 | 746 |
| 750121 | 482139 | 482158 | AATGTTGCCGAAAGAAAAGA | 73 | 747 |
| 750122 | 482156 | 482175 | ACAAGTGTCATATACTAAAT | 51 | 748 |
| 750123 | 482174 | 482193 | AAATTTAACCAAGGAGTTAC | 48 | 749 |
| 750124 | 482246 | 482265 | AGCCATCTAAAAGAGAAATT | 38 | 750 |
| 750125 | 482396 | 482415 | GATCAAGAAGTAAAATTATC | 74 | 751 |
| 750126 | 482685 | 482704 | CACATGATAATCTCAATTAT | 52 | 752 |
| 750127 | 482916 | 482935 | GAAAAATTCACTCTATAGGT | 58 | 753 |

TABLE 12-continued

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750128 | 482988 | 483007 | CTATAGAGAGATAGATATTA | 52 | 754 |
| 750129 | 483017 | 483036 | AGAAAAATGTCTTTCCAAAT | 43 | 755 |
| 750130 | 483089 | 483108 | CAAATACTTAAATCAACTGT | 50 | 756 |
| 750131 | 483255 | 483274 | GGAGGGAGGAAAATTATTTC | 14 | 757 |
| 750132 | 483297 | 483316 | AGCAAACAACAGCAACATGC | 56 | 758 |
| 750133 | 483323 | 483342 | AAAATACTTTAGAAAAGTCA | 73 | 759 |
| 750134 | 483365 | 483384 | CAGAATTCAATGGACCCACA | 33 | 760 |
| 750135 | 483809 | 483828 | TCGGCAAAGGCATTATTATT | 32 | 761 |
| 750136 | 483920 | 483939 | GCTTTCACCTATAGGTGGCC | 45 | 762 |
| 750137 | 483928 | 483947 | GATGTTAAGCTTTCACCTAT | 25 | 763 |
| 750138 | 483967 | 483986 | TACCCAGGGTAGGATTCATG | 17 | 764 |
| 750139 | 483970 | 483989 | GCATACCCAGGGTAGGATTC | 13 | 765 |
| 750140 | 483972 | 483991 | GTGCATACCCAGGGTAGGAT | 9 | 766 |
| 750141 | 483975 | 483994 | CATGTGCATACCCAGGGTAG | 16 | 767 |
| 750142 | 483979 | 483998 | AGATCATGTGCATACCCAGG | 34 | 768 |
| 750143 | 483982 | 484001 | AGAAGATCATGTGCATACCC | 36 | 769 |
| 750144 | 483984 | 484003 | TAAGAAGATCATGTGCATAC | 44 | 770 |
| 750145 | 483987 | 484006 | AATTAAGAAGATCATGTGCA | 119 | 771 |
| 750146 | 484085 | 484104 | GTTCAGATGAACAATAAGCA | 45 | 772 |
| 750147 | 484311 | 484330 | ACTCATGCTGGTTACTAGGG | 30 | 773 |
| 750148 | 484598 | 484617 | TCATATGGGTGGTCGCTAAT | 24 | 774 |
| 750149 | 484719 | 484738 | ACACTAACGATGAACTCTAA | 55 | 775 |
| 750150 | 484721 | 484740 | TAACACTAACGATGAACTCT | 42 | 776 |
| 750151 | 485136 | 485155 | TTAAAACTCAACCCAGTGCA | 29 | 777 |
| 750152 | 485344 | 485363 | ATTCCTAGAGAAAACCTAGG | 82 | 778 |
| 750153 | 485478 | 485497 | AGAACAATGTTTCTTATGAA | 72 | 779 |
| 750154 | 485865 | 485884 | GAAACTGGGATATTACCAAT | 45 | 780 |
| 750155 | 485871 | 485890 | AAAATGGAAACTGGGATATT | 37 | 781 |
| 750156 | 486052 | 486071 | AAAAATTAAAGGCCAACAGA | 46 | 782 |
| 750157 | 486157 | 486176 | TTATGGCAGGTAGTGAAAGG | 47 | 783 |
| 750158 | 486265 | 486284 | ACAATATGCAAAAATTAAAT | 74 | 784 |
| 750159 | 486400 | 486419 | CATTCTCCAACATAGATCCT | 41 | 785 |
| 750160 | 486568 | 486587 | CAATAATAGAGACTTTACCA | 79 | 786 |
| 750161 | 486812 | 486831 | ATATATTATGTAAATGTAAC | 78 | 787 |
| 750162 | 486824 | 486843 | AGGATGGAAAAGATATATTA | 76 | 788 |
| 750163 | 486842 | 486861 | AAACAGGTTGAAAATGAAAG | 79 | 789 |

TABLE 12-continued

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750164 | 487049 | 487068 | AAAGGCAATATTGAAGGAAA | 72 | 790 |
| 750165 | 487267 | 487286 | GAATTGAGTTAATAATTCCT | 57 | 791 |
| 750166 | 487304 | 487323 | TCTCACAGAGAAAGAGGTGG | 21 | 792 |
| 750167 | 487314 | 487333 | TTTTCTATAATCTCACAGAG | 43 | 793 |
| 750168 | 487341 | 487360 | GGCTCAGAAAACATCCTTTT | 35 | 794 |
| 750169 | 487437 | 487456 | ATTTAATTTACACTTAATTA | 93 | 795 |
| 750170 | 487464 | 487483 | ACTTTCCTCTGCTTATAACT | 22 | 796 |
| 750171 | 487469 | 487488 | ACTATACTTTCCTCTGCTTA | 28 | 797 |
| 750172 | 487589 | 487608 | AGCAATTAGAAATCACATGA | 21 | 798 |
| 750173 | 487724 | 487743 | AAAGCAGTAAACAATAAGTG | 53 | 799 |
| 750174 | 487739 | 487758 | TCATATGTAAATCCAAAAGC | 57 | 800 |
| 750175 | 487772 | 487791 | CATTGTAAGGATAAGAGATA | 27 | 801 |
| 750176 | 487784 | 487803 | CAGTTTGAATTACATTGTAA | 29 | 802 |
| 750177 | 487804 | 487823 | AATTGAACTTAAATTGGCAT | 32 | 803 |
| 750178 | 487831 | 487850 | CTGCATAGGAGTAGAGTTTT | 31 | 804 |
| 750179 | 487877 | 487896 | AAGATGGAATTTGCGACATC | 50 | 805 |
| 750180 | 487921 | 487940 | ACATAAAAATGTATAAATCC | 70 | 806 |
| 750181 | 488018 | 488037 | ACTGATAAAGGTAAGCACAT | 31 | 807 |

TABLE 13

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617456 | 463905 | 463924 | CAACTGTTACCAAGACTTCA | 13 | 32 |
| 617457 | 465003 | 465022 | ATCTGCGAATAGAGGCCCTC | 38 | 33 |
| 617460 | 466539 | 466558 | TAGGTTGCATAAAGCCAGGC | 16 | 36 |
| 617461 | 466981 | 467000 | CACACATCTTGTTCCCTCAA | 11 | 37 |
| 617557 | 483977 | 483996 | ATCATGTGCATACCCAGGGT | 13 | 172 |
| 750398 | 510078 | 510097 | CAGAGAGGAGAGAAGGACAA | 45 | 808 |
| 750399 | 510104 | 510123 | GGCTAGGAAAATTCTCCTGG | 39 | 809 |
| 750400 | 510207 | 510226 | AGGGAGAGCTGTCCTAAGGC | 27 | 810 |
| 750401 | 510214 | 510233 | GATATCCAGGGAGAGCTGTC | 23 | 811 |
| 750402 | 510269 | 510288 | TTGAAGGGAAAATTATTAAT | 43 | 812 |
| 750403 | 510319 | 510338 | AGCTGGACGGACAGTGTTGC | 47 | 813 |
| 750404 | 510407 | 510426 | CAAGACATGCTAGGGACTCT | 38 | 814 |

TABLE 13-continued

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750405 | 510408 | 510427 | CCAAGACATGCTAGGGACTC | 30 | 815 |
| 750406 | 510416 | 510435 | GCCACAGTCCAAGACATGCT | 49 | 816 |
| 750407 | 510442 | 510461 | GCAGATAATCTGAAGATAGA | 43 | 817 |
| 750408 | 510515 | 510534 | TTTATTACAAACTGAAAGAG | 42 | 818 |
| 750409 | 510609 | 510628 | GGTCAGATAATGAGGGCCTT | 20 | 819 |
| 750410 | 510701 | 510720 | AGGATAGGTGTATGTGAGTG | 31 | 820 |
| 750411 | 510729 | 510748 | ATGAAGGTCAAGCCGAATCT | 50 | 821 |
| 750412 | 510798 | 510817 | AAAAGAAGTATGTGAAAGTA | 45 | 822 |
| 750413 | 510997 | 511016 | TGTCTCTAATCCTATTCCAA | 12 | 823 |
| 750414 | 511100 | 511119 | AGTCTTCATGATTTGGTAAA | 37 | 824 |
| 750415 | 511341 | 511360 | AGTAAGAGGCAGAATTATGT | 54 | 825 |
| 750416 | 511441 | 511460 | GGGCAGCAACAGCTCTTGAA | 16 | 826 |
| 750417 | 511503 | 511522 | TAATAATTAACAGTGACTGG | 24 | 827 |
| 750418 | 511529 | 511548 | AAGTCATTCCCCACCCTGGC | ND | 828 |
| 750419 | 511555 | 511574 | TCCAGCAGGGTGTATTCCAG | 47 | 829 |
| 750420 | 511567 | 511586 | TCAGCTGTGGTTTCCAGCAG | 34 | 830 |
| 750421 | 511579 | 511598 | GCTTAGAGAATCTCAGCTGT | 49 | 831 |
| 750422 | 511594 | 511613 | GGTTGGAAGCTGCCAGCTTA | 22 | 832 |
| 750423 | 511668 | 511687 | AATGGACTGCCGGCCTGGAG | 47 | 833 |
| 750424 | 511893 | 511912 | TGAACTACTTGGAGACCTTC | 55 | 834 |
| 750425 | 511895 | 511914 | AGTGAACTACTTGGAGACCT | 45 | 835 |
| 750426 | 512282 | 512301 | TCTTTTATTAAACCTAGTTT | 60 | 836 |
| 750427 | 512318 | 512337 | TTAGCTAGCTGTGGGTTTGC | 25 | 837 |
| 750428 | 512392 | 512411 | ACAAGAGCAGACATCTTTTT | 60 | 838 |
| 750429 | 512564 | 512583 | TGTAGCTTTTCTAAAATTCT | 34 | 839 |
| 750430 | 512570 | 512589 | GTATATTGTAGCTTTTCTAA | 16 | 840 |
| 750431 | 513010 | 513029 | CTTGATGGCTGTAGCTTGGT | 21 | 841 |
| 750432 | 513074 | 513093 | TTTCTGGATTCTCAGTCTTA | 28 | 842 |
| 750433 | 513189 | 513208 | TGCATTGGTATCTGTATATC | 23 | 843 |
| 750434 | 513219 | 513238 | GTTTCCTATTTCATCCATTT | 25 | 844 |
| 750435 | 513378 | 513397 | CTGGAGTGTAAGTAAATTCA | 33 | 845 |
| 750436 | 513442 | 513461 | ATACTCTTTCCACATTTCAG | 19 | 846 |
| 750437 | 513450 | 513469 | TCCTCTTGATACTCTTTCCA | 34 | 847 |
| 750438 | 513459 | 513478 | CTTAGGGTCTCCTCTTGATA | 32 | 848 |
| 750439 | 513467 | 513486 | CAGAGTGTCTTAGGGTCTCC | 27 | 849 |
| 750440 | 513620 | 513639 | ATATTTCTCAAATACTCTTC | 48 | 850 |

TABLE 13-continued

Reduction of UBE3A-ATS RNA by 8,000 nM 5-10-5 MOE gapmers with mixed PO/PS internucleoside linkages in vitro (40,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 750441 | 513760 | 513779 | TGTGCTAGAACACTATCTTG | 62 | 851 |
| 750442 | 513793 | 513812 | TGACTCTCATCTCCCTCTTC | 70 | 852 |
| 750443 | 513796 | 513815 | CCCTGACTCTCATCTCCCTC | 50 | 853 |
| 750444 | 513875 | 513894 | CCTTCCTTCTTTATACTGCC | 46 | 854 |
| 750445 | 513944 | 513963 | CATCAAAATCTCTCATTCCT | 22 | 855 |
| 750446 | 513947 | 513966 | AATCATCAAAATCTCTCATT | 35 | 856 |
| 750447 | 513951 | 513970 | CCCCAATCATCAAAATCTCT | 70 | 857 |
| 750448 | 514039 | 514058 | TAGTCAGTAGTCCTAAAAAC | 58 | 858 |
| 750449 | 514073 | 514092 | AGACCTCTGTCTCTGGGATT | 54 | 859 |
| 750450 | 514159 | 514178 | AAAGTCCTTACCTGTTCTTG | 36 | 860 |
| 750451 | 514326 | 514345 | TTCACCGAAAGTACAGTCTT | 54 | 861 |
| 750452 | 514330 | 514349 | TAGTTTCACCGAAAGTACAG | ND | 862 |
| 750453 | 514439 | 514458 | AAGTCTTTTCTCCCCTCCCC | 28 | 863 |
| 750454 | 514504 | 514523 | TCAACAGTGTTAGTGTGTAA | 45 | 864 |
| 750455 | 514513 | 514532 | CCTTTTACCTCAACAGTGTT | 35 | 865 |
| 750456 | 514673 | 514692 | AGACTAGTCCCTGTGTAGTC | 27 | 866 |
| 750457 | 514676 | 514695 | CCAAGACTAGTCCCTGTGTA | 40 | 867 |
| 750458 | 514701 | 514720 | AACTGTCAGAGGAAGAAATG | 62 | 868 |
| 750459 | 514861 | 514880 | CGAACAGAACTTGCCGATGT | 37 | 869 |
| 750460 | 514920 | 514939 | TTGTATAGGGAGATGATAGA | 39 | 870 |
| 750461 | 515069 | 515088 | TAACCTTTTATTATTATAGA | 55 | 871 |
| 750462 | 515111 | 515130 | TAAACTAAAGTAACTGGTTT | 55 | 872 |
| 750463 | 515143 | 515162 | CCAGGAAGCTCTGGAGGGAA | 23 | 873 |
| 750464 | 515187 | 515206 | ACTCTATTATATATTTTGGT | 28 | 874 |
| 750465 | 515215 | 515234 | GTTATAAAGTACTTTTTTT | 78 | 875 |
| 750466 | 515242 | 515261 | GGATACTTCCTCTACCCCAA | 30 | 876 |
| 750467 | 515247 | 515266 | ACAGTGGATACTTCCTCTAC | 40 | 877 |
| 750468 | 515318 | 515337 | CTGCCTTTTCATTACTATTT | 30 | 878 |
| 750469 | 515500 | 515519 | GTTTTAAAGTGGTAATTGAA | 44 | 879 |

TABLE 14

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617557 | 483977 | 483996 | ATCATGTGCATACCCAGGGT | 44 | 172 |
| 699781 | 483977 | 483996 | ATCATGTGCATACCCAGGGT | 51 | 172 |
| 749882 | 460115 | 460134 | ACTTTATAGTGTGGATGGTA | 39 | 586 |
| 750519 | 349103* | 349122* | GTCATCACCTCTCTTCAGGA | 17 | 181 |
| 1065269 | 432253 | 432272 | TCATCATCAACCTAACCGAG | 92 | 880 |
| 1065285 | 433960 | 433979 | CCATCTTGGAACCGGATGAC | 65 | 881 |
| 1065301 | 442413 | 442432 | GTAATTGAGGTGGCCATATC | 101 | 882 |
| 1065317 | 443132 | 443151 | GAGTCCTAAATGTCTCATAC | 81 | 883 |
| 1065333 | 444649 | 444668 | GGTTTTAGTCCACTGGTTCA | 44 | 884 |
| 1065349 | 445540 | 445559 | CTAGTCATGTATCTACAGCC | 88 | 885 |
| 1065365 | 446609 | 446628 | GTATATGGCTTACACAGGCT | 82 | 886 |
| 1065381 | 447599 | 447618 | GAGATTTCAGACTACCTGTA | 64 | 887 |
| 1065397 | 448125 | 448144 | ATTGACCCAGCCCATGGCAC | 97 | 888 |
| 1065413 | 448713 | 448732 | GCGCATTGAGCAAAATTCCA | 73 | 889 |
| 1065429 | 449066 | 449085 | GCATAACGATAATCATGTGG | 116 | 890 |
| 1065445 | 449627 | 449646 | GGCTATAGGCCATTTATTCA | 111 | 891 |
| 1065461 | 451295 | 451314 | TTGAATAACTACCTAGGCTC | 86 | 892 |
| 1065477 | 452310 | 452329 | CCGGTGCAGGAATCCAGGAT | 98 | 893 |
| 1065493 | 453797 | 453816 | TAACAATAAGATAAAGGCGC | 123 | 894 |
| 1065509 | 454580 | 454599 | GGCAAGCAAAGACTACACCG | 55 | 895 |
| 1065525 | 455169 | 455188 | GCTCCTAACATTGTATCCCC | 94 | 896 |
| 1065541 | 455476 | 455495 | CTCTACCAAGCTATCCAAGT | 78 | 897 |
| 1065557 | 456768 | 456787 | GTCCTATTGGAGGGCCGCAC | 39 | 898 |
| 1065573 | 457320 | 457339 | GTCCTCCAATAAGCTTCTGA | 48 | 899 |
| 1065589 | 458165 | 458184 | GGGACAATACTGCAATCCTT | 63 | 900 |
| 1065605 | 458957 | 458976 | AGAGACCTCAAGACCTATAG | 15 | 901 |
| 1065621 | 460348 | 460367 | GACTACTTCAACCTGATACC | 30 | 902 |
| 1065637 | 460957 | 460976 | GGGCATCATTAACATAAGCT | 69 | 903 |
| 1065652 | 461602 | 461621 | ACAAACGGGCTATGTGAGAT | 50 | 904 |
| 1065667 | 463052 | 463071 | CACTGAGTTTTGTAGTTCG | 32 | 905 |
| 1065682 | 463885 | 463904 | GGCAGTTGTGATAGTCAACA | 75 | 906 |
| 1065698 | 464994 | 465013 | TAGAGGCCCTCTTGTTTCAA | 44 | 907 |
| 1065713 | 465247 | 465266 | GGATTTATTGGTCATCTCG | 30 | 908 |
| 1065729 | 465664 | 465683 | GTAGTTACTTATACTGGTTC | 62 | 909 |
| 1065745 | 466276 | 466295 | GTGGGTTCCTGATGGAGTCC | 79 | 910 |
| 1065761 | 466540 | 466559 | CTAGGTTGCATAAAGCCAGG | 64 | 911 |

TABLE 14-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 1065777 | 467942 | 467961 | GCCTTAAAAGGGTTCCCTGT | 64 | 912 |
| 1065793 | 470287 | 470306 | GGTCATGATGTATGCCATTA | 39 | 913 |
| 1065809 | 474125 | 474144 | ATCTAGCTTGAATGGATACC | 55 | 914 |
| 1065825 | 475454 | 475473 | GTTCTTTCTCGGTCAAACTA | 41 | 915 |
| 1065841 | 476084 | 476103 | TACGAGTTGCTGGTTTCAGC | 46 | 916 |
| 1065857 | 478470 | 478489 | GGTTAGGGCTATGTTATGTT | 31 | 917 |
| 1065873 | 480382 | 480401 | GATTCCACTTGTGTATGCAC | 33 | 918 |
| 1065889 | 482148 | 482167 | CATATACTAAATGTTGCCGA | 30 | 919 |
| 1065905 | 483368 | 483387 | ATACAGAATTCAATGGACCC | 55 | 920 |
| 1065936 | 485657 | 485676 | GCCTAGGACCAGTTGGTTCA | 48 | 921 |
| 1065952 | 487409 | 487428 | GGCTGTTGTACATTCCTAGT | 65 | 922 |
| 1065968 | 489096 | 489115 | CCCTAAGCTTAGATATACCC | 88 | 923 |
| 1065984 | 489740 | 489759 | AGGTGGGAAACCGGTTCCCA | 100 | 924 |
| 1066000 | 493977 | 493996 | GGTCGGTCCCCACCAAAGGA | 58 | 925 |
| 1066016 | 496817 | 496836 | GCCATGTACGACCCTCATCA | 76 | 926 |
| 1066032 | 498218 | 498237 | TACTATAATACGGGACCTCA | 70 | 927 |
| 1066048 | 499683 | 499702 | ATCACATTCAAGGTAGCCCC | 48 | 928 |
| 1066064 | 500605 | 500624 | TGACCAGCAATAGGCTCTGC | 37 | 929 |
| 1066080 | 500895 | 500914 | ACTGGCCTTTGGGTCGGATA | 81 | 930 |
| 1066096 | 501395 | 501414 | GGAGTCCCCAGATAATGCAT | 91 | 931 |
| 1066112 | 501767 | 501786 | GGATGGGCTAAGAGTCACCT | 74 | 932 |
| 1066128 | 502370 | 502389 | GGTATTAAGGCCCTTGGCCA | 104 | 933 |
| 1066144 | 502741 | 502760 | GGCCCGATGACACCAGCCAC | 87 | 934 |
| 1066160 | 502949 | 502968 | TAACAGTCCTGTAACCAGAC | 90 | 935 |
| 1066176 | 503331 | 503350 | CCCCCTGAGATCCATGAGGT | 125 | 936 |
| 1066192 | 503867 | 503886 | CAGTTGTGCAGTTGTTAACT | 86 | 937 |
| 1066208 | 504141 | 504160 | AACCAGATGGCTGAGCTATT | 89 | 938 |
| 1066224 | 504518 | 504537 | TTAGGCCATACCTCTTCCAT | 77 | 939 |
| 1066240 | 505065 | 505084 | TTAGTCTGTTGTGTGACTCC | 73 | 940 |
| 1066256 | 505644 | 505663 | CCACCTAAGAGCTATCCGCT | 75 | 941 |
| 1066272 | 505945 | 505964 | GGCCGACCAGCTCTGAAAGT | 120 | 942 |
| 1066288 | 506275 | 506294 | ACCAGGGTGGTATTATAAAG | 102 | 943 |
| 1066304 | 506773 | 506792 | CAGGTTGTGGAGGTTGTTCC | 96 | 944 |
| 1066320 | 507371 | 507390 | GTTGTCTGGCATGGAGATCC | 60 | 945 |
| 1066336 | 507929 | 507948 | GTTGATTGGAGGCACTGCAG | 62 | 946 |
| 1066352 | 508488 | 508507 | TGGTGAGTAAATCAATCACG | 106 | 947 |

TABLE 14-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 1066368 | 509007 | 509026 | CCCTTCAACATGTGTTAACG | 62 | 948 |
| 1066384 | 509917 | 509936 | CGTGGCTGTACCTGCAGTGC | 49 | 949 |
| 1066400 | 510393 | 510412 | GACTCTGATTGATTCAGTGC | 93 | 950 |
| 1066416 | 510817 | 510836 | AGTACAAACCACTAAGGGTA | 114 | 951 |
| 1066432 | 511629 | 511648 | GTGCCATATAATGTTGAAGC | 71 | 952 |
| 1066448 | 511804 | 511823 | CGTGTCTGAACTGGCCTGTG | 75 | 953 |

TABLE 15

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 28 | 172 |
| 749882 | 460115 | 460134 | ACTTTATAGTGTGGATGGTA | 25 | 586 |
| 750519 | 349103# | 349122# | GTCATCACCTCTCTTCAGGA | 17 | 181 |
| 1065270 | 432284 | 432303 | CATAACCTCTCCTCGAGACA | 96 | 954 |
| 1065286 | 434182 | 434201 | TCTGTCACGCTTCCCTTGGC | 61 | 955 |
| 1065302 | 442470 | 442489 | TCACTGGTGTGGTATCATGC | 49 | 956 |
| 1065318 | 443199 | 443218 | GATTGCATCTCTTGCAGCAC | 63 | 957 |
| 1065334 | 444722 | 444741 | CTCACCTGTGTATATGAGTC | 93 | 958 |
| 1065350 | 445583 | 445602 | ACACTGTTAGAGCCCCCACA | 71 | 959 |
| 1065366 | 446657 | 446676 | GCATAGGAATGGGACCATAG | 88 | 960 |
| 1065382 | 447672 | 447691 | GCATCATACAGTGTATGC | 80 | 961 |
| 1065398 | 448219 | 448238 | CTTGTCTCACAATTGTTACC | 83 | 962 |
| 1065414 | 448721 | 448740 | TAACTGTAGCGCATTGAGCA | 91 | 963 |
| 1065430 | 449092 | 449111 | GCTAGTCACTCATTGAGAAG | 110 | 964 |
| 1065446 | 449633 | 449652 | TAGATAGGCTATAGGCCATT | 85 | 965 |
| 1065462 | 451694 | 451713 | GCATATATCTTAACTCACCC | 56 | 966 |
| 1065478 | 452315 | 452334 | AAAAGCCGGTGCAGGAATCC | 82 | 967 |
| 1065494 | 453918 | 453937 | TAAGTGCCCATGGCATAGTC | 65 | 968 |
| 1065510 | 454719 | 454738 | GAGTGCTGAAGAACATCCCC | 75 | 969 |
| 1065526 | 455213 | 455232 | CAAGTCTACTACCAATAAGT | 89 | 970 |
| 1065542 | 455567 | 455586 | CGTCAGCATTGCTTGATCTC | 89 | 971 |
| 1065558 | 456773 | 456792 | TATTTGTCCTATTGGAGGGC | ND | 972 |
| 1065574 | 457363 | 457382 | CATGGTGAGGGTCTCAATGA | 40 | 973 |
| 1065590 | 458238 | 458257 | GAGACATGTGCCAGTTCAAG | 19 | 974 |

TABLE 15-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065606 | 458987 | 459006 | GGACACTGGCACATCTATAG | 64 | 975 |
| 1065622 | 460362 | 460381 | CTGTATAACTGATTGACTAC | 51 | 976 |
| 1065638 | 461068 | 461087 | GCTCATCTATGGATTGCATT | 49 | 977 |
| 1065653 | 461604 | 461623 | GTACAAACGGGCTATGTGAG | 30 | 978 |
| 1065668 | 463144 | 463163 | AGCTATAGGTACCTGAAGTT | 49 | 979 |
| 1065683 | 464365 | 464384 | CTTAGCTTGCCCAGAGCATA | 57 | 980 |
| 1065699 | 464999 | 465018 | GCGAATAGAGGCCCTCTTGT | 49 | 981 |
| 1065714 | 465287 | 465306 | GATGTGTATAGGTGTTGGTC | 55 | 982 |
| 1065730 | 465808 | 465827 | CCATTTTGGTGCTATAACCC | 43 | 983 |
| 1065746 | 466283 | 466302 | CTTATAGGTGGGTTCCTGAT | 40 | 984 |
| 1065762 | 466543 | 466562 | TCTCTAGGTTGCATAAAGCC | 69 | 985 |
| 1065778 | 468007 | 468026 | GCACTTGTATAGTTCATCCC | 37 | 986 |
| 1065794 | 470316 | 470335 | ATCCTGCATCCGAGGCATGA | 76 | 987 |
| 1065810 | 474167 | 474186 | GTGGTTGCCTTAGTATTACA | 24 | 988 |
| 1065826 | 475512 | 475531 | CTGTAAGGTGATATCTATAC | 28 | 989 |
| 1065842 | 476090 | 476109 | TGTTCATACGAGTTGCTGGT | 52 | 990 |
| 1065858 | 478533 | 478552 | CGCAATGTATCAGGCAACAG | 29 | 991 |
| 1065874 | 480393 | 480412 | GAGGGCACAATGATTCCACT | 65 | 992 |
| 1065890 | 482162 | 482181 | GGAGTTACAAGTGTCATATA | 37 | 993 |
| 1065906 | 483424 | 483443 | GGCTCTATGCACTTAAGGGA | 42 | 994 |
| 1065921 | 483978 | 483997 | GATCATGTGCATACCCAGGG | 35 | 995 |
| 1065937 | 485769 | 485788 | GGTCAGATTCCTAAATACGC | 26 | 996 |
| 1065953 | 487600 | 487619 | GTGTCATATGTAGCAATTAG | 25 | 997 |
| 1065969 | 489319 | 489338 | CACCTGTATAGGAGAATTGT | 100 | 998 |
| 1065985 | 489776 | 489795 | CCACTCCCGTGGCAACATGA | 85 | 999 |
| 1066001 | 493985 | 494004 | GGGTAAGAGGTCGGTCCCCA | 48 | 1000 |
| 1066017 | 496821 | 496840 | GGAGGCCATGTACGACCCTC | 80 | 1001 |
| 1066033 | 498225 | 498244 | GCTGCAATACTATAATACGG | 56 | 1002 |
| 1066049 | 499792 | 499811 | AGCTGAGGTCACCGATCAGA | 83 | 1003 |
| 1066065 | 500610 | 500629 | AACAGTGACCAGCAATAGGC | 64 | 1004 |
| 1066081 | 500898 | 500917 | CTAACTGGCCTTTGGGTCGG | 107 | 1005 |
| 1066097 | 501399 | 501418 | GGGAGGAGTCCCCAGATAAT | 24 | 1006 |
| 1066113 | 501802 | 501821 | GGCCCAAGTGATGACATATC | 50 | 1007 |
| 1066129 | 502410 | 502429 | GTAAGGCATGGTCTTCCTTG | 79 | 1008 |
| 1066145 | 502746 | 502765 | AATATGGCCCGATGACACCA | 85 | 1009 |
| 1066161 | 502956 | 502975 | GCAAGATTAACAGTCCTGTA | 53 | 1010 |
| 1066177 | 503342 | 503361 | TCAGCTCAACACCCCCTGAG | 96 | 1011 |

TABLE 15-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1066193 | 503872 | 503891 | AGGGTCAGTTGTGCAGTTGT | 39 | 1012 |
| 1066209 | 504260 | 504279 | GCAAGGAATCATGTGGCTCC | 70 | 1013 |
| 1066225 | 504526 | 504545 | CCAAAGATTTAGGCCATACC | 55 | 1014 |
| 1066241 | 505106 | 505125 | GTAACCTTCACATAAGCTGC | 48 | 1015 |
| 1066257 | 505654 | 505673 | GGCCTAGCTTCCACCTAAGA | 104 | 1016 |
| 1066273 | 505949 | 505968 | CGCTGGCCGACCAGCTCTGA | ND | 1017 |
| 1066289 | 506280 | 506299 | CGTCTACCAGGGTGGTATTA | 41 | 1018 |
| 1066305 | 506779 | 506798 | ATACTCCAGGTTGTGGAGGT | 84 | 1019 |
| 1066321 | 507481 | 507500 | CAAATTGGTGAATGTTCCCC | 44 | 1020 |
| 1066337 | 508000 | 508019 | TCTCATGACCACCTAATTGA | 72 | 1021 |
| 1066353 | 508571 | 508590 | CCGTGCTGCTTTCTTGAGTG | 92 | 1022 |
| 1066369 | 509052 | 509071 | ACATGCTTGCATCCAGGCCC | 53 | 1023 |
| 1066385 | 510017 | 510036 | CGGAACCCACAGTAGAGGCA | 46 | 1024 |
| 1066401 | 510398 | 510417 | CTAGGGACTCTGATTGATTC | 45 | 1025 |
| 1066417 | 510827 | 510846 | ACCAGGCATAAGTACAAACC | 62 | 1026 |
| 1066433 | 511633 | 511652 | CTGAGTGCCATATAATGTTG | 71 | 1027 |
| 1066449 | 511822 | 511841 | AAGGCTCTCAGGGTAAGACG | 42 | 1028 |

TABLE 16

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 52 | 172 |
| 749882 | 460115 | 460134 | ACTTTATAGTGTGGATGGTA | 22 | 586 |
| 750519 | 349103# | 349122# | GTCATCACCTCTCTTCAGGA | 12 | 181 |
| 1065259 | 430439 | 430458 | CGTGGAACACTGACCCATCA | 73 | 1029 |
| 1065275 | 432915 | 432934 | CAGCATGTAACTCATGTTGT | 75 | 1030 |
| 1065291 | 441514 | 441533 | GTTCTAAAGTCGGTTGTGTC | 57 | 1031 |
| 1065307 | 442648 | 442667 | AGAGTAGGCCAGGTGTCAAA | 60 | 1032 |
| 1065323 | 443577 | 443596 | TACCAGTGAGTAAACTGGCC | 89 | 1033 |
| 1065339 | 444914 | 444933 | GTACTCCCCATGCACACTTG | 48 | 1034 |
| 1065355 | 445958 | 445977 | ACGGATTATCATACCCTCCC | 115 | 1035 |
| 1065371 | 446805 | 446824 | GTCTTGTAAACCCTTACCAG | 83 | 1036 |
| 1065387 | 447818 | 447837 | CCGTTACTTAAGCTGTGGTA | 88 | 1037 |
| 1065403 | 448458 | 448477 | TAGTGCCAGTAGGACTTACT | 75 | 1038 |

TABLE 16-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065419 | 448827 | 448846 | GGACCCTTAAGTCATAAAGA | 78 | 1039 |
| 1065435 | 449209 | 449228 | GACCAAATGAGCATCACATC | 69 | 1040 |
| 1065451 | 449704 | 449723 | CCTGTATGTATGGCTTATGC | 73 | 1041 |
| 1065467 | 452181 | 452200 | ATCCATAGTGATCTGGGAAC | 77 | 1042 |
| 1065483 | 453133 | 453152 | ACTATAATTGGGAATGGTCA | 77 | 1043 |
| 1065499 | 454160 | 454179 | GATTTGACCCTTATGGAGAC | 104 | 1044 |
| 1065515 | 454855 | 454874 | TATTCCCTATCCAGGGTAGA | 96 | 1045 |
| 1065531 | 455296 | 455315 | TTATCCTGTTGCAATAGAAC | 81 | 1046 |
| 1065547 | 456499 | 456518 | ATTAGATTAAAATCTGGCCG | 93 | 1047 |
| 1065563 | 456886 | 456905 | GACTCATAAGACAGGATGCC | 87 | 1048 |
| 1065579 | 457738 | 457757 | CCAGCCAGGTGTCTTATATC | 18 | 1049 |
| 1065595 | 458523 | 458542 | CAGTTGTGTATTGACTAAGT | 23 | 1050 |
| 1065611 | 459549 | 459568 | AAGACTATCCTGGTATGACT | 56 | 1051 |
| 1065627 | 460624 | 460643 | TCGATGTTCTTGCTTCCCTG | 32 | 1052 |
| 1065642 | 461446 | 461465 | GGCAGCTCCTGACAAATTAG | 22 | 1053 |
| 1065658 | 461694 | 461713 | AGACCCTCCCTTAATGTAA | 53 | 1054 |
| 1065673 | 463249 | 463268 | ACCTGGGTATTGCTGTCCAA | 41 | 1055 |
| 1065688 | 464458 | 464477 | CTCACCCTTTACTAAGGTGC | 75 | 1056 |
| 1065703 | 465140 | 465159 | CCATTGGTATGAGAGATGCT | 72 | 1057 |
| 1065719 | 465386 | 465405 | GTCAGACTTATTGAGGATGG | 27 | 1058 |
| 1065735 | 465932 | 465951 | TTACTCCTCTGGTGTGCTGA | 29 | 1059 |
| 1065751 | 466372 | 466391 | GCGCACTTGGGAGCCAGCCA | 68 | 1060 |
| 1065767 | 467076 | 467095 | TTACTGACTGGCCTTAGGAG | 38 | 1061 |
| 1065783 | 468351 | 468370 | GTAGTATGCATTGACAAGCT | 32 | 1062 |
| 1065799 | 471923 | 471942 | GAGTATATTACCTCCAGGTT | 27 | 1063 |
| 1065815 | 474614 | 474633 | GTATTGCTGCTCTAGCTCTA | 49 | 1064 |
| 1065831 | 475841 | 475860 | ACGGACCTCATACAGTGAGT | 31 | 1065 |
| 1065847 | 476213 | 476232 | GGGCTCTTGGAAGTCTAGTT | 59 | 1066 |
| 1065863 | 479124 | 479143 | ACATACTTGGTTGCAGACGC | 26 | 1067 |
| 1065879 | 480825 | 480844 | TAGGTTTGCGGATGCCAGTG | 50 | 1068 |
| 1065895 | 482771 | 482790 | TACACAGTGGGATTTGCCCC | 59 | 1069 |
| 1065911 | 483853 | 483872 | ATGGCCTGACTAGGCATTGA | 76 | 1070 |
| 1065926 | 484302 | 484321 | GGTTACTAGGGCCAGAGAAT | 42 | 1071 |
| 1065942 | 486355 | 486374 | TGTTAATAGACTGCGATTAT | 56 | 1072 |
| 1065958 | 487839 | 487858 | GGGCGGAGCTGCATAGGAGT | 51 | 1073 |
| 1065974 | 489522 | 489541 | ACAATGGACCACCTAAGACC | 96 | 1074 |
| 1065990 | 489953 | 489972 | CAACCCTTACTCTGCCAGGG | 80 | 1075 |

TABLE 16-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1066006 | 494491 | 494510 | TGTGCAATAGCCTAAATGCC | 82 | 1076 |
| 1066022 | 497436 | 497455 | CTACTATGAAGTTATGCACC | 69 | 1077 |
| 1066038 | 499100 | 499119 | GTTAGCCTTACAGCAAATAC | 52 | 1078 |
| 1066054 | 500359 | 500378 | TACTAATTAGCAAGCCACTG | 52 | 1079 |
| 1066070 | 500766 | 500785 | GTGTCAAATCAATTTGTGCC | 47 | 1080 |
| 1066086 | 501001 | 501020 | CTAAGCACATCCGATAGTCA | 49 | 1081 |
| 1066102 | 501563 | 501582 | GGAGTGCTCTTTGTGGATGC | 39 | 1082 |
| 1066118 | 502117 | 502136 | ACCCATGGCTCATCAGTGGG | 91 | 1083 |
| 1066134 | 502447 | 502466 | GGCAGCTCTTTGTAGGCCCA | 60 | 1084 |
| 1066150 | 502782 | 502801 | GGAGTGGGTTCCTATAAGGA | 53 | 1085 |
| 1066166 | 503100 | 503119 | GGACTAATAGGCCTTTCTAC | 61 | 1086 |
| 1066182 | 503399 | 503418 | CTACAGTACCAGGTCATTTG | 45 | 1087 |
| 1066198 | 503946 | 503965 | CACCACCAACCTTAAATAGT | 80 | 1088 |
| 1066214 | 504395 | 504414 | CCATGCCACAGATTGGCTTG | 64 | 1089 |
| 1066230 | 504654 | 504673 | CGGAGCCTTACGCTTGGCTG | 66 | 1090 |
| 1066246 | 505185 | 505204 | CAGTCTGTCTCTGTGTACCG | 46 | 1091 |
| 1066262 | 505741 | 505760 | GGTTGACAGGACATGCTGTC | 58 | 1092 |
| 1066278 | 506119 | 506138 | GTTAGCCGAGCATTGGCTTC | 84 | 1093 |
| 1066294 | 506589 | 506608 | CCCATGGTGGTGGAATGCTG | 102 | 1094 |
| 1066310 | 506992 | 507011 | TCCCGCACCATGCATTCTGA | 43 | 1095 |
| 1066326 | 507684 | 507703 | TCAGCTTCCTTCAGTGGGCG | 65 | 1096 |
| 1066342 | 508193 | 508212 | GATCTCACACATGGCACTGC | 71 | 1097 |
| 1066358 | 508691 | 508710 | TACCAGTAAAGGGTAGTATA | 49 | 1098 |
| 1066374 | 509110 | 509129 | GTAAATATACACTTGGGCCC | 73 | 1099 |
| 1066390 | 510117 | 510136 | TAGCTGAACCTGTGGCTAGG | 60 | 1100 |
| 1066406 | 510654 | 510673 | AGTGTCAGGCTGTAAGGGAT | 59 | 1101 |
| 1066422 | 510901 | 510920 | GCCATAGGTTTCAGGCTGAT | 46 | 1102 |
| 1066438 | 511707 | 511726 | GAGATGGGCTATGAGCCATC | 84 | 1103 |

TABLE 17

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 32 | 172 |
| 749882 | 460115 | 460134 | ACTTTATAGTGTGGATGGTA | 21 | 586 |

TABLE 17-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 750519 | 349103# | 349122# | GTCATCACCTCTCTTCAGGA | 8 | 181 |
| 1065264 | 430601 | 430620 | GGACCAGCGGGCCGAACGCA | 101 | 1104 |
| 1065280 | 433410 | 433429 | ATGCAAAGGTGTCGATTTGT | 47 | 1105 |
| 1065296 | 441815 | 441834 | GGTCCATAGATGTCAGTTAC | 27 | 1106 |
| 1065312 | 442767 | 442786 | ATTAATGTTCTATGGTGGAT | 46 | 1107 |
| 1065328 | 443839 | 443858 | GGAGTAGAATGCCCACTGGG | 53 | 1108 |
| 1065344 | 445212 | 445231 | GAGACCTGAATATACCTTAC | 55 | 1109 |
| 1065360 | 446498 | 446517 | GGTATGCCAGGTTTTTGACA | 49 | 1110 |
| 1065376 | 447152 | 447171 | CCGTGTAATGACACACCTCT | 67 | 1111 |
| 1065392 | 447922 | 447941 | AGGCTATAGTCAAAGGGTGG | 46 | 1112 |
| 1065408 | 448614 | 448633 | GTGTCAGTCAATCATTGAGA | 75 | 1113 |
| 1065424 | 449001 | 449020 | GGTCTTATTTACCATTGGCA | 63 | 1114 |
| 1065440 | 449470 | 449489 | TAACATGTTGCTTGCACTCC | 85 | 1115 |
| 1065456 | 450017 | 450036 | GCTCAAACTAGAATACCCCA | 81 | 1116 |
| 1065472 | 452261 | 452280 | GTCTAGGTCTCACGCTGTGT | 96 | 1117 |
| 1065488 | 453235 | 453254 | GACAGTGGAGTCAAGTTGGT | 106 | 1118 |
| 1065504 | 454462 | 454481 | GGACTCCACACACCTACTAG | 107 | 1119 |
| 1065520 | 455019 | 455038 | GTGGGATGGCTGTCAATGCT | 56 | 1120 |
| 1065536 | 455341 | 455360 | GATAATTGAGGAGTTCACCA | 81 | 1121 |
| 1065552 | 220313 456682 | 220332 456701 | GATCCAAACAAGCACCCTCC | 85 | 1122 |
| 1065568 | 457020 | 457039 | TATCACAGTTGCTTGACCCT | 70 | 1123 |
| 1065584 | 457982 | 458001 | GATCTATTATGAGGGCATCA | 39 | 1124 |
| 1065600 | 458571 | 458590 | AGCTTTAGTATGTCGAGAAC | 20 | 1125 |
| 1065616 | 460107 | 460126 | GTGTGGATGGTATCCTGGTC | 26 | 1126 |
| 1065632 | 460711 | 460730 | GGAATGCTTGATCTGTGGGC | 25* | 1127 |
| 1065647 | 461518 | 461537 | GCTAGACTAGTTGAAATCGG | 44 | 1128 |
| 1065663 | 462056 | 462075 | CCCTCCCATCAGTGAAGATT | 78 | 1129 |
| 1065677 | 463767 | 463786 | GCTTTAGAGGTCAAATAGTG | 50 | 1130 |
| 1065693 | 464784 | 464803 | CTGGTCTTCCTCGAGGATAG | 69 | 1131 |
| 1065708 | 465236 | 465255 | GTCATCTCGGGTATATAAAT | 30 | 1132 |
| 1065724 | 465561 | 465580 | GGACAAGTCTTATAGAGAAC | 52 | 1133 |
| 1065740 | 466229 | 466248 | GTTCCAAGTATGGGCTGCTG | 44 | 1134 |
| 1065756 | 466426 | 466445 | GTCAACATGTGCTTGCAAGC | 35 | 1135 |
| 1065772 | 467425 | 467444 | GCTGTTGATACGCTCCTTCA | 37 | 1136 |
| 1065788 | 469130 | 469149 | GAGGCACTGAAGTTCACTAC | 37 | 1137 |
| 1065804 | 472937 | 472956 | AGGGTCCCACTTGTTTAGGT | 44 | 1138 |

TABLE 17-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065820 | 474883 | 474902 | CGTATTAAGGTGTTGTATGA | 40 | 1139 |
| 1065836 | 475943 | 475962 | CCTTGTGACAATAGTAGTGA | 54 | 1140 |
| 1065852 | 476443 | 476462 | GGCTAGATGGAGCTTGAGCC | 94 | 1141 |
| 1065868 | 479997 | 480016 | CGTGAGCTATCTGTACAAAA | 24 | 1142 |
| 1065884 | 481441 | 481460 | GTGCATAATGGTCTACCACA | 32 | 1143 |
| 1065900 | 482857 | 482876 | TGAAGATAGGTCAGTTAACG | 58 | 1144 |
| 1065916 | 483925 | 483944 | GTTAAGCTTTCACCTATAGG | 33 | 1145 |
| 1065931 | 484601 | 484620 | TGATCATATGGGTGGTCGCT | 46 | 1146 |
| 1065947 | 487134 | 487153 | ATTGTCCTCCTGGTAACCAC | 28 | 1147 |
| 1065963 | 488572 | 488591 | GGGACTGGTGCCACACCATC | 55 | 1148 |
| 1065979 | 489629 | 489648 | CTAACCTGGATCTCAGATAG | 75 | 1149 |
| 1065995 | 493844 | 493863 | CTGGGCCCCAATTCAGTAAT | 98 | 1150 |
| 1066011 | 495399 | 495418 | TTGGTAAAGGAGGGAATCGG | ND | 1151 |
| 1066027 | 498030 | 498049 | TCCAGGATATATGTTAGTCC | 46 | 1152 |
| 1066043 | 499291 | 499310 | TAGCTACAATAAGTTGTAGC | 94 | 1153 |
| 1066059 | 500494 | 500513 | GAGGGCCATGTTAAAGGCCT | 119 | 1154 |
| 1066075 | 500861 | 500880 | TTTTGGTAGGTAACTACGGG | 41 | 1155 |
| 1066091 | 501335 | 501354 | TGTAGCTCAGCTCAATGTGT | 58 | 1156 |
| 1066107 | 501628 | 501647 | GAACTGCACTGGGTTGTCTC | 58 | 1157 |
| 1066123 | 502162 | 502181 | GTATTGCACTCACATACTGT | 61 | 1158 |
| 1066139 | 502579 | 502598 | AGCCAATGCGCAAGAAAAGT | 69 | 1159 |
| 1066155 | 502824 | 502843 | CATAGGCATAAAGCCTCCTA | 79 | 1160 |
| 1066171 | 503139 | 503158 | TCCCAGAAATGGTCCTCGCA | 86 | 1161 |
| 1066187 | 503480 | 503499 | ATGTGGGTCTGCACCAAGTT | 86 | 1162 |
| 1066203 | 504077 | 504096 | GGTGAACTCCTGTGACTGAT | 52 | 1163 |
| 1066219 | 504441 | 504460 | GTGGAGTAGGTATATTAGTC | 32 | 1164 |
| 1066235 | 504825 | 504844 | GTATTCCTGAAGTAGTCCTG | 36 | 1165 |
| 1066251 | 505330 | 505349 | AGAAATTGGGCCGCCTCTGT | 58 | 1166 |
| 1066267 | 505817 | 505836 | GTGCTTAGTGAACTGTGGGC | 55 | 1167 |
| 1066283 | 506185 | 506204 | CCGGCATGCATCAGCTCTGA | 34 | 1168 |
| 1066299 | 506693 | 506712 | TAAGAAGCTTGCCTTTCGAT | 96 | 1169 |
| 1066315 | 507250 | 507269 | GCAGTGCTACTGTGCCCTTA | 58 | 1170 |
| 1066331 | 507818 | 507837 | TCCAGCCCTCAGTATATAGA | 62 | 1171 |
| 1066347 | 508285 | 508304 | CCGAAGTGGAAGTAGTCATG | 63 | 1172 |
| 1066363 | 508790 | 508809 | TGAATGCCACCGTGATTGCA | 50 | 1173 |
| 1066379 | 509416 | 509435 | CGTAGTGTCATCACCATAAA | 45 | 1174 |
| 1066395 | 510227 | 510246 | GTTGTGTCTGAGGGATATCC | 45 | 1175 |

TABLE 17-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1066411 | 510718 | 510737 | GCCGAATCTTGACATACAGG | 55 | 1176 |
| 1066427 | 511241 | 511260 | GATTACCAAAAAGGGACCAG | 48 | 1177 |
| 1066443 | 511766 | 511785 | CTCCTACCAATAATGGAGTC | 76 | 1178 |

TABLE 18

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 38 | 172 |
| 749882 | 460115 | 460134 | ACTTTATAGTGTGGATGGTA | 32 | 586 |
| 750519 | 349103# | 349122# | GTCATCACCTCTCTTCAGGA | 17 | 181 |
| 1065265 | 430612 | 430631 | CGGACACACTGGGACCAGCG | 90 | 1179 |
| 1065281 | 433463 | 433482 | GCTCCTATCAAGCTTTTCCC | 46 | 1180 |
| 1065297 | 441909 | 441928 | TGAGGTGCATTTTCTAGCCC | 78 | 1181 |
| 1065313 | 442830 | 442849 | ATCTATGGAGTCATCTCCCC | 76 | 1182 |
| 1065329 | 443979 | 443998 | GGTAGAGGTTAATCTATGTC | 59 | 1183 |
| 1065345 | 445310 | 445329 | CGTCGGTAAAGGAAGCTACT | 58 | 1184 |
| 1065361 | 446510 | 446529 | TCATAAGGACAAGGTATGCC | 73 | 1185 |
| 1065377 | 447310 | 447329 | GGACCTCATTAGATCAGTCA | 90 | 1186 |
| 1065393 | 448007 | 448026 | GGCAGTTGAGTGGTGTCAGT | 99 | 1187 |
| 1065409 | 448628 | 448647 | GGATTGCATCACATGTGTCA | 55 | 1188 |
| 1065425 | 449017 | 449036 | TATAAGTGTCCATAAAGGTC | 90 | 1189 |
| 1065441 | 449475 | 449494 | GGCATTAACATGTTGCTTGC | 66 | 1190 |
| 1065457 | 450095 | 450114 | GAATTGATAAGTGGTCTTCT | 86 | 1191 |
| 1065473 | 452266 | 452285 | GGGAAGTCTAGGTCTCACGC | ND | 1192 |
| 1065489 | 453243 | 453262 | CTACATATGACAGTGGAGTC | 89 | 1193 |
| 1065505 | 454467 | 454486 | TGAGTGGACTCCACACACCT | 84 | 1194 |
| 1065521 | 455028 | 455047 | GATATTGCAGTGGGATGGCT | 60 | 1195 |
| 1065537 | 455360 | 455379 | CGTGATAGTGCTATTGTGAG | 60 | 1196 |
| 1065553 | 220317 456686 | 220336 456705 | CATCGATCCAAACAAGCACC | 74 | 1197 |
| 1065569 | 457233 | 457252 | GCTTAGCTACTCACCCCTGT | 70 | 1198 |
| 1065585 | 457989 | 458008 | CCCACTTGATCTATTATGAG | 64 | 1199 |
| 1065601 | 458790 | 458809 | CCCTAATATAGGGCAGATGA | 59 | 1200 |
| 1065617 | 460108 | 460127 | AGTGTGGATGGTATCCTGGT | 44 | 1201 |
| 1065633 | 460736 | 460755 | GGATTTGAGCCTGCTATGTC | 15* | 1202 |

TABLE 18-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065648 | 461524 | 461543 | CATTCAGCTAGACTAGTTGA | 70 | 1203 |
| 1065664 | 462061 | 462080 | TATGGCCCTCCCATCAGTGA | 49 | 1204 |
| 1065678 | 463775 | 463794 | TAGATTGGGCTTTAGAGGTC | 33 | 1205 |
| 1065694 | 464788 | 464807 | ACATCTGGTCTTCCTCGAGG | 61 | 1206 |
| 1065709 | 465237 | 465256 | GGTCATCTCGGGTATATAAA | 17 | 1207 |
| 1065725 | 465591 | 465610 | ACCGAAGGAGTTCCTTTAGC | 40 | 1208 |
| 1065741 | 466233 | 466252 | GGCAGTTCCAAGTATGGGCT | 76 | 1209 |
| 1065757 | 466438 | 466457 | GTGGAGCCAGCTGTCAACAT | 66 | 1210 |
| 1065773 | 467718 | 467737 | TGGAATGTATCCTGTACGGG | 52 | 1211 |
| 1065789 | 469377 | 469396 | GTGTTATACTATTGTGGTGC | 42 | 1212 |
| 1065805 | 472944 | 472963 | GTTTGTTAGGGTCCCACTTG | 49 | 1213 |
| 1065821 | 474901 | 474920 | TCTGCTATTGTTGGATATCG | 33 | 1214 |
| 1065837 | 475988 | 476007 | ATGGTTAGTTTAAGAAATCG | 65 | 1215 |
| 1065853 | 478295 | 478314 | GAGTCCTGGTTGATGTGGTG | 65 | 1216 |
| 1065869 | 480141 | 480160 | ACGGGCATGCTTTATAATTA | 73 | 1217 |
| 1065885 | 481448 | 481467 | AACCTTTGTGCATAATGGTC | 82 | 1218 |
| 1065901 | 482908 | 482927 | CACTCTATAGGTTCAAGCAG | 37 | 1219 |
| 1065917 | 483964 | 483983 | CCAGGGTAGGATTCATGGTC | 63 | 1220 |
| 1065932 | 484673 | 484692 | TGTTGTATGCAGGTTCATCA | 31 | 1221 |
| 1065948 | 487139 | 487158 | GATACATTGTCCTCCTGGTA | 35 | 1222 |
| 1065964 | 488637 | 488656 | ACACTTGAAGCTGTTGAGTC | 66 | 1223 |
| 1065980 | 489652 | 489671 | CGTGAAGGAATGATCTCTCT | 61 | 1224 |
| 1065996 | 493855 | 493874 | CCTAATCTATGCTGGGCCCC | 75 | 1225 |
| 1066012 | 495430 | 495449 | GAGAGTAAGTTACTAGAGGC | 59 | 1226 |
| 1066028 | 498180 | 498199 | TGGGCAGATTGATCACCTAG | 93 | 1227 |
| 1066044 | 499495 | 499514 | TACTAGGCCTGCTCTACTGG | 71 | 1228 |
| 1066060 | 500523 | 500542 | TTAGAGGTCAAGCCCTGTGT | 63 | 1229 |
| 1066076 | 500885 | 500904 | GGGTCGGATATAGCTTTTAC | 31 | 1230 |
| 1066092 | 501340 | 501359 | GCTTATGTAGCTCAGCTCAA | 33 | 1231 |
| 1066108 | 501701 | 501720 | TTGGGACATCCCAAAGTTAC | 80 | 1232 |
| 1066124 | 502205 | 502224 | GGAACATCATGTTAGCCATC | 44 | 1233 |
| 1066140 | 502588 | 502607 | GATGCATCAAGCCAATGCGC | 41 | 1234 |
| 1066156 | 502882 | 502901 | GAACCTCTACAGAGAGACTA | 65 | 1235 |
| 1066172 | 503154 | 503173 | GTTCTGTATACACCATCCCA | 56 | 1236 |
| 1066188 | 503485 | 503504 | GCAAAATGTGGGTCTGCACC | 96 | 1237 |
| 1066204 | 504082 | 504101 | TAACTGGTGAACTCCTGTGA | 98 | 1238 |

TABLE 18-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1066220 | 504449 | 504468 | CCCCAGAAGTGGAGTAGGTA | ND | 1239 |
| 1066236 | 504866 | 504885 | CCTCAAGATCAACAGACCCC | 81 | 1240 |
| 1066252 | 505543 | 505562 | CAGTCAGGTACAGGTGTTGG | 52 | 1241 |
| 1066268 | 505823 | 505842 | GTGAGGGTGCTTAGTGAACT | 54 | 1242 |
| 1066284 | 506196 | 506215 | GTCAGAACAATCCGGCATGC | 50 | 1243 |
| 1066300 | 506730 | 506749 | GAGTGCTCCACACTTCTGTC | 65 | 1244 |
| 1066316 | 507254 | 507273 | GCTTGCAGTGCTACTGTGCC | 95 | 1245 |
| 1066332 | 507900 | 507919 | TCGATACCTGCTTTTGTGAC | 69 | 1246 |
| 1066348 | 508290 | 508309 | CATAACCGAAGTGGAAGTAG | 71 | 1247 |
| 1066364 | 508901 | 508920 | TACTTCATGACTGCCTAGTT | 78 | 1248 |
| 1066380 | 509434 | 509453 | AAGAAGGGCATATATCTACG | 72 | 1249 |
| 1066396 | 510312 | 510331 | CGGACAGTGTTGCTGTTAGG | 39 | 1250 |
| 1066412 | 510724 | 510743 | GGTCAAGCCGAATCTTGACA | 68 | 1251 |
| 1066428 | 511490 | 511509 | TGACTGGGTAAGGCAGGATC | 50 | 1252 |
| 1066444 | 511770 | 511789 | AGTACTCCTACCAATAATGG | 77 | 1253 |

TABLE 19

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 17 | 172 |
| 749882 | 460115 | 460134 | ACTTTATAGTGTGGATGGTA | 26 | 586 |
| 750519 | 349103# | 349122# | GTCATCACCTCTCTTCAGGA | 12 | 181 |
| 1065271 | 432577 | 432596 | GGCAGTGCATTCAACTGTAG | 75 | 1254 |
| 1065287 | 440156 | 440175 | CGTGGGTTAGTCCAAGTAAC | 49 | 1255 |
| 1065303 | 442546 | 442565 | GCCCATTATGTAGTCTATAG | 37 | 1256 |
| 1065319 | 443234 | 443253 | GACGAAGGCAGTCACTCTGC | 88 | 1257 |
| 1065335 | 444735 | 444754 | GGGAGAACTACATCTCACCT | 63 | 1258 |
| 1065351 | 445658 | 445677 | CCCCATTACCACGGTCTCTT | 63 | 1259 |
| 1065367 | 446675 | 446694 | AGCAGTCTTTATCTACAGGC | 85 | 1260 |
| 1065383 | 447745 | 447764 | TTGATGACCTGGTAAGGGAT | 76 | 1261 |
| 1065399 | 448290 | 448309 | CGCAATAAGATTCCATTGCC | 83 | 1262 |
| 1065415 | 448725 | 448744 | ACGATAACTGTAGCGCATTG | 70 | 1263 |
| 1065431 | 449100 | 449119 | GCAAGTATGCTAGTCACTCA | 82 | 1264 |
| 1065447 | 449637 | 449656 | CCATTAGATAGGCTATAGGC | 77 | 1265 |
| 1065463 | 452066 | 452085 | TCGCCGCTGATTTTAAAGAT | 97 | 1266 |

TABLE 19-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065479 | 452320 | 452339 | GGTTCAAAAGCCGGTGCAGG | 83 | 1267 |
| 1065495 | 453926 | 453945 | GTTGTTCTTAAGTGCCCATG | 61 | 1268 |
| 1065511 | 454740 | 454759 | GCACTTTGCATGAGAATAGG | 60 | 1269 |
| 1065527 | 455219 | 455238 | TCCAGACAAGTCTACTACCA | 69 | 1270 |
| 1065543 | 455585 | 455604 | TCTACTCCTTGCTACAAACG | 84 | 1271 |
| 1065575 | 457378 | 457397 | CAATAGTGTAGGTGACATGG | 36 | 1273 |
| 1065591 | 458400 | 458419 | GCATGTGGGCCTCTATTAAG | 8 | 1274 |
| 1065607 | 459079 | 459098 | GTATGGTATCTTGCAGTAGC | 15 | 1275 |
| 1065623 | 460427 | 460446 | ATAGCCCTTTCAGCACACTT | 16 | 1276 |
| 1065639 | 461343 | 461362 | GCTGGCAATATGTCAACCTT | 36 | 1277 |
| 1065654 | 461605 | 461624 | TGTACAAACGGGCTATGTGA | 30 | 1278 |
| 1065669 | 463151 | 463170 | CATATGAAGCTATAGGTACC | 22 | 1279 |
| 1065684 | 464383 | 464402 | GGTAGTTCACAACTCTTCCT | 59 | 1280 |
| 1065700 | 465002 | 465021 | TCTGCGAATAGAGGCCCTCT | 49 | 1281 |
| 1065715 | 465301 | 465320 | GACACGCTGACTATGATGTG | 77 | 1282 |
| 1065731 | 465875 | 465894 | CTTGCCCATGGATGGTTGTC | 71 | 1283 |
| 1065747 | 466287 | 466306 | GTGGCTTATAGGTGGGTTCC | ND | 1284 |
| 1065763 | 466945 | 466964 | GGTTGTATGCCTTCTGCATT | 44 | 1285 |
| 1065779 | 468014 | 468033 | CCTTGCAGCACTTGTATAGT | 44 | 1286 |
| 1065795 | 470319 | 470338 | ACTATCCTGCATCCGAGGCA | 23 | 1287 |
| 1065811 | 474227 | 474246 | ATATAATTGAGGGCCACCAT | 74 | 1288 |
| 1065827 | 475597 | 475616 | CCTTTAGAGGGATTTGTGTA | 34 | 1289 |
| 1065843 | 476097 | 476116 | CTTAACATGTTCATACGAGT | 47 | 1290 |
| 1065859 | 478733 | 478752 | GCTGATCACATTACCCATCC | 24 | 1291 |
| 1065875 | 480518 | 480537 | GATGTATCACGCAAACAATT | 81 | 1292 |
| 1065891 | 482167 | 482186 | ACCAAGGAGTTACAAGTGTC | 62 | 1293 |
| 1065907 | 483587 | 483606 | GGCCAGGATGGTCAACCTTA | 50 | 1294 |
| 1065922 | 484119 | 484138 | TTTTTGCCACAGCCGCTTGG | 193 | 1295 |
| 1065938 | 485811 | 485830 | CGAATAATTGCATGCCAACT | 68 | 1296 |
| 1065954 | 487606 | 487625 | GGTTTAGTGTCATATGTAGC | 23 | 1297 |
| 1065970 | 489324 | 489343 | GCACACACCTGTATAGGAGA | 43 | 1298 |
| 1065986 | 489780 | 489799 | CCTGCCACTCCCGTGGCAAC | 95 | 1299 |
| 1066002 | 493989 | 494008 | TTATGGGTAAGAGGTCGGTC | ND | 1300 |
| 1066018 | 496826 | 496845 | GGTATGGAGGCCATGTACGA | 84 | 1301 |
| 1066034 | 498510 | 498529 | GCGCCCGGCAAGAGATTCAC | ND | 1302 |
| 1066050 | 499912 | 499931 | TTGCATAATAGGAGGTCCTT | 51 | 1303 |

TABLE 19-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1066066 | 500662 | 500681 | GGGCTTACAACCTCTCAATT | 74 | 1304 |
| 1066082 | 500899 | 500918 | CCTAACTGGCCTTTGGGTCG | 80 | 1305 |
| 1066098 | 501446 | 501465 | GTCTGCACAGGTGGCATAGA | 53 | 1306 |
| 1066114 | 501817 | 501836 | GTCCAGAGGTCATATGGCCC | 54 | 1307 |
| 1066130 | 502416 | 502435 | GCATAAGTAAGGCATGGTCT | 41 | 1308 |
| 1066146 | 502755 | 502774 | CTTCGGGCAAATATGGCCCG | 76 | 1309 |
| 1066162 | 503036 | 503055 | GGTGCTACAGTCATACTATC | 62 | 1310 |
| 1066178 | 503346 | 503365 | GTGATCAGCTCAACACCCCC | 65 | 1311 |
| 1066194 | 503878 | 503897 | TAATAAAGGGTCAGTTGTGC | 39 | 1312 |
| 1066210 | 504270 | 504289 | CACTGCCTAAGCAAGGAATC | 86 | 1313 |
| 1066226 | 504530 | 504549 | TGCCCCAAAGATTTAGGCCA | 69 | 1314 |
| 1066242 | 505115 | 505134 | TCAGACATGGTAACCTTCAC | 40 | 1315 |
| 1066258 | 505660 | 505679 | ATTGCAGGCCTAGCTTCCAC | 51 | 1316 |
| 1066274 | 506031 | 506050 | GGTATTGAGTAGGACTTCTC | 34 | 1317 |
| 1066290 | 506402 | 506421 | CTTAAGGAGGCAACTCCTGA | 51 | 1318 |
| 1066306 | 506781 | 506800 | ATATACTCCAGGTTGTGGAG | 66 | 1319 |
| 1066322 | 507526 | 507545 | GAGCCAGGTTCCTGTTCACG | 33 | 1320 |
| 1066338 | 508110 | 508129 | CCGTCTTTAGGAACTTAAAT | 43 | 1321 |
| 1066354 | 508581 | 508600 | AGCACAACCCCGTGCTGCT | 88 | 1322 |
| 1066370 | 509058 | 509077 | TACCCAACATGCTTGCATCC | 58 | 1323 |
| 1066386 | 510022 | 510041 | ATACACGGAACCCACAGTAG | 70 | 1324 |
| 1066402 | 510402 | 510421 | CATGCTAGGGACTCTGATTG | 69 | 1325 |
| 1066418 | 510832 | 510851 | GTTAGACCAGGCATAAGTAC | 44 | 1326 |
| 1066434 | 511638 | 511657 | TGCAGCTGAGTGCCATATAA | 56 | 1327 |
| 1066450 | 511890 | 511909 | ACTACTTGGAGACCTTCACC | 57 | 1328 |

TABLE 20

Reduction of UBE3A-ATS RNA by 7,000 nm 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 35 | 172 |
| 749882 | 460115 | 460134 | ACTTTATAGTGTGGATGGTA | 26 | 586 |
| 749902 | 461442 | 461461 | GCTCCTGACAAATTAGCACT | 61 | 1329 |
| 750519 | 349103# | 349122# | GTCATCACCTCTCTTCAGGA | 20 | 181 |
| 1065258 | 430419 | 430438 | CGGATGCAGGGCACCCTTGG | 96 | 1330 |
| 1065274 | 432770 | 432789 | CATGATATAAGGAGAAACGC | 63 | 1331 |

TABLE 20-continued

Reduction of UBE3A-ATS RNA by 7,000 nm 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065290 | 440729 | 440748 | ATCTTGCGGCTGTCTCCCAG | 64 | 1332 |
| 1065306 | 442613 | 442632 | TCCCATAGTTATATGGCTCA | 60 | 1333 |
| 1065322 | 443476 | 443495 | CTGCATGTTAGATTGGGCAT | 48 | 1334 |
| 1065338 | 444879 | 444898 | GCTGTGATGCTAGGATGCAT | 84 | 1335 |
| 1065354 | 445874 | 445893 | AGACATAGACCCCAGACGGT | 83 | 1336 |
| 1065370 | 446795 | 446814 | CCCTTACCAGAATAGCATCC | 81 | 1337 |
| 1065386 | 447803 | 447822 | TGGTAGACCACTGATTCCCC | 63 | 1338 |
| 1065402 | 448415 | 448434 | AGCAAGGGTCTTAGTGCCAA | 60 | 1339 |
| 1065418 | 448742 | 448761 | GTCTGTATATTTAGACCACG | 83 | 1340 |
| 1065434 | 449159 | 449178 | GTCAACATTATATCGATGCA | 64 | 1341 |
| 1065450 | 449697 | 449716 | GTATGGCTTATGCATGCTAT | 86 | 1342 |
| 1065466 | 452137 | 452156 | TGGGCAGGTCAACTTGGTAT | 66 | 1343 |
| 1065482 | 453037 | 453056 | AAAAGGTGATTAGGCGGCCG | 88 | 1344 |
| 1065498 | 454156 | 454175 | TGACCCTTATGGAGACTTAT | 74 | 1345 |
| 1065514 | 454846 | 454865 | TCCAGGGTAGAAGACTAGCA | 63 | 1346 |
| 1065530 | 455286 | 455305 | GCAATAGAACAGATGGCCAT | 97 | 1347 |
| 1065546 | 455764 | 455783 | GTACCAAAGTGGCTGCTCAC | 89 | 1348 |
| 1065562 | 456866 | 456885 | ACTGCCCTCTTCGAAGAGAT | 71 | 1349 |
| 1065578 | 457715 | 457734 | GATTATCTCAGACATGCCAT | 20 | 1350 |
| 1065594 | 458488 | 458507 | CCTTAAGCAAGGAGTTCACT | 39 | 1351 |
| 1065610 | 459543 | 459562 | ATCCTGGTATGACTGTCAGT | 45 | 1352 |
| 1065626 | 460538 | 460557 | GGCTCTCATCTAAATAAGCC | 75 | 1353 |
| 1065657 | 461674 | 461693 | AACCCTAAGGTGAAGTCTGT | 65 | 1354 |
| 1065672 | 463245 | 463264 | GGGTATTGCTGTCCAAATGG | 20 | 1355 |
| 1065687 | 464409 | 464428 | GTGTTATGGTTCCCATTCAG | 32 | 1356 |
| 1065702 | 465012 | 465031 | CCTGCTCAAATCTGCGAATA | 58 | 1357 |
| 1065718 | 465382 | 465401 | GACTTATTGAGGATGGTGTG | 53 | 1358 |
| 1065734 | 465894 | 465913 | TGAACTCCCACAAGGTACTC | 52 | 1359 |
| 1065750 | 466341 | 466360 | AGGCATTTGGAGCATTCGGG | 16 | 1360 |
| 1065766 | 467050 | 467069 | ACTTTCATCAGTTAGTCAGG | 30 | 1361 |
| 1065782 | 468343 | 468362 | CATTGACAAGCTATTGCAGC | 44 | 1362 |
| 1065798 | 470982 | 471001 | TTTTATGGCTTATAGCAGCG | 50 | 1363 |
| 1065814 | 474563 | 474582 | CACGCCCAAATGGAACTCTA | 38 | 1364 |
| 1065830 | 475827 | 475846 | GTGAGTTATAGAGTGTTCCC | 39 | 1365 |
| 1065846 | 476165 | 476184 | TGGGCACTTAGGAGTTCCTA | 73 | 1366 |
| 1065862 | 479069 | 479088 | GCTGTATCTGTGGTTTAGCA | 67 | 1367 |

TABLE 20-continued

Reduction of UBE3A-ATS RNA by 7,000 nm 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065878 | 480818 | 480837 | GCGGATGCCAGTGGCCGAGA | 40 | 1368 |
| 1065894 | 482519 | 482538 | GCTATACCCCTAGGATCAGA | 31 | 1369 |
| 1065910 | 483843 | 483862 | TAGGCATTGAATGAGGGCCC | 71 | 1370 |
| 1065925 | 484245 | 484264 | GTATGGACTTGTCTTATGGC | 57 | 1371 |
| 1065941 | 486351 | 486370 | AATAGACTGCGATTATACAA | 48 | 1372 |
| 1065957 | 487807 | 487826 | CGCAATTGAACTTAAATTGG | 56 | 1373 |
| 1065973 | 489517 | 489536 | GGACCACCTAAGACCTCAAG | 50 | 1374 |
| 1065989 | 489908 | 489927 | GGCTAAAGTAATCTTATGGG | 48 | 1375 |
| 1066005 | 494490 | 494509 | GTGCAATAGCCTAAATGCCA | 69 | 1376 |
| 1066021 | 497267 | 497286 | GGATTAGGCAGCTTCACTAC | 44 | 1377 |
| 1066037 | 499088 | 499107 | GCAAATACAATGGTAATCGC | 30 | 1378 |
| 1066053 | 500286 | 500305 | CTGGTGTACATTGGATATGA | 57 | 1379 |
| 1066069 | 500694 | 500713 | GCAAGAGGTACTGTAAGCCC | 70 | 1380 |
| 1066085 | 500993 | 501012 | ATCCGATAGTCAAACTATGA | 52 | 1381 |
| 1066101 | 501532 | 501551 | AAACACCCTTCCAATGAGGG | 75 | 1382 |
| 1066117 | 501986 | 502005 | GTTCACTAGCATCTGCTACA | 46 | 1383 |
| 1066133 | 502443 | 502462 | GCTCTTTGTAGGCCCAAGGG | 38 | 1384 |
| 1066149 | 502776 | 502795 | GGTTCCTATAAGGAATAGGC | 73 | 1385 |
| 1066165 | 503096 | 503115 | TAATAGGCCTTTCTACAGCT | 77 | 1386 |
| 1066181 | 503374 | 503393 | CCCCAGGGTCATAGGAGTGT | 80 | 1387 |
| 1066197 | 503944 | 503963 | CCACCAACCTTAAATAGTAG | 70 | 1388 |
| 1066213 | 504390 | 504409 | CCACAGATTGGCTTGGAATG | 74 | 1389 |
| 1066229 | 504650 | 504669 | GCCTTACGCTTGGCTGACAT | 73 | 1390 |
| 1066245 | 505179 | 505198 | GTCTCTGTGTACCGAGCTCA | 63 | 1391 |
| 1066261 | 505724 | 505743 | GTCTGGTGGCCAAGTGCTTC | 70 | 1392 |
| 1066277 | 506116 | 506135 | AGCCGAGCATTGGCTTCATA | 73 | 1393 |
| 1066293 | 506584 | 506603 | GGTGGTGGAATGCTGTCCAC | 89 | 1394 |
| 1066309 | 506869 | 506888 | CTCCACCAAATACTTAGCCC | 67 | 1395 |
| 1066325 | 507649 | 507668 | TAAATGTCAGGAGGTCCCCC | 55 | 1396 |
| 1066341 | 508126 | 508145 | CCTTGGGTTATTCTTACCGT | 55 | 1397 |
| 1066357 | 508680 | 508699 | GGTAGTATAAGAATGGTTCC | 54 | 1398 |
| 1066373 | 509104 | 509123 | ATACACTTGGGCCCAAATGG | 78 | 1399 |
| 1066389 | 510039 | 510058 | GCTAGCATTTGAGAGTTATA | 43 | 1400 |
| 1066405 | 510647 | 510666 | GGCTGTAAGGGATTAAGATG | 79 | 1401 |
| 1066421 | 510853 | 510872 | CTGTTACAGGGAGACAATCT | 56 | 1402 |
| 1066437 | 511678 | 511697 | ACCCTGCACAAATGGACTGC | 103 | 1403 |

TABLE 21

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 42 | 172 |
| 749882 | 460115 | 460134 | ACTTTATAGTGTGGATGGTA | 33 | 586 |
| 750519 | 349103# | 349122# | GTCATCACCTCTCTTCAGGA | 21 | 181 |
| 1065268 | 432234 | 432253 | GGGCACCCCGTCACCGTGC | 82 | 1404 |
| 1065284 | 433765 | 433784 | AGATTTTCCGACCTATGTCA | 62 | 1405 |
| 1065300 | 442386 | 442405 | ATCGCCATGGTCACTTGCCA | 63 | 1406 |
| 1065316 | 443032 | 443051 | GGCAAAGCAAGTTCGCCACA | 91 | 1407 |
| 1065332 | 444610 | 444629 | ATCATACAGGTCACTTGGCT | 63 | 1408 |
| 1065348 | 445505 | 445524 | ATTGGACTAGGTAACAGTGA | 103 | 1409 |
| 1065364 | 446595 | 446614 | CAGGCTATTTCTTAGTGGAC | 59 | 1410 |
| 1065380 | 447562 | 447581 | CAAGGGTAACCTATAGCTGA | 116 | 1411 |
| 1065396 | 448099 | 448118 | GCATATGCACACTTGGATCA | 89 | 1412 |
| 1065412 | 448676 | 448695 | ACCCTGAAAACAATCAATCG | 102 | 1413 |
| 1065428 | 449061 | 449080 | ACGATAATCATGTGGCCTGA | 85 | 1414 |
| 1065444 | 449593 | 449612 | GACTAACTATACAGGTCTCT | 107 | 1415 |
| 1065460 | 451288 | 451307 | ACTACCTAGGCTCACTTGCT | 83 | 1416 |
| 1065476 | 452297 | 452316 | CCAGGATGCTAATGTCCTA | 69 | 1417 |
| 1065492 | 453781 | 453800 | GCGCTTTCACCAAGAAATTT | 78 | 1418 |
| 1065508 | 454575 | 454594 | GCAAAGACTACACCGTGACA | 109 | 1419 |
| 1065524 | 455153 | 455172 | CCCCTGCATTCAGCTTATAG | 85 | 1420 |
| 1065540 | 455467 | 455486 | GCTATCCAAGTGACACAGTA | 77 | 1421 |
| 1065556 | 456757 | 456776 | GGGCCGCACATCTGGACCTC | 104 | 1422 |
| 1065572 | 457293 | 457312 | TACAAAACGACCTAAAGACC | 83 | 1423 |
| 1065588 | 458156 | 458175 | CTGCAATCCTTAAGACTTGA | 37 | 1424 |
| 1065604 | 458952 | 458971 | CCTCAAGACCTATAGGACCT | 37 | 1425 |
| 1065620 | 460284 | 460303 | ATACATTGCCAGCACTAAGG | 60 | 1426 |
| 1065636 | 460849 | 460868 | GATTTACCACACATATAGGC | 36 | 1427 |
| 1065651 | 461597 | 461616 | CGGGCTATGTGAGATAATTC | 15 | 1428 |
| 1065666 | 462686 | 462705 | GGCTGACATGCCCCTTTTAA | 142 | 1429 |
| 1065681 | 463881 | 463900 | GTTGTGATAGTCAACAATTG | 89 | 1430 |
| 1065697 | 464991 | 465010 | AGGCCCTCTTGTTTCAATTG | 63 | 1431 |
| 1065712 | 465246 | 465265 | GATTTATTGGTCATCTCGG | 30 | 1432 |
| 1065728 | 465606 | 465625 | GCCTTTCTATTTCAGACCGA | 35 | 1433 |
| 1065744 | 466263 | 466282 | GGAGTCCATGAAGTAACTGG | 62 | 1434 |
| 1065760 | 466538 | 466557 | AGGTTGCATAAAGCCAGGCC | 55 | 1435 |
| 1065776 | 467801 | 467820 | CCCTCTTAGTGATTGGTGGT | 63 | 1436 |
| 1065792 | 470049 | 470068 | GGTTGGCAGTCTTCACCAGT | 62 | 1437 |

TABLE 21-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065808 | 474120 | 474139 | GCTTGAATGGATACCAATTA | 40 | 1438 |
| 1065824 | 475447 | 475466 | CTCGGTCAAACTAATAATAC | 53 | 1439 |
| 1065840 | 476015 | 476034 | CCAGTTTTCGCCCGTTACCT | 32 | 1440 |
| 1065856 | 478440 | 478459 | GTAGCTATAGGTGTCACATA | 21 | 1441 |
| 1065872 | 480351 | 480370 | GCCTCAAATATGTGATGCAC | 45 | 1442 |
| 1065888 | 482108 | 482127 | GAATGGCAATACATCCGTGT | 80 | 1443 |
| 1065904 | 483359 | 483378 | TCAATGGACCCACATGATCA | 63 | 1444 |
| 1065920 | 483971 | 483990 | TGCATACCCAGGGTAGGATT | 29 | 1445 |
| 1065935 | 485084 | 485103 | TCTAATACTACAACGATGGA | 84 | 1446 |
| 1065951 | 487204 | 487223 | AACCTTCCTAAAATCCCCGA | 52 | 1447 |
| 1065967 | 489085 | 489104 | GATATACCCAGTTAATCAGT | 63 | 1448 |
| 1065983 | 489731 | 489750 | ACCGGTTCCCAATTTTCTCC | 78 | 140 |
| 1065999 | 493889 | 493908 | TTGGCAGATGTAACCTATTC | 52 | 1449 |
| 1066015 | 496809 | 496828 | CGACCCTCATCACTTTTTGA | 73 | 1450 |
| 1066031 | 498209 | 498228 | ACGGGACCTCAATACTCTAC | 56 | 1451 |
| 1066047 | 499678 | 499697 | ATTCAAGGTAGCCCCAATAC | 89 | 1452 |
| 1066063 | 500578 | 500597 | CTACTGGCATCAGTCAAAAC | 84 | 150 |
| 1066079 | 500894 | 500913 | CTGGCCTTTGGGTCGGATAT | 86 | 1453 |
| 1066095 | 501390 | 501409 | CCCCAGATAATGCATAGATC | 98 | 1454 |
| 1066111 | 501763 | 501782 | GGGCTAAGAGTCACCTGTAT | 59 | 1455 |
| 1066127 | 502360 | 502379 | CCCTTGGCCACCTGACTTCG | 77 | 1456 |
| 1066143 | 502629 | 502648 | TTGGCTCAGTGTTCACTTCG | 52 | 1457 |
| 1066159 | 502939 | 502958 | GTAACCAGACCCAAGGCACT | 62 | 1458 |
| 1066175 | 503325 | 503344 | GAGATCCATGAGGTATATAC | 55 | 1459 |
| 1066191 | 503815 | 503834 | GCCCAGTGCCCTATAGGTCA | 67 | 1460 |
| 1066207 | 504127 | 504146 | GCTATTTCATTAAGTCACCC | 39 | 1461 |
| 1066223 | 504502 | 504521 | CCATGGAATGGCTGTCATGC | 72 | 1462 |
| 1066239 | 504974 | 504993 | TTATCTTCTTAGGGTCGACT | 38 | 1463 |
| 1066255 | 505635 | 505654 | AGCTATCCGCTTCCCAAGGG | 47 | 1464 |
| 1066271 | 505906 | 505925 | CCCTGAGATGCTAGTTGGGC | 85 | 1465 |
| 1066287 | 506256 | 506275 | GTATGTCCTTGGAGGTGAGC | 88 | 1466 |
| 1066303 | 506744 | 506763 | GCCTTTCATTTTGGGAGTGC | 48 | 1467 |
| 1066319 | 507364 | 507383 | GGCATGGAGATCCAACCTGT | 96 | 1468 |
| 1066335 | 507919 | 507938 | GGCACTGCAGGATAGCCATT | 95 | 1469 |
| 1066351 | 508470 | 508489 | CGTTATCCTAAGAAGTGACT | 58 | 1470 |
| 1066367 | 509003 | 509022 | TCAACATGTGTTAACGGAAC | 63 | 1471 |

TABLE 21-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1066383 | 509910 | 509929 | GTACCTGCAGTGCATAGAGC | 52 | 1472 |
| 1066399 | 510387 | 510406 | GATTGATTCAGTGCTCATGC | 49 | 1473 |
| 1066415 | 510747 | 510766 | ACTGCAGATAGGTAGGTGAT | 43 | 1474 |
| 1066431 | 511593 | 511612 | GTTGGAAGCTGCCAGCTTAG | 96 | 1475 |
| 1066447 | 511795 | 511814 | ACTGGCCTGTGGCAGTTAAC | 80 | 1476 |

TABLE 22

Reduction of UBE3A-ATS RNA by 7,000 nM 5-10-5 MOE gapmers with with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 617557 | 483977 | 483996 | ATCATGTGCATACCCAGGGT | 28 | 172 |
| 749882 | 460115 | 460134 | ACTTTATAGTGTGGATGGTA | 24 | 586 |
| 750519 | 349103# | 349122# | GTCATCACCTCTCTTCAGGA | 17 | 181 |
| 1065261 | 430489 | 430508 | GCGCTGGCTCACGCATGCTC | 65 | 1477 |
| 1065277 | 432989 | 433008 | CCTAGAGTTTCCTTCTCCCG | 79 | 1478 |
| 1065293 | 441703 | 441722 | GGGATGCCAATGCCTCCAAC | 97 | 1479 |
| 1065309 | 442707 | 442726 | TAAATTGCCCTGGGTGCAGC | 71 | 1480 |
| 1065325 | 443778 | 443797 | GCCCTTTCAGGACCAACTGG | 107 | 1481 |
| 1065341 | 445116 | 445135 | GTTGGGCAAACAAGTTACCC | 92 | 1482 |
| 1065357 | 446183 | 446202 | GGGACCCCAATTTACTACGC | 112 | 1483 |
| 1065373 | 446912 | 446931 | CTTCTTGCAAGGATTGGCAC | 69 | 1484 |
| 1065389 | 447847 | 447866 | ACTGAGATGTGTGATACTCC | 70 | 1485 |
| 1065405 | 448471 | 448490 | CCACTCAATAGAATAGTGCC | 123 | 1486 |
| 1065421 | 448838 | 448857 | CCCAATTGCAAGGACCCTTA | 80 | 1487 |
| 1065437 | 449334 | 449353 | GAACATGTAGCCATAATGCC | 65 | 1488 |
| 1065453 | 449867 | 449886 | GAGTGGCATCCTTAAATCCT | 66 | 1489 |
| 1065469 | 452204 | 452223 | TAATTGGTCAAGTAAACAGC | 73 | 1490 |
| 1065485 | 453199 | 453218 | TCCACCGTTACTGATTATCT | 51 | 1491 |
| 1065501 | 454230 | 454249 | CAAGTCCCACCATGTTAATC | 87 | 1492 |
| 1065517 | 454913 | 454932 | GTTAGGATCTATTTGACAGC | 67 | 1493 |
| 1065533 | 455318 | 455337 | AGGCCTGCTCCGAATGTGTT | 107 | 1494 |
| 1065549 | 456627 | 456646 | GTGCATGGTTATCTAATGCA | 87 | 1495 |
| 1065565 | 456917 | 456936 | TTGGGTCACTAGGCACACTA | 110 | 1496 |
| 1065581 | 457899 | 457918 | TGACTAGTTCGATAAGTTTT | 48 | 1497 |
| 1065597 | 458561 | 458580 | TGTCGAGAACTCAAAAGGTG | 31 | 1498 |
| 1065613 | 459646 | 459665 | CTGTATAGTTTACCCAGGCA | 24 | 1499 |

TABLE 22-continued

Reduction of UBE3A-ATS RNA by 7,000 nM 5-10-5 MOE gapmers with with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 1065629 | 460641 | 460660 | CAGAGTGCATTGGCAACTCG | 50 | 1500 |
| 1065644 | 461457 | 461476 | GATCTTGGTAAGGCAGCTCC | 29 | 1501 |
| 1065660 | 461891 | 461910 | CAATTTGGTCCCATTGTAGT | 84 | 1502 |
| 1065675 | 463503 | 463522 | TCTATCAAGGCTGTTATTGG | 40 | 1503 |
| 1065690 | 464528 | 464547 | GCTCAGTTAGGTTAGTGCAC | 23 | 1504 |
| 1065705 | 465162 | 465181 | TCTAGGGCTCCAGTTTATGT | 78 | 1505 |
| 1065721 | 465442 | 465461 | CTTTGGTTATGTACATTGCC | 73 | 1506 |
| 1065737 | 466098 | 466117 | GCCTGTATGTCTTGAGAAAC | 78 | 1507 |
| 1065753 | 466388 | 466407 | CTCGCTTTTCACAGGAGCGC | 36 | 1508 |
| 1065769 | 467300 | 467319 | TCACAGAGTAGTCTATTGGT | 43 | 1509 |
| 1065785 | 468922 | 468941 | GTAAGTATAGATGCCTCTCC | 33 | 1510 |
| 1065801 | 472475 | 472494 | GCAAACTTTAGGAGTGTGTT | 60 | 1511 |
| 1065817 | 474799 | 474818 | GGTATTGACACCTCCAACTG | 18 | 1512 |
| 1065833 | 475854 | 475873 | ATATAAGGGTAATACGGACC | 39 | 1513 |
| 1065849 | 476362 | 476381 | GCCCCCTGCCGTGTGAAAGA | 72 | 1514 |
| 1065865 | 479579 | 479598 | CTTCAAGACTAAGGTAGGGA | 38 | 1515 |
| 1065881 | 480923 | 480942 | GTATGCGAAGCGAACGAAGC | 75 | 1516 |
| 1065897 | 482786 | 482805 | CCTAAAAAACCCGTGTACAC | 62 | 1517 |
| 1065913 | 483907 | 483926 | GGTGGCCTTCAGTCAGTACA | 57 | 1518 |
| 1065928 | 484317 | 484336 | GCCCAGACTCATGCTGGTTA | 96 | 1519 |
| 1065944 | 486448 | 486467 | ATACTTCACCTAATAGCACC | 86 | 1520 |
| 1065960 | 488086 | 488105 | GGAGTTCTTTAGGTTGGAAC | 62 | 1521 |
| 1065976 | 489542 | 489561 | GCAACTATGGGTGGAGACAT | 53 | 1522 |
| 1065992 | 493191 | 493210 | TCGGGCCAGGTCCAGGCGCA | 52 | 1523 |
| 1066008 | 495127 | 495146 | GCTGTCATATGGGAACTACG | 57 | 1524 |
| 1066024 | 497743 | 497762 | CAAACCTACGCCAATAAAGA | 86 | 1525 |
| 1066040 | 499138 | 499157 | TTTATCGCTTAAAGTAGCCT | 83 | 1526 |
| 1066056 | 500407 | 500426 | CGTATATCGAATACCCTCAA | 33 | 1527 |
| 1066072 | 500818 | 500837 | GTAAGAGTTAGCTATTCCCC | 30 | 1528 |
| 1066088 | 501153 | 501172 | CAGTAAAGAGCCACCTAAGG | 71 | 1529 |
| 1066104 | 501574 | 501593 | GGCAAGGCTAAGGAGTGCTC | 54 | 1530 |
| 1066120 | 502129 | 502148 | GCTACCCATTAGACCCATGG | 34 | 1531 |
| 1066136 | 502502 | 502521 | GGAGTCCCTGTGTCATTGGA | 37 | 1532 |
| 1066152 | 502803 | 502822 | GGATGTAGCCCATCAACCCT | 77 | 1533 |
| 1066168 | 503118 | 503137 | CCAGTTAATCTCTGACATGG | 57 | 1534 |
| 1066184 | 503422 | 503441 | AGGTGATGACACCCCTACCA | 57 | 1535 |

TABLE 22-continued

Reduction of UBE3A-ATS RNA by 7,000 nM 5-10-5 MOE gapmers with with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (%UTC) | SEQ ID NO |
|---|---|---|---|---|---|
| 1066200 | 503960 | 503979 | GGGTGTCTCTTTGACACCAC | 76 | 1536 |
| 1066216 | 504419 | 504438 | AGGCAGTCAGGGTAATGCTA | 76 | 1537 |
| 1066232 | 504667 | 504686 | CCTTCTGTCCCAACGGAGCC | 111 | 1538 |
| 1066248 | 505213 | 505232 | CTCTCGCTGAGGACACATCA | 64 | 1539 |
| 1066264 | 505791 | 505810 | ACCACAGGGTACTATTCTGG | 64 | 1540 |
| 1066280 | 506126 | 506145 | CTGCTCTGTTAGCCGAGCAT | 75 | 1541 |
| 1066296 | 506634 | 506653 | GCTTGTATGCCCCACTGGAG | 59 | 1542 |
| 1066312 | 507213 | 507232 | GCTTGCCATGTTTTATAGAC | 80 | 1543 |
| 1066328 | 507762 | 507781 | CTCAGGATCGCTGGCCATTT | 62 | 1544 |
| 1066344 | 508223 | 508242 | GCCTAAAGGTAGTTCTCCCT | 57 | 1545 |
| 1066360 | 508731 | 508750 | CAGGAGGGTGTCAACCAGAC | 75 | 1546 |
| 1066376 | 509178 | 509197 | GGCAGATAACCTCCAAGTGC | 95 | 1547 |
| 1066392 | 510128 | 510147 | CACATAGACCATAGCTGAAC | 56 | 1548 |
| 1066408 | 510668 | 510687 | GTCTAGTATGTCTGAGTGTC | 87 | 1549 |
| 1066424 | 511065 | 511084 | GACTCGGGACATTTAGGATG | 72 | 1550 |
| 1066440 | 511730 | 511749 | ATAGGCCACGCTGGTCACTG | 48 | 1551 |

TABLE 23

Reduction of UBE3A-ATS RNA by 7,000 nM 5-10-5 MOE gapmers with with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 39 | 172 |
| 749882 | 460115 | 460134 | ACTTTATAGTGTGGATGGTA | 16 | 586 |
| 750519 | 349103# | 349122# | GTCATCACCTCTCTTCAGGA | 14 | 181 |
| 1065260 | 430471 | 430490 | TCATCCTCTATGGACCCACG | 83 | 1552 |
| 1065276 | 432973 | 432992 | CCCGACTTACATTACCTACC | 69 | 1553 |
| 1065292 | 441621 | 441640 | ATGATCTGCTGTTCAGTGCG | 45 | 1554 |
| 1065308 | 442687 | 442706 | AGGCCAAGTGGTGCTCTTCC | 58 | 1555 |
| 1065324 | 443691 | 443710 | ATTCAGATACTAGTTTACCC | 36 | 1556 |
| 1065340 | 445011 | 445030 | TCTAGGTAGGCTGAGCCTCA | 89 | 1557 |
| 1065356 | 445972 | 445991 | TTGTCTTGGAACATACGGAT | 81 | 1558 |
| 1065372 | 446901 | 446920 | GATTGGCACTATTTTGAGCC | 113 | 1559 |
| 1065388 | 447835 | 447854 | GATACTCCAAATATGACCCG | 80 | 1560 |
| 1065404 | 448465 | 448484 | AATAGAATAGTGCCAGTAGG | 70 | 1561 |
| 1065420 | 448833 | 448852 | TTGCAAGGACCCTTAAGTCA | 87 | 1562 |
| 1065436 | 449328 | 449347 | GTAGCCATAATGCCATAGTC | 61 | 1563 |

TABLE 23-continued

Reduction of UBE3A-ATS RNA by 7,000 nM 5-10-5 MOE gapmers with with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065452 | 449862 | 449881 | GCATCCTTAAATCCTGGTTG | 97 | 1564 |
| 1065468 | 452186 | 452205 | GCAATATCCATAGTGATCTG | 84 | 1565 |
| 1065484 | 453194 | 453213 | CGTTACTGATTATCTTATCC | 72 | 1566 |
| 1065500 | 454225 | 454244 | CCCACCATGTTAATCAAGGC | 69 | 1567 |
| 1065516 | 454863 | 454882 | CAGGTGTATATTCCCTATCC | 70 | 1568 |
| 1065532 | 455309 | 455328 | CCGAATGTGTTATTTATCCT | 58 | 1569 |
| 1065548 | 456621 | 456640 | GGTTATCTAATGCATCATCA | 71 | 1570 |
| 1065564 | 456909 | 456928 | CTAGGCACACTAAAGTGCAC | 84 | 1571 |
| 1065580 | 457802 | 457821 | GATGCAATCACAGCAAGTAC | 68 | 1572 |
| 1065596 | 458560 | 458579 | GTCGAGAACTCAAAAGGTGA | 51 | 1573 |
| 1065612 | 459639 | 459658 | GTTTACCCAGGCAATGGCTC | 70 | 1574 |
| 1065628 | 460629 | 460648 | GCAACTCGATGTTCTTGCTT | 79 | 1575 |
| 1065643 | 461453 | 461472 | TTGGTAAGGCAGCTCCTGAC | 58 | 1576 |
| 1065659 | 461886 | 461905 | TGGTCCCATTGTAGTTGTGT | 50 | 1577 |
| 1065674 | 463502 | 463521 | CTATCAAGGCTGTTATTGGT | 29 | 1578 |
| 1065689 | 464477 | 464496 | GCTTCTAACTAACATGCCTC | 61 | 1579 |
| 1065704 | 465158 | 465177 | GGGCTCCAGTTTATGTATCC | 79 | 1580 |
| 1065720 | 465418 | 465437 | TAGCCTGCATGGTTTACAGT | 72 | 1581 |
| 1065736 | 466030 | 466049 | GGGCTCTTGTTACTGAGCTG | 79 | 1582 |
| 1065752 | 466382 | 466401 | TTTCACAGGAGCGCACTTGG | 55 | 1583 |
| 1065768 | 467295 | 467314 | GAGTAGTCTATTGGTGTTCC | 27 | 1584 |
| 1065784 | 468404 | 468423 | CCCTACCCTTGCATGCTATG | 75 | 1585 |
| 1065800 | 471928 | 471947 | CCATTGAGTATATTACCTCC | 45 | 1586 |
| 1065816 | 474789 | 474808 | CCTCCAACTGTAATCATTGA | 65 | 1587 |
| 1065832 | 475846 | 475865 | GTAATACGGACCTCATACAG | 61 | 1588 |
| 1065848 | 476316 | 476335 | ACTACTTGTCCCCTGGGCTT | 45 | 1589 |
| 1065864 | 479256 | 479275 | CTTGCTTGTATGGTCTGATG | 63 | 1590 |
| 1065880 | 480830 | 480849 | AAAAGTAGGTTTGCGGATGC | 61 | 1591 |
| 1065896 | 482778 | 482797 | ACCCGTGTACACAGTGGGAT | 60 | 1592 |
| 1065912 | 483896 | 483915 | GTCAGTACACAAGCAGGTAG | 68 | 1593 |
| 1065927 | 484309 | 484328 | TCATGCTGGTTACTAGGGCC | 42 | 1594 |
| 1065943 | 486378 | 486397 | GTTAGGCCACAAGACTTAAT | 51 | 1595 |
| 1065959 | 488046 | 488065 | CTCAAACCCGTATAAAGATG | 58 | 1596 |
| 1065975 | 489527 | 489546 | GACATACAATGGACCACCTA | 70 | 1597 |
| 1065991 | 489961 | 489980 | GGAAGTTCCAACCCTTACTC | 64 | 1598 |
| 1066007 | 494921 | 494940 | GAATCCACTACATGGGATTA | 110 | 1599 |

TABLE 23-continued

Reduction of UBE3A-ATS RNA by 7,000 nM 5-10-5 MOE gapmers with with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1066023 | 497674 | 497693 | GACTAAGCCCGAAAGTTAGC | 79 | 1600 |
| 1066039 | 499133 | 499152 | CGCTTAAAGTAGCCTAAGGA | 41 | 1601 |
| 1066055 | 500400 | 500419 | CGAATACCCTCAACTTCACC | 59 | 1602 |
| 1066071 | 500797 | 500816 | CAACCTTGATAGCAGCTTAT | 38 | 1603 |
| 1066087 | 501007 | 501026 | GTGAAACTAAGCACATCCGA | 77 | 1604 |
| 1066103 | 501569 | 501588 | GGCTAAGGAGTGCTCTTTGT | 66 | 1605 |
| 1066119 | 502125 | 502144 | CCCATTAGACCCATGGCTCA | 21 | 1606 |
| 1066135 | 502465 | 502484 | TACAACAGTCCCAGGCTAGG | 51 | 1607 |
| 1066151 | 502799 | 502818 | GTAGCCCATCAACCCTGGGA | 72 | 1608 |
| 1066167 | 503107 | 503126 | CTGACATGGACTAATAGGCC | 47 | 1609 |
| 1066183 | 503415 | 503434 | GACACCCTACCATGGCTAC | 54 | 1610 |
| 1066199 | 503956 | 503975 | GTCTCTTTGACACCACCAAC | 62 | 1611 |
| 1066215 | 504408 | 504427 | GTAATGCTATCTTCCATGCC | 47 | 1612 |
| 1066231 | 504661 | 504680 | GTCCCAACGGAGCCTTACGC | 62 | 1613 |
| 1066247 | 505200 | 505219 | CACATCAGCTGTTAGCAGTC | 64 | 1614 |
| 1066263 | 505749 | 505768 | ACTCTGTAGGTTGACAGGAC | 59 | 1615 |
| 1066279 | 506121 | 506140 | CTGTTAGCCGAGCATTGGCT | 88 | 1616 |
| 1066295 | 506628 | 506647 | ATGCCCCACTGGAGAAGTCT | 77 | 1617 |
| 1066311 | 506997 | 507016 | CGTCTTCCCGCACCATGCAT | 40 | 1618 |
| 1066327 | 507699 | 507718 | CGTGTCACTTTCAGGTCAGC | 59 | 1619 |
| 1066343 | 508216 | 508235 | GGTAGTTCTCCCTTCTGTCA | 73 | 1620 |
| 1066359 | 508726 | 508745 | GGGTGTCAACCAGACTTCCA | ND | 1621 |
| 1066375 | 509128 | 509147 | GCTCATCACAACTGGGTGGT | 35 | 1622 |
| 1066391 | 510121 | 510140 | ACCATAGCTGAACCTGTGGC | 62 | 1623 |
| 1066407 | 510659 | 510678 | GTCTGAGTGTCAGGCTGTAA | 68 | 1624 |
| 1066423 | 510905 | 510924 | GTGTGCCATAGGTTTCAGGC | 18 | 1625 |
| 1066439 | 511725 | 511744 | CCACGCTGGTCACTGAAAGA | 70 | 1626 |

TABLE 24

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 49 | 172 |
| 749882 | 460115 | 460134 | ACTTTATAGTGTGGATGGTA | 25 | 586 |

TABLE 24-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 750519 | 349103# | 349122# | GTCATCACCTCTCTTCAGGA | 10 | 181 |
| 1065266 | 432182 | 432201 | CCGCTCAATGCAGGACACCA | 79 | 1627 |
| 1065282 | 433495 | 433514 | TGCTCCATAGGTAAGATGGT | 82 | 1628 |
| 1065298 | 442149 | 442168 | TAGGCACTGCCTTTGTTGCG | 87 | 1629 |
| 1065314 | 442877 | 442896 | GTCGAAGACAATATAACATC | 59 | 1630 |
| 1065330 | 444418 | 444437 | ATCAGGGCACATGGAGTTGT | 21 | 1631 |
| 1065346 | 445359 | 445378 | CCCTTAGGTGGGAGTCTTCC | 128 | 1632 |
| 1065362 | 446536 | 446555 | GGCTCTAGACCATTGACTCA | 72 | 1633 |
| 1065378 | 447498 | 447517 | GTAGTGCCTCAATGATCCAC | 62 | 1634 |
| 1065394 | 448042 | 448061 | GGTAAAGTGGACTGGATGCC | 66 | 1635 |
| 1065410 | 448635 | 448654 | CTCATGAGGATTGCATCACA | 71 | 1636 |
| 1065426 | 449041 | 449060 | AGGAACGGCCCTGACTGTCA | 110 | 1637 |
| 1065442 | 449492 | 449511 | CCATATCAATAACAATTGGC | 111 | 1638 |
| 1065458 | 450273 | 450292 | GGAACTCCAGCCAGTGAATA | 96 | 1639 |
| 1065474 | 452270 | 452289 | ATGAGGGAAGTCTAGGTCTC | 80 | 1640 |
| 1065490 | 453360 | 453379 | ACATAGGCACTCTACTAGCT | 101 | 1641 |
| 1065506 | 454514 | 454533 | TATCAGTCATAGCTACACAC | 104 | 1642 |
| 1065522 | 455119 | 455138 | GGTGGATGTCTGACTTGACT | 61 | 1643 |
| 1065538 | 455426 | 455445 | GCTAAAGTTGTGGTCTACCA | 83 | 1644 |
| 1065554 | 220324 456693 | 220343 456712 | TTCTCATCATCGATCCAAAC | 60 | 1645 |
| 1065570 | 457238 | 457257 | TAATGGCTTAGCTACTCACC | 90 | 1646 |
| 1065586 | 457994 | 458013 | GAGAACCCACTTGATCTATT | 24 | 1647 |
| 1065602 | 458938 | 458957 | GGACCTCAGGAGATTGTACA | 35 | 1648 |
| 1065618 | 460111 | 460130 | TATAGTGTGGATGGTATCCT | 31 | 1649 |
| 1065634 | 460744 | 460763 | GTACACAGGGATTTGAGCCT | 12* | 1650 |
| 1065649 | 461528 | 461547 | GGAACATTCAGCTAGACTAG | 40 | 1651 |
| 1065665 | 462567 | 462586 | TAAATTGGTCTGGTTACAAG | 56 | 1652 |
| 1065679 | 463779 | 463798 | CCTATAGATTGGGCTTTAGA | 48 | 1653 |
| 1065695 | 464905 | 464924 | GTCTATATTTGGTAAGACAC | 69 | 1654 |
| 1065710 | 465240 | 465259 | ATTGGTCATCTCGGGTATAT | 18 | 1655 |
| 1065726 | 465596 | 465615 | TTCAGACCGAAGGAGTTCCT | 60 | 1656 |
| 1065742 | 466244 | 466263 | GTAGGATCTATGGCAGTTCC | 59 | 1657 |
| 1065758 | 466448 | 466467 | GTTCTACAGAGTGGAGCCAG | 65 | 1658 |
| 1065774 | 467791 | 467810 | GATTGGTGGTTTATTCATCG | 47 | 1659 |
| 1065790 | 469893 | 469912 | TACCCATTGCAAGTTAACTA | 73 | 1660 |

TABLE 24-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065806 | 473260 | 473279 | TCCTAATAGTTGGAGGTGGT | ND | 1661 |
| 1065822 | 474959 | 474978 | CAGCCTAATATGTGTCATCC | 40 | 1662 |
| 1065838 | 476003 | 476022 | CGTTACCTCAATTCTATGGT | 49 | 1663 |
| 1065854 | 478299 | 478318 | ACTGGAGTCCTGGTTGATGT | 67 | 1664 |
| 1065870 | 480146 | 480165 | ACAAAACGGGCATGCTTTAT | 63 | 1665 |
| 1065886 | 481476 | 481495 | GCGGATAAATTGGATTTATC | 37 | 1666 |
| 1065902 | 483108 | 483127 | AGGCAATGGACTTAGTACAC | 21 | 1667 |
| 1065918 | 483965 | 483984 | CCCAGGGTAGGATTCATGGT | 45 | 1668 |
| 1065933 | 484683 | 484702 | CAAGTGATGATGTTGTATGC | 87 | 1669 |
| 1065949 | 487192 | 487211 | ATCCCCGAATGGGAGAGATT | 107 | 1670 |
| 1065965 | 489067 | 489086 | GTGAACGAATACTGTGGCAT | 59 | 1671 |
| 1065981 | 489671 | 489690 | CCAACCTGTCATGGGACTGC | 45 | 1672 |
| 1065997 | 493859 | 493878 | TAGGCCTAATCTATGCTGGG | 44 | 1673 |
| 1066013 | 496023 | 496042 | TCTCAAAAGACATTCGGTAC | 137 | 1674 |
| 1066029 | 498183 | 498202 | CCATGGGCAGATTGATCACC | 102 | 1675 |
| 1066045 | 499515 | 499534 | TGCCTAAGGGAGTTTGTCAC | 73 | 1676 |
| 1066061 | 500527 | 500546 | ATGTTTAGAGGTCAAGCCCT | 91 | 1677 |
| 1066077 | 500886 | 500905 | TGGGTCGGATATAGCTTTTA | 58 | 1678 |
| 1066093 | 501347 | 501366 | GACATCTGCTTATGTAGCTC | 45 | 1679 |
| 1066109 | 501708 | 501727 | AGTTACTTTGGGACATCCCA | 68 | 1680 |
| 1066125 | 502209 | 502228 | GTTTGGAACATCATGTTAGC | 49 | 1681 |
| 1066141 | 502595 | 502614 | TCCAACTGATGCATCAAGCC | 43 | 1682 |
| 1066157 | 502904 | 502923 | GCCTATATCCAACCAGCTAC | 73 | 1683 |
| 1066173 | 503217 | 503236 | CGTTGGAAACTTCAAAGGCA | 69 | 1684 |
| 1066189 | 503506 | 503525 | CCTTGGTTGTGGTGAAACCC | 72 | 1685 |
| 1066205 | 504087 | 504106 | TATCTTAACTGGTGAACTCC | 73 | 1686 |
| 1066221 | 504477 | 504496 | GGATGGTTGACCTCAAAATT | 30 | 1687 |
| 1066237 | 504952 | 504971 | TGGTTACCCATACAGTATAT | 42 | 1688 |
| 1066253 | 505549 | 505568 | GCTTTTCAGTCAGGTACAGG | 29 | 1689 |
| 1066269 | 505828 | 505847 | GACCTGTGAGGGTGCTTAGT | 81 | 1690 |
| 1066285 | 506235 | 506254 | GTTTGACCAGCTCCTTGTTG | 76 | 1691 |
| 1066301 | 506734 | 506753 | TTGGGAGTGCTCCACACTTC | 72 | 1692 |
| 1066317 | 507331 | 507350 | GATGCCCTGGTCCTAGCTTC | 60 | 1693 |
| 1066333 | 507909 | 507928 | GATAGCCATTCGATACCTGC | 56 | 1694 |
| 1066349 | 508297 | 508316 | GCTTCTACATAACCGAAGTG | 116 | 1695 |

TABLE 24-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1066365 | 508933 | 508952 | CTAGTGCCTATTACAATCTG | 61 | 1696 |
| 1066381 | 509882 | 509901 | CATGTGCTTTGTGGACCCAT | 47 | 1697 |
| 1066397 | 510318 | 510337 | GCTGGACGGACAGTGTTGCT | 61 | 1698 |
| 1066413 | 510733 | 510752 | GGTGATGAAGGTCAAGCCGA | 103 | 1699 |
| 1066429 | 511561 | 511580 | GTGGTTTCCAGCAGGGTGTA | 20 | 1700 |
| 1066445 | 511777 | 511796 | ACTAAAGAGTACTCCTACCA | 110 | 1701 |

TABLE 25

Reduction of UBE3A-ATS RNA by 7,000 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 617557 | 483977 | 483996 | ATCATGTGCATACCCAGGGT | 34 | 172 |
| 749882 | 460115 | 460134 | ACTTTATAGTGTGGATGGTA | 30 | 586 |
| 749921 | 462626 | 462645 | GTAATGATTTGCCCTCCTAC | 32 | 1702 |
| 750519 | 349103# | 349122# | GTCATCACCTCTCTTCAGGA | 17 | 181 |
| 1065267 | 432208 | 432227 | CCAGCGGGACCTGGACAAGC | 62 | 1703 |
| 1065283 | 433699 | 433718 | GGTGTAGTGGCAAGAAGTTC | 59 | 1704 |
| 1065299 | 442231 | 442250 | CCCCCTAGCTTTCCAATGGG | 82 | 1705 |
| 1065315 | 442923 | 442942 | GTCTCCACATAATCCTATTG | 48 | 1706 |
| 1065331 | 444553 | 444572 | ACATCCCATTAATCATCGCT | 49 | 1707 |
| 1065347 | 445388 | 445407 | TCAGATTACCTGAAGGTGTA | 104 | 1708 |
| 1065363 | 446582 | 446601 | AGTGGACAGATACGGTCCGT | 95 | 1709 |
| 1065379 | 447508 | 447527 | TCAGTTGTGAGTAGTGCCTC | 75 | 1710 |
| 1065395 | 448074 | 448093 | GCTTACCAGAGATGGTTTCC | 111 | 1711 |
| 1065411 | 448658 | 448677 | CGTAGGGCAAAAGTAAGGAT | 71 | 1712 |
| 1065427 | 449050 | 449069 | GTGGCCTGAAGGAACGGCCC | 92 | 1713 |
| 1065443 | 449532 | 449551 | GACCTTCAATTGATCAGTCT | 112 | 1714 |
| 1065459 | 450791 | 450810 | CCTGTCTGGTACTCCCATAT | 69 | 1715 |
| 1065475 | 452275 | 452294 | TCAATATGAGGGAAGTCTAG | 73 | 1716 |
| 1065491 | 453366 | 453385 | TTAACTACATAGGCACTCTA | 76 | 1717 |
| 1065507 | 454568 | 454587 | CTACACCGTGACAAAAGAGC | 76 | 1718 |
| 1065523 | 455125 | 455144 | AGCACAGGTGGATGTCTGAC | 82 | 1719 |
| 1065539 | 455450 | 455469 | GTAGTTGTATCTTGAATGGG | 65 | 1720 |

TABLE 25-continued

Reduction of UBE3A-ATS RNA by 7,000 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065555 | 220380 456749 | 220399 456768 | CATCTGGACCTCAGATTGAC | 64 | 1721 |
| 1065571 | 457288 | 457307 | AACGACCTAAAGACCTAGCA | 36 | 1722 |
| 1065587 | 458044 | 458063 | CTTGAGTAACTACTCATGAC | 83 | 1723 |
| 1065603 | 458946 | 458965 | GACCTATAGGACCTCAGGAG | 33 | 1724 |
| 1065619 | 460118 | 460137 | CTAACTTTATAGTGTGGATG | 18 | 1725 |
| 1065635 | 460843 | 460862 | CCACACATATAGGCTAGCCA | 9 | 1726 |
| 1065650 | 461573 | 461592 | GGTCATCATATTGAACCAAT | 44 | 1727 |
| 1065680 | 463826 | 463845 | GATTTCCTTACTGAGTGAGC | 29 | 1728 |
| 1065696 | 464909 | 464928 | GGTAGTCTATATTTGGTAAG | 17 | 1729 |
| 1065711 | 465242 | 465261 | TTATTGGTCATCTCGGGTAT | 47 | 1730 |
| 1065727 | 465600 | 465619 | CTATTTCAGACCGAAGGAGT | 32 | 1731 |
| 1065743 | 466251 | 466270 | GTAACTGGTAGGATCTATGG | 49 | 1732 |
| 1065759 | 466496 | 466515 | TTTTTAGGGTAGTGTCCTGA | 92 | 1733 |
| 1065775 | 467797 | 467816 | CTTAGTGATTGGTGGTTTAT | 54 | 1734 |
| 1065791 | 469899 | 469918 | GGGATTTACCCATTGCAAGT | ND | 1735 |
| 1065807 | 473264 | 473283 | GCCATCCTAATAGTTGGAGG | 44 | 1736 |
| 1065823 | 475306 | 475325 | GGTTAAGTCTGCTCTTTCAC | 25 | 1737 |
| 1065839 | 476008 | 476027 | TCGCCCGTTACCTCAATTCT | 60 | 1738 |
| 1065855 | 478307 | 478326 | GCTATTACACTGGAGTCCTG | 45 | 1739 |
| 1065871 | 480150 | 480169 | CAATACAAAACGGGCATGCT | 94 | 1740 |
| 1065887 | 481747 | 481766 | GATCATTCCCTGTGGTAAAG | 68 | 1741 |
| 1065903 | 483112 | 483131 | GCTTAGGCAATGGACTTAGT | 11 | 1742 |
| 1065919 | 483969 | 483988 | CATACCCAGGGTAGGATTCA | 43 | 1743 |
| 1065934 | 484722 | 484741 | ATAACACTAACGATGAACTC | 37 | 1744 |
| 1065950 | 487198 | 487217 | CCTAAAATCCCCGAATGGGA | 98 | 1745 |
| 1065966 | 489079 | 489098 | CCCAGTTAATCAGTGAACGA | 77 | 1746 |
| 1065982 | 489676 | 489695 | ATGTTCCAACCTGTCATGGG | 71 | 1747 |
| 1065998 | 493867 | 493886 | GATGAGATTAGGCCTAATCT | 43 | 1748 |
| 1066014 | 496564 | 496583 | CCATCTACTATTAATGAGCT | 58 | 1749 |
| 1066030 | 498186 | 498205 | TCACCATGGGCAGATTGATC | 109 | 1750 |
| 1066046 | 499672 | 499691 | GGTAGCCCCAATACAGATTC | 26 | 72 |
| 1066062 | 500564 | 500583 | CAAAACATGTTCTGACCTCG | 93 | 1751 |
| 1066078 | 500892 | 500911 | GGCCTTTGGGTCGGATATAG | 93 | 1752 |
| 1066094 | 501356 | 501375 | CGTCAAACTGACATCTGCTT | 38 | 1753 |
| 1066110 | 501733 | 501752 | AGTTAACACCTATCAAGTTG | 58 | 1754 |

TABLE 25-continued

Reduction of UBE3A-ATS RNA by 7,000 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1066126 | 502355 | 502374 | GGCCACCTGACTTCGGCCCA | 115 | 1755 |
| 1066142 | 502599 | 502618 | GACTTCCAACTGATGCATCA | 42 | 1756 |
| 1066158 | 502919 | 502938 | GACCCTTCTGTGAAAGCCTA | 61 | 1757 |
| 1066174 | 503279 | 503298 | GACTGCATCTCAATCCTATG | 62 | 1758 |
| 1066190 | 503636 | 503655 | GCCCATATGCTTGAACAATT | 40 | 1759 |
| 1066206 | 504088 | 504107 | GTATCTTAACTGGTGAACTC | 55 | 1760 |
| 1066222 | 504484 | 504503 | GCAGTTTGGATGGTTGACCT | 43 | 1761 |
| 1066238 | 504963 | 504982 | GGGTCGACTGATGGTTACCC | 80 | 1762 |
| 1066254 | 505594 | 505613 | ATAGGAGCTGAATAGTAGGG | 37 | 1763 |
| 1066270 | 505833 | 505852 | TCAAAGACCTGTGAGGGTGC | 78 | 1764 |
| 1066286 | 506243 | 506262 | GGTGAGCTGTTTGACCAGCT | 49 | 1765 |
| 1066302 | 506739 | 506758 | TCATTTTGGGAGTGCTCCAC | 53 | 1766 |
| 1066318 | 507359 | 507378 | GGAGATCCAACCTGTGTGGA | 79 | 1767 |
| 1066334 | 507915 | 507934 | CTGCAGGATAGCCATTCGAT | 69 | 1768 |
| 1066350 | 508354 | 508373 | CATTATTCAATTAAGGGTGG | 15 | 1769 |
| 1066366 | 508999 | 509018 | CATGTGTTAACGGAACTGAG | 85 | 1770 |
| 1066382 | 509901 | 509920 | GTGCATAGAGCAGACTGTAC | 103 | 1771 |
| 1066398 | 510328 | 510347 | GGTTTTGAGAGCTGGACGGA | 57 | 1772 |
| 1066414 | 510740 | 510759 | ATAGGTAGGTGATGAAGGTC | 75 | 1773 |
| 1066430 | 511586 | 511605 | GCTGCCAGCTTAGAGAATCT | 95 | 1774 |
| 1066446 | 511781 | 511800 | GTTAACTAAAGAGTACTCCT | 92 | 1775 |

TABLE 26

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 617557 | 483977 | 483996 | ATCATGTGCATACCCAGGGT | 35 | 172 |
| 749882 | 460115 | 460134 | ACTTTATAGTGTGGATGGTA | 42 | 586 |
| 749960 | 465003 | 465022 | ATCTGCGAATAGAGGCCCTC | 56 | 33 |
| 750519 | 349103* | 349122* | GTCATCACCTCTCTTCAGGA | 16 | 181 |
| 1065272 | 432587 | 432606 | GTAGGAGATAGGCAGTGCAT | 25 | 1776 |
| 1065288 | 440174 | 440193 | AATTATACTGTCCTACTTCG | 65 | 1777 |
| 1065304 | 442560 | 442579 | GTACCCCAGAAATAGCCCAT | 45 | 1778 |
| 1065320 | 443271 | 443290 | CATCACTAGCCTAGTGATCT | 114 | 1779 |

TABLE 26-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065336 | 444826 | 444845 | GGGTGCTGTCAACTGTCCCA | 45 | 1780 |
| 1065352 | 445690 | 445709 | GGCAAAGTACATACTGATCC | 54 | 1781 |
| 1065368 | 446725 | 446744 | CCTGTGCGGTAGCACTTGCC | 80 | 1782 |
| 1065384 | 447772 | 447791 | GGGCCAAGCACATAGGTATC | 74 | 1783 |
| 1065400 | 448306 | 448325 | CGTGCAAAACAAGTTTCGCA | 91 | 1784 |
| 1065416 | 448729 | 448748 | GACCACGATAACTGTAGCGC | 62 | 1785 |
| 1065432 | 449105 | 449124 | TCCTGGCAAGTATGCTAGTC | 73 | 1786 |
| 1065448 | 449643 | 449662 | ACTGATCCATTAGATAGGCT | 53 | 1787 |
| 1065464 | 452074 | 452093 | AGAACACTTCGCCGCTGATT | 76 | 1788 |
| 1065480 | 452327 | 452346 | AACATAAGGTTCAAAAGCCG | 86 | 1789 |
| 1065496 | 454063 | 454082 | CATAGATGATCCCATAATAG | 77 | 1790 |
| 1065512 | 454746 | 454765 | CCGAAAGCACTTTGCATGAG | 70 | 1791 |
| 1065528 | 455227 | 455246 | ATCCTTGATCCAGACAAGTC | 76 | 1792 |
| 1065544 | 455606 | 455625 | ATCATACAGGCATCTCAGCC | 68 | 1793 |
| 1065560 | 220447 456816 | 220466 456835 | TGTCACTGAGGGATCCCCAA | 83 | 1794 |
| 1065576 | 457383 | 457402 | GGATTCAATAGTGTAGGTGA | 15 | 1795 |
| 1065592 | 458407 | 458426 | GTACAATGCATGTGGGCCTC | ND | 1796 |
| 1065608 | 459102 | 459121 | ACTGGCATATTCCGATTATA | 24 | 1797 |
| 1065624 | 460467 | 460486 | CGTATTGGACCTTTCAATGA | 28 | 1798 |
| 1065640 | 461349 | 461368 | ATTGAAGCTGGCAATATGTC | 67 | 1799 |
| 1065655 | 461608 | 461627 | GCATGTACAAACGGGCTATG | 33 | 1800 |
| 1065670 | 463188 | 463207 | GGAATCTTGTAGAGGATTGG | 51 | 1801 |
| 1065685 | 464393 | 464412 | TCAGCACTTAGGTAGTTCAC | 27 | 1802 |
| 1065716 | 465309 | 465328 | TGTCTTTTGACACGCTGACT | 60 | 1803 |
| 1065732 | 465880 | 465899 | GTACTCTTGCCCATGGATGG | 42 | 1804 |
| 1065748 | 466292 | 466311 | CCCCTGTGGCTTATAGGTGG | 93 | 1805 |
| 1065764 | 466995 | 467014 | GGATGAACCTGCTTCACACA | 45 | 1806 |
| 1065780 | 468051 | 468070 | CAGATTTGCCAGGTAAAGCG | 58 | 1807 |
| 1065796 | 470320 | 470339 | AACTATCCTGCATCCGAGGC | 33 | 1808 |
| 1065812 | 474393 | 474412 | GGTCAACCAATTTGCTATTC | 23 | 1809 |
| 1065828 | 475722 | 475741 | GGTCTTGGGATTATAGTTTG | 32 | 1810 |
| 1065844 | 476155 | 476174 | GGAGTTCCTAACTCTCAATC | 78 | 1811 |
| 1065860 | 478826 | 478845 | TCTACTGAGGAACCCATCAC | 86 | 1812 |
| 1065876 | 480715 | 480734 | CGTTGCATAACATGTGTATT | 46 | 1813 |
| 1065892 | 482259 | 482278 | TACACCTGCAACAAGCCATC | 85 | 1814 |

TABLE 26-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1065908 | 483816 | 483835 | GAGCAAATCGGCAAAGGCAT | 43 | 1815 |
| 1065923 | 484156 | 484175 | CCAAGTGGCTTGTGGTGAAA | 87 | 1816 |
| 1065939 | 485817 | 485836 | GAACTACGAATAATTGCATG | 49 | 1817 |
| 1065955 | 487610 | 487629 | CAATGGTTTAGTGTCATATG | 27 | 1818 |
| 1065971 | 489454 | 489473 | AGTAGCTGTTTAGGCTGGAC | 58 | 1819 |
| 1065987 | 489784 | 489803 | TTGCCCTGCCACTCCCGTGG | 76 | 1820 |
| 1066003 | 494419 | 494438 | GGGATATATCACTTGGAGCT | ND | 1821 |
| 1066019 | 496833 | 496852 | CAGATTAGGTATGGAGGCCA | 49 | 1822 |
| 1066035 | 498902 | 498921 | ACGGATTAGATTCTCCAACA | 36 | 1823 |
| 1066051 | 499936 | 499955 | AGGACACATCAAGCTAGCTA | 55 | 1824 |
| 1066067 | 500680 | 500699 | AAGCCCTTTGCTTTTTCGGG | 81 | 1825 |
| 1066083 | 500908 | 500927 | GTGTTTTGACCTAACTGGCC | 65 | 1826 |
| 1066099 | 501472 | 501491 | CGTGGGTATGGTTTTCCTCT | 75 | 1827 |
| 1066115 | 501905 | 501924 | TCCAACGAGTGATAATTCAC | 81 | 1828 |
| 1066131 | 502423 | 502442 | AATTGATGCATAAGTAAGGC | 51 | 1829 |
| 1066147 | 502762 | 502781 | ATAGGCACTTCGGGCAAATA | 67 | 1830 |
| 1066163 | 503043 | 503062 | GGATTTAGGTGCTACAGTCA | 38 | 1831 |
| 1066179 | 503356 | 503375 | GTTAGCCCAGGTGATCAGCT | 57 | 1832 |
| 1066195 | 503886 | 503905 | ATTGCAACTAATAAAGGGTC | 79 | 1833 |
| 1066211 | 504295 | 504314 | GCTCTCATGTGAGAGTATGA | 81 | 1834 |
| 1066227 | 504544 | 504563 | TCATGAATTCAGGTTGCCCC | 42 | 1835 |
| 1066243 | 505149 | 505168 | CTTTGGTTGGAAGTTAGACC | 46 | 1836 |
| 1066259 | 505666 | 505685 | CTGCTTATTGCAGGCCTAGC | 69 | 1837 |
| 1066275 | 506042 | 506061 | CAGTTGAGAACGGTATTGAG | 67 | 1838 |
| 1066291 | 506447 | 506466 | GTCTGTCTTTAGGGTCACCC | 47 | 1839 |
| 1066307 | 506828 | 506847 | GCTTTAGGATGGTGTGGATC | 60 | 1840 |
| 1066323 | 507587 | 507606 | CTCTCACTGACTAGCTTTCG | 57 | 1841 |
| 1066339 | 508114 | 508133 | CTTACCGTCTTTAGGAACTT | 47 | 1842 |
| 1066355 | 508585 | 508604 | GGACAGCACAACCCCCGTGC | 94 | 1843 |
| 1066371 | 509070 | 509089 | CCCTACAATGCATACCCAAC | 58 | 1844 |
| 1066387 | 510027 | 510046 | GAGTTATACACGGAACCCAC | 56 | 1845 |
| 1066403 | 510410 | 510429 | GTCCAAGACATGCTAGGGAC | 71 | 1846 |
| 1066419 | 510839 | 510858 | CAATCTAGTTAGACCAGGCA | 31 | 1847 |
| 1066435 | 511667 | 511686 | ATGGACTGCCGGCCTGGAGC | 49 | 1848 |
| 1066451 | 511894 | 511913 | GTGAACTACTTGGAGACCTT | 50 | 1849 |

TABLE 27

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 617557 | 483977 | 483996 | ATCATGTGCATACCCAGGGT | 31 | 172 |
| 749882 | 460115 | 460134 | ACTTTATAGTGTGGATGGTA | 17 | 586 |
| 750519 | 349103# | 349122# | GTCATCACCTCTCTTCAGGA | 16 | 181 |
| 1065273 | 432754 | 432773 | ACGCAACTGAGACAATCCAT | 33 | 1850 |
| 1065289 | 440229 | 440248 | GTGGCTGTGCTGGATATTAC | 48 | 1851 |
| 1065305 | 442574 | 442593 | GAGCAAAATGGTCAGTACCC | 43 | 1852 |
| 1065321 | 443357 | 443376 | GATAGGTCAGTCACTCACTG | 40 | 1853 |
| 1065337 | 444867 | 444886 | GGATGCATTGGTGTCAAGAG | 47 | 1854 |
| 1065353 | 445763 | 445782 | GGTTTACACATGATAGGAAC | 80 | 1855 |
| 1065369 | 446772 | 446791 | AACAACGGTTGCAGGGACAG | 29 | 1856 |
| 1065385 | 447787 | 447806 | CCCCGTGTACAGTAAGGGCC | 73 | 1857 |
| 1065401 | 448408 | 448427 | GTCTTAGTGCCAAATATCCA | 52 | 1858 |
| 1065417 | 448735 | 448754 | TATTTAGACCACGATAACTG | 100 | 1859 |
| 1065433 | 449118 | 449137 | TCCCTCTTGTAGATCCTGGC | 40 | 1860 |
| 1065449 | 449666 | 449685 | GAGATATGATTAGTACTGGA | 63 | 1861 |
| 1065465 | 452079 | 452098 | GAGATAGAACACTTCGCCGC | 39 | 1862 |
| 1065481 | 453032 | 453051 | GTGATTAGGCGGCCGGGCGC | 119 | 1863 |
| 1065497 | 454151 | 454170 | CTTATGGAGACTTATATACC | 61 | 1864 |
| 1065513 | 454842 | 454861 | GGGTAGAAGACTAGCATACA | 22 | 1865 |
| 1065529 | 455233 | 455252 | GTACTTATCCTTGATCCAGA | 48 | 1866 |
| 1065545 | 455636 | 455655 | AGCACAAGATTGGTTCCATT | 47 | 1867 |
| 1065561 | 456827 | 456846 | GGGTACTATGTTGTCACTGA | N.D | 1868 |
| 1065577 | 457571 | 457590 | ATGAACCATGGAGTCTCTAT | 77 | 1869 |
| 1065593 | 458456 | 458475 | GGCTTTATACTTTACCCAAC | 15 | 1870 |
| 1065609 | 459265 | 459284 | GTAGATAACTTTACCTTGAC | 14 | 1871 |
| 1065625 | 460511 | 460530 | GTTTATAGGGTGGTTGGTTC | N.D. | 1872 |
| 1065641 | 461413 | 461432 | GGGTTACTTTCCAATAGAGT | 11 | 1873 |
| 1065656 | 461610 | 461629 | AGGCATGTACAAACGGGCTA | 73 | 1874 |
| 1065671 | 463193 | 463212 | GTTCTGGAATCTTGTAGAGG | 11 | 1875 |
| 1065686 | 464398 | 464417 | CCCATTCAGCACTTAGGTAG | 23 | 1876 |
| 1065701 | 465011 | 465030 | CTGCTCAAATCTGCGAATAG | 73 | 1877 |
| 1065717 | 465374 | 465393 | GAGGATGGTGTGTATGTTAT | 31 | 1878 |
| 1065733 | 465889 | 465908 | TCCCACAAGGTACTCTTGCC | 61 | 1879 |
| 1065749 | 466296 | 466315 | GCATCCCTGTGGCTTATAG | 65 | 1880 |
| 1065765 | 467043 | 467062 | TCAGTTAGTCAGGTTAGGGA | 7 | 1881 |
| 1065781 | 468335 | 468354 | AGCTATTGCAGCTATGGGTT | 35 | 1882 |
| 1065797 | 470401 | 470420 | GTTCAACCATCGAGATGATC | 64 | 1883 |

TABLE 27-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1065813 | 474404 | 474423 | GATAGGGTTTAGGTCAACCA | 20 | 1884 |
| 1065829 | 475726 | 475745 | ATCTGGTCTTGGGATTATAG | 26 | 1885 |
| 1065845 | 476159 | 476178 | CTTAGGAGTTCCTAACTCTC | 56 | 1886 |
| 1065861 | 478935 | 478954 | GTTTTGGAGATTGTGTTACG | 57 | 1887 |
| 1065877 | 480733 | 480752 | GGAGCCAGGTAGAGTTAACG | 41 | 1888 |
| 1065893 | 482489 | 482508 | GGATAGTTGTGAACAACTTC | 70 | 1889 |
| 1065909 | 483839 | 483858 | CATTGAATGAGGGCCCAAAC | 77 | 1890 |
| 1065924 | 484241 | 484260 | GGACTTGTCTTATGGCTGCC | N.D. | 1891 |
| 1065940 | 485829 | 485848 | TGATTATTCAGAGAACTACG | 47 | 1892 |
| 1065956 | 487697 | 487716 | CGTTGGCATTTAAGTCTGAG | 35 | 1893 |
| 1065972 | 489491 | 489510 | CTGGGTTGAGACTATTCAGG | 64 | 1894 |
| 1065988 | 489844 | 489863 | CCATTGAAGAAAAACCCGCG | 52 | 1895 |
| 1066004 | 494452 | 494471 | GCACTACTGTAAGGGTCATG | 48 | 1896 |
| 1066020 | 497158 | 497177 | ACAAGGGTAGTGTTACACTG | 42 | 1897 |
| 1066036 | 499081 | 499100 | CAATGGTAATCGCATATACT | 53 | 1898 |
| 1066052 | 500210 | 500229 | GACTAATCCTCTTAAGTTCA | 45 | 1899 |
| 1066068 | 500689 | 500708 | AGGTACTGTAAGCCCTTTGC | 80 | 1900 |
| 1066084 | 500972 | 500991 | AACTTTTACACGCTAGTGGG | 68 | 1901 |
| 1066100 | 501490 | 501509 | CCCTTTGTTCATACTGAACG | 69 | 1902 |
| 1066116 | 501913 | 501932 | AGCTTCCCTCCAACGAGTGA | 78 | 1903 |
| 1066132 | 502433 | 502452 | GGCCCAAGGGAATTGATGCA | 45 | 1904 |
| 1066148 | 502766 | 502785 | AGGAATAGGCACTTCGGGCA | 58 | 1905 |
| 1066164 | 503051 | 503070 | GGAACCCAGGATTAGGTGC | 50 | 1906 |
| 1066180 | 503368 | 503387 | GGTCATAGGAGTGTTAGCCC | 44 | 1907 |
| 1066196 | 503900 | 503919 | GGTTGGATTGCTTTATTGCA | 85 | 1908 |
| 1066212 | 504299 | 504318 | GCCTGCTCTCATGTGAGAGT | 47 | 1909 |
| 1066228 | 504644 | 504663 | CGCTTGGCTGACATTTAGGG | 38 | 1910 |
| 1066244 | 505169 | 505188 | ACCGAGCTCAAGAACTGTGA | 59 | 1911 |
| 1066260 | 505670 | 505689 | TGGCCTGCTTATTGCAGGCC | 73 | 1912 |
| 1066276 | 506047 | 506066 | GTTTTCAGTTGAGAACGGTA | 41 | 1913 |
| 1066292 | 506493 | 506512 | GGGACCTCCTTATATTCACC | 35 | 1914 |
| 1066308 | 506833 | 506852 | CCCCTGCTTTAGGATGGTGT | 134 | 1915 |
| 1066324 | 507637 | 507656 | GGTCCCCCAGAAGGCTTGA | 56 | 1916 |
| 1066340 | 508118 | 508137 | TATTCTTACCGTCTTTAGGA | 39 | 1917 |
| 1066356 | 508640 | 508659 | GGATGGAGCTGTTGTGGCAT | 57 | 1918 |
| 1066372 | 509076 | 509095 | GCATTACCCTACAATGCATA | 84 | 1919 |

TABLE 27-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1066388 | 510035 | 510054 | GCATTTGAGAGTTATACACG | 33 | 1920 |
| 1066404 | 510596 | 510615 | GGGCCTTATAGACCATACCA | 65 | 1921 |
| 1066420 | 510844 | 510863 | GGAGACAATCTAGTTAGACC | 30 | 1922 |
| 1066436 | 511673 | 511692 | GCACAAATGGACTGCCGGCC | 89 | 1923 |
| 1066452 | 511964 | 511983 | GAGAGTCATACTCCTGACAG | 53 | 1924 |

TABLE 28

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 617557 | 483977 | 483996 | ATCATGTGCATACCCAGGGT | 24 | 172 |
| 749882 | 460115 | 460134 | ACTTTATAGTGTGGATGGTA | 27 | 586 |
| 750519 | 349103# | 349122# | GTCATCACCTCTCTTCAGGA | 7 | 181 |
| 1065262 | 430574 | 430593 | CTCCGGGCTCACCACCTGGT | 82 | 1925 |
| 1065278 | 433033 | 433052 | TCTATACACTGCTGTTGACG | 52 | 1926 |
| 1065294 | 441732 | 441751 | GCTTGCTAAACCTGTCCATT | 40 | 1927 |
| 1065310 | 442717 | 442736 | CTGGATGGTATAAATTGCCC | 43 | 1928 |
| 1065326 | 443811 | 443830 | GTTGCCGCTTTGGTGAACCT | 69 | 1929 |
| 1065342 | 445129 | 445148 | GTGCACTGATACAGTTGGGC | 31 | 1930 |
| 1065358 | 446360 | 446379 | CCATCAAGTAGGCCAGTCAC | 37 | 1931 |
| 1065374 | 446952 | 446971 | GGAATAACCCATACCCCCCA | 97 | 1932 |
| 1065390 | 447883 | 447902 | GCATGACTCCTAATTGCTGT | 59 | 1933 |
| 1065406 | 448539 | 448558 | GAGCTCAGTCTTCACTAGTT | 46 | 1934 |
| 1065422 | 448919 | 448938 | GTCAGGCACCAGATTGCTCA | 70 | 1935 |
| 1065438 | 449442 | 449461 | ATGATCATACTGGAGCCAGG | 8 | 1936 |
| 1065454 | 449875 | 449894 | ACCTACCAGAGTGGCATCCT | 47 | 1937 |
| 1065470 | 452250 | 452269 | ACGCTGTGTGAATCAAAAGC | 85 | 1938 |
| 1065486 | 453211 | 453230 | AGTGTTCTTACATCCACCGT | 62 | 1939 |
| 1065502 | 454279 | 454298 | CATGCCAATCGCATGCAAGC | 71 | 1940 |
| 1065518 | 454967 | 454986 | GTCAGGAGTTAACTATGAAC | 95 | 1941 |
| 1065534 | 455326 | 455345 | CACCAGTTAGGCCTGCTCCG | 94 | 1942 |
| 1065550 | 456651 | 456670 | CGTTTCCACAGCCAGGCTTA | 83 | 1943 |
| 1065566 | 456921 | 456940 | AGTCTTGGGTCACTAGGCAC | 81 | 1944 |
| 1065582 | 457908 | 457927 | CCAATATTTTGACTAGTTCG | 23 | 1945 |
| 1065598 | 458568 | 458587 | TTTAGTATGTCGAGAACTCA | 31 | 1946 |
| 1065614 | 459652 | 459671 | TGAAACCTGTATAGTTTACC | 70 | 1947 |

TABLE 28-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1065630 | 460652 | 460671 | CTAACCATAGACAGAGTGCA | 33 | 1948 |
| 1065645 | 461463 | 461482 | CATCATGATCTTGGTAAGGC | 18 | 1949 |
| 1065661 | 461898 | 461917 | GACCCCACAATTTGGTCCCA | 62 | 1950 |
| 1065676 | 463668 | 463687 | GACTATCTCAGCACTAGGGA | 26 | 1951 |
| 1065691 | 464558 | 464577 | GCCCTGTAGTATGTGGATAC | 46 | 1952 |
| 1065706 | 465231 | 465250 | CTCGGGTATATAAATTAATG | 43 | 1953 |
| 1065722 | 465480 | 465499 | GGATCTAGAATGATTGGTTG | 75 | 1954 |
| 1065738 | 466218 | 466237 | GGGCTGCTGTTTGAGTCCCC | 65 | 1955 |
| 1065754 | 466397 | 466416 | AGATACTCACTCGCTTTTCA | 20 | 1956 |
| 1065770 | 467416 | 467435 | ACGCTCCTTCATTTCATGCA | 46 | 1957 |
| 1065786 | 468925 | 468944 | GCTGTAAGTATAGATGCCTC | 35 | 1958 |
| 1065802 | 472661 | 472680 | ATTAGTTGACTCTATAAACG | 70 | 1959 |
| 1065818 | 474805 | 474824 | AAGTTTGGTATTGACACCTC | 36 | 1960 |
| 1065834 | 475858 | 475877 | CTTGATATAAGGGTAATACG | 58 | 1961 |
| 1065850 | 476393 | 476412 | GGCTCAGGCAAAGTAGCTTC | 93 | 1962 |
| 1065866 | 479584 | 479603 | GCCATCTTCAAGACTAAGGT | 50 | 1963 |
| 1065882 | 480932 | 480951 | CGAAAAATAGTATGCGAAGC | 32 | 1964 |
| 1065898 | 482792 | 482811 | GGAGACCCTAAAAAACCCGT | 67 | 1965 |
| 1065914 | 483913 | 483932 | CCTATAGGTGGCCTTCAGTC | 30 | 1966 |
| 1065929 | 484322 | 484341 | GGCAAGCCCAGACTCATGCT | 86 | 1967 |
| 1065945 | 486491 | 486510 | CGTCAACACTATAGATGAAT | 40 | 1968 |
| 1065961 | 488332 | 488351 | CCACTCATGTACATGAGATC | 44 | 1969 |
| 1065977 | 489547 | 489566 | GGCAAGCAACTATGGGTGGA | 26 | 1970 |
| 1065993 | 493198 | 493217 | GTTTACTTCGGGCCAGGTCC | 97 | 1971 |
| 1066009 | 495221 | 495240 | ACCCCTAGGAATAATGTTGC | 36 | 1972 |
| 1066025 | 497750 | 497769 | AGCGATACAAACCTACGCCA | 71 | 1973 |
| 1066041 | 499146 | 499165 | GGCAAGTTTTTATCGCTTAA | 48 | 1974 |
| 1066057 | 500425 | 500444 | AGTATTTTAGCCGGGATACG | 53 | 1975 |
| 1066073 | 500846 | 500865 | ACGGGTTCCTATTTGTCAGG | 54 | 1976 |
| 1066089 | 501208 | 501227 | GTGAGCTTTACTCTGCAATA | 31 | 1977 |
| 1066105 | 501601 | 501620 | GCCTTATTGGAGAGAGAACT | 91 | 1978 |
| 1066121 | 502134 | 502153 | TCAGTGCTACCCATTAGACC | 35 | 1979 |
| 1066137 | 502512 | 502531 | CATACATGGAGGAGTCCCTG | 59 | 1980 |
| 1066153 | 502809 | 502828 | TCCTAAGGATGTAGCCCATC | 55 | 1981 |
| 1066169 | 503123 | 503142 | CGCATCCAGTTAATCTCTGA | 84 | 1982 |
| 1066185 | 503437 | 503456 | GTCCCAGTTGGATTAAGGTG | 64 | 1983 |

TABLE 28-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1066201 | 503970 | 503989 | CTGTACAGGAGGGTGTCTCT | N.D. | 1984 |
| 1066217 | 504426 | 504445 | TAGTCTAAGGCAGTCAGGGT | 28 | 1985 |
| 1066233 | 504757 | 504776 | ATCTAGACTCTGCCTGGTTA | 51 | 1986 |
| 1066249 | 505218 | 505237 | GGACACTCTCGCTGAGGACA | 21 | 1987 |
| 1066265 | 505800 | 505819 | GGCACTATGACCACAGGGTA | 35 | 1988 |
| 1066281 | 506127 | 506146 | TCTGCTCTGTTAGCCGAGCA | 77 | 1989 |
| 1066297 | 506641 | 506660 | GCACAATGCTTGTATGCCCC | 57 | 1990 |
| 1066313 | 507239 | 507258 | GTGCCCTTACTGTTAAATCC | 48 | 1991 |
| 1066329 | 507766 | 507785 | TTTGCTCAGGATCGCTGGCC | 93 | 1992 |
| 1066345 | 508230 | 508249 | AGCCTCTGCCTAAAGGTAGT | 64 | 1993 |
| 1066361 | 508780 | 508799 | CGTGATTGCAAAGTCCAAGG | 47 | 1994 |
| 1066377 | 509247 | 509266 | CAGTAGTGGTATCAAATCTG | 36 | 1995 |
| 1066393 | 510133 | 510152 | TCCAGCACATAGACCATAGC | 60 | 1996 |
| 1066409 | 510676 | 510695 | GGTGGAAAGTCTAGTATGTC | 73 | 1997 |
| 1066425 | 511077 | 511096 | GACCCATGGAAAGACTCGGG | 119 | 1998 |
| 1066441 | 511737 | 511756 | GTTTCCCATAGGCCACGCTG | 81 | 1999 |

TABLE 29

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 617557 | 483977 | 483996 | ATCATGTGCATACCCAGGGT | 35 | 172 |
| 749882 | 460115 | 460134 | ACTTTATAGTGTGGATGGTA | 26 | 586 |
| 749935 | 463695 | 463714 | AGTGGTTGCTATCCTGCTAA | 65 | 2000 |
| 750519 | 349103* | 349122* | GTCATCACCTCTCTTCAGGA | 16 | 181 |
| 1065263 | 430586 | 430605 | ACGCAAGTCCTCCTCCGGGC | 73 | 2001 |
| 1065279 | 433138 | 433157 | TCAAGGGAACTAACTCCTCC | 91 | 2002 |
| 1065295 | 441764 | 441783 | GATTGATCATGTTATGCCCT | 34 | 2003 |
| 1065311 | 442754 | 442773 | GGTGGATTGGAGTTGCTACA | 74 | 2004 |
| 1065327 | 443823 | 443842 | TGGGACACATATGTTGCCGC | 81 | 2005 |
| 1065343 | 445173 | 445192 | CTGAAGCAAAGCTTATAGGC | 91 | 2006 |
| 1065359 | 446483 | 446502 | TGACACTGAGTAATCTGCGA | 71 | 2007 |
| 1065375 | 446994 | 447013 | TGTAAGATTCCCCCAAGGGT | 103 | 2008 |
| 1065391 | 447907 | 447926 | GGTGGGATTACATCTCTTAT | 97 | 2009 |
| 1065407 | 448582 | 448601 | CGTGATATTCATGTTGTCTG | 89 | 2010 |

TABLE 29-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065423 | 448947 | 448966 | CGAAGCCAAAGGTACTTGAG | 100 | 2011 |
| 1065439 | 449461 | 449480 | GCTTGCACTCCATCATATAA | 126 | 2012 |
| 1065455 | 449988 | 450007 | AGGACCAGCCAGTCTAGTTT | 47 | 2013 |
| 1065471 | 452256 | 452275 | GGTCTCACGCTGTGTGAATC | 90 | 2014 |
| 1065487 | 453229 | 453248 | GGAGTCAAGTTGGTTAATAG | 136 | 2015 |
| 1065503 | 454339 | 454358 | GGGCGAAAGTATATCAGGCA | N.D. | 2016 |
| 1065519 | 455012 | 455031 | GGCTGTCAATGCTGATATAT | 82 | 2017 |
| 1065535 | 455332 | 455351 | GGAGTTCACCAGTTAGGCCT | 88 | 2018 |
| 1065551 | 456669 | 456688 | ACCCTCCCAACAAATAAGCG | 160 | 2019 |
| 1065567 | 456925 | 456944 | AGCAAGTCTTGGGTCACTAG | 72 | 2020 |
| 1065583 | 457969 | 457988 | GGCATCAATCAACAAGCACC | 49 | 2021 |
| 1065599 | 458570 | 458589 | GCTTTAGTATGTCGAGAACT | 19 | 2022 |
| 1065615 | 460105 | 460124 | GTGGATGGTATCCTGGTCAA | 46 | 2023 |
| 1065631 | 460660 | 460679 | GCATGATTCTAACCATAGAC | 31 | 2024 |
| 1065646 | 461468 | 461487 | GTACTCATCATGATCTTGGT | 26 | 2025 |
| 1065662 | 462030 | 462049 | GGAATAGGGCTCTGCTTATT | 60 | 2026 |
| 1065692 | 464776 | 464795 | CCTCGAGGATAGTTTCACTG | 76 | 2027 |
| 1065707 | 465234 | 465253 | CATCTCGGGTATATAAATTA | 77 | 2028 |
| 1065723 | 465484 | 465503 | TGTTGGATCTAGAATGATTG | 71 | 2029 |
| 1065739 | 466222 | 466241 | GTATGGGCTGCTGTTTGAGT | 55 | 2030 |
| 1065755 | 466403 | 466422 | CTGCAGAGATACTCACTCGC | 55 | 2031 |
| 1065771 | 467421 | 467440 | TTGATACGCTCCTTCATTTC | 75 | 2032 |
| 1065787 | 468927 | 468946 | ATGCTGTAAGTATAGATGCC | 86 | 2033 |
| 1065803 | 472669 | 472688 | CGTTGAATATTAGTTGACTC | 74 | 2034 |
| 1065819 | 474875 | 474894 | GGTGTTGTATGATAATGTGT | 72 | 2035 |
| 1065835 | 475935 | 475954 | CAATAGTAGTGATGACTTCC | 41 | 2036 |
| 1065851 | 476439 | 476458 | AGATGGAGCTTGAGCCATCC | 76 | 2037 |
| 1065867 | 479607 | 479626 | GCCCCACAGTAGAAATGTGG | 87 | 2038 |
| 1065883 | 481338 | 481357 | AGTCAACAAGACAACTCGAT | 62 | 2039 |
| 1065899 | 482839 | 482858 | CGTTATTCAGTCTCAGGGAG | 28 | 2040 |
| 1065915 | 483919 | 483938 | CTTTCACCTATAGGTGGCCT | 67 | 2041 |
| 1065930 | 484442 | 484461 | GAGTAATGGACTTCTGGTCT | 133 | 2042 |
| 1065946 | 486772 | 486791 | GTGTGAGGGAATCTAAGATC | 54 | 2043 |
| 1065962 | 488566 | 488585 | GGTGCCACACCATCAAAAGA | 63 | 2044 |
| 1065978 | 489581 | 489600 | GCTGCAGTGGTACCACAGAC | 91 | 2045 |
| 1065994 | 493203 | 493222 | AAGAAGTTTACTTCGGGCCA | 59 | 2046 |

TABLE 29-continued

Reduction of UBE3A-ATS RNA by 7,000 nM 5-10-5 MOE gapmers with mixed PO/PS internucleoside linkages in vitro (37,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1066010 | 495383 | 495402 | TCGGGAGTTGTTAGTCCAAG | 62 | 2047 |
| 1066026 | 497873 | 497892 | GCTCCCAAACAACTAATAGT | 76 | 2048 |
| 1066042 | 499204 | 499223 | TCAAAATCACGAAAGGCGGG | 71 | 2049 |
| 1066058 | 500430 | 500449 | TTAGAAGTATTTTAGCCGGG | 44 | 2050 |
| 1066074 | 500857 | 500876 | GGTAGGTAACTACGGGTTCC | 59 | 2051 |
| 1066090 | 501222 | 501241 | CACCCCTGTAAACAGTGAGC | 96 | 2052 |
| 1066106 | 501609 | 501628 | CTGCTCAAGCCTTATTGGAG | 120 | 2053 |
| 1066122 | 502140 | 502159 | GTGGAATCAGTGCTACCCAT | 77 | 2054 |
| 1066138 | 502527 | 502546 | AGCTGGGCACTCATACATAC | 55 | 2055 |
| 1066154 | 502813 | 502832 | AGCCTCCTAAGGATGTAGCC | 108 | 2056 |
| 1066170 | 503131 | 503150 | ATGGTCCTCGCATCCAGTTA | 54 | 2057 |
| 1066186 | 503444 | 503463 | CAGCACTGTCCCAGTTGGAT | 61 | 2058 |
| 1066202 | 503986 508752 | 504005 508771 | GTTGATTCACTGCACACTGT | 80 | 2059 |
| 1066218 | 504433 | 504452 | GGTATATTAGTCTAAGGCAG | 43 | 2060 |
| 1066234 | 504789 | 504808 | GCGAAGCCTTCTCAAAGACT | 92 | 2061 |
| 1066250 | 505323 | 505342 | GGGCCGCCTCTGTTATTGTG | 88 | 2062 |
| 1066266 | 505808 | 505827 | GAACTGTGGGCACTATGACC | 86 | 2063 |
| 1066282 | 506165 | 506184 | CCTTTGGAGCTTTGACTGGC | 76 | 2064 |
| 1066298 | 506677 | 506696 | CGATTTCCTGCCAGTGGCTG | 79 | 2065 |
| 1066314 | 507244 | 507263 | CTACTGTGCCCTTACTGTTA | 83 | 2066 |
| 1066330 | 507795 | 507814 | GAAGACTTAGGTCTCAAGCT | 62 | 2067 |
| 1066346 | 508274 | 508293 | GTAGTCATGTAGAACAGCAC | 78 | 2068 |
| 1066362 | 508784 | 508803 | CCACCGTGATTGCAAAGTCC | 69 | 2069 |
| 1066378 | 509252 | 509271 | GGGCACAGTAGTGGTATCAA | 22 | 2070 |
| 1066394 | 510203 | 510222 | AGAGCTGTCCTAAGGCAATT | 54 | 2071 |
| 1066410 | 510711 | 510730 | CTTGACATACAGGATAGGTG | 52 | 2072 |
| 1066426 | 511088 | 511107 | TTGGTAAATTAGACCCATGG | 110 | 2073 |
| 1066442 | 511744 | 511763 | GATGTATGTTTCCCATAGGC | 56 | 2074 |

TABLE 30

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 51 | 172 |
| 749882 | 460115 | 460134 | ACTTTATAGTGTGGATGGTA | 46 | 586 |
| 750519 | 349103* | 349122* | GTCATCACCTCTCTTCAGGA | 28 | 181 |
| 1165442 | 449002 | 449021 | AGGTCTTATTTACCATTGGC | 72 | 2377 |
| 1165447 | 449444 | 449463 | TAATGATCATACTGGAGCCA | 87 | 2378 |
| 1165449 | 452253 | 452272 | CTCACGCTGTGTGAATCAAA | 101 | 2379 |
| 1165455 | 452265 | 452284 | GGAAGTCTAGGTCTCACGCT | 88 | 2380 |
| 1165467 | 453362 | 453381 | CTACATAGGCACTCTACTAG | 96 | 2381 |
| 1165471 | 454154 | 454173 | ACCCTTATGGAGACTTATAT | 96 | 2382 |
| 1165477 | 454461 | 454480 | GACTCCACACACCTACTAGA | 97 | 2383 |
| 1165483 | 454578 | 454597 | CAAGCAAAGACTACACCGTG | 106 | 2384 |
| 1165487 | 454848 | 454867 | TATCCAGGGTAGAAGACTAG | 83 | 2385 |
| 1165493 | 454861 | 454880 | GGTGTATATTCCCTATCCAG | 89 | 2386 |
| 1165499 | 455020 | 455039 | AGTGGGATGGCTGTCAATGC | 82 | 2387 |
| 1165510 | 220439 456808 | 220458 456827 | AGGGATCCCCAAATAGAGCC | 96 | 2388 |
| 1165516 | 457018 | 457037 | TCACAGTTGCTTGACCCTTA | 79 | 2389 |
| 1165522 | 457572 | 457591 | TATGAACCATGGAGTCTCTA | 69 | 2390 |
| 1165528 | 458791 | 458810 | TCCCTAATATAGGGCAGATG | 88 | 2391 |
| 1165534 | 458942 | 458961 | TATAGGACCTCAGGAGATTG | 52 | 2392 |
| 1165539 | 458950 | 458969 | TCAAGACCTATAGGACCTCA | 37 | 2393 |
| 1165546 | 459550 | 459569 | AAAGACTATCCTGGTATGAC | 65 | 2394 |
| 1165557 | 460735 | 460754 | GATTTGAGCCTGCTATGTCT | 16* | 2395 |
| 1165565 | 461525 | 461544 | ACATTCAGCTAGACTAGTTG | 58 | 2396 |
| 1165570 | 461901 | 461920 | TGAGACCCCACAATTTGGTC | 89 | 2397 |
| 1165572 | 464385 | 464404 | TAGGTAGTTCACAACTCTTC | 68 | 2398 |
| 1165582 | 464562 | 464581 | ATATGCCCTGTAGTATGTGG | 77 | 2399 |
| 1165587 | 465245 | 465264 | ATTTTATTGGTCATCTCGGG | 47 | 2400 |
| 1165592 | 465387 | 465406 | TGTCAGACTTATTGAGGATG | 67 | 2401 |
| 1165594 | 465891 | 465910 | ACTCCCACAAGGTACTCTTG | 84 | 2402 |
| 1165598 | 466249 | 466268 | AACTGGTAGGATCTATGGCA | 40 | 2403 |
| 1165603 | 467301 | 467320 | TTCACAGAGTAGTCTATTGG | 84 | 2404 |
| 1165609 | 468352 | 468371 | TGTAGTATGCATTGACAAGC | 58 | 2405 |
| 1165612 | 482161 | 482180 | GAGTTACAAGTGTCATATAC | 48 | 2406 |
| 1165618 | 483960 | 483979 | GGTAGGATTCATGGTCCAAA | 64 | 2407 |
| 1165625 | 485656 | 485675 | CCTAGGACCAGTTGGTTCAC | 99 | 2408 |
| 1165633 | 489492 | 489511 | ACTGGGTTGAGACTATTCAG | 68 | 2409 |

TABLE 30-continued

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1165638 | 489521 | 489540 | CAATGGACCACCTAAGACCT | 104 | 2410 |
| 1165641 | 493854 | 493873 | CTAATCTATGCTGGGCCCCA | 89 | 2411 |
| 1165647 | 493864 | 493883 | GAGATTAGGCCTAATCTATG | 116 | 2412 |
| 1165653 | 496830 | 496849 | ATTAGGTATGGAGGCCATGT | 69 | 2413 |
| 1165664 | 499674 | 499693 | AAGGTAGCCCCAATACAGAT | 87 | 2414 |
| 1165668 | 500690 | 500709 | GAGGTACTGTAAGCCCTTTG | 115 | 2415 |
| 1165673 | 500906 | 500925 | GTTTTGACCTAACTGGCCTT | 86 | 2416 |
| 1165678 | 501567 | 501586 | CTAAGGAGTGCTCTTTGTGG | 59 | 2417 |
| 1165684 | 502371 | 502390 | AGGTATTAAGGCCCTTGGCC | 95 | 2418 |
| 1165690 | 502378 | 502397 | GTATACAAGGTATTAAGGCC | 69 | 2419 |
| 1165695 | 502449 | 502468 | TAGGCAGCTCTTTGTAGGCC | 82 | 2420 |
| 1165701 | 503155 | 503174 | AGTTCTGTATACACCATCCC | 51 | 2421 |
| 1165707 | 503361 | 503380 | GGAGTGTTAGCCCAGGTGAT | 95 | 2422 |
| 1165713 | 503367 | 503386 | GTCATAGGAGTGTTAGCCCA | 84 | 2423 |
| 1165719 | 503421 | 503440 | GGTGATGACACCCCTACCAT | 106 | 2424 |
| 1165725 | 503507 | 503526 | GCCTTGGTTGTGGTGAAACC | 64 | 2425 |
| 1165729 | 504076 | 504095 | GTGAACTCCTGTGACTGATA | 52 | 2426 |
| 1165736 | 504431 | 504450 | TATATTAGTCTAAGGCAGTC | 47 | 2427 |
| 1165747 | 505173 | 505192 | GTGTACCGAGCTCAAGAACT | 51 | 2428 |
| 1165753 | 505181 | 505200 | CTGTCTCTGTGTACCGAGCT | 64 | 2429 |
| 1165766 | 505320 | 505339 | CCGCCTCTGTTATTGTGATA | 78 | 2430 |
| 1165772 | 505327 | 505346 | AATTGGGCCGCCTCTGTTAT | 74 | 2431 |
| 1165778 | 505542 | 505561 | AGTCAGGTACAGGTGTTGGA | 56 | 2432 |
| 1165783 | 505745 | 505764 | TGTAGGTTGACAGGACATGC | 64 | 2433 |
| 1165789 | 505821 | 505840 | GAGGGTGCTTAGTGAACTGT | 87 | 2434 |
| 1165795 | 505830 | 505849 | AAGACCTGTGAGGGTGCTTA | 87 | 2435 |
| 1165800 | 506448 | 506467 | AGTCTGTCTTTAGGGTCACC | 57 | 2436 |
| 1165806 | 507907 | 507926 | TAGCCATTCGATACCTGCTT | 76 | 2437 |
| 1165812 | 507914 | 507933 | TGCAGGATAGCCATTCGATA | 75 | 2438 |
| 1165823 | 508791 | 508810 | ATGAATGCCACCGTGATTGC | 94 | 2439 |
| 1165828 | 510228 | 510247 | AGTTGTGTCTGAGGGATATC | 64 | 2440 |
| 1165839 | 448411 | 448430 | AGGGTCTTAGTGCCAAATAT | 102 | 2441 |
| 1165852 | 455763 | 455782 | TACCAAAGTGGCTGCTCACC | 76 | 2442 |
| 1165854 | 460426 | 460445 | TAGCCCTTTCAGCACACTTC | 44 | 2443 |
| 1165856 | 461342 | 461361 | CTGGCAATATGTCAACCTTA | 55 | 2444 |
| 1165864 | 464515 | 464534 | AGTGCACAGATAATGACTAG | 91 | 2445 |

TABLE 30-continued

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1165880 | 484240 | 484259 | GACTTGTCTTATGGCTGCCT | 90 | 2446 |
| 1165884 | 486440 | 486459 | CCTAATAGCACCAGAATAGT | 104 | 2447 |
| 1165891 | 499666 | 499685 | CCCAATACAGATTCAGTGGC | 89 | 2448 |
| 1165901 | 504818 | 504837 | TGAAGTAGTCCTGCCCTTTC | 86 | 2449 |
| 1165902 | 505216 | 505235 | ACACTCTCGCTGAGGACACA | 74 | 2450 |
| 1165908 | 506966 | 506985 | GGGCATTCAGTGCTCCCTCC | 106 | 2451 |

TABLE 31

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 617557 | 483977 | 483996 | ATCATGTGCATACCCAGGGT | 53 | 172 |
| 749882 | 460115 | 460134 | ACTTTATAGTGTGGATGGTA | 50 | 586 |
| 750519 | 349103* | 349122* | GTCATCACCTCTCTTCAGGA | 31 | 181 |
| 1165439 | 448413 | 448432 | CAAGGGTCTTAGTGCCAAAT | 106 | 2452 |
| 1165444 | 449095 | 449114 | TATGCTAGTCACTCATTGAG | 113 | 2453 |
| 1165451 | 452258 | 452277 | TAGGTCTCACGCTGTGTGAA | 97 | 2454 |
| 1165457 | 452268 | 452287 | GAGGGAAGTCTAGGTCTCAC | 89 | 2455 |
| 1165468 | 453365 | 453384 | TAACTACATAGGCACTCTAC | 79 | 2456 |
| 1165473 | 454161 | 454180 | AGATTTGACCCTTATGGAGA | 115 | 2457 |
| 1165479 | 454465 | 454484 | AGTGGACTCCACACACCTAC | 108 | 2458 |
| 1165485 | 454843 | 454862 | AGGGTAGAAGACTAGCATAC | 96 | 22 |
| 1165489 | 454857 | 454876 | TATATTCCCTATCCAGGGTA | 92 | 2459 |
| 1165495 | 454865 | 454884 | GACAGGTGTATATTCCCTAT | 116 | 2460 |
| 1165505 | 456628 | 456647 | TGTGCATGGTTATCTAATGC | 74 | 2461 |
| 1165512 | 457013 | 457032 | GTTGCTTGACCCTTAATTCA | 108 | 2462 |
| 1165518 | 457022 | 457041 | CATATCACAGTTGCTTGACC | 132 | 2463 |
| 1165524 | 457984 | 458003 | TTGATCTATTATGAGGGCAT | 22 | 2464 |
| 1165530 | 458935 | 458954 | CCTCAGGAGATTGTACAACA | 47 | 2465 |
| 1165542 | 459545 | 459564 | CTATCCTGGTATGACTGTCA | 39 | 2466 |
| 1165548 | 460110 | 460129 | ATAGTGTGGATGGTATCCTG | 57 | 2467 |
| 1165553 | 460508 | 460527 | TATAGGGTGGTTGGTTCAAA | 29 | 2468 |
| 1165559 | 460844 | 460863 | ACCACACATATAGGCTAGCC | 39 | 2469 |
| 1165566 | 461527 | 461546 | GAACATTCAGCTAGACTAGT | 64 | 2470 |

TABLE 31-continued

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1165574 | 464388 | 464407 | ACTTAGGTAGTTCACAACTC | 55 | 2471 |
| 1165579 | 464557 | 464576 | CCCTGTAGTATGTGGATACT | 97 | 2472 |
| 1165583 | 465239 | 465258 | TTGGTCATCTCGGGTATATA | 43 | 2473 |
| 1165589 | 465380 | 465399 | CTTATTGAGGATGGTGTGTA | 64 | 2474 |
| 1165605 | 467802 | 467821 | TCCCTCTTAGTGATTGGTGG | 80 | 2475 |
| 1165614 | 483844 | 483863 | CTAGGCATTGAATGAGGGCC | 93 | 2476 |
| 1165620 | 483962 | 483981 | AGGGTAGGATTCATGGTCCA | 95 | 2477 |
| 1165627 | 486353 | 486372 | TTAATAGACTGCGATTATAC | 100 | 2478 |
| 1165630 | 489097 | 489116 | TCCCTAAGCTTAGATATACC | 76 | 2479 |
| 1165634 | 489516 | 489535 | GACCACCTAAGACCTCAAGG | 73 | 2480 |
| 1165643 | 493860 | 493879 | TTAGGCCTAATCTATGCTGG | 84 | 2481 |
| 1165649 | 493866 | 493885 | ATGAGATTAGGCCTAATCTA | 108 | 2482 |
| 1165655 | 496832 | 496851 | AGATTAGGTATGGAGGCCAT | 85 | 2483 |
| 1165660 | 499668 | 499687 | GCCCCAATACAGATTCAGTG | 94 | 2484 |
| 1165675 | 500909 | 500928 | GGTGTTTTGACCTAACTGGC | 81 | 2485 |
| 1165680 | 501762 | 501781 | GGCTAAGAGTCACCTGTATC | 85 | 2486 |
| 1165686 | 502373 | 502392 | CAAGGTATTAAGGCCCTTGG | 92 | 2487 |
| 1165691 | 502438 | 502457 | TTGTAGGCCCAAGGGAATTG | 105 | 2488 |
| 1165696 | 502451 | 502470 | GCTAGGCAGCTCTTTGTAGG | 65 | 2489 |
| 1165703 | 503357 | 503376 | TGTTAGCCCAGGTGATCAGC | 69 | 2490 |
| 1165709 | 503363 | 503382 | TAGGAGTGTTAGCCCAGGTG | 56 | 2491 |
| 1165715 | 503370 | 503389 | AGGGTCATAGGAGTGTTAGC | 65 | 2492 |
| 1165721 | 503424 | 503443 | TAAGGTGATGACACCCCTAC | 109 | 2493 |
| 1165726 | 503871 | 503890 | GGGTCAGTTGTGCAGTTGTT | 46 | 2494 |
| 1165738 | 504434 | 504453 | AGGTATATTAGTCTAAGGCA | 49 | 2495 |
| 1165743 | 504977 | 504996 | CTATTATCTTCTTAGGGTCG | 57 | 2496 |
| 1165749 | 505175 | 505194 | CTGTGTACCGAGCTCAAGAA | 65 | 2497 |
| 1165755 | 505198 | 505217 | CATCAGCTGTTAGCAGTCTG | 82 | 2498 |
| 1165760 | 505219 | 505238 | AGGACACTCTCGCTGAGGAC | 64 | 2499 |
| 1165768 | 505322 | 505341 | GGCCGCCTCTGTTATTGTGA | 91 | 2500 |
| 1165774 | 505329 | 505348 | GAAATTGGGCCGCCTCTGTT | 91 | 2501 |
| 1165779 | 505651 | 505670 | CTAGCTTCCACCTAAGAGCT | 111 | 2502 |
| 1165785 | 505750 | 505769 | AACTCTGTAGGTTGACAGGA | 78 | 2503 |
| 1165791 | 505824 | 505843 | TGTGAGGGTGCTTAGTGAAC | 77 | 2504 |
| 1165796 | 505836 | 505855 | CTGTCAAAGACCTGTGAGGG | 78 | 2505 |
| 1165808 | 507910 | 507929 | GGATAGCCATTCGATACCTG | 101 | 2506 |

TABLE 31-continued

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1165814 | 508119 | 508138 | TTATTCTTACCGTCTTTAGG | 70 | 2507 |
| 1165825 | 509129 | 509148 | AGCTCATCACAACTGGGTGG | 86 | 2508 |
| 1165842 | 449667 | 449686 | AGAGATATGATTAGTACTGG | 105 | 2509 |
| 1165850 | 455030 | 455049 | GTGATATTGCAGTGGGATGG | 89 | 2510 |
| 1165853 | 458945 | 458964 | ACCTATAGGACCTCAGGAGA | 70 | 2511 |
| 1165857 | 461416 | 461435 | ACTGGGTTACTTTCCAATAG | 61 | 2512 |
| 1165861 | 463093 | 463112 | CAATTTACTTGATACAGGGC | 43 | 2513 |
| 1165869 | 465393 | 465412 | GTCAATTGTCAGACTTATTG | 54 | 2514 |
| 1165873 | 466100 | 466119 | GGGCCTGTATGTCTTGAGAA | 88 | 2515 |
| 1165874 | 467294 | 467313 | AGTAGTCTATTGGTGTTCCT | 68 | 2516 |
| 1165876 | 468356 | 468375 | ATACTGTAGTATGCATTGAC | 79 | 2517 |
| 1165882 | 484300 | 484319 | TTACTAGGGCCAGAGAATCC | 94 | 2518 |
| 1165889 | 493623 | 493642 | CAGATGACTAGCCTCCAAAC | 102 | 2519 |
| 1165892 | 499910 | 499929 | GCATAATAGGAGGTCCTTAA | 46 | 2520 |
| 1165894 | 500764 | 500783 | GTCAAATCAATTTGTGCCAC | 72 | 2521 |
| 1165900 | 504422 | 504441 | CTAAGGCAGTCAGGGTAATG | 55 | 2522 |
| 1165905 | 506694 | 506713 | TTAAGAAGCTTGCCTTTCGA | 115 | 2523 |
| 1165909 | 507901 | 507920 | TTCGATACCTGCTTTTGTGA | 111 | 2524 |
| 1165914 | 511254 | 511273 | CTGATGATTTGTTGATTACC | 84 | 2525 |

TABLE 32

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 617557 | 483977 | 483996 | ATCATGTGCATACCCAGGGT | 49 | 172 |
| 749882 | 460115 | 460134 | ACTTTATAGTGTGGATGGTA | 33 | 586 |
| 750519 | 349103* | 349122* | GTCATCACCTCTCTTCAGGA | 22 | 181 |
| 1165440 | 448459 | 448478 | ATAGTGCCAGTAGGACTTAC | 98 | 2526 |
| 1165445 | 449097 | 449116 | AGTATGCTAGTCACTCATTG | 68 | 2527 |
| 1165452 | 452259 | 452278 | CTAGGTCTCACGCTGTGTGA | 84 | 2528 |
| 1165458 | 452271 | 452290 | TATGAGGGAAGTCTAGGTCT | 64 | 2529 |
| 1165474 | 454162 | 454181 | AAGATTTGACCCTTATGGAG | 96 | 2530 |
| 1165480 | 454466 | 454485 | GAGTGGACTCCACACACCTA | 80 | 2531 |
| 1165490 | 454858 | 454877 | GTATATTCCCTATCCAGGGT | 93 | 2532 |
| 1165496 | 454866 | 454885 | TGACAGGTGTATATTCCCTA | 55 | 2533 |

TABLE 32-continued

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1165501 | 455031 | 455050 | AGTGATATTGCAGTGGGATG | 77 | 2534 |
| 1165506 | 220320 456689 | 220339 456708 | CATCATCGATCCAAACAAGC | 102 | 2535 |
| 1165513 | 457015 | 457034 | CAGTTGCTTGACCCTTAATT | 76 | 2536 |
| 1165519 | 457364 | 457383 | ACATGGTGAGGGTCTCAATG | 33 | 2537 |
| 1165525 | 457986 | 458005 | ACTTGATCTATTATGAGGGC | 35 | 2538 |
| 1165531 | 458936 | 458955 | ACCTCAGGAGATTGTACAAC | 42 | 2539 |
| 1165536 | 458947 | 458966 | AGACCTATAGGACCTCAGGA | 28 | 2540 |
| 1165543 | 459546 | 459565 | ACTATCCTGGTATGACTGTC | 40 | 2541 |
| 1165549 | 460112 | 460131 | TTATAGTGTGGATGGTATCC | 49 | 2542 |
| 1165554 | 460509 | 460528 | TTATAGGGTGGTTGGTTCAA | 24 | 2543 |
| 1165560 | 460845 | 460864 | TACCACACATATAGGCTAGC | 43 | 2544 |
| 1165567 | 461671 | 461690 | CCTAAGGTGAAGTCTGTGTA | 58 | 2545 |
| 1165575 | 464389 | 464408 | CACTTAGGTAGTTCACAACT | 59 | 2546 |
| 1165580 | 464559 | 464578 | TGCCCTGTAGTATGTGGATA | 69 | 2547 |
| 1165584 | 465241 | 465260 | TATTGGTCATCTCGGGTATA | 51 | 2548 |
| 1165595 | 466246 | 466265 | TGGTAGGATCTATGGCAGTT | 35 | 2549 |
| 1165600 | 467297 | 467316 | CAGAGTAGTCTATTGGTGTT | 83 | 2550 |
| 1165606 | 467803 | 467822 | CTCCCTCTTAGTGATTGGTG | 84 | 2551 |
| 1165610 | 468403 | 468422 | CCTACCCTTGCATGCTATGT | 88 | 2552 |
| 1165615 | 483850 | 483869 | GCCTGACTAGGCATTGAATG | 79 | 2553 |
| 1165622 | 484301 | 484320 | GTTACTAGGGCCAGAGAATC | 105 | 2554 |
| 1165628 | 486354 | 486373 | GTTAATAGACTGCGATTATA | 43 | 2555 |
| 1165631 | 489098 | 489117 | CTCCCTAAGCTTAGATATAC | 88 | 2556 |
| 1165635 | 489518 | 489537 | TGGACCACCTAAGACCTCAA | 73 | 139 |
| 1165644 | 493861 | 493880 | ATTAGGCCTAATCTATGCTG | 89 | 2557 |
| 1165650 | 493868 | 493887 | AGATGAGATTAGGCCTAATC | 136 | 2558 |
| 1165656 | 496834 | 496853 | ACAGATTAGGTATGGAGGCC | 57 | 2559 |
| 1165661 | 499670 | 499689 | TAGCCCCAATACAGATTCAG | 55 | 2560 |
| 1165666 | 499911 | 499930 | TGCATAATAGGAGGTCCTTA | 54 | 2561 |
| 1165670 | 500864 | 500883 | TACTTTTGGTAGGTAACTAC | 70 | 2562 |
| 1165676 | 500910 | 500929 | AGGTGTTTTGACCTAACTGG | 80 | 2563 |
| 1165681 | 501764 | 501783 | TGGGCTAAGAGTCACCTGTA | 109 | 2564 |
| 1165687 | 502374 | 502393 | ACAAGGTATTAAGGCCCTTG | 106 | 2565 |
| 1165692 | 502439 | 502458 | TTTGTAGGCCCAAGGGAATT | 119 | 2566 |
| 1165697 | 502740 | 502759 | GCCCGATGACACCAGCCACT | 61 | 2567 |

TABLE 32-continued

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1165704 | 503358 | 503377 | GTGTTAGCCCAGGTGATCAG | 66 | 2568 |
| 1165710 | 503364 | 503383 | ATAGGAGTGTTAGCCCAGGT | 62 | 2569 |
| 1165716 | 503418 | 503437 | GATGACACCCCTACCATGGC | 63 | 2570 |
| 1165722 | 503425 | 503444 | TTAAGGTGATGACACCCCTA | 102 | 2571 |
| 1165727 | 503873 | 503892 | AAGGGTCAGTTGTGCAGTTG | 43 | 2572 |
| 1165733 | 504427 | 504446 | TTAGTCTAAGGCAGTCAGGG | 50 | 2573 |
| 1165739 | 504435 | 504454 | TAGGTATATTAGTCTAAGGC | 50 | 2574 |
| 1165744 | 505167 | 505186 | CGAGCTCAAGAACTGTGACT | 65 | 2575 |
| 1165750 | 505176 | 505195 | TCTGTGTACCGAGCTCAAGA | 41 | 2576 |
| 1165756 | 505199 | 505218 | ACATCAGCTGTTAGCAGTCT | 45 | 2577 |
| 1165761 | 505220 | 505239 | GAGGACACTCTCGCTGAGGA | 78 | 2578 |
| 1165769 | 505324 | 505343 | TGGGCCGCCTCTGTTATTGT | 79 | 2579 |
| 1165775 | 505331 | 505350 | TAGAAATTGGGCCGCCTCTG | 63 | 2580 |
| 1165780 | 505652 | 505671 | CCTAGCTTCCACCTAAGAGC | 78 | 2581 |
| 1165786 | 505751 | 505770 | GAACTCTGTAGGTTGACAGG | 43 | 2582 |
| 1165792 | 505826 | 505845 | CCTGTGAGGGTGCTTAGTGA | 76 | 2583 |
| 1165797 | 506166 | 506185 | ACCTTTGGAGCTTTGACTGG | 90 | 2584 |
| 1165804 | 507902 | 507921 | ATTCGATACCTGCTTTTGTG | 95 | 2585 |
| 1165809 | 507911 | 507930 | AGGATAGCCATTCGATACCT | 70 | 2586 |
| 1165837 | 511896 | 511915 | AAGTGAACTACTTGGAGACC | 38 | 2587 |
| 1165843 | 449698 | 449717 | TGTATGGCTTATGCATGCTA | 75 | 2588 |
| 1165847 | 453368 | 453387 | TATTAACTACATAGGCACTC | 58 | 2589 |
| 1165848 | 454844 | 454863 | CAGGGTAGAAGACTAGCATA | 109 | 2590 |
| 1165858 | 461430 | 461449 | TTAGCACTTCTATAACTGGG | 40 | 2591 |
| 1165862 | 463776 | 463795 | ATAGATTGGGCTTTAGAGGT | 45 | 2592 |
| 1165867 | 465383 | 465402 | AGACTTATTGAGGATGGTGT | 47 | 2593 |
| 1165870 | 465563 | 465582 | TAGGACAAGTCTTATAGAGA | 48 | 2594 |
| 1165878 | 483974 | 483993 | ATGTGCATACCCAGGGTAGG | 58 | 2595 |
| 1165890 | 493850 | 493869 | TCTATGCTGGGCCCCAATTC | 87 | 2596 |
| 1165906 | 506772 | 506791 | AGGTTGTGGAGGTTGTTCCT | 72 | 2597 |
| 1165911 | 508171 | 508190 | ACCTGCAGTTATTTAGCCAT | 68 | 2598 |
| 1165912 | 509171 | 509190 | AACCTCCAAGTGCTTCAAGC | 60 | 2599 |

TABLE 33

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1065438 | 449442 | 449461 | ATGATCATACTGGAGCCAGG | 95 | 1936 |
| 1165509 | 220406 | 220425 | CTTATTTGTCCTATTGGAGG | 91 | 2600 |
| | 456775 | 456794 | | | |
| 1178377 | 220315 | 220334 | TCGATCCAAACAAGCACCCT | 98 | 2601 |
| | 456684 | 456703 | | | |
| 1178379 | 220318 | 220337 | TCATCGATCCAAACAAGCAC | 132 | 2602 |
| | 456687 | 456706 | | | |
| 1178384 | 456753 | 456772 | CGCACATCTGGACCTCAGAT | 98 | 2603 |
| 1178386 | 456755 | 456774 | GCCGCACATCTGGACCTCAG | 129 | 2604 |
| 1178388 | 456758 | 456777 | AGGGCCGCACATCTGGACCT | 115 | 2605 |
| 1178390 | 456760 | 456779 | GGAGGGCCGCACATCTGGAC | 70 | 2606 |
| 1178392 | 456762 | 456781 | TTGGAGGGCCGCACATCTGG | 106 | 2607 |
| 1178394 | 456764 | 456783 | TATTGGAGGGCCGCACATCT | 123 | 2608 |
| 1178396 | 456766 | 456785 | CCTATTGGAGGGCCGCACAT | 136 | 2609 |
| 1178398 | 456769 | 456788 | TGTCCTATTGGAGGGCCGCA | 100 | 2610 |
| 1178400 | 456771 | 456790 | TTTGTCCTATTGGAGGGCCG | 104 | 2611 |
| 1178404 | 220455 | 220474 | TACTATGTTGTCACTGAGGG | 83 | 2612 |
| | 456824 | 456843 | | | |
| 1178406 | 220457 | 220476 | GGTACTATGTTGTCACTGAG | 68 | 2613 |
| | 456826 | 456845 | | | |
| 1178408 | 456864 | 456883 | TGCCCTCTTCGAAGAGATAG | 87 | 2614 |
| 1178411 | 456914 | 456933 | GGTCACTAGGCACACTAAAG | 87 | 2615 |
| 1178413 | 456916 | 456935 | TGGGTCACTAGGCACACTAA | 87 | 2616 |
| 1178415 | 456923 | 456942 | CAAGTCTTGGGTCACTAGGC | 93 | 2617 |
| 1178417 | 456926 | 456945 | AAGCAAGTCTTGGGTCACTA | 72 | 2618 |
| 1178418 | 457232 | 457251 | CTTAGCTACTCACCCCTGTT | 111 | 2619 |
| 1178420 | 457237 | 457256 | AATGGCTTAGCTACTCACCC | 79 | 104 |
| 1178422 | 457240 | 457259 | GATAATGGCTTAGCTACTCA | 77 | 2620 |
| 1178423 | 457286 | 457305 | CGACCTAAAGACCTAGCAAA | 55 | 2621 |
| 1178425 | 457289 | 457308 | AAACGACCTAAAGACCTAGC | 50 | 2622 |
| 1178426 | 457294 | 457313 | GTACAAAACGACCTAAAGAC | 77 | 2623 |
| 1178428 | 457574 | 457593 | ATTATGAACCATGGAGTCTC | 47 | 2624 |
| 1179735 | 448291 | 448310 | TCGCAATAAGATTCCATTGC | 106 | 2625 |
| 1179742 | 448305 | 448324 | GTGCAAAACAAGTTTCGCAA | 119 | 2626 |
| 1179745 | 448453 | 448472 | CCAGTAGGACTTACTAAATC | 79 | 2627 |
| 1179747 | 448455 | 448474 | TGCCAGTAGGACTTACTAAA | 99 | 2628 |
| 1179749 | 448457 | 448476 | AGTGCCAGTAGGACTTACTA | 76 | 2629 |
| 1179751 | 448630 | 448649 | GAGGATTGCATCACATGTGT | 118 | 2630 |

TABLE 33-continued

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1179753 | 448715 | 448734 | TAGCGCATTGAGCAAAATTC | 75 | 2631 |
| 1179755 | 448717 | 448736 | TGTAGCGCATTGAGCAAAAT | 75 | 2632 |
| 1179757 | 448719 | 448738 | ACTGTAGCGCATTGAGCAAA | 83 | 2633 |
| 1179759 | 448722 | 448741 | ATAACTGTAGCGCATTGAGC | 103 | 2634 |
| 1179761 | 448724 | 448743 | CGATAACTGTAGCGCATTGA | 68 | 2635 |
| 1179763 | 448727 | 448746 | CCACGATAACTGTAGCGCAT | 91 | 2636 |
| 1179765 | 448730 | 448749 | AGACCACGATAACTGTAGCG | 84 | 2637 |
| 1179767 | 448732 | 448751 | TTAGACCACGATAACTGTAG | 104 | 2638 |
| 1179769 | 448734 | 448753 | ATTTAGACCACGATAACTGT | 114 | 2639 |
| 1179770 | 448737 | 448756 | TATATTTAGACCACGATAAC | 106 | 2640 |
| 1179772 | 448740 | 448759 | CTGTATATTTAGACCACGAT | 78 | 2641 |
| 1179774 | 448828 | 448847 | AGGACCCTTAAGTCATAAAG | 75 | 2642 |
| 1179776 | 448834 | 448853 | ATTGCAAGGACCCTTAAGTC | 75 | 2643 |
| 1179778 | 448841 | 448860 | TATCCCAATTGCAAGGACCC | 131 | 2644 |
| 1179781 | 448948 | 448967 | ACGAAGCCAAAGGTACTTGA | 124 | 2645 |
| 1179783 | 449034 | 449053 | GCCCTGACTGTCATTCATAT | 86 | 2646 |
| 1179785 | 449037 | 449056 | ACGGCCCTGACTGTCATTCA | 98 | 2647 |
| 1179787 | 449039 | 449058 | GAACGGCCCTGACTGTCATT | 117 | 2648 |
| 1179789 | 449042 | 449061 | AAGGAACGGCCCTGACTGTC | 78 | 2649 |
| 1179791 | 449044 | 449063 | TGAAGGAACGGCCCTGACTG | 101 | 2650 |
| 1179793 | 449046 | 449065 | CCTGAAGGAACGGCCCTGAC | 108 | 2651 |
| 1179795 | 449049 | 449068 | TGGCCTGAAGGAACGGCCCT | 119 | 2652 |
| 1179797 | 449052 | 449071 | ATGTGGCCTGAAGGAACGGC | 76 | 2653 |
| 1179799 | 449058 | 449077 | ATAATCATGTGGCCTGAAGG | 104 | 2654 |
| 1179801 | 449060 | 449079 | CGATAATCATGTGGCCTGAA | 79 | 2655 |
| 1179803 | 449063 | 449082 | TAACGATAATCATGTGGCCT | 61 | 2656 |
| 1179805 | 449065 | 449084 | CATAACGATAATCATGTGGC | 81 | 2657 |
| 1179807 | 449101 | 449120 | GGCAAGTATGCTAGTCACTC | 73 | 2658 |
| 1179809 | 449103 | 449122 | CTGGCAAGTATGCTAGTCAC | 105 | 2659 |
| 1179811 | 449106 | 449125 | ATCCTGGCAAGTATGCTAGT | 83 | 2660 |
| 1179813 | 449108 | 449127 | AGATCCTGGCAAGTATGCTA | 103 | 2661 |
| 1179815 | 449110 | 449129 | GTAGATCCTGGCAAGTATGC | 68 | 2662 |
| 1179817 | 449115 | 449134 | CTCTTGTAGATCCTGGCAAG | 78 | 2663 |
| 1179818 | 449157 | 449176 | CAACATTATATCGATGCAAT | 89 | 2664 |
| 1179820 | 449160 | 449179 | TGTCAACATTATATCGATGC | 109 | 2665 |
| 1179822 | 449163 | 449182 | ACTTGTCAACATTATATCGA | 78 | 2666 |

TABLE 33-continued

Reduction of UBE3A-ATS RNA by 8,000 nM 5-10-5 MOE gapmers with mixed PO/PS internucleoside linkages in vitro (20,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1179825 | 448297 | 448316 | CAAGTTTCGCAATAAGATTC | 72 | 2667 |
| 1179833 | 456498 | 456517 | TTAGATTAAAATCTGGCCGG | 92 | 2668 |
| 1179834 | 456912 | 456931 | TCACTAGGCACACTAAAGTG | 107 | 2669 |
| 1179838 | 457298 | 457317 | AGATGTACAAAACGACCTAA | 99 | 2670 |
| 1179840 | 457386 | 457405 | TAAGGATTCAATAGTGTAGG | 34 | 2671 |
| 1179842 | 457503 | 457522 | GGCACACCTGGATTTCACTA | 12 | 2672 |
| 1179845 | 448416 | 448435 | GAGCAAGGGTCTTAGTGCCA | 108 | 2673 |
| 1179847 | 448625 | 448644 | TTGCATCACATGTGTCAGTC | 102 | 2674 |
| 1179849 | 448843 | 448862 | TTTATCCCAATTGCAAGGAC | 86 | 2675 |

Example 2: Effect of 5-10-5 MOE Gapmer Modified Oligonucleotides on Human UBE3A-ATS RNA In Vitro, Single Dose Modified oligonucleotides complementary to human UBE3A-ATS nucleic acid were tested for their effect on UBE3A-ATS RNA levels in vitro.

The modified oligonucleotides in the tables below are 5-10-5 gapmers. The gapmers are 20 nucleosides in length, wherein the central gap segment consists of ten 2'-β-D-deoxynucleosides and the 5' and 3' wing segments each consists of five 2'-MOE nucleosides. The sugar motif for the gapmers is (from 5' to 3'): eeeeedddddddddeeeee; wherein represents a 2'-β-D-deoxyribosyl sugar moiety, and 'e' represents a 2'-MOE sugar moiety.

Each internucleoside linkage of Compound IDs 617456, 617457, 617460, 617461, and 617557 is a phosphorothioate internucleoside linkage. All other compounds have an internucleoside linkage motif of: soooosssssssssssooss, wherein each "s" represents a phosphorothioate internucleoside linkage and each "o" represents a phosphodiester internucleoside linkage.

All cytosine residues are 5-methylcytosines.

"Start site" indicates the 5'-most nucleoside to which the modified oligonucleotide is complementary in target nucleic acid sequence. "Stop site" indicates the 3'-most nucleoside to which the modified oligonucleotide is complementary in the target nucleic acid sequence. Each modified oligonucleotide listed in the Tables below is 100% complementary to SEQ ID NO: 1. Start and stop sites for Compound 750519 are marked with a hashtag (#) in several tables below. The complete list of start sites for Compound 750519 are listed in Table 4b.

Human IPS cell derived ReproNeuro™ Neurons (Repro-CELL) were cultured per manufacturer instructions at 40,000 cells per well and were treated with 8,000 nM of modified oligonucleotide by free uptake. After a treatment period of approximately 5 days, total RNA was isolated from the cells and UBE3A-ATS RNA levels were measured by quantitative real-time RTPCR. Human UBE3A-ATS primer probe set RTS4796 (described herein in Example 1) was used to measure RNA levels. UBE3A-ATS RNA levels were normalized to total RNA content, as measured by RIBOGREEN®. Reduction of UBE3A-ATS is presented in the tables below as percent UBE3A-ATS RNA amount relative to untreated control (UTC) cells. Each table represents results from an individual assay plate. The values marked with an asterisk (*) indicate that the modified oligonucleotide is complementary to the amplicon region of the primer probe set. Additional assays may be used to measure the potency and efficacy of the modified oligonucleotides complementary to the amplicon region.

TABLE 34

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 38 | 172 |
| 749882 | 460115 | 460134 | ACTTTATAGTGTGGATGGTA | 30 | 586 |
| 750519 | 349103* | 349122* | GTCATCACCTCTCTTCAGGA | 23 | 181 |
| 1165438 | 448412 | 448431 | AAGGGTCTTAGTGCCAAATA | 75 | 2075 |
| 1165443 | 449094 | 449113 | ATGCTAGTCACTCATTGAGA | 65 | 2076 |

TABLE 34-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1165448 | 449641 | 449660 | TGATCCATTAGATAGGCTAT | 80 | 2077 |
| 1165450 | 452254 | 452273 | TCTCACGCTGTGTGAATCAA | 81 | 2078 |
| 1165456 | 452267 | 452286 | AGGGAAGTCTAGGTCTCACG | 54 | 2079 |
| 1165472 | 454155 | 454174 | GACCCTTATGGAGACTTATA | 77 | 2080 |
| 1165478 | 454464 | 454483 | GTGGACTCCACACACCTACT | 62 | 2081 |
| 1165484 | 454579 | 454598 | GCAAGCAAAGACTACACCGT | 48 | 2082 |
| 1165488 | 454856 | 454875 | ATATTCCCTATCCAGGGTAG | 91 | 2083 |
| 1165494 | 454862 | 454881 | AGGTGTATATTCCCTATCCA | 76 | 2084 |
| 1165500 | 455029 | 455048 | TGATATTGCAGTGGGATGGC | 59 | 2085 |
| 1165504 | 456625 | 456644 | GCATGGTTATCTAATGCATC | 60 | 2086 |
| 1165511 | 220440 456809 | 220459 456828 | GAGGGATCCCCAAATAGAGC | 51 | 2087 |
| 1165517 | 457019 | 457038 | ATCACAGTTGCTTGACCCTT | 63 | 2088 |
| 1165523 | 457983 | 458002 | TGATCTATTATGAGGGCATC | 25 | 2089 |
| 1165529 | 458792 | 458811 | TTCCCTAATATAGGGCAGAT | 49 | 2090 |
| 1165535 | 458943 | 458962 | CTATAGGACCTCAGGAGATT | 42 | 2091 |
| 1165540 | 458951 | 458970 | CTCAAGACCTATAGGACCTC | 50 | 2092 |
| 1165547 | 460109 | 460128 | TAGTGTGGATGGTATCCTGG | 55 | 2093 |
| 1165552 | 460506 | 460525 | TAGGGTGGTTGGTTCAAAAT | 24 | 2094 |
| 1165558 | 460842 | 460861 | CACACATATAGGCTAGCCAA | 44 | 2095 |
| 1165562 | 461414 | 461433 | TGGGTTACTTTCCAATAGAG | 27 | 2096 |
| 1165573 | 464387 | 464406 | CTTAGGTAGTTCACAACTCT | 37 | 2097 |
| 1165578 | 464556 | 464575 | CCTGTAGTATGTGGATACTG | 40 | 2098 |
| 1165588 | 465372 | 465391 | GGATGGTGTGTATGTTATGA | 32 | 2099 |
| 1165599 | 467293 | 467312 | GTAGTCTATTGGTGTTCCTT | 45 | 2100 |
| 1165604 | 467418 | 467437 | ATACGCTCCTTCATTTCATG | 49 | 2101 |
| 1165613 | 483363 | 483382 | GAATTCAATGGACCCACATG | 67 | 2102 |
| 1165619 | 483961 | 483980 | GGGTAGGATTCATGGTCCAA | 43 | 2103 |
| 1165626 | 486352 | 486371 | TAATAGACTGCGATTATACA | 64 | 2104 |
| 1165642 | 493857 | 493876 | GGCCTAATCTATGCTGGGCC | 63 | 2105 |
| 1165648 | 493865 | 493884 | TGAGATTAGGCCTAATCTAT | 79 | 2106 |
| 1165654 | 496831 | 496850 | GATTAGGTATGGAGGCCATG | 48 | 2107 |
| 1165659 | 499667 | 499686 | CCCCAATACAGATTCAGTGG | 75 | 2108 |
| 1165665 | 499676 | 499695 | TCAAGGTAGCCCCAATACAG | 44 | 2109 |
| 1165669 | 500693 | 500712 | CAAGAGGTACTGTAAGCCCT | 87 | 2110 |
| 1165674 | 500907 | 500926 | TGTTTTGACCTAACTGGCCT | 75 | 2111 |
| 1165679 | 501761 | 501780 | GCTAAGAGTCACCTGTATCC | 53 | 2112 |

TABLE 34-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1165685 | 502372 | 502391 | AAGGTATTAAGGCCCTTGGC | 54 | 2113 |
| 1165702 | 503347 | 503366 | GGTGATCAGCTCAACACCCC | 73 | 2114 |
| 1165708 | 503362 | 503381 | AGGAGTGTTAGCCCAGGTGA | 53 | 2115 |
| 1165714 | 503369 | 503388 | GGGTCATAGGAGTGTTAGCC | 77 | 2116 |
| 1165720 | 503423 | 503442 | AAGGTGATGACACCCCTACC | 67 | 2117 |
| 1165730 | 504128 | 504147 | AGCTATTTCATTAAGTCACC | 43 | 2118 |
| 1165737 | 504432 | 504451 | GTATATTAGTCTAAGGCAGT | 30 | 2119 |
| 1165742 | 504976 | 504995 | TATTATCTTCTTAGGGTCGA | 37 | 2120 |
| 1165748 | 505174 | 505193 | TGTGTACCGAGCTCAAGAAC | 55 | 2121 |
| 1165754 | 505184 | 505203 | AGTCTGTCTCTGTGTACCGA | 70 | 2122 |
| 1165759 | 505217 | 505236 | GACACTCTCGCTGAGGACAC | 58 | 2123 |
| 1165767 | 505321 | 505340 | GCCGCCTCTGTTATTGTGAT | 56 | 2124 |
| 1165773 | 505328 | 505347 | AAATTGGGCCGCCTCTGTTA | 41 | 2125 |
| 1165784 | 505746 | 505765 | CTGTAGGTTGACAGGACATG | 50 | 2126 |
| 1165790 | 505822 | 505841 | TGAGGGTGCTTAGTGAACTG | 78 | 2127 |
| 1165801 | 506449 | 506468 | GAGTCTGTCTTTAGGGTCAC | 42 | 2128 |
| 1165803 | 507899 | 507918 | CGATACCTGCTTTTGTGACA | 54 | 2129 |
| 1165807 | 507908 | 507927 | ATAGCCATTCGATACCTGCT | 56 | 2130 |
| 1165813 | 507916 | 507935 | ACTGCAGGATAGCCATTCGA | 72 | 2131 |
| 1165824 | 508792 | 508811 | TATGAATGCCACCGTGATTG | 79 | 2132 |
| 1165846 | 453364 | 453383 | AACTACATAGGCACTCTACT | 78 | 2133 |
| 1165859 | 461526 | 461545 | AACATTCAGCTAGACTAGTT | 43 | 2134 |
| 1165860 | 461902 | 461921 | ATGAGACCCCACAATTTGGT | 79 | 2135 |
| 1165866 | 464995 | 465014 | ATAGAGGCCCTCTTGTTTCA | 60 | 2136 |
| 1165868 | 465391 | 465410 | CAATTGTCAGACTTATTGAG | 66 | 2137 |
| 1165872 | 465893 | 465912 | GAACTCCCACAAGGTACTCT | 45 | 2138 |
| 1165875 | 468353 | 468372 | CTGTAGTATGCATTGACAAG | 53 | 2139 |
| 1165881 | 484299 | 484318 | TACTAGGGCCAGAGAATCCA | 55 | 2140 |
| 1165885 | 488335 | 488354 | AAGCCACTCATGTACATGAG | 55 | 2141 |
| 1165887 | 489494 | 489513 | AAACTGGGTTGAGACTATTC | 42 | 2142 |
| 1165888 | 489580 | 489599 | CTGCAGTGGTACCACAGACC | 40 | 2143 |
| 1165896 | 502392 | 502411 | TGACTACACATCTTGTATAC | 73 | 2144 |
| 1165897 | 502450 | 502469 | CTAGGCAGCTCTTTGTAGGC | 25 | 2145 |
| 1165898 | 503807 | 503826 | CCCTATAGGTCAAAATGCC | 51 | 2146 |

TABLE 34-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 1165903 | 505544 | 505563 | TCAGTCAGGTACAGGTGTTG | 58 | 2147 |
| 1165904 | 505834 | 505853 | GTCAAAGACCTGTGAGGGTG | 63 | 2148 |
| 1165913 | 510480 | 510499 | GGTCTTTGCAGTTAAGTTAT | 65 | 2149 |

TABLE 35

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC)) | SEQ ID NO |
|---|---|---|---|---|---|
| 617557 | 483977 | 483996 | ATCATGTGCATACCCAGGGT | 52 | 172 |
| 749882 | 460115 | 460134 | ACTTTATAGTGTGGATGGTA | 38 | 586 |
| 750519 | 349103* | 349122* | GTCATCACCTCTCTTCAGGA | 26 | 181 |
| 1165437 | 448410 | 448429 | GGGTCTTAGTGCCAAATATC | 112 | 2150 |
| 1165454 | 452264 | 452283 | GAAGTCTAGGTCTCACGCTG | 84 | 2151 |
| 1165466 | 453361 | 453380 | TACATAGGCACTCTACTAGC | 96 | 2152 |
| 1165470 | 454153 | 454172 | CCCTTATGGAGACTTATATA | 81 | 2153 |
| 1165476 | 454164 | 454183 | TGAAGATTTGACCCTTATGG | 114 | 2154 |
| 1165482 | 454577 | 454596 | AAGCAAAGACTACACCGTGA | 80 | 2155 |
| 1165486 | 454847 | 454866 | ATCCAGGGTAGAAGACTAGC | 75 | 2156 |
| 1165492 | 454860 | 454879 | GTGTATATTCCCTATCCAGG | 83 | 2157 |
| 1165498 | 455016 | 455035 | GGATGGCTGTCAATGCTGAT | 84 | 2158 |
| 1165502 | 455214 | 455233 | ACAAGTCTACTACCAATAAG | 57 | 2159 |
| 1165508 | 220325 456694 | 220344 456713 | ATTCTCATCATCGATCCAAA | 58 | 2160 |
| 1165515 | 457017 | 457036 | CACAGTTGCTTGACCCTTAA | 58 | 2161 |
| 1165521 | 457382 | 457401 | GATTCAATAGTGTAGGTGAC | 29 | 2162 |
| 1165527 | 458789 | 458808 | CCTAATATAGGGCAGATGAT | 53 | 2163 |
| 1165533 | 458939 | 458958 | AGGACCTCAGGAGATTGTAC | 29 | 2164 |
| 1165538 | 458949 | 458968 | CAAGACCTATAGGACCTCAG | 29 | 2165 |
| 1165545 | 459548 | 459567 | AGACTATCCTGGTATGACTG | 22 | 2166 |
| 1165551 | 460353 | 460372 | TGATTGACTACTTCAACCTG | 64 | 2167 |
| 1165556 | 460512 | 460531 | CGTTTATAGGGTGGTTGGTT | 38 | 2168 |
| 1165564 | 461520 | 461539 | CAGCTAGACTAGTTGAAATC | 51 | 2169 |
| 1165569 | 461900 | 461919 | GAGACCCCACAATTTGGTCC | 94 | 2170 |
| 1165571 | 463886 | 463905 | AGGCAGTTGTGATAGTCAAC | 93 | 2171 |
| 1165577 | 464397 | 464416 | CCATTCAGCACTTAGGTAGT | 29 | 2172 |
| 1165581 | 464561 | 464580 | TATGCCCTGTAGTATGTGGA | 56 | 2173 |

TABLE 35-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1165586 | 465244 | 465263 | TTTTATTGGTCATCTCGGGT | 27 | 2174 |
| 1165591 | 465385 | 465404 | TCAGACTTATTGAGGATGGT | 47 | 2175 |
| 1165597 | 466248 | 466267 | ACTGGTAGGATCTATGGCAG | 43 | 2176 |
| 1165602 | 467299 | 467318 | CACAGAGTAGTCTATTGGTG | 62 | 2177 |
| 1165608 | 467805 | 467824 | GTCTCCCTCTTAGTGATTGG | 25 | 2178 |
| 1165611 | 474168 | 474187 | AGTGGTTGCCTTAGTATTAC | 20 | 2179 |
| 1165617 | 483858 | 483877 | TGTAAATGGCCTGACTAGGC | 75 | 2180 |
| 1165624 | 485655 | 485674 | CTAGGACCAGTTGGTTCACT | 72 | 2181 |
| 1165637 | 489520 | 489539 | AATGGACCACCTAAGACCTC | 85 | 2182 |
| 1165640 | 493853 | 493872 | TAATCTATGCTGGGCCCAA | 76 | 2183 |
| 1165646 | 493863 | 493882 | AGATTAGGCCTAATCTATGC | 94 | 2184 |
| 1165652 | 496808 | 496827 | GACCCTCATCACTTTTTGAC | 66 | 2185 |
| 1165658 | 498508 | 498527 | GCCCGGCAAGAGATTCACTT | 79 | 2186 |
| 1165663 | 499673 | 499692 | AGGTAGCCCCAATACAGATT | 60 | 2187 |
| 1165667 | 500493 | 500512 | AGGGCCATGTTAAAGGCCTC | 82 | 2188 |
| 1165672 | 500901 | 500920 | GACCTAACTGGCCTTTGGGT | 64 | 2189 |
| 1165683 | 502143 | 502162 | TATGTGGAATCAGTGCTACC | 75 | 2190 |
| 1165689 | 502377 | 502396 | TATACAAGGTATTAAGGCCC | 55 | 2191 |
| 1165694 | 502446 | 502465 | GCAGCTCTTTGTAGGCCCAA | 25 | 2192 |
| 1165700 | 503099 | 503118 | GACTAATAGGCCTTTCTACA | 59 | 2193 |
| 1165706 | 503360 | 503379 | GAGTGTTAGCCCAGGTGATC | 57 | 2194 |
| 1165712 | 503366 | 503385 | TCATAGGAGTGTTAGCCCAG | 36 | 2195 |
| 1165718 | 503420 | 503439 | GTGATGACACCCCTACCATG | 96 | 2196 |
| 1165724 | 503427 | 503446 | GATTAAGGTGATGACACCCC | 27 | 2197 |
| 1165728 | 503943 | 503962 | CACCAACCTTAAATAGTAGG | 63 | 2198 |
| 1165735 | 504429 | 504448 | TATTAGTCTAAGGCAGTCAG | 78 | 2199 |
| 1165741 | 504653 | 504672 | GGAGCCTTACGCTTGGCTGA | 55 | 2200 |
| 1165746 | 505172 | 505191 | TGTACCGAGCTCAAGAACTG | 58 | 2201 |
| 1165752 | 505180 | 505199 | TGTCTCTGTGTACCGAGCTC | 59 | 2202 |
| 1165758 | 505215 | 505234 | CACTCTCGCTGAGGACACAT | 60 | 2203 |
| 1165765 | 505319 | 505338 | CGCCTCTGTTATTGTGATAT | 83 | 2204 |
| 1165771 | 505326 | 505345 | ATTGGGCCGCCTCTGTTATT | 54 | 2205 |
| 1165777 | 505333 | 505352 | TGTAGAAATTGGGCCGCCTC | 41 | 2206 |
| 1165782 | 505744 | 505763 | GTAGGTTGACAGGACATGCT | 75 | 2207 |
| 1165788 | 505819 | 505838 | GGGTGCTTAGTGAACTGTGG | 30 | 2208 |
| 1165794 | 505829 | 505848 | AGACCTGTGAGGGTGCTTAG | 84 | 2209 |
| 1165799 | 506279 | 506298 | GTCTACCAGGGTGGTATTAT | 70 | 2210 |

TABLE 35-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1165802 | 506782 | 506801 | TATATACTCCAGGTTGTGGA | 44 | 2211 |
| 1165805 | 507906 | 507925 | AGCCATTCGATACCTGCTTT | 50 | 2212 |
| 1165811 | 507913 | 507932 | GCAGGATAGCCATTCGATAC | 78 | 2213 |
| 1165822 | 508789 | 508808 | GAATGCCACCGTGATTGCAA | 51 | 2214 |
| 1165827 | 510129 | 510148 | GCACATAGACCATAGCTGAA | 32 | 2215 |
| 1165840 | 448466 | 448485 | CAATAGAATAGTGCCAGTAG | 74 | 2216 |
| 1165841 | 449441 | 449460 | TGATCATACTGGAGCCAGGT | 60 | 2217 |
| 1165845 | 452251 | 452270 | CACGCTGTGTGAATCAAAAG | 87 | 2218 |
| 1165855 | 460974 | 460993 | GTGTTTATCCAAACCAAGGG | 21 | 2219 |
| 1165871 | 465890 | 465909 | CTCCCACAAGGTACTCTTGC | 72 | 2220 |
| 1165879 | 484093 | 484112 | GGATGTCAGTTCAGATGAAC | 74 | 2221 |
| 1165883 | 486393 | 486412 | CAACATAGATCCTCTGTTAG | 74 | 2222 |
| 1165886 | 489101 | 489120 | CTGCTCCCTAAGCTTAGATA | 58 | 2223 |
| 1165895 | 501152 | 501171 | AGTAAAGAGCCACCTAAGGG | 100 | 2224 |

TABLE 36

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617557 | 483977 | 483996 | ATCATGTGCATACCCAGGGT | 40 | 172 |
| 749882 | 460115 | 460134 | ACTTTATAGTGTGGATGGTA | 75 | 586 |
| 750519 | 349103* | 349122* | GTCATCACCTCTCTTCAGGA | 28 | 181 |
| 1165436 | 448409 | 448428 | GGTCTTAGTGCCAAATATCC | 46 | 2225 |
| 1165441 | 448460 | 448479 | AATAGTGCCAGTAGGACTTA | 71 | 2226 |
| 1165446 | 449099 | 449118 | CAAGTATGCTAGTCACTCAT | 40 | 2227 |
| 1165453 | 452260 | 452279 | TCTAGGTCTCACGCTGTGTG | 53 | 2228 |
| 1165460 | 453213 | 453232 | ATAGTGTTCTTACATCCACC | 59 | 2229 |
| 1165469 | 454152 | 454171 | CCTTATGGAGACTTATATAC | 103 | 2230 |
| 1165475 | 454163 | 454182 | GAAGATTTGACCCTTATGGA | 91 | 2231 |
| 1165481 | 454576 | 454595 | AGCAAAGACTACACCGTGAC | 69 | 2232 |
| 1165491 | 454859 | 454878 | TGTATATTCCCTATCCAGGG | 106 | 2233 |
| 1165497 | 455015 | 455034 | GATGGCTGTCAATGCTGATA | 53 | 2234 |
| 1165507 | 220321 456690 | 220340 456709 | TCATCATCGATCCAAACAAG | 58 | 2235 |
| 1165514 | 457016 | 457035 | ACAGTTGCTTGACCCTTAAT | 126 | 2236 |
| 1165520 | 457379 | 457398 | TCAATAGTGTAGGTGACATG | 63 | 2237 |

TABLE 36-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1165526 | 458398 | 458417 | ATGTGGGCCTCTATTAAGAT | 47 | 2238 |
| 1165532 | 458937 | 458956 | GACCTCAGGAGATTGTACAA | 45 | 2239 |
| 1165537 | 458948 | 458967 | AAGACCTATAGGACCTCAGG | 53 | 2240 |
| 1165544 | 459547 | 459566 | GACTATCCTGGTATGACTGT | 57 | 2241 |
| 1165550 | 460352 | 460371 | GATTGACTACTTCAACCTGA | 23 | 2242 |
| 1165555 | 460510 | 460529 | TTTATAGGGTGGTTGGTTCA | 30 | 2243 |
| 1165561 | 460850 | 460869 | GGATTTACCACACATATAGG | 39 | 2244 |
| 1165563 | 461451 | 461470 | GGTAAGGCAGCTCCTGACAA | 32 | 2245 |
| 1165568 | 461899 | 461918 | AGACCCCACAATTTGGTCCC | 51 | 2246 |
| 1165576 | 464390 | 464409 | GCACTTAGGTAGTTCACAAC | 41 | 2247 |
| 1165585 | 465243 | 465262 | TTTATTGGTCATCTCGGGTA | 44 | 2248 |
| 1165590 | 465384 | 465403 | CAGACTTATTGAGGATGGTG | 30 | 2249 |
| 1165593 | 465564 | 465583 | TTAGGACAAGTCTTATAGAG | 20 | 2250 |
| 1165596 | 466247 | 466266 | CTGGTAGGATCTATGGCAGT | 32 | 2251 |
| 1165601 | 467298 | 467317 | ACAGAGTAGTCTATTGGTGT | 67 | 2252 |
| 1165607 | 467804 | 467823 | TCTCCCTCTTAGTGATTGGT | 45 | 2253 |
| 1165616 | 483851 | 483870 | GGCCTGACTAGGCATTGAAT | 16 | 2254 |
| 1165621 | 483976 | 483995 | TCATGTGCATACCCAGGGTA | 76 | 2255 |
| 1165623 | 485654 | 485673 | TAGGACCAGTTGGTTCACTG | 66 | 2256 |
| 1165629 | 486356 | 486375 | ATGTTAATAGACTGCGATTA | 102 | 2257 |
| 1165632 | 489099 | 489118 | GCTCCCTAAGCTTAGATATA | 85 | 2258 |
| 1165636 | 489519 | 489538 | ATGGACCACCTAAGACCTCA | 79 | 2259 |
| 1165639 | 493852 | 493871 | AATCTATGCTGGGCCCCAAT | 52 | 2260 |
| 1165645 | 493862 | 493881 | GATTAGGCCTAATCTATGCT | 71 | 2261 |
| 1165651 | 496565 | 496584 | TCCATCTACTATTAATGAGC | 81 | 2262 |
| 1165657 | 497266 | 497285 | GATTAGGCAGCTTCACTACT | 52 | 2263 |
| 1165662 | 499671 | 499690 | GTAGCCCAATACAGATTCA | 35 | 2264 |
| 1165671 | 500900 | 500919 | ACCTAACTGGCCTTTGGGTC | 111 | 2265 |
| 1165677 | 500913 | 500932 | TCAAGGTGTTTTGACCTAAC | 64 | 2266 |
| 1165682 | 501766 | 501785 | GATGGGCTAAGAGTCACCTG | 99 | 2267 |
| 1165688 | 502375 | 502394 | TACAAGGTATTAAGGCCCTT | 98 | 2268 |
| 1165693 | 502442 | 502461 | CTCTTTGTAGGCCCAAGGGA | 66 | 2269 |
| 1165698 | 502763 | 502782 | AATAGGCACTTCGGGCAAAT | 75 | 2270 |
| 1165705 | 503359 | 503378 | AGTGTTAGCCCAGGTGATCA | 71 | 2271 |
| 1165711 | 503365 | 503384 | CATAGGAGTGTTAGCCCAGG | 61 | 2272 |
| 1165717 | 503419 | 503438 | TGATGACACCCCTACCATGG | 96 | 2273 |

TABLE 36-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1165723 | 503426 | 503445 | ATTAAGGTGATGACACCCCT | 81 | 2274 |
| 1165734 | 504428 | 504447 | ATTAGTCTAAGGCAGTCAGG | 96 | 2275 |
| 1165740 | 504436 | 504455 | GTAGGTATATTAGTCTAAGG | 51 | 2276 |
| 1165745 | 505171 | 505190 | GTACCGAGCTCAAGAACTGT | 71 | 2277 |
| 1165751 | 505178 | 505197 | TCTCTGTGTACCGAGCTCAA | 58 | 2278 |
| 1165757 | 505214 | 505233 | ACTCTCGCTGAGGACACATC | 73 | 2279 |
| 1165762 | 505223 | 505242 | AATGAGGACACTCTCGCTGA | 76 | 2280 |
| 1165770 | 505325 | 505344 | TTGGGCCGCCTCTGTTATTG | 51 | 2281 |
| 1165776 | 505332 | 505351 | GTAGAAATTGGGCCGCCTCT | 35 | 2282 |
| 1165781 | 505743 | 505762 | TAGGTTGACAGGACATGCTG | 66 | 2283 |
| 1165787 | 505815 | 505834 | GCTTAGTGAACTGTGGGCAC | 72 | 2284 |
| 1165793 | 505827 | 505846 | ACCTGTGAGGGTGCTTAGTG | 62 | 2285 |
| 1165798 | 506277 | 506296 | CTACCAGGGTGGTATTATAA | 33 | 2286 |
| 1165810 | 507912 | 507931 | CAGGATAGCCATTCGATACC | 44 | 2287 |
| 1165821 | 508786 | 508805 | TGCCACCGTGATTGCAAAGT | 61 | 2288 |
| 1165826 | 510127 | 510146 | ACATAGACCATAGCTGAACC | 65 | 2289 |
| 1165844 | 449863 | 449882 | GGCATCCTTAAATCCTGGTT | 66 | 2290 |
| 1165849 | 454845 | 454864 | CCAGGGTAGAAGACTAGCAT | 74 | 2291 |
| 1165851 | 455058 | 455077 | GAACCCTTTGGTCTAAGCAA | 80 | 2292 |
| 1165863 | 463777 | 463796 | TATAGATTGGGCTTTAGAGG | 76 | 2293 |
| 1165865 | 464560 | 464579 | ATGCCCTGTAGTATGTGGAT | 74 | 2294 |
| 1165877 | 473792 | 473811 | GTAATGCTGTTGTACACTAG | 59 | 2295 |
| 1165893 | 499914 | 499933 | TTTTGCATAATAGGAGGTCC | 62 | 2296 |
| 1165899 | 503942 | 503961 | ACCAACCTTAAATAGTAGGA | 61 | 2297 |
| 1165907 | 506780 | 506799 | TATACTCCAGGTTGTGGAGG | 55 | 2298 |
| 1165910 | 507903 | 507922 | CATTCGATACCTGCTTTTGT | 71 | 2299 |

TABLE 37

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1065438 | 449442 | 449461 | ATGATCATACTGGAGCCAGG | 65 | 1936 |
| 1178376 | 220314 456683 | 220333 456702 | CGATCCAAACAAGCACCCTC | 80 | 2300 |
| 1178378 | 220316 456685 | 220335 456704 | ATCGATCCAAACAAGCACCC | 69 | 2301 |

TABLE 37-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1178380 | 220319 | 220338 | ATCATCGATCCAAACAAGCA | 55 | 2302 |
|  | 456688 | 456707 |  |  |  |
| 1178385 | 456754 | 456773 | CCGCACATCTGGACCTCAGA | 97 | 2303 |
| 1178387 | 456756 | 456775 | GGCCGCACATCTGGACCTCA | 89 | 2304 |
| 1178389 | 456759 | 456778 | GAGGGCCGCACATCTGGACC | 94 | 2305 |
| 1178391 | 456761 | 456780 | TGGAGGGCCGCACATCTGGA | 83 | 2306 |
| 1178393 | 456763 | 456782 | ATTGGAGGGCCGCACATCTG | 93 | 2307 |
| 1178395 | 456765 | 456784 | CTATTGGAGGGCCGCACATC | 63 | 2308 |
| 1178397 | 456767 | 456786 | TCCTATTGGAGGGCCGCACA | 90 | 2309 |
| 1178399 | 456770 | 456789 | TTGTCCTATTGGAGGGCCGC | 64 | 2310 |
| 1178401 | 220403 | 220422 | ATTTGTCCTATTGGAGGGCC | 101 | 2311 |
|  | 456772 | 456791 |  |  |  |
| 1178403 | 220452 | 220471 | TATGTTGTCACTGAGGGATC | 78 | 2312 |
|  | 456821 | 456840 |  |  |  |
| 1178405 | 220456 | 220475 | GTACTATGTTGTCACTGAGG | 80 | 2313 |
|  | 456825 | 456844 |  |  |  |
| 1178407 | 456863 | 456882 | GCCCTCTTCGAAGAGATAGA | 90 | 2314 |
| 1178409 | 456865 | 456884 | CTGCCCTCTTCGAAGAGATA | 58 | 2315 |
| 1178410 | 456913 | 456932 | GTCACTAGGCACACTAAAGT | 62 | 2316 |
| 1178412 | 456915 | 456934 | GGGTCACTAGGCACACTAAA | 76 | 2317 |
| 1178414 | 456922 | 456941 | AAGTCTTGGGTCACTAGGCA | 63 | 2318 |
| 1178416 | 456924 | 456943 | GCAAGTCTTGGGTCACTAGG | 81 | 2319 |
| 1178419 | 457236 | 457255 | ATGGCTTAGCTACTCACCCC | 68 | 2320 |
| 1178421 | 457239 | 457258 | ATAATGGCTTAGCTACTCAC | 60 | 2321 |
| 1178424 | 457287 | 457306 | ACGACCTAAAGACCTAGCAA | 49 | 2322 |
| 1178427 | 457297 | 457316 | GATGTACAAAACGACCTAAA | 60 | 2323 |
| 1179741 | 448298 | 448317 | ACAAGTTTCGCAATAAGATT | 55 | 2324 |
| 1179743 | 448414 | 448433 | GCAAGGGTCTTAGTGCCAAA | 78 | 2325 |
| 1179744 | 448450 | 448469 | GTAGGACTTACTAAATCATC | 75 | 2326 |
| 1179746 | 448454 | 448473 | GCCAGTAGGACTTACTAAAT | 57 | 2327 |
| 1179748 | 448456 | 448475 | GTGCCAGTAGGACTTACTAA | 62 | 2328 |
| 1179750 | 448629 | 448648 | AGGATTGCATCACATGTGTC | 56 | 2329 |
| 1179752 | 448714 | 448733 | AGCGCATTGAGCAAAATTCC | 82 | 2330 |
| 1179754 | 448716 | 448735 | GTAGCGCATTGAGCAAAATT | 76 | 2331 |
| 1179756 | 448718 | 448737 | CTGTAGCGCATTGAGCAAAA | 83 | 2332 |
| 1179758 | 448720 | 448739 | AACTGTAGCGCATTGAGCAA | 52 | 2333 |
| 1179760 | 448723 | 448742 | GATAACTGTAGCGCATTGAG | 85 | 2334 |

TABLE 37-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1179762 | 448726 | 448745 | CACGATAACTGTAGCGCATT | 38 | 2335 |
| 1179764 | 448728 | 448747 | ACCACGATAACTGTAGCGCA | 67 | 2336 |
| 1179766 | 448731 | 448750 | TAGACCACGATAACTGTAGC | 80 | 2337 |
| 1179768 | 448733 | 448752 | TTTAGACCACGATAACTGTA | 54 | 2338 |
| 1179771 | 448738 | 448757 | GTATATTTAGACCACGATAA | 58 | 2339 |
| 1179773 | 448741 | 448760 | TCTGTATATTTAGACCACGA | 49 | 2340 |
| 1179775 | 448831 | 448850 | GCAAGGACCCTTAAGTCATA | 72 | 2341 |
| 1179777 | 448836 | 448855 | CAATTGCAAGGACCCTTAAG | 99 | 2342 |
| 1179779 | 448842 | 448861 | TTATCCCAATTGCAAGGACC | 49 | 2343 |
| 1179780 | 448920 | 448939 | AGTCAGGCACCAGATTGCTC | 112 | 2344 |
| 1179782 | 448949 | 448968 | AACGAAGCCAAAGGTACTTG | 80 | 2345 |
| 1179784 | 449036 | 449055 | CGGCCCTGACTGTCATTCAT | 71 | 2346 |
| 1179786 | 449038 | 449057 | AACGGCCCTGACTGTCATTC | 53 | 2347 |
| 1179788 | 449040 | 449059 | GGAACGGCCCTGACTGTCAT | 95 | 2348 |
| 1179790 | 449043 | 449062 | GAAGGAACGGCCCTGACTGT | 70 | 2349 |
| 1179792 | 449045 | 449064 | CTGAAGGAACGGCCCTGACT | 105 | 2350 |
| 1179794 | 449047 | 449066 | GCCTGAAGGAACGGCCCTGA | 111 | 2351 |
| 1179796 | 449051 | 449070 | TGTGGCCTGAAGGAACGGCC | 100 | 2352 |
| 1179798 | 449054 | 449073 | TCATGTGGCCTGAAGGAACG | 68 | 2353 |
| 1179800 | 449059 | 449078 | GATAATCATGTGGCCTGAAG | 49 | 2354 |
| 1179802 | 449062 | 449081 | AACGATAATCATGTGGCCTG | 86 | 2355 |
| 1179804 | 449064 | 449083 | ATAACGATAATCATGTGGCC | 52 | 2356 |
| 1179806 | 449096 | 449115 | GTATGCTAGTCACTCATTGA | 91 | 2357 |
| 1179808 | 449102 | 449121 | TGGCAAGTATGCTAGTCACT | 12 | 2358 |
| 1179810 | 449104 | 449123 | CCTGGCAAGTATGCTAGTCA | 76 | 2359 |
| 1179812 | 449107 | 449126 | GATCCTGGCAAGTATGCTAG | 103 | 2360 |
| 1179814 | 449109 | 449128 | TAGATCCTGGCAAGTATGCT | 71 | 2361 |
| 1179816 | 449111 | 449130 | TGTAGATCCTGGCAAGTATG | 79 | 2362 |
| 1179819 | 449158 | 449177 | TCAACATTATATCGATGCAA | 66 | 2363 |
| 1179821 | 449162 | 449181 | CTTGTCAACATTATATCGAT | 61 | 2364 |
| 1179823 | 449164 | 449183 | AACTTGTCAACATTATATCG | 79 | 2365 |
| 1179824 | 448294 | 448313 | GTTTCGCAATAAGATTCCAT | 98 | 2366 |
| 1179835 | 457231 | 457250 | TTAGCTACTCACCCCTGTTC | 74 | 2367 |
| 1179836 | 457241 | 457260 | AGATAATGGCTTAGCTACTC | 63 | 2368 |
| 1179837 | 457290 | 457309 | AAAACGACCTAAAGACCTAG | 92 | 2369 |
| 1179839 | 457384 | 457403 | AGGATTCAATAGTGTAGGTG | 25 | 2370 |

TABLE 37-continued

Reduction of UBE3A-ATS RNA by 8,000 nM 5-10-5 MOE gapmers with mixed PO/PS internucleoside linkages in vitro

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 1179841 | 457502 | 457521 | GCACACCTGGATTTCACTAC | 33 | 2371 |
| 1179843 | 457505 | 457524 | TTGGCACACCTGGATTTCAC | 28 | 2372 |
| 1179844 | 457674 | 457693 | ATAACTTACCTTGTTGCAAC | 65 | 2373 |
| 1179846 | 448600 | 448619 | TTGAGAAGAAAACCCTATCG | 82 | 2374 |
| 1179848 | 448736 | 448755 | ATATTTAGACCACGATAACT | 83 | 2375 |
| 1179850 | 449117 | 449136 | CCCTCTTGTAGATCCTGGCA | 51 | 2376 |

Example 3: Effect of 5-10-5 MOE Gapmer Modified Oligonucleotides on Human UBE3A-ATS RNA In Vitro, Single Dose Modified oligonucleotides complementary to human UBE3A-ATS nucleic acid were tested for their effect on UBE3A-ATS RNA levels in vitro, essentially as described in Example 1, except that human UBE3A-ATS primer probe set LTS01075 (forward sequence GCCCGAAGTGCCTATTCCTT, designated herein as SEQ ID NO: 5; reverse sequence TGGTCAGGAGAACATAGGCATAAA, designated herein as SEQ ID NO: 6; probe sequence ACTCCCAGGGTTGATGGGCTACATCC, designated herein as SEQ ID NO: 7) was used to measure RNA levels.

The modified oligonucleotides in the tables below are 5-10-5 gapmers. The gapmers are 20 nucleosides in length, wherein the central gap segment consists of ten 2'-β-D-deoxynucleosides and the 3' and 5' wing segments each consists of five 2'-MOE nucleosides. The sugar motif for the gapmer is (from 5' to 3'): eeeeedddddddddeeeee; wherein represents a 2'-β-D-deoxyribosyl sugar moiety, and 'e' represents a 2'-MOE sugar moiety. Each internucleoside linkage of Compound IDs 617456, 617457, 617460, 617461, and 617557 is a phosphorothioate internucleoside linkage. All other compounds have an internucleoside linkage motif of: soooosssssssssssooss, wherein each "s" represents a phosphorothioate internucleoside linkage and each "o" represents a phosphodiester internucleoside linkage.

All cytosine residues are 5-methylcytosines.

"Start site" indicates the 5'-most nucleoside to which the modified oligonucleotide is complementary in the target nucleic acid. "Stop site" indicates the 3'-most nucleoside to which the modified oligonucleotide is complementary in the target nucleic acid. Each modified oligonucleotide listed in the Tables below is 100% complementary to SEQ ID NO: 1.

Reduction of UBE3A-ATS RNA is presented in the tables below as percent UBE3A-ATS RNA amount relative to untreated control (UTC) cells. The values marked with an asterisk (*) indicate that the modified oligonucleotide is complementary to the amplicon region of the primer probe set. Additional assays may be used to measure the potency and efficacy of the modified oligonucleotides complementary to the amplicon region.

TABLE 38

Reduction of UBE3A-ATS RNA by 7,000 nM 5-10-5 MOE gapmers with PS internucleoside linkages in vitro (35,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 617456 | 463905 | 463924 | CAACTGTTACCAAGACTTCA | 25 | 32 |
| 617457 | 465003 | 465022 | ATCTGCGAATAGAGGCCCTC | 14 | 33 |
| 617460 | 466539 | 466558 | TAGGTTGCATAAAGCCAGGC | 22 | 36 |
| 617461 | 466981 | 467000 | CACACATCTTGTTCCCTCAA | 15 | 37 |
| 617557 | 483977 | 483996 | ATCATGTGCATACCCAGGGT | 17 | 172 |
| 699779 | 463905 | 463924 | CAACTGTTACCAAGACTTCA | 42 | 32 |
| 749897 | 461087 | 461106 | AATAATATTACTGCCAAATG | 85 | 2676 |
| 749898 | 461222 | 461241 | TGAATCAATTTTCAATATTT | 104 | 2677 |
| 749899 | 461325 | 461344 | TTATAAACTTCAGCAGAGTC | 41 | 2678 |
| 749900 | 461397 | 461416 | GAGTTGTTATTTGCATTAAG | 44 | 2679 |
| 749901 | 461431 | 461450 | ATTAGCACTTCTATAACTGG | 49 | 2680 |

TABLE 38-continued

Reduction of UBE3A-ATS RNA by 7,000 nM 5-10-5 MOE gapmers with PS internucleoside linkages in vitro (35,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 749902 | 461442 | 461461 | GCTCCTGACAAATTAGCACT | 91 | 1329 |
| 749903 | 461455 | 461474 | TCTTGGTAAGGCAGCTCCTG | 64 | 2681 |
| 749904 | 461467 | 461486 | TACTCATCATGATCTTGGTA | 54 | 2682 |
| 749905 | 461516 | 461535 | TAGACTAGTTGAAATCGGAA | 46 | 2683 |
| 749906 | 461556 | 461575 | AATTCTAAAAGTCCTCTCTT | 69 | 2684 |
| 749907 | 461590 | 461609 | TGTGAGATAATTCAGGAGGT | 11 | 2685 |
| 749908 | 461810 | 461829 | ATTCACTTTATAAACACTGA | 68 | 2686 |
| 749909 | 461895 | 461914 | CCCACAATTTGGTCCCATTG | 39 | 2687 |
| 749910 | 462029 | 462048 | GAATAGGGCTCTGCTTATTT | 57 | 2688 |
| 749911 | 462064 | 462083 | TTTTATGGCCCTCCCATCAG | 81 | 2689 |
| 749912 | 462098 | 462117 | CATGAATTTAATTCTTTAAA | 80 | 2690 |
| 749913 | 462126 | 462145 | CATTGTGGAATTAAATTAAC | 54 | 2691 |
| 749914 | 462141 | 462160 | TTTCTAATTCAATATCATTG | 59 | 2692 |
| 749915 | 462149 | 462168 | TCCTCTTATTTCTAATTCAA | 54 | 2693 |
| 749916 | 462159 | 462178 | CAAGAGATATTCCTCTTATT | 41 | 2694 |
| 749917 | 462212 | 462231 | CAATAAATAGGTCAGAAATG | 84 | 2695 |
| 749918 | 462406 | 462425 | CTAAGTTTCTTAAGGTAAAA | 65 | 2696 |
| 749919 | 462607 | 462626 | CATTTTCAAATATTGGTATT | 77 | 2697 |
| 749920 | 462625 | 462644 | TAATGATTTGCCCTCCTACA | 51 | 2698 |
| 749921 | 462626 | 462645 | GTAATGATTTGCCCTCCTAC | 26 | 1702 |
| 749922 | 462674 | 462693 | CCTTTTAAATAATTTTTCCT | 66 | 2699 |
| 749923 | 462992 | 463011 | AAAATGTTGGCATACATTTT | 70 | 2700 |
| 749924 | 462993 | 463012 | AAAAATGTTGGCATACATTT | 69 | 2701 |
| 749925 | 463248 | 463267 | CCTGGGTATTGCTGTCCAAA | 36 | 2702 |
| 749926 | 463307 | 463326 | TATGTTCCTAAGGAATAATG | 113 | 2703 |
| 749927 | 463318 | 463337 | TTCTTTGCATTTATGTTCCT | 40 | 2704 |
| 749928 | 463319 | 463338 | TTTCTTTGCATTTATGTTCC | 36 | 2705 |
| 749929 | 463453 | 463472 | TTACTCTGACTTTCCAGAAG | 70 | 2706 |
| 749930 | 463474 | 463493 | GGAGTAGATTTTGGAGTTT | 43 | 2707 |
| 749931 | 463512 | 463531 | TCAACTATTTCTATCAAGGC | 22 | 2708 |
| 749932 | 463519 | 463538 | ATTAATTTCAACTATTTCTA | 87 | 2709 |
| 749933 | 463601 | 463620 | TCTTACTGATTCAGCCATTT | 27 | 2710 |
| 749934 | 463663 | 463682 | TCTCAGCACTAGGGAGAAAA | 56 | 2711 |
| 749935 | 463695 | 463714 | AGTGGTTGCTATCCTGCTAA | 71 | 2000 |
| 749936 | 463788 | 463807 | AATATAAATCCTATAGATTG | 71 | 2712 |
| 749937 | 463805 | 463824 | CTGAGTCAGTCCAAATGAAT | 40 | 2713 |

TABLE 38-continued

Reduction of UBE3A-ATS RNA by 7,000 nM 5-10-5 MOE gapmers with PS internucleoside linkages in vitro (35,000 cells/well)

| Compound Number | SEQ ID NO: 1 Start Site | SEQ ID NO: 1 Stop Site | Sequence (5' to 3') | UBE3A-ATS (% UTC) | SEQ ID NO |
|---|---|---|---|---|---|
| 749938 | 463840 | 463859 | TACCTTGAAATTGAGATTTC | 50 | 2714 |
| 749939 | 463853 | 463872 | TCTTTTTGACCAATACCTTG | 34 | 2715 |
| 749940 | 463871 | 463890 | TCAACAATTGCCATGGATTC | 78 | 2716 |
| 749941 | 463895 | 463914 | CAAGACTTCAGGCAGTTGTG | 54 | 2717 |
| 749942 | 463898 | 463917 | TACCAAGACTTCAGGCAGTT | 51 | 2718 |
| 749943 | 463900 | 463919 | GTTACCAAGACTTCAGGCAG | 35 | 2719 |
| 749944 | 463903 | 463922 | ACTGTTACCAAGACTTCAGG | 37 | 2720 |
| 749945 | 463907 | 463926 | CCCAACTGTTACCAAGACTT | 27 | 2721 |
| 749946 | 463910 | 463929 | TATCCCAACTGTTACCAAGA | 37 | 2722 |
| 749947 | 463912 | 463931 | TTTATCCCAACTGTTACCAA | 29 | 2723 |
| 749948 | 463915 | 463934 | TTGTTTATCCCAACTGTTAC | 42 | 2724 |
| 749949 | 463926 | 463945 | TGATCAGCTTCTTGTTTATC | 29 | 2725 |
| 749950 | 464355 | 464374 | CCAGAGCATAAAAGGAAAGC | 87 | 2726 |
| 749951 | 464377 | 464396 | TCACAACTCTTCCTTAGCTT | 28 | 2727 |
| 749952 | 464525 | 464544 | CAGTTAGGTTAGTGCACAGA | 44 | 2728 |
| 749953 | 464530 | 464549 | CTGCTCAGTTAGGTTAGTGC | 31 | 2729 |
| 749954 | 464542 | 464561 | ATACTGAAGTCTCTGCTCAG | 53 | 2730 |
| 749955 | 464738 | 464757 | TGTGCCATATTTTCTATTT | 41 | 2731 |
| 749956 | 464993 | 465012 | AGAGGCCCTCTTGTTTCAAT | 36 | 2732 |
| 749957 | 464996 | 465015 | AATAGAGGCCCTCTTGTTTC | 42 | 2733 |
| 749958 | 464998 | 465017 | CGAATAGAGGCCCTCTTGTT | 59 | 2734 |
| 749959 | 465001 | 465020 | CTGCGAATAGAGGCCCTCTT | 35 | 2735 |
| 749960 | 465003 | 465022 | ATCTGCGAATAGAGGCCCTC | 30 | 33 |
| 749961 | 465005 | 465024 | AAATCTGCGAATAGAGGCCC | 33 | 2736 |
| 749962 | 465008 | 465027 | CTCAAATCTGCGAATAGAGG | 34 | 2737 |
| 749963 | 465010 | 465029 | TGCTCAAATCTGCGAATAGA | 67 | 2738 |
| 749964 | 465013 | 465032 | GCCTGCTCAAATCTGCGAAT | 24 | 2739 |
| 749965 | 465050 | 465069 | AGTTGACATATCTTCAAGTT | 69 | 2740 |
| 749966 | 465057 | 465076 | TAATCTCAGTTGACATATCT | 55 | 2741 |
| 749967 | 465059 | 465078 | GATAATCTCAGTTGACATAT | 42 | 2742 |

Example 4: Effect of Modified Oligonucleotides on Human UBE3A-ATS RNA In Vitro, Multiple Doses Modified oligonucleotides selected from the examples above were tested at various doses in human IPS derived iCell GABANeurons (Cellular Dynamics). Cells were plated at a density of 35,000-60,000 cells per well, maintained per manufacturer instructions, and treated with modified oligonucleotides by free uptake at various concentrations as specified in the tables below. After a treatment period of approximately 6 days, total RNA was isolated from the cells and UBE3A-ATS RNA levels were measured by quantitative real-time PCR. Human UBE3A-ATS primer probe set RTS4796, described hereinabove, was used to measure RNA levels. UBE3A-ATS RNA levels were normalized according to total RNA content, as measured by RIBOGREEN®. Reduction of UBE3A-ATS RNA is presented in the tables below as percent UBE3A-ATS RNA amount relative to untreated control (UTC) cells.

Where possible, the half maximal inhibitory concentration (IC$_{50}$) of each modified oligonucleotide was calculated using a linear regression on a log/linear plot of the data in excel. In some cases, an IC$_{50}$ could not be reliably calculated and the data point is marked as "N.C.". Values marked with "N.D." indicate that a value was not determined in this experiment.

TABLE 39

Dose-dependent percent reduction of human UBE3A-ATS RNA in vitro (60,000 cells/well)

| Compound Number | UBE3A-ATS expression (% UTC) | | | |
|---|---|---|---|---|
| | 740.7 nM | 2,222 nM | 6,666 nM | 20,000 nM |
| 617456 | 43 | 35 | 16 | 11 |
| 617457 | 38 | 32 | 27 | 18 |
| 617460 | 28 | 29 | 24 | 15 |
| 617461 | 40 | 19 | 11 | 12 |
| 617557 | 23 | 18 | 20 | 16 |

TABLE 40

Dose-dependent percent reduction of human UBE3A-ATS RNA in vitro (60,000 cells/well)

| Compound Number | UBE3A-ATS expression (% UTC) | | | |
|---|---|---|---|---|
| | 740.7 nM | 2,222 nM | 6,666 nM | 20,000 nM |
| 617456 | 48 | 38 | 17 | 15 |
| 617457 | 35 | 27 | 18 | 18 |
| 617460 | 29 | 31 | 24 | 18 |
| 617461 | 38 | 24 | 13 | 12 |
| 617557 | 23 | 17 | 14 | 13 |

TABLE 41

Dose-dependent percent reduction of human UBE3A-ATS RNA in vitro (60,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617456 | 41 | 26 | 15 | 20 | N.C. |
| 617557 | 69 | 43 | 24 | 30 | 1.9 |
| 749969 | 46 | 15 | 12 | 5 | N.C. |
| 749991 | 43 | 27 | 19 | 13 | N.C. |
| 750028 | 54 | 31 | 24 | 15 | N.C. |
| 750030 | 57 | 37 | 23 | 14 | 1.0 |
| 750032 | 40 | 18 | 14 | 7 | N.C. |
| 750326 | 76 | 60 | 38 | 25 | 3.8 |
| 750329 | 60 | 57 | 33 | 16 | 2.1 |
| 750344 | 63 | 77 | 49 | 29 | 5.6 |
| 750350 | 67 | 71 | 59 | 35 | 8.6 |
| 750359 | 110 | 56 | 38 | 41 | 6.7 |
| 750360 | 69 | 47 | 39 | 38 | 3.3 |
| 750365 | 58 | 60 | 38 | 22 | 2.4 |
| 750366 | 87 | 58 | 44 | 24 | 4.6 |
| 750386 | 76 | 57 | 42 | 40 | 5.3 |
| 750517 | 30 | 25 | 12 | 8 | N.C. |
| 750519 | 45 | 23 | 10 | 8 | N.C. |
| 750542 | 96 | 71 | 55 | 41 | 9.9 |
| 750549 | 92 | 54 | 40 | 24 | 4.3 |

TABLE 42

Dose-dependent percent reduction of human UBE3A-ATS RNA in vitro (60,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 85 | 57 | 37 | 25 | 4.1 |
| 749861 | 47 | 31 | 25 | 14 | N.C. |
| 749863 | 83 | 52 | 34 | 23 | 3.5 |
| 749869 | 46 | 30 | 18 | 11 | N.C. |
| 749882 | 84 | 60 | 40 | 27 | 4.5 |
| 749885 | 61 | 53 | 31 | 20 | 2.0 |
| 749893 | 63 | 36 | 25 | 13 | 1.3 |
| 749894 | 28 | 21 | 10 | 11 | N.C. |
| 750040 | 78 | 59 | 46 | 32 | 5.1 |
| 750051 | 47 | 18 | 21 | 23 | N.C. |
| 750092 | 80 | 54 | 40 | 28 | 3.9 |
| 750100 | 82 | 67 | 59 | 51 | N.C. |
| 750270 | 43 | 34 | 25 | 21 | N.C. |
| 750292 | 58 | 37 | 28 | 26 | 1.0 |
| 750312 | 57 | 54 | 41 | 30 | 2.3 |
| 750325 | 101 | 94 | 68 | 46 | 18.4 |
| 750413 | 98 | 60 | 35 | 28 | 4.9 |
| 750416 | 94 | 48 | 38 | 15 | 3.7 |
| 750430 | 85 | 47 | 33 | 24 | 3.3 |
| 750431 | 136 | 125 | 90 | 62 | N.C. |

TABLE 43

Dose-dependent percent reduction of human UBE3A-ATS RNA in vitro (35,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617459 | 118 | 69 | 33 | 20 | 5.4 |
| 617470 | 84 | 51 | 28 | 13 | 2.9 |
| 617473 | 44 | 33 | 30 | 20 | N.C. |
| 617536 | 100 | 54 | 57 | 24 | 5.9 |
| 617547 | 122 | 52 | 29 | 18 | 4.6 |
| 617593 | 81 | 75 | 32 | 21 | 4.2 |
| 749794 | 89 | 102 | 66 | 52 | N.C. |
| 750418 | 135 | 132 | 105 | 51 | N.C. |
| 750439 | 98 | 60 | 44 | 26 | 5.4 |
| 750452 | 113 | 94 | 78 | 51 | N.C. |

TABLE 44

Dose-dependent percent reduction of human UBE3A-ATS RNA in vitro (35,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 129 | 53 | 32 | 28 | 5.5 |
| 749796 | 84 | 31 | 29 | 17 | 2.3 |
| 749816 | 94 | 56 | 46 | 22 | 4.8 |
| 749907 | 65 | 57 | 21 | 16 | 2.1 |
| 749921 | 50 | 47 | 25 | 18 | 1.0 |
| 749931 | 246 | 39 | 32 | 12 | 6.3 |
| 749933 | 51 | 41 | 26 | 11 | 0.9 |
| 749937 | 74 | 46 | 27 | 16 | 2.3 |
| 749944 | 116 | N/A | 74 | 40 | 15.3 |
| 749956 | 136 | 74 | 18 | 27 | 5.7 |
| 749964 | 75 | 80 | 35 | 17 | 4.2 |
| 750131 | 73 | 50 | 36 | 25 | 2.9 |
| 750139 | 35 | 29 | 21 | 15 | N.C. |
| 750140 | 27 | 27 | 13 | 11 | N.C. |
| 750141 | 52 | 61 | 25 | 24 | 1.6 |
| 750196 | 107 | 95 | 129 | 47 | N.C. |
| 750210 | 53 | 38 | 26 | 23 | 0.8 |
| 750214 | 34 | 70 | 47 | 41 | N.C. |

TABLE 44-continued

Dose-dependent percent reduction of human UBE3A-ATS RNA in vitro (35,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 750228 | 109 | 105 | 95 | 70 | N.C. |
| 750242 | 77 | 70 | 36 | 15 | 3.8 |

TABLE 45

Dose-dependent percent reduction of human UBE3A-ATS RNA in vitro (35,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 80 | 59 | 31 | 13 | 3.1 |
| 750519 | 87 | 67 | 41 | 27 | 5.2 |
| 1065438 | 120 | 90 | 88 | 95 | N.C. |
| 1065582 | 65 | 61 | 41 | 29 | 3.4 |
| 1065597 | 142 | 135 | 111 | 103 | N.C. |
| 1065599 | 63 | 47 | 47 | 26 | 2.5 |
| 1065613 | 96 | 70 | 65 | 39 | 11.5 |
| 1065631 | 60 | 61 | 48 | 26 | 3.4 |
| 1065644 | 64 | 65 | 42 | 27 | 3.8 |
| 1065645 | 68 | 50 | 36 | 19 | 2.4 |
| 1065646 | 52 | 55 | 34 | 16 | 1.5 |
| 1065676 | 50 | 38 | 33 | 23 | N.C. |
| 1065690 | 56 | 53 | 38 | 24 | 1.9 |
| 1065754 | 74 | 56 | 57 | 27 | 5.1 |
| 1065817 | 94 | 76 | 42 | 38 | 7.6 |
| 1065899 | 59 | 56 | 46 | 30 | 3.0 |
| 1066072 | 133 | 108 | 86 | 63 | N.C. |
| 1066249 | 73 | 60 | 70 | 48 | N.C. |
| 1066378 | 116 | 114 | 87 | 52 | N.C. |

TABLE 46

Dose-dependent percent reduction of human UBE3A-ATS RNA by modified oligonucleotides in vitro (42,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 83 | 54 | 31 | 13 | 3.1 |
| 750519 | 63 | 48 | 43 | 26 | 2.4 |
| 1065578 | 77 | 36 | 36 | 24 | 2.4 |
| 1065579 | 55 | 58 | 30 | 66 | N.C. |
| 1065595 | 75 | 60 | 32 | 19 | 3.1 |
| 1065642 | 52 | 58 | 40 | 27 | 2.0 |
| 1065672 | 85 | 67 | 42 | 18 | 4.5 |
| 1065674 | 64 | 69 | 40 | 22 | 3.5 |
| 1065719 | 76 | 62 | 46 | 38 | 6.1 |
| 1065750 | 38 | 28 | 25 | 28 | N.C. |
| 1065766 | 78 | 52 | 32 | 37 | 3.7 |
| 1065768 | 86 | 66 | 43 | 30 | 5.5 |
| 1065799 | 66 | 52 | 41 | 34 | 3.2 |
| 1065863 | 54 | 60 | 46 | 27 | 2.6 |
| 1065894 | 82 | 100 | 52 | 52 | N.C. |
| 1066037 | 66 | 70 | 56 | 62 | N.C. |
| 1066119 | 82 | 116 | 101 | 72 | N.C. |
| 1066375 | 116 | 98 | 68 | 77 | N.C. |
| 1066423 | 39 | 70 | 63 | 46 | N.C. |

TABLE 47

Dose-dependent percent reduction of human UBE3A-ATS RNA in vitro (42,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 65 | 52 | 23 | 8 | 1.9 |
| 1065324 | 86 | 90 | 67 | 43 | 18.4 |
| 1065369 | 107 | 91 | 108 | 83 | N.C. |
| 1065465 | 97 | 96 | 97 | 100 | N.C. |
| 1065513 | 156 | 104 | 66 | 70 | N.C. |
| 1065558 | 116 | 125 | 92 | 112 | N.C. |
| 1065592 | 85 | 84 | 50 | 23 | 6.5 |
| 1065624 | 87 | 71 | 39 | 20 | 4.7 |
| 1065667 | 64 | 59 | 35 | 21 | 2.7 |
| 1065747 | 91 | 65 | 55 | N/A | N.C. |
| 1065955 | 84 | 55 | 43 | 23 | 4.1 |
| 1066002 | 94 | 75 | 68 | 50 | N.C. |
| 1066003 | 90 | 73 | 49 | 43 | 9.5 |
| 1066034 | 137 | 120 | 101 | 67 | N.C. |
| 1066201 | 98 | 110 | 84 | 79 | N.C. |
| 1066273 | 101 | 95 | 108 | 104 | N.C. |
| 1066359 | 111 | 96 | 101 | 81 | N.C. |
| 1066420 | 70 | 43 | 27 | 33 | 2.2 |

TABLE 48

Dose-dependent percent reduction of human UBE3A-ATS RNA in vitro (42,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 70 | 46 | 23 | 10 | 1.9 |
| 1065654 | 96 | 87 | 54 | 43 | 11.9 |
| 1065680 | 78 | 63 | 41 | 28 | 4.5 |
| 1065686 | 63 | 64 | 62 | 24 | 5.1 |
| 1065735 | 102 | 66 | 41 | 41 | 7.4 |
| 1065785 | 81 | 74 | 52 | 50 | 14.7 |
| 1065829 | 64 | 59 | 45 | 31 | 3.7 |
| 1065858 | 69 | 49 | 28 | 23 | 2.2 |
| 1065859 | 52 | 36 | 28 | 20 | N.C. |
| 1065901 | 89 | 69 | 73 | 55 | N.C. |
| 1065914 | 108 | 111 | 82 | 74 | N.C. |
| 1065977 | 106 | 87 | 101 | 76 | N.C. |
| 1066009 | 88 | 71 | 130 | 84 | N.C. |
| 1066046 | 84 | 59 | 43 | 36 | 5.5 |
| 1066089 | 46 | 71 | 58 | 41 | N.C. |
| 1066217 | 67 | 64 | 46 | 41 | 6.5 |
| 1066221 | 59 | 49 | 39 | 31 | 2.0 |
| 1066311 | 93 | 75 | 73 | 49 | N.C. |
| 1066377 | 94 | 73 | 51 | 35 | 7.9 |
| 1066396 | 100 | 75 | 82 | 54 | N.C. |

TABLE 49

Dose-dependent percent reduction of human UBE3A-ATS RNA in vitro (42,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 66 | 47 | 21 | 6 | 1.7 |
| 750519 | 75 | 58 | 36 | 25 | 3.5 |
| 1065272 | 90 | 63 | 38 | 33 | 5.4 |
| 1065576 | 21 | 28 | 19 | 13 | N.C. |
| 1065590 | 74 | 49 | 31 | 27 | 2.8 |
| 1065591 | 83 | 60 | 29 | 13 | 3.2 |
| 1065607 | 68 | 47 | 28 | 17 | 2.1 |
| 1065608 | 72 | 38 | 18 | 13 | 1.7 |
| 1065623 | 46 | 28 | 21 | 13 | N.C. |
| 1065669 | 89 | 75 | 57 | 28 | 7.6 |

TABLE 49-continued

Dose-dependent percent reduction of human
UBE3A-ATS RNA in vitro (42,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 1065685 | 64 | 34 | 19 | 20 | 1.2 |
| 1065795 | 100 | 86 | 56 | 38 | 10.8 |
| 1065810 | 62 | 46 | 23 | 22 | 1.6 |
| 1065812 | 77 | 67 | 36 | 24 | 4.1 |
| 1065826 | 108 | 93 | 54 | 43 | 12.1 |
| 1065937 | 86 | 61 | 60 | 37 | 8.7 |
| 1065953 | 77 | 46 | 34 | 29 | 3.0 |
| 1065954 | 78 | 62 | 45 | 38 | 6.1 |
| 1066097 | 133 | 121 | 119 | 125 | N.C. |

TABLE 50

Dose-dependent percent reduction of human
UBE3A-ATS RNA in vitro (42,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 39 | 43 | 25 | 13 | N.C. |
| 750519 | 44 | 36 | 34 | 17 | N.C. |
| 1065605 | 50 | 48 | 29 | 19 | N.C. |
| 1065619 | 95 | 73 | 47 | 5 | 4.6 |
| 1065621 | 5 | 63 | 44 | 21 | 4.6 |
| 1065635 | 48 | 29 | 19 | 4 | N.C. |
| 1065651 | 13 | 8 | 29 | 10 | N.C. |
| 1065696 | 77 | 71 | 61 | 7 | 4.7 |
| 1065712 | 58 | 40 | 34 | 20 | 1.3 |
| 1065713 | 4 | 4 | 7 | 6 | N.C. |
| 1065728 | 73 | 54 | 42 | 25 | 3.5 |
| 1065823 | 7 | 9 | 10 | N/A | N.C. |
| 1065840 | 73 | 61 | 41 | 32 | 4.4 |
| 1065856 | 78 | 49 | 37 | 24 | 3.2 |
| 1065857 | 10 | 61 | 49 | 28 | 5.1 |
| 1065889 | 58 | 81 | 61 | 62 | N.C. |
| 1065903 | 85 | 65 | 60 | 6 | 4.6 |
| 1065920 | 53 | 42 | 40 | 26 | 1.0 |
| 1066350 | 89 | 101 | 78 | 21 | 11.3 |

TABLE 51

Dose-dependent percent reduction of human
UBE3A-ATS RNA in vitro (42,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 14 | 16 | 3 | 0 | N.C. |
| 750519 | 31 | 27 | 22 | 12 | N.C. |
| 1065296 | 78 | 56 | 45 | 7 | 3.2 |
| 1065330 | 13 | 5 | 4 | 3 | N.C. |
| 1065586 | 5 | 44 | 22 | 11 | N.C. |
| 1065600 | 79 | 55 | 36 | 4 | 2.9 |
| 1065616 | 84 | 75 | 65 | 5 | 5.4 |
| 1065708 | 9 | 8 | 6 | N/A | N.C. |
| 1065709 | 6 | 4 | 4 | 4 | N.C. |
| 1065710 | 52 | 33 | 16 | 9 | N.C. |
| 1065821 | 110 | 58 | 29 | 16 | 4.3 |
| 1065868 | 73 | 42 | 28 | 6 | 2.0 |
| 1065902 | 8 | 60 | 35 | 24 | 3.6 |
| 1065932 | 51 | 42 | 35 | 17 | 0.9 |
| 1065947 | 65 | 48 | 38 | 10 | 2.1 |
| 1066076 | 81 | 76 | 41 | 22 | 5.0 |
| 1066092 | 80 | 49 | 40 | 27 | 3.6 |
| 1066253 | 0 | 71 | 31 | 21 | 4.5 |
| 1066429 | 28 | 17 | 6 | 6 | N.C. |

TABLE 52

Dose-dependent percent reduction of human
UBE3A-ATS RNA in vitro (42,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 617557 | 37 | 17 | 29 | 12 | N.C. |
| 750519 | 50 | 40 | 40 | 20 | N.C. |
| 1065295 | 78 | 73 | 74 | 49 | N.C. |
| 1065473 | 31 | 29 | 16 | 11 | N.C. |
| 1065503 | 105 | 107 | 107 | 77 | N.C. |
| 1065561 | 66 | 44 | 21 | 13 | 1.7 |
| 1065593 | 59 | 45 | 30 | 6 | 1.5 |
| 1065609 | 59 | 50 | 34 | 6 | 1.7 |
| 1065625 | 70 | 56 | 41 | 22 | 3.2 |
| 1065641 | 43 | 31 | 18 | 7 | N.C. |
| 1065671 | 55 | 49 | 30 | 8 | 1.4 |
| 1065678 | 75 | 78 | 54 | 33 | 8.0 |
| 1065765 | 64 | 46 | 28 | 12 | 1.8 |
| 1065791 | 7 | 58 | 44 | 30 | 4.1 |
| 1065806 | 24 | 72 | 82 | 74 | N.C. |
| 1065813 | 12 | 11 | 11 | 7 | N.C. |
| 1065924 | 107 | 94 | 79 | 41 | 18.4 |
| 1066011 | 94 | 85 | 83 | 50 | N.C. |
| 1066220 | 24 | 83 | 75 | 62 | N.C. |

TABLE 53

Dose-dependent percent reduction of human
UBE3A-ATS RNA in vitro (40,000 cells/well)

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 750519 | 83 | 53 | 21 | 14 | 2.8 |
| 1165521 | 55 | 38 | 32 | 27 | 0.9 |
| 1165524 | 42 | 33 | 26 | 14 | N.C. |
| 1165536 | 47 | 39 | 32 | 21 | N.C. |
| 1165545 | 62 | 49 | 32 | 33 | 2.0 |
| 1165552 | 53 | 35 | 24 | 16 | 0.8 |
| 1165553 | 55 | 34 | 24 | 18 | 0.8 |
| 1165554 | 63 | 55 | 29 | 19 | 2.1 |
| 1165555 | 53 | 43 | 21 | 22 | 0.9 |
| 1165562 | 72 | 69 | 35 | 23 | 3.8 |
| 1165577 | 65 | 59 | 33 | 28 | 2.8 |
| 1165588 | 78 | 57 | 33 | 38 | 4.3 |
| 1165590 | 44 | 41 | 30 | 21 | N.C. |
| 1165593 | 85 | 92 | 83 | 50 | N.C. |
| 1165611 | 47 | 39 | 25 | 21 | N.C. |
| 1165724 | 80 | 71 | 57 | 54 | N.C. |
| 1165788 | 66 | 71 | 42 | 25 | 4.2 |
| 1165798 | 73 | 81 | 86 | 52 | N.C. |
| 1179842 | 78 | 37 | 27 | 20 | 2.2 |

Example 5: Effect of Modified Oligonucleotides on Human UBE3A-ATS RNA In Vitro, Multiple Doses Modified oligonucleotides selected from the examples above were tested at various doses in human IPS derived ReproNeuro™ Neurons (Repro CELL). Cells were plated at a density of 20,000 cells per well, maintained per manufacturer instructions, and treated with modified oligonucleotides by free uptake at various concentrations as specified in the tables below. After a treatment period of approximately 5 days, total RNA was isolated from the cells and UBE3A-ATS RNA levels were measured by quantitative real-time PCR. Human UBE3A-ATS primer probe set RTS4796, described hereinabove, was used to measure RNA levels. UBE3A-ATS RNA levels were normalized according to total RNA content, as measured by RIBOGREEN®. Reduction of UBE3A-ATS RNA is presented in the tables below as percent UBE3A-ATS RNA amount relative to untreated control (UTC) cells.

The half maximal inhibitory concentration (IC$_{50}$) of each modified oligonucleotide was calculated using a linear regression on a log/linear plot of the data in excel. In cases where IC$_{50}$ could not be calculated, IC$_{50}$s are marked as N.C. (Not Calculated).

TABLE 54

Dose-dependent percent reduction of human UBE3A-ATS RNA in vitro

| Compound Number | UBE3A-ATS expression (% UTC) | | | | IC$_{50}$ (µM) |
|---|---|---|---|---|---|
| | 740.7 nM | 2,222 nM | 6,666 nM | 20,000 nM | |
| 750519 | 73 | 54 | 19 | 11 | 2.3 |
| 1165523 | 75 | 60 | 43 | 33 | 4.7 |
| 1165533 | 60 | 50 | 18 | 33 | 1.5 |
| 1165538 | 64 | 47 | 34 | 26 | 2.1 |
| 1165550 | 65 | 62 | 47 | 32 | 4.5 |
| 1165563 | 69 | 51 | 41 | 29 | 3.1 |
| 1165586 | 62 | 50 | 35 | 32 | 2.3 |
| 1165596 | 88 | 72 | 69 | 43 | 16.4 |
| 1165608 | 88 | 89 | 62 | 54 | N.C. |
| 1165616 | 89 | 88 | 80 | 74 | N.C. |
| 1165694 | 71 | 57 | 55 | 50 | 15.0 |
| 1165737 | 71 | 55 | 53 | 46 | 9.1 |
| 1165827 | 72 | 59 | 65 | 42 | 13.6 |
| 1165855 | 60 | 60 | 37 | 19 | 2.5 |
| 1165897 | 78 | 76 | 54 | 50 | N.C. |
| 1179808 | 101 | 100 | 85 | 75 | N.C. |
| 1179839 | 58 | 41 | 26 | 23 | 1.2 |
| 1179841 | 68 | 45 | 38 | 26 | 2.4 |
| 1179843 | 52 | 57 | 36 | 21 | 1.7 |

Example 6: Effect of Modified Oligonucleotides on Human UBE3A-ATS RNA and UBE3A RNA In Vitro, Multiple Doses Modified oligonucleotides selected from the examples above were tested at various doses in 10-week differentiated human neuronal cells derived from Angelman Syndrome patient derived IPS cells (Protocols and cells described in Chamberlain SJ., et al., *Induced pluripotent stem cell models of the genomic imprinting disorders Angelman and Prader-Willi syndromes*. PNAS, 2010. 41: 17668-17673). At the end of the 10-week differentiation period, cells were treated with modified oligonucleotides by free uptake at various concentrations as specified in the tables below. After a treatment period of approximately 6 days, total RNA was isolated from the cells. Both UBE3A-ATS RNA and UBE3A RNA levels were measured by quantitative real-time PCR. Human UBE3A-ATS primer probe set RTS4796 was used to measure UBE3A-ATS RNA levels as described above. Human UBE3A primer probe set RTS35984 (forward sequence CACCCTGATGTCACCGAATG, designated herein as SEQ ID NO: 8; reverse sequence GCGTTCTATTAGATGCTTTGCAG, designated herein as SEQ ID NO: 9; probe sequence ACTGAGGTTCTCCTGATCTTTTACAAGCTG, designated herein as SEQ ID NO: 10) was used to measure UBE3A RNA levels. RNA levels were adjusted according to total RNA content, as measured by RIBOGREEN®. Reduction of UBE3A-ATS RNA or induction of UBE3A RNA is presented in the tables below as percent UBE3A-ATS RNA amount or percent UBE3A RNA relative to untreated control (UTC) cells. Values marked with "N.D." indicate that a value was not determined in this experiment.

Several modified oligonucleotides were found to reduce UBE3A-ATS RNA accompanied by concurrent increase in UBE3A RNA in Angelman's patient IPS cell derived neurons.

TABLE 55

Reduction of UBE3A-ATS RNA and increase of UBE3A RNA in Angelman Syndrome IPS cell derived neurons

| Compound ID | UBE3A-ATS RNA (% UTC) (RTS4796) | | | UBE3A RNA (% UTC) (RTS35984) | | |
|---|---|---|---|---|---|---|
| | 741 nM | 2222 nM | 6667 nM | 741 nM | 2222 nM | 6667 nM |
| 617557 | 17 | 16 | N.D. | 142 | 151 | N.D. |
| 750140 | 7 | N.D. | N.D. | 226 | N.D. | N.D. |
| 750139 | 35 | 10 | 3 | 104 | 196 | 194 |
| 750131 | 29 | 25 | N.D. | 49 | 53 | N.D. |
| 750141 | 22 | N.D. | N.D. | 89 | N.D. | N.D. |
| 750242 | 42 | N.D. | N.D. | 45 | N.D. | N.D. |
| 750210 | 49 | 14 | 6 | 122 | 101 | 166 |
| 750214 | 53 | 56 | 13 | 87 | 154 | 85 |
| 749907 | 16 | 13 | 7 | 133 | 298 | 205 |
| 749931 | 35 | 17 | 11 | 152 | 271 | 260 |
| 749964 | 27 | 15 | 6 | 144 | 160 | 202 |
| 749921 | 25 | 12 | N.D. | 73 | 98 | N.D. |
| 749933 | 42 | 10 | 13 | 116 | 92 | 210 |
| 749956 | 51 | 33 | N.D. | 94 | 103 | N.D. |
| 749937 | 52 | 27 | 7 | 104 | 131 | 137 |
| 749796 | 73 | 67 | N.D. | 81 | 79 | N.D. |
| 749816 | 75 | N.D. | 19 | 63 | N.D. | 27 |
| 749969 | 33 | 14 | 10 | 171 | 249 | 305 |
| 749991 | 32 | 15 | 15 | 193 | 165 | 276 |

TABLE 56

Reduction of UBE3A-ATS RNA and increase of UBE3A RNA in Angelman Syndrome IPS cell derived neurons

| Compound ID | UBE3A-ATS RNA (% UTC) (RTS4796) | | | UBE3A RNA (% UTC) (RTS35984) | | |
|---|---|---|---|---|---|---|
| | 741 nM | 2222 nM | 6667 nM | 741 nM | 2222 nM | 6667 nM |
| 617557 | 54 | 51 | 39 | 144 | 365 | 252 |
| 750140 | 22 | 37 | N.D. | 345 | 328 | N.D. |
| 750517 | 34 | 30 | 19 | 269 | 328 | 418 |
| 750549 | 60 | 72 | 72 | 337 | 225 | 309 |
| 750542 | 64 | 70 | 22 | 98 | 113 | 234 |
| 617456 | 58 | 35 | 26 | 142 | 176 | 253 |
| 750519 | 33 | 26 | 18 | 374 | 440 | 447 |
| 750360 | 93 | 113 | 59 | 151 | 221 | 204 |
| 750359 | 32 | 31 | 27 | 267 | 134 | 229 |
| 750386 | 35 | 40 | 17 | 182 | 282 | 320 |
| 750366 | 77 | 45 | 37 | 87 | 122 | 185 |
| 750344 | 51 | 50 | 30 | 91 | 139 | 150 |
| 750326 | 67 | 49 | 31 | 106 | 108 | 166 |
| 750350 | 68 | 66 | 102 | 111 | 132 | 138 |
| 750365 | 74 | 63 | 37 | 122 | 160 | 183 |
| 750329 | 88 | 82 | N.D. | 154 | 148 | N.D. |
| 750028 | 81 | N.D. | 14 | 324 | N.D. | 448 |
| 750030 | 87 | 30 | 22 | 221 | 307 | 373 |
| 750032 | 47 | 17 | 13 | 202 | 323 | 254 |

TABLE 57

Reduction of UBE3A-ATS RNA and increase of UBE3A RNA in Angelman Syndrome IPS cell derived neurons

| Compound ID | UBE3A-ATS RNA (% UTC) (RTS4796) | | | UBE3A RNA (% UTC) (RTS35984) | | |
|---|---|---|---|---|---|---|
| | 741 nM | 2222 nM | 6667 nM | 741 nM | 2222 nM | 6667 nM |
| 617557 | 28 | 54 | N.D. | 318 | 411 | N.D. |
| 750140 | 19 | 20 | 10 | 619 | 542 | 132 |
| 750040 | 38 | 49 | 25 | 171 | 192 | 318 |
| 750051 | 21 | 21 | 13 | 106 | 544 | 416 |
| 750092 | 40 | 32 | 12 | 175 | 507 | 118 |
| 749894 | 12 | 19 | 6 | 143 | 2085 | 605 |
| 749869 | 10 | 11 | 13 | 376 | 802 | 1504 |
| 749882 | 34 | 31 | 19 | 502 | 907 | 926 |
| 749863 | 45 | 42 | 22 | 326 | 2584 | 927 |
| 749893 | 34 | 10 | 7 | 215 | 428 | 1023 |
| 749885 | 22 | 12 | 10 | 105 | 233 | 614 |
| 749861 | 19 | 11 | 8 | 209 | 236 | 466 |
| 750292 | 28 | 15 | 13 | 123 | 318 | 645 |
| 750270 | 18 | 14 | 10 | 267 | 578 | 584 |
| 750312 | 39 | 19 | 12 | 87 | 289 | 420 |
| 750413 | 46 | 49 | 20 | 123 | 375 | 143 |
| 750416 | 49 | N.D. | N.D. | 119 | N.D. | N.D. |
| 750430 | 33 | 21 | 12 | 329 | 359 | 241 |
| 750439 | 40 | 31 | 19 | 188 | 197 | 183 |

TABLE 58

Reduction of UBE3A-ATS RNA and increase of UBE3A RNA in Angelman Syndrome IPS cell derived neurons

| Compound ID | UBE3A-ATS RNA (% UTC) (RTS4796) | | | UBE3A RNA (% UTC) (RTS35984) | | |
|---|---|---|---|---|---|---|
| | 741 nM | 2222 nM | 6667 nM | 741 nM | 2222 nM | 6667 nM |
| 617557 | 60 | 39 | N.D. | 266 | 161 | N.D. |
| 617557 | 65 | 23 | 8 | 229 | 204 | 122 |
| 750140 | 18 | 29 | N.D. | 312 | 222 | N.D. |
| 617470 | 36 | 34 | 23 | 141 | 191 | 317 |
| 617473 | 29 | 37 | 20 | 91 | 162 | 87 |
| 617459 | 38 | 18 | 8 | 80 | 155 | 191 |
| 617547 | 31 | 19 | 28 | 52 | 145 | 226 |
| 617536 | 83 | 28 | 109 | 165 | 108 | 265 |
| 617593 | 67 | 142 | 107 | 100 | 73 | 83 |
| 750544 | 98 | 107 | 51 | 221 | 258 | 307 |
| 750554 | 65 | 72 | 88 | 57 | 80 | 55 |
| 750540 | 46 | 26 | 29 | 202 | 344 | 458 |
| 750567 | 62 | 49 | 31 | 86 | 108 | 227 |
| 749984 | 47 | 42 | N.D. | 68 | 99 | 277 |
| 750009 | 31 | 39 | 22 | 65 | 92 | 217 |
| 749865 | 44 | N.D. | 12 | 201 | N.D. | 249 |
| 749860 | 36 | 22 | 9 | 285 | 265 | 263 |
| 750006 | 32 | 17 | 66 | 241 | 329 | 513 |
| 582468 | 102 | 79 | 33 | 120 | 33 | 62 |
| 141923 | 150 | 169 | 100 | 135 | 126 | 53 |

TABLE 59

Reduction of UBE3A-ATS RNA and increase of UBE3A RNA in Angelman Syndrome IPS cell derived neurons

| Compound ID | UBE3A-ATS RNA (% UTC) (RTS4796) | | | | UBE3A RNA (% UTC) (RTS35984) | | | |
|---|---|---|---|---|---|---|---|---|
| | 741 nM | 2222 nM | 6667 nM | 20000 nM | 741 nM | 2222 nM | 6667 nM | 20000 nM |
| 749894 | 20 | 13 | 11 | 10 | 301 | 200 | 159 | 546 |
| 749969 | 47 | 44 | 45 | 51 | 125 | 88 | 85 | 205 |
| 750032 | 16 | 17 | 12 | 17 | 215 | 190 | 182 | 236 |
| 750140 | 26 | 33 | 13 | 22 | 252 | 429 | 160 | 222 |
| 1065690 | 18 | 7 | 11 | 9 | 313 | 295 | 203 | 254 |
| 1065868 | 32 | 17 | 9 | 9 | 249 | 303 | 211 | 143 |
| 1065579 | 20 | 19 | 25 | 7 | 155 | 134 | 133 | 231 |
| 1065858 | 22 | 24 | 25 | 17 | 190 | 239 | 229 | 249 |
| 1065859 | 55 | 57 | 36 | 29 | 117 | 141 | 199 | 193 |
| 1065812 | 25 | 29 | 9 | 10 | 133 | 120 | 185 | 163 |
| 749860 | 35 | 21 | 14 | 11 | 129 | 250 | 196 | 278 |
| 1065593 | 18 | 10 | 7 | 9 | 228 | 181 | 211 | 261 |
| 1065953 | 15 | 11 | 12 | 10 | 148 | 269 | 243 | 221 |
| 1065856 | 15 | 18 | 11 | 9 | 292 | 286 | 103 | 234 |
| 1065937 | 21 | 26 | 12 | 10 | 93 | 205 | 225 | 208 |
| 1065728 | 35 | 24 | 20 | 12 | 132 | 143 | 144 | 198 |
| 750139 | 38 | 28 | 13 | 14 | 176 | 229 | 248 | 315 |
| 617557 | 55 | 23 | 30 | 33 | 166 | 206 | 193 | 226 |
| 750519 | 15 | 15 | 5 | 3 | 173 | 101 | 220 | 324 |

TABLE 60

Reduction of UBE3A-ATS RNA and increase of UBE3A RNA in Angelman Syndrome IPS cell derived neurons

| Compound ID | UBE3A-ATS RNA (% UTC) (RTS4796) | | | | UBE3A RNA (% UTC) (RTS35984) | | | |
|---|---|---|---|---|---|---|---|---|
| | 741 nM | 2222 nM | 6667 nM | 20000 nM | 741 nM | 2222 nM | 6667 nM | 20000 nM |
| 1066092 | 138 | 160 | 98 | 55 | 247 | 253 | 254 | 111 |
| 1065902 | 92 | 85 | 55 | 42 | 168 | 231 | 203 | 304 |
| 1065840 | 57 | 54 | 37 | 22 | 209 | 176 | 141 | 307 |
| 1066253 | 77 | 37 | 52 | 36 | 182 | 167 | 184 | 236 |
| 1065785 | 93 | 35 | 41 | 54 | 155 | 198 | 225 | 240 |
| 1065821 | 40 | 19 | 20 | 20 | 220 | 288 | 215 | 276 |
| 750006 | 78 | 33 | 33 | 56 | 132 | 119 | 168 | 185 |
| 750028 | 36 | 17 | 16 | 19 | 173 | 235 | 189 | 216 |
| 617557 | 37 | 26 | 13 | 23 | 194 | 166 | 214 | 241 |

TABLE 61

Reduction of UBE3A-ATS RNA and increase of UBE3A
RNA in Angelman Syndrome IPS cell derived neurons

| | UBE3A-ATS RNA (% UTC) (RTS4796) | | | | UBE3A RNA (% UTC) (RTS35984) | | | |
|---|---|---|---|---|---|---|---|---|
| Compound ID | 741 nM | 2222 nM | 6667 nM | 20000 nM | 741 nM | 2222 nM | 6667 nM | 20000 nM |
| 750519 | 41 | 26 | 11 | 8 | 138 | 158 | 148 | 158 |
| 1065671 | 106 | 81 | 108 | 61 | 213 | 189 | 387 | 235 |
| 617557 | 69 | 52 | 37 | 35 | 129 | 132 | 210 | 195 |
| 1065686 | 101 | 101 | 81 | 88 | 145 | 105 | 118 | 164 |
| 750359 | 121 | 70 | 79 | 48 | 108 | 119 | 134 | 131 |
| 1065817 | 75 | 78 | 40 | N.D. | 119 | 174 | 131 | N.D. |
| 750386 | 100 | 65 | 58 | 50 | 106 | 155 | 190 | 128 |
| 749894 | 58 | 40 | 19 | 20 | 176 | 187 | 159 | 244 |
| 1065591 | 68 | 51 | 52 | 34 | 138 | 132 | 227 | 155 |
| 750140 | 178 | 165 | 133 | 129 | 129 | 117 | 98 | 142 |
| 750032 | 95 | 56 | 40 | 31 | 109 | 144 | 126 | 172 |
| 1065599 | 73 | 45 | 42 | 33 | 135 | 131 | 188 | 210 |
| 1065690 | 66 | 48 | 35 | 29 | 182 | 175 | 211 | 185 |
| 1065868 | 132 | 125 | 107 | 90 | 93 | 125 | 113 | 99 |
| 1065645 | 83 | 47 | 50 | 25 | 169 | 144 | 287 | 158 |
| 1065858 | 78 | 46 | 22 | 18 | 175 | 192 | 162 | 227 |
| 1065856 | 76 | 66 | 49 | 35 | 138 | 195 | 167 | 165 |
| 1065667 | 137 | 127 | 137 | 94 | 115 | 116 | 163 | 134 |
| 1066092 | 133 | 126 | 87 | 75 | 100 | 113 | 104 | 106 |

Example 7: Design and Synthesis of Modified Oligonucleotides Complementary to a Human UBE3A-ATS Nucleic Acid Modified oligonucleotides were synthesized as indicated in the tables below.

The compounds in Table 62 are 4-10-6 MOE gapmers. The gapmers are 20 nucleosides in length, wherein the central gap segment consists of ten 2'-O-D-deoxynucleosides, the 5' wing segment consists of four 2'-MOE nucleosides, and the 3' wing segment consists of six 2'-MOE nucleosides. The sugar motif of the gapmers is (from 5' to 3'): eeeedddddddddddeeeeee; wherein 'd' represents a 2'-β-D-deoxyriboxyl sugar moiety, and 'e' represents a 2'-MOE sugar moiety. The gapmers have an internucleoside linkage motif of (from 5' to 3'): sooosssssssssssooss; wherein "s" represents a phosphorothioate internucleoside linkage and "o" represents a phosphodiester internucleoside linkage. All cytosine residues are 5-methylcytosines.

TABLE 62

4-10-6 MOE gapmers with a mixed PO/PS
internucleoside linkages complementary
to human UBE3A-ATS

| Compound ID | SEQ ID NO: 1 Start Site | SEQ ID NO: 1 Stop Site | SEQUENCE | SEQ ID NO |
|---|---|---|---|---|
| 1263473 | 460996 | 461015 | TTTTTCCATTTTTCTCTTAG | 2745 |
| 1263474 | 460997 | 461016 | GTTTTTCCATTTTTCTCTTA | 2746 |
| 1263475 | 460999 | 461018 | GTGTTTTTCCATTTTTCTCT | 598 |
| 1263476 | 461000 | 461019 | TGTGTTTTTCCATTTTTCTC | 2747 |
| 1263477 | 461001 | 461020 | GTGTGTTTTTCCATTTTTCT | 2748 |
| 1263478 | 461002 | 461021 | TGTGTGTTTTTCCATTTTTC | 2749 |

TABLE 62-continued 4-10-6 MOE gapmers with a mixed PO/PS
internucleoside linkages complementary
to human UBE3A-ATS

| Compound ID | SEQ ID NO: 1 Start Site | SEQ ID NO: 1 Stop Site | SEQUENCE | SEQ ID NO |
|---|---|---|---|---|
| 1263479 | 465235 | 465254 | TCATCTCGGGTATATAAATT | 2750 |
| 1263480 | 465236 | 465255 | GTCATCTCGGGTATATAAAT | 1132 |
| 1263481 | 465237 | 465256 | GGTCATCTCGGGTATATAAA | 1207 |
| 1263482 | 465238 | 465257 | TGGTCATCTCGGGTATATAA | 318 |
| 1263483 | 465239 | 465258 | TTGGTCATCTCGGGTATATA | 2473 |
| 1263484 | 465240 | 465259 | ATTGGTCATCTCGGGTATAT | 1655 |
| 1263485 | 465241 | 465260 | TATTGGTCATCTCGGGTATA | 2548 |
| 1263486 | 468985 | 469004 | TCACCATTTTGACCTTCTTA | 2751 |
| 1263487 | 468986 | 469005 | TTCACCATTTTGACCTTCTT | 2752 |
| 1263488 | 468987 | 469006 | CTTCACCATTTTGACCTTCT | 2753 |
| 1263489 | 468988 | 469007 | GCTTCACCATTTTGACCTTC | 377 |
| 1263490 | 468989 | 469008 | TGCTTCACCATTTTGACCTT | 2754 |
| 1263491 | 468990 | 469009 | CTGCTTCACCATTTTGACCT | 2755 |
| 1263492 | 468991 | 469010 | ACTGCTTCACCATTTTGACC | 2756 |
| 1263494 | 464526 | 464545 | TCAGTTAGGTTAGTGCACAG | 2757 |
| 1263495 | 464527 | 464546 | CTCAGTTAGGTTAGTGCACA | 2758 |
| 1263496 | 464528 | 464547 | GCTCAGTTAGGTTAGTGCAC | 1504 |
| 1263497 | 464529 | 464548 | TGCTCAGTTAGGTTAGTGCA | 2759 |

TABLE 62-continued 4-10-6 MOE gapmers with a mixed PO/PS internucleoside linkages complementary to human UBE3A-ATS

| Compound ID | SEQ ID NO: 1 Start Site | SEQ ID NO: 1 Stop Site | SEQUENCE | SEQ ID NO |
|---|---|---|---|---|
| 1263498 | 464530 | 464549 | CTGCTCAGTTAGGTTAGTGC | 2729 |
| 1263499 | 464531 | 464550 | TCTGCTCAGTTAGGTTAGTG | 2760 |
| 1263500 | 479994 | 480013 | GAGCTATCTGTACAAAATGG | 2761 |
| 1263501 | 479995 | 480014 | TGAGCTATCTGTACAAAATG | 2743 |
| 1263502 | 479996 | 480015 | GTGAGCTATCTGTACAAAAT | 2744 |
| 1263503 | 479997 | 480016 | CGTGAGCTATCTGTACAAAA | 1142 |
| 1263532 | 483970 | 483989 | GCATACCCAGGGTAGGATTC | 765 |
| 1263534 | 483971 | 483990 | TGCATACCCAGGGTAGGATT | 1445 |
| 1263536 | 483972 | 483991 | GTGCATACCCAGGGTAGGAT | 766 |
| 1263539 | 483973 | 483992 | TGTGCATACCCAGGGTAGGA | 2762 |
| 1263541 | 483974 | 483993 | ATGTGCATACCCAGGGTAGG | 2595 |
| 1273009 | 457735 | 457754 | GCCAGGTGTCTTATATCTAT | 2852 |
| 1273010 | 474393 | 474412 | GGTCAACCAATTTGCTATTC | 1809 |
| 1273011 | 474394 | 474413 | AGGTCAACCAATTTGCTATT | 2853 |
| 1273012 | 474396 | 474415 | TTAGGTCAACCAATTTGCTA | 2854 |
| 1273013 | 457736 | 457755 | AGCCAGGTGTCTTATATCTA | 2855 |
| 1273014 | 478535 | 478554 | AACGCAATGTATCAGGCAAC | 2856 |
| 1273015 | 478536 | 478555 | AAACGCAATGTATCAGGCAA | 2857 |
| 1273016 | 478730 | 478749 | GATCACATTACCCATCCGTT | 2858 |
| 1273017 | 478731 | 478750 | TGATCACATTACCCATCCGT | 2859 |
| 1273018 | 478732 | 478751 | CTGATCACATTACCCATCCG | 2860 |
| 1273019 | 474395 | 474414 | TAGGTCAACCAATTTGCTAT | 2861 |
| 1273020 | 478733 | 478752 | GCTGATCACATTACCCATCC | 1291 |
| 1273021 | 478734 | 478753 | TGCTGATCACATTACCCATC | 2862 |
| 1273022 | 478735 | 478754 | TTGCTGATCACATTACCCAT | 2863 |

The compounds in Table 63 are 5-10-5 MOE gapmers. The gapmers are 20 nucleosides in length, wherein the central gap segment consists of ten 2'-O-D-deoxyribonucleosides and the 5' and 3' wing segments each consist of five 2'-MOE nucleosides. The sugar motif for the gapmers is (from 5' to 3'): eeeeedddddddddddeeeee; wherein 'd' represents a 2'-β-D-deoxyribosyl sugar moiety, and 'e' represents a 2'-MOE sugar moiety. The gapmers have an internucleoside linkage motif of (from 5' to 3'): soooosssssssssssooss, wherein "s" represents a phosphorothioate internucleoside linkage and "o" represents a phosphodiester internucleoside linkage. All cytosine residues are 5-methylcytosines.

TABLE 63

5-10-5 MOE gapmers with a mixed PO/PS internucleoside linkages complementary to human UBE3A-ATS

| Compound ID | SEQ ID NO: 1 Start Site | SEQ ID NO: 1 Stop Site | SEQUENCE | SEQ ID NO |
|---|---|---|---|---|
| 1263451 | 460996 | 461015 | TTTTTCCATTTTTCTCTTAG | 2745 |
| 1263452 | 460997 | 461016 | GTTTTTCCATTTTTCTCTTA | 2746 |
| 1263453 | 461000 | 461019 | TGTGTTTTTCCATTTTTCTC | 2747 |
| 1263454 | 461001 | 461020 | GTGTGTTTTTCCATTTTTCT | 2748 |
| 1263455 | 461002 | 461021 | TGTGTGTTTTTCCATTTTTC | 2749 |
| 1263456 | 465235 | 465254 | TCATCTCGGGTATATAAATT | 2750 |
| 1263460 | 468985 | 469004 | TCACCATTTTGACCTTCTTA | 2751 |
| 1263461 | 468986 | 469005 | TTCACCATTTTGACCTTCTT | 2752 |
| 1263462 | 468987 | 469006 | CTTCACCATTTTGACCTTCT | 2753 |
| 1263463 | 468989 | 469008 | TGCTTCACCATTTTGACCTT | 2754 |
| 1263464 | 468990 | 469009 | CTGCTTCACCATTTTGACCT | 2755 |
| 1263465 | 468991 | 469010 | ACTGCTTCACCATTTTGACC | 2756 |
| 1263466 | 464526 | 464545 | TCAGTTAGGTTAGTGCACAG | 2757 |
| 1263467 | 464527 | 464546 | CTCAGTTAGGTTAGTGCACA | 2758 |
| 1263468 | 464529 | 464548 | TGCTCAGTTAGGTTAGTGCA | 2759 |
| 1263469 | 464531 | 464550 | TCTGCTCAGTTAGGTTAGTG | 2760 |
| 1263470 | 479994 | 480013 | GAGCTATCTGTACAAAATGG | 2761 |
| 1263471 | 479995 | 480014 | TGAGCTATCTGTACAAAATG | 2743 |
| 1263472 | 479996 | 480015 | GTGAGCTATCTGTACAAAAT | 2744 |
| 1263538 | 483973 | 483992 | TGTGCATACCCAGGGTAGGA | 2762 |
| 1272943 | 467048 | 467067 | TTTCATCAGTTAGTCAGGTT | 2786 |
| 1272944 | 465605 | 465624 | CCTTTCTATTTCAGACCGAA | 2787 |
| 1272945 | 465607 | 465626 | TGCCTTTCTATTTCAGACCG | 2788 |
| 1272946 | 465608 | 465627 | GTGCCTTTCTATTTCAGACC | 2789 |
| 1272947 | 465609 | 465628 | AGTGCCTTTCTATTTCAGAC | 2790 |
| 1272948 | 468919 | 468938 | AGTATAGATGCCTCTCCTCT | 2791 |
| 1272949 | 468920 | 468939 | AAGTATAGATGCCTCTCCTC | 2792 |
| 1272950 | 468921 | 468940 | TAAGTATAGATGCCTCTCCT | 2793 |
| 1272951 | 474796 | 474815 | ATTGACACCTCCAACTGTAA | 2794 |
| 1272952 | 474798 | 474817 | GTATTGACACCTCCAACTGT | 2795 |
| 1272953 | 474800 | 474819 | TGGTATTGACACCTCCAACT | 2796 |
| 1272954 | 474801 | 474820 | TTGGTATTGACACCTCCAAC | 2797 |
| 1272955 | 474802 | 474821 | TTTGGTATTGACACCTCCAA | 2798 |
| 1272956 | 476012 | 476031 | GTTTTCGCCCGTTACCTCAA | 2799 |
| 1272957 | 476013 | 476032 | AGTTTTCGCCCGTTACCTCA | 2800 |

TABLE 63-continued 5-10-5 MOE gapmers with a mixed PO/PS internucleoside linkages complementary to human UBE3A-ATS

| Compound ID | SEQ ID NO: 1 Start Site | SEQ ID NO: 1 Stop Site | SEQUENCE | SEQ ID NO |
|---|---|---|---|---|
| 1272958 | 476014 | 476033 | CAGTTTTCGCCCGTTACCTC | 2801 |
| 1272959 | 476017 | 476036 | CTCCAGTTTTCGCCCGTTAC | 2802 |
| 1272960 | 467052 | 467071 | ACACTTTCATCAGTTAGTCA | 2803 |
| 1272961 | 476018 | 476037 | TCTCCAGTTTTCGCCCGTTA | 2804 |
| 1272962 | 478437 | 478456 | GCTATAGGTGTCACATATTC | 2805 |
| 1272963 | 478442 | 478461 | TTGTAGCTATAGGTGTCACA | 2806 |
| 1272964 | 478443 | 478462 | TTTGTAGCTATAGGTGTCAC | 2807 |
| 1272965 | 483106 | 483125 | GCAATGGACTTAGTACACAA | 2808 |
| 1272966 | 483107 | 483126 | GGCAATGGACTTAGTACACA | 2809 |
| 1272967 | 483110 | 483129 | TTAGGCAATGGACTTAGTAC | 2810 |
| 1272968 | 483111 | 483130 | CTTAGGCAATGGACTTAGTA | 2811 |
| 1272969 | 485766 | 485785 | CAGATTCCTAAATACGCACA | 2812 |
| 1272970 | 485767 | 485786 | TCAGATTCCTAAATACGCAC | 2813 |
| 1272971 | 485768 | 485787 | GTCAGATTCCTAAATACGCA | 2814 |
| 1272972 | 485771 | 485790 | GTGGTCAGATTCCTAAATAC | 2815 |
| 1272973 | 487601 | 487620 | AGTGTCATATGTAGCAATTA | 2816 |
| 1272974 | 487603 | 487622 | TTAGTGTCATATGTAGCAAT | 2817 |
| 1272975 | 501337 | 501356 | TATGTAGCTCAGCTCAATGT | 2818 |
| 1272976 | 501339 | 501358 | CTTATGTAGCTCAGCTCAAT | 2819 |
| 1272977 | 501342 | 501361 | CTGCTTATGTAGCTCAGCTC | 2820 |
| 1272978 | 468734 | 468753 | AAAATCCATTTGTCCAGTCT | 2821 |
| 1272979 | 505552 | 505571 | TTTGCTTTTCAGTCAGGTAC | 2822 |
| 1272980 | 468735 | 468754 | TAAAATCCATTTGTCCAGTC | 2823 |
| 1272981 | 468736 | 468755 | CTAAAATCCATTTGTCCAGT | 2824 |
| 1272982 | 506110 | 506129 | GCATTGGCTTCATATTTCTC | 2825 |
| 1272983 | 506112 | 506131 | GAGCATTGGCTTCATATTTC | 2826 |
| 1272984 | 508942 | 508961 | CATTATTCTCTAGTGCCTAT | 2827 |
| 1272985 | 508943 | 508962 | TCATTATTCTCTAGTGCCTA | 2828 |
| 1272986 | 508947 | 508966 | GTCTTCATTATTCTCTAGTG | 2829 |
| 1272987 | 508948 | 508967 | AGTCTTCATTATTCTCTAGT | 2830 |
| 1272988 | 458439 | 458458 | AACTTCATCAATATTTCCCC | 2831 |
| 1272989 | 458397 | 458416 | TGTGGGCCTCTATTAAGATC | 2832 |
| 1272990 | 458399 | 458418 | CATGTGGGCCTCTATTAAGA | 2833 |
| 1272991 | 458401 | 458420 | TGCATGTGGGCCTCTATTAA | 2834 |
| 1272992 | 458453 | 458472 | TTTATACTTTACCCAACTTC | 2835 |
| 1272993 | 458454 | 458473 | CTTTATACTTTACCCAACTT | 2836 |
| 1272994 | 458455 | 458474 | GCTTTATACTTTACCCAACT | 2837 |
| 1272995 | 458440 | 458459 | CAACTTCATCAATATTTCCC | 2838 |
| 1272996 | 458457 | 458476 | TGGCTTTATACTTTACCCAA | 2839 |
| 1272997 | 458458 | 458477 | TTGGCTTTATACTTTACCCA | 2840 |
| 1272998 | 458459 | 458478 | TTTGGCTTTATACTTTACCC | 2841 |
| 1272999 | 458569 | 458588 | CTTTAGTATGTCGAGAACTC | 2842 |
| 1273000 | 458441 | 458460 | CCAACTTCATCAATATTTCC | 2843 |
| 1273001 | 461466 | 461485 | ACTCATCATGATCTTGGTAA | 2844 |
| 1273002 | 463053 | 463072 | TCACTGAGTTTTTGTAGTTC | 2845 |
| 1273003 | 463191 | 463210 | TCTGGAATCTTGTAGAGGAT | 2846 |
| 1273004 | 463192 | 463211 | TTCTGGAATCTTGTAGAGGA | 2847 |
| 1273005 | 467047 | 467066 | TTCATCAGTTAGTCAGGTTA | 2848 |
| 1273006 | 464395 | 464414 | ATTCAGCACTTAGGTAGTTC | 2849 |
| 1273007 | 464399 | 464418 | TCCCATTCAGCACTTAGGTA | 2850 |
| 1273008 | 464400 | 464419 | TTCCCATTCAGCACTTAGGT | 2851 |
| 1273061 | 468982 | 469001 | CCATTTTGACCTTCTTAGCC | 2872 |
| 1273062 | 468983 | 469002 | ACCATTTTGACCTTCTTAGC | 2873 |
| 1273063 | 465232 | 465251 | TCTCGGGTATATAAATTAAT | 2874 |
| 1273064 | 465233 | 465252 | ATCTCGGGTATATAAATTAA | 2875 |
| 1273065 | 468992 | 469011 | AACTGCTTCACCATTTTGAC | 2876 |
| 1273066 | 468993 | 469012 | TAACTGCTTCACCATTTTGA | 2877 |
| 1273067 | 468994 | 469013 | TTAACTGCTTCACCATTTTG | 2878 |
| 1273068 | 464522 | 464541 | TTAGGTTAGTGCACAGATAA | 2879 |
| 1273069 | 464523 | 464542 | GTTAGGTTAGTGCACAGATA | 2880 |
| 1273070 | 464534 | 464553 | GTCTCTGCTCAGTTAGGTTA | 2881 |
| 1273071 | 479991 | 480010 | CTATCTGTACAAAATGGAAC | 2882 |
| 1273072 | 479992 | 480011 | GCTATCTGTACAAAATGGAA | 2883 |
| 1273073 | 479993 | 480012 | AGCTATCTGTACAAAATGGA | 2884 |
| 1273084 | 457732 | 457751 | AGGTGTCTTATATCTATGAT | 2885 |
| 1273085 | 457742 | 457761 | GAAACCAGCCAGGTGTCTTA | 2886 |
| 1273086 | 474391 | 474410 | TCAACCATTTGCTATTCAT | 2887 |
| 1273087 | 474392 | 474411 | GTCAACCAATTTGCTATTCA | 2888 |
| 1273088 | 457733 | 457752 | CAGGTGTCTTATATCTATGA | 2889 |
| 1273089 | 474394 | 474413 | AGGTCAACCAATTTGCTATT | 2853 |

TABLE 63-continued 5-10-5 MOE gapmers with a mixed PO/PS internucleoside linkages complementary to human UBE3A-ATS

| Compound ID | SEQ ID NO: 1 Start Site | SEQ ID NO: 1 Stop Site | SEQUENCE | SEQ ID NO |
|---|---|---|---|---|
| 1273090 | 474395 | 474414 | TAGGTCAACCAATTTGCTAT | 2861 |
| 1273091 | 474396 | 474415 | TTAGGTCAACCAATTTGCTA | 2854 |
| 1273092 | 474397 | 474416 | TTTAGGTCAACCAATTTGCT | 2890 |
| 1273093 | 474398 | 474417 | GTTTAGGTCAACCAATTTGC | 2891 |
| 1273094 | 474399 | 474418 | GGTTTAGGTCAACCAATTTG | 2892 |
| 1273095 | 478527 | 478546 | GTATCAGGCAACAGAATCTC | 2893 |
| 1273096 | 478528 | 478547 | TGTATCAGGCAACAGAATCT | 2894 |
| 1273097 | 478529 | 478548 | ATGTATCAGGCAACAGAATC | 2895 |
| 1273098 | 457734 | 457753 | CCAGGTGTCTTATATCTATG | 2896 |
| 1273099 | 478535 | 478554 | AACGCAATGTATCAGGCAAC | 2856 |
| 1273101 | 478537 | 478556 | AAAACGCAATGTATCAGGCA | 2897 |
| 1273102 | 478538 | 478557 | TAAAACGCAATGTATCAGGC | 2898 |
| 1273103 | 457735 | 457754 | GCCAGGTGTCTTATATCTAT | 2852 |
| 1273104 | 478727 | 478746 | CACATTACCCATCCGTTCTT | 2899 |
| 1273105 | 478728 | 478747 | TCACATTACCCATCCGTTCT | 2900 |
| 1273106 | 478729 | 478748 | ATCACATTACCCATCCGTTC | 2901 |
| 1273107 | 478730 | 478749 | GATCACATTACCCATCCGTT | 2858 |
| 1273108 | 478731 | 478750 | TGATCACATTACCCATCCGT | 2859 |
| 1273109 | 478732 | 478751 | CTGATCACATTACCCATCCG | 2860 |
| 1273110 | 478734 | 478753 | TGCTGATCACATTACCCATC | 2862 |
| 1273111 | 478735 | 478754 | TTGCTGATCACATTACCCAT | 2863 |
| 1273112 | 457736 | 457755 | AGCCAGGTGTCTTATATCTA | 2855 |
| 1273113 | 478737 | 478756 | TCTTGCTGATCACATTACCC | 2902 |
| 1273114 | 478738 | 478757 | TTCTTGCTGATCACATTACC | 2903 |
| 1273115 | 457737 | 457756 | CAGCCAGGTGTCTTATATCT | 2904 |

The compounds in Table 64 are 6-10-4 MOE gapmers. The gapmers are 20 nucleosides in length, wherein the central gap segment consists of ten 2'-O-D-deoxynucleosides, the 5' wing segment consists of six 2'-MOE nucleosides, and the 3' wing segment consists of four 2'-MOE nucleosides. The sugar motif of the gapmers is (from 5' to 3'): eeeeeedddddddddddeeee; wherein 'd' represents a 2'-β-D-deoxyriboxyl sugar moiety, and 'e' represents a 2'-MOE sugar moiety. The gapmers have an internucleoside linkage motif of (from 5' to 3'): sooooosssssssssssoss, wherein "s" represents a phosphorothioate internucleoside linkage and "o" represents a phosphodiester internucleoside linkage. All cytosine residues are 5-methylcytosines.

TABLE 64

6-10-4 MOE gapmers with a mixed PO/PS internucleoside linkages complementary to human UBE3A-ATS

| Compound ID | SEQ ID NO: 1 Start Site | SEQ ID NO: 1 Stop Site | SEQUENCE | SEQ ID NO |
|---|---|---|---|---|
| 1263457 | 479995 | 480014 | TGAGCTATCTGTACAAAATG | 2743 |
| 1263458 | 479996 | 480015 | GTGAGCTATCTGTACAAAAT | 2744 |
| 1263459 | 479997 | 480016 | CGTGAGCTATCTGTACAAAA | 1142 |
| 1263504 | 460996 | 461015 | TTTTTCCATTTTTCTCTTAG | 2745 |
| 1263505 | 460997 | 461016 | GTTTTTCCATTTTTCTCTTA | 2746 |
| 1263506 | 460999 | 461018 | GTGTTTTTCCATTTTTCTCT | 598 |
| 1263507 | 461000 | 461019 | TGTGTTTTTCCATTTTTCTC | 2747 |
| 1263508 | 461001 | 461020 | GTGTGTTTTTCCATTTTTCT | 2748 |
| 1263509 | 461002 | 461021 | TGTGTGTTTTTCCATTTTTC | 2749 |
| 1263510 | 465235 | 465254 | TCATCTCGGGTATATAAATT | 2750 |
| 1263511 | 465236 | 465255 | GTCATCTCGGGTATATAAAT | 1132 |
| 1263512 | 465237 | 465256 | GGTCATCTCGGGTATATAAA | 1207 |
| 1263513 | 465238 | 465257 | TGGTCATCTCGGGTATATAA | 318 |
| 1263514 | 465239 | 465258 | TTGGTCATCTCGGGTATATA | 2473 |
| 1263515 | 465240 | 465259 | ATTGGTCATCTCGGGTATAT | 1655 |
| 1263516 | 465241 | 465260 | TATTGGTCATCTCGGGTATA | 2548 |
| 1263517 | 468985 | 469004 | TCACCATTTTGACCTTCTTA | 2751 |
| 1263518 | 468986 | 469005 | TTCACCATTTTGACCTTCTT | 2752 |
| 1263519 | 468987 | 469006 | CTTCACCATTTTGACCTTCT | 2753 |
| 1263520 | 468988 | 469007 | GCTTCACCATTTTGACCTTC | 377 |
| 1263521 | 468989 | 469008 | TGCTTCACCATTTTGACCTT | 2754 |
| 1263522 | 468990 | 469009 | CTGCTTCACCATTTTGACCT | 2755 |
| 1263523 | 468991 | 469010 | ACTGCTTCACCATTTTGACC | 2756 |
| 1263524 | 464525 | 464544 | CAGTTAGGTTAGTGCACAGA | 2728 |
| 1263525 | 464526 | 464545 | TCAGTTAGGTTAGTGCACAG | 2757 |
| 1263526 | 464527 | 464546 | CTCAGTTAGGTTAGTGCACA | 2758 |
| 1263527 | 464528 | 464547 | GCTCAGTTAGGTTAGTGCAC | 1504 |
| 1263528 | 464529 | 464548 | TGCTCAGTTAGGTTAGTGCA | 2759 |
| 1263529 | 464530 | 464549 | CTGCTCAGTTAGGTTAGTGC | 2729 |
| 1263530 | 464531 | 464550 | TCTGCTCAGTTAGGTTAGTG | 2760 |
| 1263531 | 479994 | 480013 | GAGCTATCTGTACAAAATGG | 2761 |
| 1263533 | 483970 | 483989 | GCATACCCAGGGTAGGATTC | 765 |
| 1263535 | 483971 | 483990 | TGCATACCCAGGGTAGGATT | 1445 |
| 1263537 | 483972 | 483991 | GTGCATACCCAGGGTAGGAT | 766 |
| 1263540 | 483973 | 483992 | TGTGCATACCCAGGGTAGGA | 2762 |

TABLE 64-continued

6-10-4 MOE gapmers with a mixed PO/PS internucleoside linkages complementary to human UBE3A-ATS

| Compound ID | SEQ ID NO: 1 Start Site | SEQ ID NO: 1 Stop Site | SEQUENCE | SEQ ID NO |
|---|---|---|---|---|
| 1263542 | 483974 | 483993 | ATGTGCATACCCAGGGTAGG | 2595 |
| 1273023 | 457735 | 457754 | GCCAGGTGTCTTATATCTAT | 2852 |
| 1273024 | 457736 | 457755 | AGCCAGGTGTCTTATATCTA | 2855 |
| 1273025 | 474393 | 474412 | GGTCAACCAATTTGCTATTC | 1809 |
| 1273026 | 474394 | 474413 | AGGTCAACCAATTTGCTATT | 2853 |
| 1273027 | 474395 | 474414 | TAGGTCAACCAATTTGCTAT | 2861 |
| 1273028 | 474396 | 474415 | TTAGGTCAACCAATTTGCTA | 2854 |
| 1273029 | 478535 | 478554 | AACGCAATGTATCAGGCAAC | 2856 |
| 1273030 | 478536 | 478555 | AAACGCAATGTATCAGGCAA | 2857 |
| 1273031 | 478730 | 478749 | GATCACATTACCCATCCGTT | 2858 |
| 1273032 | 478731 | 478750 | TGATCACATTACCCATCCGT | 2859 |
| 1273033 | 478732 | 478751 | CTGATCACATTACCCATCCG | 2860 |
| 1273034 | 478733 | 478752 | GCTGATCACATTACCCATCC | 1291 |
| 1273035 | 478734 | 478753 | TGCTGATCACATTACCCATC | 2862 |
| 1273036 | 478735 | 478754 | TTGCTGATCACATTACCCAT | 2863 |

The compounds in Table 65 are 4-8-6 MOE gapmers. The gapmers are 18 nucleosides in length, wherein the central gap segment consists of eight 2'-β-D-deoxynucleosides, the 5' segment consists of four 2'-MOE nucleosides, and the 3' wing segment consists of six 2'-MOE nucleosides. The sugar motif of the gapmers is (from 5' to 3'): eeeedddddddeeeeee; wherein 'd' represents a 2'-β-D-deoxyriboxyl sugar moiety, and 'e' represents a 2'-MOE sugar moiety. The gapmers have an internucleoside linkage motif of (from 5' to 3'): sooossssssssooss; wherein "s" represents a phosphorothioate internucleoside linkage and "o" represents a phosphodiester internucleoside linkage. All cytosine residues are 5-methylcytosines.

TABLE 65

4-8-6 MOE gapmers with a mixed PO/PS internucleoside linkages complementary to human UBE3A-ATS

| Compound ID | SEQ ID NO: 1 Start Site | SEQ ID NO: 1 Stop Site | SEQUENCE | SEQ ID NO |
|---|---|---|---|---|
| 1263403 | 465237 | 465254 | TCATCTCGGGTATATAAA | 2768 |
| 1263404 | 465238 | 465255 | GTCATCTCGGGTATATAA | 2769 |
| 1263405 | 465239 | 465256 | GGTCATCTCGGGTATATA | 2770 |
| 1263406 | 465240 | 465257 | TGGTCATCTCGGGTATAT | 2771 |
| 1263407 | 465241 | 465258 | TTGGTCATCTCGGGTATA | 2772 |
| 1263408 | 468987 | 469004 | TCACCATTTTGACCTTCT | 2773 |
| 1263409 | 468988 | 469005 | TTCACCATTTTGACCTTC | 2774 |
| 1263410 | 468989 | 469006 | CTTCACCATTTTGACCTT | 2775 |
| 1263411 | 468991 | 469008 | TGCTTCACCATTTTGACC | 2776 |
| 1263412 | 464527 | 464544 | CAGTTAGGTTAGTGCACA | 2777 |
| 1263413 | 464528 | 464545 | TCAGTTAGGTTAGTGCAC | 2778 |
| 1263414 | 464529 | 464546 | CTCAGTTAGGTTAGTGCA | 2779 |
| 1263415 | 464530 | 464547 | GCTCAGTTAGGTTAGTGC | 2780 |
| 1263416 | 464531 | 464548 | TGCTCAGTTAGGTTAGTG | 2781 |
| 1263417 | 479996 | 480013 | GAGCTATCTGTACAAAAT | 2782 |
| 1263418 | 479997 | 480014 | TGAGCTATCTGTACAAAA | 2783 |
| 1263419 | 479998 | 480015 | GTGAGCTATCTGTACAAA | 2784 |
| 1263420 | 479999 | 480016 | CGTGAGCTATCTGTACAA | 2785 |
| 1263543 | 483971 | 483988 | CATACCCAGGGTAGGATT | 2763 |
| 1263546 | 483972 | 483989 | GCATACCCAGGGTAGGAT | 2764 |
| 1263549 | 483973 | 483990 | TGCATACCCAGGGTAGGA | 2765 |
| 1263552 | 483974 | 483991 | GTGCATACCCAGGGTAGG | 2766 |
| 1263557 | 483975 | 483992 | TGTGCATACCCAGGGTAG | 2767 |
| 1273037 | 457737 | 457754 | GCCAGGTGTCTTATATCT | 2864 |
| 1273038 | 478535 | 478552 | CGCAATGTATCAGGCAAC | 2865 |
| 1273039 | 478536 | 478553 | ACGCAATGTATCAGGCAA | 2866 |
| 1273040 | 478732 | 478749 | GATCACATTACCCATCCG | 2867 |
| 1273041 | 478733 | 478750 | TGATCACATTACCCATCC | 2868 |
| 1273042 | 478735 | 478752 | GCTGATCACATTACCCAT | 2869 |
| 1273043 | 457738 | 457755 | AGCCAGGTGTCTTATATC | 2870 |
| 1273060 | 474393 | 474410 | TCAACCAATTTGCTATTC | 2871 |

The compounds in Table 66 are 5-8-5 MOE gapmers. The gapmers are 18 nucleosides in length, wherein the central gap segment consists of eight 2'-β-D-deoxynucleosides and the 5' and 3' wing segments each consists of five 2'-MOE nucleosides. The sugar motif of the gapmers is (from 5' to 3'): eeeeedddddddeeeee; wherein 'd' represents a 2'-β-D-deoxyriboxyl sugar moiety, and 'e' represents a 2'-MOE sugar moiety. The gapmers have an internucleoside linkage motif of (from 5' to 3'): sooossssssssooss; wherein "s" represents a phosphorothioate internucleoside linkage and "o" represents a phosphodiester internucleoside linkage. All cytosine residues are 5-methylcytosines.

TABLE 66

5-8-5 MOE gapmers with a mixed PO/PS internucleoside linkages complementary to human UBE3A-ATS

| Compound ID | SEQ ID NO: 1 Start Site | SEQ ID NO: 1 Stop Site | SEQUENCE | SEQ ID NO |
|---|---|---|---|---|
| 1263421 | 465237 | 465254 | TCATCTCGGGTATATAAA | 2768 |
| 1263422 | 465238 | 465255 | GTCATCTCGGGTATATAA | 2769 |
| 1263423 | 465239 | 465256 | GGTCATCTCGGGTATATA | 2770 |
| 1263424 | 465240 | 465257 | TGGTCATCTCGGGTATAT | 2771 |
| 1263425 | 465241 | 465258 | TTGGTCATCTCGGGTATA | 2772 |
| 1263426 | 468987 | 469004 | TCACCATTTTGACCTTCT | 2773 |
| 1263427 | 464527 | 464544 | CAGTTAGGTTAGTGCACA | 2777 |
| 1263428 | 464528 | 464545 | TCAGTTAGGTTAGTGCAC | 2778 |
| 1263429 | 464529 | 464546 | CTCAGTTAGGTTAGTGCA | 2779 |
| 1263430 | 464530 | 464547 | GCTCAGTTAGGTTAGTGC | 2780 |
| 1263431 | 464531 | 464548 | TGCTCAGTTAGGTTAGTG | 2781 |
| 1263432 | 479996 | 480013 | GAGCTATCTGTACAAAAT | 2782 |
| 1263433 | 479997 | 480014 | TGAGCTATCTGTACAAAA | 2783 |
| 1263434 | 479998 | 480015 | GTGAGCTATCTGTACAAA | 2784 |
| 1263435 | 479999 | 480016 | CGTGAGCTATCTGTACAA | 2785 |
| 1263544 | 483971 | 483988 | CATACCCAGGGTAGGATT | 2763 |
| 1263547 | 483972 | 483989 | GCATACCCAGGGTAGGAT | 2764 |
| 1263550 | 483973 | 483990 | TGCATACCCAGGGTAGGA | 2765 |
| 1263553 | 483974 | 483991 | GTGCATACCCAGGGTAGG | 2766 |
| 1263554 | 483975 | 483992 | TGTGCATACCCAGGGTAG | 2767 |
| 1273052 | 457737 | 457754 | GCCAGGTGTCTTATATCT | 2864 |
| 1273053 | 457738 | 457755 | AGCCAGGTGTCTTATATC | 2870 |
| 1273054 | 474393 | 474410 | TCAACCAATTTGCTATTC | 2871 |
| 1273055 | 478535 | 478552 | CGCAATGTATCAGGCAAC | 2865 |
| 1273056 | 478536 | 478553 | ACGCAATGTATCAGGCAA | 2866 |
| 1273057 | 478732 | 478749 | GATCACATTACCCATCCG | 2867 |
| 1273058 | 478733 | 478750 | TGATCACATTACCCATCC | 2868 |
| 1273059 | 478735 | 478752 | GCTGATCACATTACCCAT | 2869 |

The compounds in Table 67 are 6-8-4 MOE gapmers. The gapmers are 18 nucleosides in length, wherein the central gap segment consists of eight 2'-β-D-deoxynucleosides, the 5' wing segment consists of six 2'-MOE nucleosides, and the 3' wing segment consists of four 2'-MOE nucleosides. The sugar motif of the gapmers is (from 5' to 3'): eeeeeeddddddd-deeee; wherein 'd' represents a 2'-β-D-deoxyriboxyl sugar moiety, and 'e' represents a 2'-MOE sugar moiety. The gapmers have an internucleoside linkage motif of (from 5' to 3'): soooossssssssssoss; wherein "s" represents a phosphoro- thioate internucleoside linkage and "o" represents a phosphodiester internucleoside linkage. All cytosine residues are 5-methylcytosines.

TABLE 67

6-8-4 MOE gapmers with a mixed PO/PS internucleoside linkages complementary to human UBE3A-ATS

| Compound ID | SEQ ID NO: 1 Start Site | SEQ ID NO: 1 Stop Site | SEQUENCE | SEQ ID NO |
|---|---|---|---|---|
| 1263436 | 465237 | 465254 | TCATCTCGGGTATATAAA | 2768 |
| 1263437 | 465238 | 465255 | GTCATCTCGGGTATATAA | 2769 |
| 1263438 | 465239 | 465256 | GGTCATCTCGGGTATATA | 2770 |
| 1263439 | 465240 | 465257 | TGGTCATCTCGGGTATAT | 2771 |
| 1263440 | 465241 | 465258 | TTGGTCATCTCGGGTATA | 2772 |
| 1263441 | 468987 | 469004 | TCACCATTTTGACCTTCT | 2773 |
| 1263442 | 464527 | 464544 | CAGTTAGGTTAGTGCACA | 2777 |
| 1263443 | 464528 | 464545 | TCAGTTAGGTTAGTGCAC | 2778 |
| 1263444 | 464529 | 464546 | CTCAGTTAGGTTAGTGCA | 2779 |
| 1263445 | 464530 | 464547 | GCTCAGTTAGGTTAGTGC | 2780 |
| 1263446 | 464531 | 464548 | TGCTCAGTTAGGTTAGTG | 2781 |
| 1263447 | 479996 | 480013 | GAGCTATCTGTACAAAAT | 2782 |
| 1263448 | 479997 | 480014 | TGAGCTATCTGTACAAAA | 2783 |
| 1263449 | 479998 | 480015 | GTGAGCTATCTGTACAAA | 2784 |
| 1263450 | 479999 | 480016 | CGTGAGCTATCTGTACAA | 2785 |
| 1263545 | 483971 | 483988 | CATACCCAGGGTAGGATT | 2763 |
| 1263548 | 483972 | 483989 | GCATACCCAGGGTAGGAT | 2764 |
| 1263551 | 483973 | 483990 | TGCATACCCAGGGTAGGA | 2765 |
| 1263555 | 483974 | 483991 | GTGCATACCCAGGGTAGG | 2766 |
| 1263556 | 483975 | 483992 | TGTGCATACCCAGGGTAG | 2767 |
| 1273044 | 457737 | 457754 | GCCAGGTGTCTTATATCT | 2864 |
| 1273045 | 457738 | 457755 | AGCCAGGTGTCTTATATC | 2870 |
| 1273046 | 474393 | 474410 | TCAACCAATTTGCTATTC | 2871 |
| 1273047 | 478535 | 478552 | CGCAATGTATCAGGCAAC | 2865 |
| 1273048 | 478536 | 478553 | ACGCAATGTATCAGGCAA | 2866 |
| 1273049 | 478732 | 478749 | GATCACATTACCCATCCG | 2867 |
| 1273050 | 478733 | 478750 | TGATCACATTACCCATCC | 2868 |
| 1273051 | 478735 | 478752 | GCTGATCACATTACCCAT | 2869 |

Example 8: Effect of Modified Oligonucleotides on Human UBE3A-ATS RNA In Vitro, Multiple Doses Modified oligonucleotides selected from the examples above were tested at various doses in human IPS derived iCell GABANeurons (Cellular Dynamics), as described in Example 4. Reduction of UBE3A-ATS RNA is presented in the tables below as percent UBE3A-ATS RNA amount relative to untreated control (UTC) cells. Where possible, the half maximal inhibitory concentration (IC$_{50}$) of each modified oligonucleotide was calculated using a linear regression on a log/linear plot of the data in excel. In some cases, an IC$_{50}$ could not be reliably calculated and the data point is marked as "N.C.". Values marked with "N.D." indicate that a value was not determined in this experiment.

TABLE 68

Dose-dependent percent reduction of human UBE3A-ATS RNA in vitro (40,000 cells/well)

| Compound Number | UBE3A-ATS expression (% UTC) | | | | | IC$_{50}$ (μM) |
|---|---|---|---|---|---|---|
| | 250 nM | 740.7 nM | 2,222 nM | 6,666 nM | 20,000 nM | |
| 750519 | 69 | 53 | 23 | N.D. | N.D. | 0.7 |
| 617557 | 66 | 54 | 34 | 25 | N.D. | 0.9 |
| 749860 | 62 | 48 | 39 | 20 | 13 | 0.7 |
| 1065593 | 44 | 32 | 21 | 11 | 9 | N.C. |
| 1263517 | 55 | 47 | 35 | 17 | 18 | 0.4 |
| 1263519 | 52 | 39 | 25 | 17 | 16 | 0.2 |
| 1263533 | 51 | 34 | 29 | 28 | 23 | 0.1 |
| 1263540 | 39 | 29 | 29 | 29 | 24 | N.C. |
| 1272994 | 51 | 39 | 28 | 14 | 10 | 0.2 |
| 1272996 | 62 | 45 | 38 | 20 | 13 | 0.6 |
| 1272997 | 73 | 53 | 39 | 24 | 18 | 1.1 |
| 1272998 | 67 | 53 | 30 | 19 | 13 | 0.8 |
| 1273030 | 68 | 54 | 33 | 30 | 22 | 1.0 |
| 1273033 | 51 | 50 | 31 | 32 | 20 | 0.4 |
| 1273049 | 57 | 41 | 32 | 24 | 21 | 0.3 |

TABLE 69

Dose-dependent percent reduction of human UBE3A-ATS RNA in vitro (40,000 cells/well)

| Compound Number | UBE3A-ATS expression (% UTC) | | | | | IC$_{50}$ (μM) |
|---|---|---|---|---|---|---|
| | 250 nM | 740.7 nM | 2,222 nM | 6,666 nM | 20,000 nM | |
| 750519 | 79 | 66 | 29 | 15 | N.D. | 1.1 |
| 1263426 | 64 | 48 | 34 | 29 | 25 | 0.7 |
| 1273042 | 92 | 72 | 58 | 43 | 40 | 5.5 |
| 1273051 | 70 | 47 | 34 | 29 | 22 | 0.9 |
| 1273055 | 71 | 58 | 47 | 40 | 27 | 1.9 |
| 1273057 | 73 | 71 | 50 | 37 | 39 | 3.4 |
| 1273058 | 80 | 69 | 58 | 48 | 34 | 4.8 |
| 1273087 | 55 | 34 | 26 | 14 | 20 | 0.2 |
| 1273107 | 63 | 59 | 36 | 26 | 26 | 1.0 |
| 1273113 | 75 | 68 | 58 | 47 | 28 | 3.6 |

TABLE 70

Dose-dependent percent reduction of human UBE3A-ATS RNA in vitro (40,000 cells/well)

| Compound Number | UBE3A-ATS expression (% UTC) | | | | | IC$_{50}$ (μM) |
|---|---|---|---|---|---|---|
| | 250 nM | 740.7 nM | 2,222 nM | 6,666 nM | 20,000 nM | |
| 750519 | 56 | 38 | 22 | 10 | 25 | 0.2 |
| 749860 | 68 | 47 | 37 | 19 | 16 | 0.8 |
| 1065645 | 66 | 45 | 31 | 19 | 12 | 0.6 |
| 1263461 | 70 | 66 | 55 | 32 | 27 | 2.3 |
| 1263486 | 74 | 48 | 44 | 25 | 21 | 1.2 |

TABLE 71

Dose-dependent percent reduction of human UBE3A-ATS RNA in vitro (40,000 cells/well)

| Compound Number | UBE3A-ATS expression (% UTC) | | | | | IC$_{50}$ (μM) |
|---|---|---|---|---|---|---|
| | 250 nM | 740.7 nM | 2,222 nM | 6,666 nM | 20,000 nM | |
| 750519 | 63 | 39 | 19 | 9 | 4 | 0.4 |
| 1263517 | 56 | 40 | 27 | 17 | 11 | 0.3 |
| 1263518 | 72 | 65 | 42 | 28 | 20 | 1.6 |
| 1263532 | 57 | 44 | 38 | 33 | 64 | 0.5 |
| 1263533 | 41 | 56 | 37 | ND | 26 | NC |

TABLE 72

Dose-dependent percent reduction of human UBE3A-ATS RNA in vitro (40,000 cells/well)

| Compound Number | UBE3A-ATS expression (% UTC) | | | | | IC$_{50}$ (μM) |
|---|---|---|---|---|---|---|
| | 250 nM | 740.7 nM | 2,222 nM | 6,666 nM | 20,000 nM | |
| 617557 | 59 | 56 | 37 | 23 | 23 | 0.8 |
| 1263537 | 70 | 86 | 82 | 77 | 59 | N.C. |
| 1272944 | 51 | 39 | 23 | 13 | 8 | 0.2 |
| 1273033 | 55 | 40 | 32 | 21 | 15 | 0.3 |
| 1273039 | 68 | 58 | 37 | 28 | 20 | 1.1 |

TABLE 73

Dose-dependent percent reduction of human UBE3A-ATS RNA in vitro (40,000 cells/well)

| Compound Number | UBE3A-ATS expression (% UTC) | | | | | IC$_{50}$ (μM) |
|---|---|---|---|---|---|---|
| | 250 nM | 740.7 nM | 2,222 nM | 6,666 nM | 20,000 nM | |
| 617557 | 70 | 57 | 38 | N.D. | N.D. | 1.0 |
| 1273050 | 81 | 75 | 76 | 62 | 41 | 16.5 |
| 1273055 | 59 | 48 | 40 | 26 | 18 | 0.6 |
| 1273062 | 54 | 37 | 28 | 18 | 13 | 0.2 |
| 1273090 | 76 | 64 | 71 | 56 | 55 | N.C. |
| 1273091 | 75 | 79 | 56 | 44 | 32 | 4.3 |

Example 9: Effect of Modified Oligonucleotides on Human UBE3A-ATS RNA and UBE3A RNA In Vitro, Multiple Doses Modified oligonucleotides selected from the examples above were tested at various doses in 10-week differentiated human neuronal cells derived from Angelman Syndrome patient derived IPS cells as described in Example 6 above. Reduction of UBE3A-ATS RNA or induction of UBE3A RNA is presented in the tables below as percent UBE3A-ATS RNA amount or percent UBE3A RNA relative to untreated control (UTC) cells. Values marked with "N.D." indicate that a value was not determined in this experiment.

Several modified oligonucleotides were found to reduce UBE3A-ATS RNA accompanied by concurrent increase in UBE3A RNA in Angelman's patient IPS cell derived neurons.

TABLE 74

Reduction of UBE3A-ATS RNA and increase of UBE3A
RNA in Angelman Syndrome IPS cell derived neurons

| | UBE3A-ATS RNA (% UTC) (RTS4796) | | | | | UBE3A RNA (% UTC) (RTS35984) | | | | |
|---|---|---|---|---|---|---|---|---|---|---|
| Compound ID | 250 nM | 741 nM | 2222 nM | 6667 nM | 20000 nM | 250 nM | 741 nM | 2222 nM | 6667 nM | 20000 nM |
| 750519 | 51 | 20 | 11 | 7 | 5 | 297 | 224 | 235 | 250 | 205 |
| 749860 | 47 | 21 | 18 | 15 | 8 | 148 | 119 | 245 | 307 | 324 |
| 1065645 | 41 | 15 | 13 | 11 | 13 | 213 | 185 | 298 | 315 | 353 |
| 1263461 | 49 | 42 | 34 | 25 | 16 | 141 | 185 | 248 | 235 | 221 |
| 1263486 | 64 | 47 | 33 | 29 | 16 | 136 | 174 | 215 | 323 | 264 |

TABLE 75

Reduction of UBE3A-ATS RNA and increase of UBE3A
RNA in Angelman Syndrome IPS cell derived neurons

| | UBE3A-ATS RNA (% UTC) (RTS4796) | | | | | UBE3A RNA (% UTC) (RTS35984) | | | | |
|---|---|---|---|---|---|---|---|---|---|---|
| Compound ID | 250 nM | 741 nM | 2222 nM | 6667 nM | 20000 nM | 250 nM | 741 nM | 2222 nM | 6667 nM | 20000 nM |
| 750519 | 46 | 22 | 13 | 7 | 7 | 259 | 274 | 520 | 482 | 272 |
| 1263517 | 37 | 29 | 16 | 12 | 12 | 230 | 261 | 462 | 521 | 283 |
| 1263518 | 66 | 39 | 29 | 21 | 18 | 187 | 183 | 269 | 496 | 277 |
| 1263532 | 39 | 26 | 21 | 17 | 24 | 192 | 162 | 393 | 390 | 357 |
| 1263533 | 34 | 25 | 24 | 18 | 29 | 296 | 367 | 389 | 371 | 548 |

TABLE 76

Reduction of UBE3A-ATS RNA and increase of UBE3A
RNA in Angelman Syndrome IPS cell derived neurons

| | UBE3A-ATS RNA (% UTC) (RTS4796) | | | | | UBE3A RNA (% UTC) (RTS35984) | | | | |
|---|---|---|---|---|---|---|---|---|---|---|
| Compound ID | 250 nM | 741 nM | 2222 nM | 6667 nM | 20000 nM | 250 nM | 741 nM | 2222 nM | 6667 nM | 20000 nM |
| 617557 | 68 | 44 | 28 | 24 | 20 | 120 | 210 | 319 | 453 | 396 |
| 1263537 | 29 | 26 | 21 | 26 | 16 | 139 | 203 | 414 | 440 | 480 |
| 1272944 | 35 | 25 | 13 | 11 | 7 | 148 | 235 | 469 | 702 | 677 |
| 1273033 | 38 | 21 | 21 | 16 | 18 | 119 | 244 | 487 | 422 | 514 |
| 1273039 | 64 | 41 | 29 | 20 | 17 | 183 | 237 | 395 | 376 | 418 |

TABLE 77

Reduction of UBE3A-ATS RNA and increase of UBE3A
RNA in Angelman Syndrome IPS cell derived neurons

| | UBE3A-ATS RNA (% UTC) (RTS4796) | | | | | UBE3A RNA (% UTC) (RTS35984) | | | | |
|---|---|---|---|---|---|---|---|---|---|---|
| Compound ID | 250 nM | 741 nM | 2222 nM | 6667 nM | 20000 nM | 250 nM | 741 nM | 2222 nM | 6667 nM | 20000 nM |
| 617557 | 63 | 50 | 33 | 28 | 27 | 126 | 230 | 347 | 335 | 368 |
| 1273050 | 64 | 48 | 59 | 41 | 28 | 165 | 152 | 240 | 457 | 483 |
| 1273055 | 44 | 31 | 38 | 22 | 17 | 541 | 664 | 1014 | 1094 | 887 |
| 1273062 | 34 | 54 | 51 | 47 | 27 | 253 | 296 | 421 | 705 | 997 |
| 1273090 | 70 | 54 | 30 | 39 | 23 | 155 | 165 | 259 | 487 | 692 |
| 1273091 | 91 | 86 | 54 | 37 | 31 | 96 | 121 | 135 | 156 | 284 |

Example 10: Tolerability of Modified Oligonucleotides Complementary to Human UBE3A-ATS in Wild-Type Mice 3 Hour Study Modified oligonucleotides described above were tested in wild-type female C57/Bl6 mice to assess the tolerability of the oligonucleotides. Wild-type female C57/Bl6 mice each received a single ICV dose of 700 µg of modified oligonucleotide listed in the table below. Each treatment group consisted of 4 mice. A group of 4 mice received PBS as a negative control for each experiment (identified in separate tables below). At 3 hours post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse and averaged within each treatment group. The results are presented in the tables below.

TABLE 78

Tolerability scores in mice at 700 µg dose

| Compound Number | 3 hr FOB |
| --- | --- |
| PBS | 0.0 |
| 749860 | 0.0 |
| 749865 | 4.0 |
| 749984 | 4.8 |
| 750006 | 3.5 |
| 750009 | 3.8 |
| 750540 | 3.5 |
| 750544 | 2.8 |
| 750567 | 5.0 |

TABLE 79

Tolerability scores in mice at 700 µg dose

| Compound Number | 3 hr FOB |
| --- | --- |
| PBS | 0 |
| 1065272 | 5.0 |
| 1065295 | 2.0 |
| 1065296 | 5.5 |
| 1065324 | 2.8 |
| 1065330 | 6.8 |
| 1065369 | 6.8 |
| 1065438 | 5.8 |
| 1065465 | 5.0 |
| 1065513 | 5.8 |
| 1065576 | 7.0 |
| 1065578 | 3.2 |
| 1065579 | 3.8 |
| 1065582 | 4.2 |
| 1065586 | 3.0 |
| 1065590 | 6.0 |
| 1065591 | 4.0 |
| 1065593 | 1.0 |
| 1065595 | 4.8 |
| 1065597 | 4.5 |
| 1065599 | 6.0 |
| 1065600 | 4.2 |
| 1065605 | 3.8 |
| 1065607 | 5.2 |
| 1065608 | 3.0 |

TABLE 80

Tolerability scores in mice at 700 µg dose

| Compound Number | 3 hr FOB |
| --- | --- |
| PBS | 0.0 |
| 1065609 | 0.0 |
| 1065613 | 0.0 |
| 1065616 | 5.5 |
| 1065619 | 5.0 |
| 1065621 | 2.0 |
| 1065623 | 3.5 |
| 1065624 | 3.5 |
| 1065631 | 1.0 |
| 1065635 | 1.0 |
| 1065641 | 1.5 |
| 1065642 | 4.0 |
| 1065644 | 6.8 |
| 1065645 | 3.0 |
| 1065646 | 2.0 |
| 1065651 | 4.0 |
| 1065654 | 7.0 |
| 1065667 | 4.0 |
| 1065669 | 1.0 |
| 1065671 | 4.0 |
| 1065672 | 6.8 |
| 1065674 | 4.0 |
| 1065676 | 2.0 |
| 1065678 | 5.0 |
| 1065680 | 1.0 |

TABLE 81

Tolerability scores in mice at 700 µg dose

| Compound Number | 3 hr FOB |
| --- | --- |
| PBS | 0 |
| 1065685 | 5.0 |
| 1065686 | 4.8 |
| 1065690 | 3.8 |
| 1065696 | 6.2 |
| 1065708 | 5.5 |
| 1065709 | 4.2 |
| 1065710 | 2.8 |
| 1065712 | 6.8 |
| 1065713 | 5.0 |
| 1065719 | 4.0 |
| 1065728 | 1.0 |
| 1065735 | 3.5 |
| 1065750 | 6.2 |
| 1065754 | 3.2 |
| 1065765 | 4.2 |
| 1065766 | 5.2 |
| 1065768 | 5.5 |
| 1065785 | 3.8 |
| 1065795 | 1.0 |
| 1065799 | 1.0 |
| 1065810 | 2.2 |
| 1065812 | 3.8 |
| 1065813 | 5.0 |
| 1065817 | 5.0 |

TABLE 82

Tolerability scores in mice at 700 μg dose

| Compound Number | 3 hr FOB |
|---|---|
| PBS | 0.0 |
| 1065821 | 6.5 |
| 1065823 | 4.0 |
| 1065826 | 3.0 |
| 1065829 | 4.8 |
| 1065840 | 4.5 |
| 1065856 | 6.2 |
| 1065857 | 6.0 |
| 1065858 | 4.0 |
| 1065859 | 0.0 |
| 1065863 | 4.8 |
| 1065868 | 3.2 |
| 1065889 | 1.0 |
| 1065894 | 3.8 |
| 1065899 | 4.5 |
| 1065901 | 4.0 |
| 1065902 | 4.0 |
| 1065903 | 5.5 |
| 1065914 | 5.0 |
| 1065920 | 2.0 |
| 1065932 | 4.5 |
| 1065937 | 1.0 |
| 1065947 | 1.2 |
| 1065953 | 6.5 |
| 1065954 | 5.5 |

TABLE 83

Tolerability scores in mice at 700 μg dose

| Compound Number | 3 hr FOB |
|---|---|
| PBS | 0.0 |
| 1065955 | 5.0 |
| 1065977 | 6.2 |
| 1066009 | 2.0 |
| 1066037 | 4.2 |
| 1066046 | 1.0 |
| 1066072 | 4.0 |
| 1066076 | 5.0 |
| 1066089 | 1.0 |
| 1066092 | 1.0 |
| 1066097 | 1.2 |
| 1066119 | 11.0 |
| 1066217 | 6.0 |
| 1066221 | 3.8 |
| 1066249 | 4.5 |
| 1066253 | 6.0 |
| 1066311 | 2.0 |
| 1066350 | 4.0 |
| 1066375 | 1.0 |
| 1066377 | 6.2 |
| 1066378 | 5.2 |
| 1066396 | 6.0 |
| 1066420 | 4.0 |
| 1066423 | 2.8 |
| 1066429 | 5.8 |

TABLE 84

Tolerability scores in mice at 700 μg dose

| Compound Number | 3 hr FOB |
|---|---|
| PBS | 0.0 |
| 749931 | 0.0 |
| 749933 | 4.0 |
| 749937 | 0.5 |
| 749944 | 3.8 |
| 749956 | 1.8 |
| 749964 | 2.0 |
| 749969 | 5.2 |
| 749991 | 2.2 |
| 750028 | 4.2 |
| 750030 | 3.2 |
| 750032 | 2.2 |
| 750040 | 4.2 |
| 750051 | 2.5 |
| 750092 | 0.8 |
| 750100 | 2.5 |
| 750131 | 0.5 |
| 750139 | 3.0 |
| 750140 | 1.2 |
| 750196 | 4.0 |
| 750210 | 3.5 |
| 750214 | 3.25 |
| 750228 | 0.0 |
| 750270 | 1.0 |
| 750292 | 0.0 |
| 750312 | 4.8 |
| 750325 | 1.0 |
| 750326 | 0.0 |
| 750329 | 5.5 |
| 750344 | 6.2 |
| 750350 | 2.8 |
| 750359 | 0.0 |
| 750360 | 3.2 |
| 750365 | 5.2 |
| 750366 | 0.0 |
| 750386 | 0.0 |
| 750413 | 0.0 |
| 750416 | 7.0 |
| 750418 | 1.8 |
| 750430 | 6.2 |
| 750431 | 5.0 |
| 750439 | 5.5 |
| 750452 | 2.5 |
| 750517 | 3.0 |
| 750519 | 1.0 |
| 750542 | 3.5 |
| 750549 | 0.0 |

TABLE 85

Tolerability scores in mice at 700 μg dose

| Compound Number | 3 hr FOB |
|---|---|
| PBS | 0.0 |
| 617456 | 4.8 |
| 617459 | 7.0 |
| 617470 | 6.5 |
| 617473 | 6.8 |
| 617536 | 6.5 |
| 617547 | 6.8 |
| 617557 | 5.2 |
| 617593 | 6.5 |
| 749794 | 5.0 |
| 749796 | 4.5 |
| 749816 | 5.8 |
| 749861 | 3.0 |
| 749863 | 5.5 |
| 749869 | 3.8 |
| 749882 | 6.8 |
| 749885 | 0.5 |
| 749893 | 1.2 |
| 749894 | 0.0 |
| 749907 | 5.0 |
| 749921 | 6.0 |

TABLE 86

Tolerability scores in mice at 700 μg dose

| Compound Number | 3 hr FOB |
|---|---|
| PBS | 0.0 |
| 1065473 | 3.2 |
| 1065561 | 6.0 |
| 1065592 | 4.0 |
| 1065625 | 7.0 |
| 1065791 | 1.0 |
| 1065924 | 1.0 |
| 1066003 | 4.0 |

TABLE 87

Tolerability scores in mice at 700 μg dose

| Compound ID | 3 hr FOB |
|---|---|
| PBS | 0.0 |
| 1263471 | 6.2 |
| 1263472 | 3.2 |
| 1263473 | 1.0 |
| 1263474 | 0.0 |
| 1263475 | 0.0 |
| 1263476 | 1.0 |
| 1263477 | 0.0 |
| 1263478 | 1.0 |
| 1263479 | 4.0 |
| 1263480 | 4.0 |
| 1263481 | 5.5 |
| 1263482 | 4.0 |
| 1263483 | 4.0 |
| 1263484 | 4.0 |
| 1263485 | 4.0 |
| 1263486 | 2.0 |
| 1263487 | 1.0 |
| 1263488 | 1.0 |
| 1263489 | 0.0 |
| 1263490 | 0.0 |
| 1263491 | 0.0 |
| 1263492 | 1.0 |
| 1263494 | 4.0 |
| 1263495 | 4.0 |
| 1263496 | 4.0 |
| 1263497 | 4.0 |
| 1263498 | 4.0 |
| 1263499 | 4.0 |
| 1263500 | 4.7 |
| 1263501 | 5.5 |
| 1263502 | 4.0 |
| 1263503 | 4.0 |
| 1263504 | 1.0 |
| 1263505 | 0.0 |
| 1263506 | 0.0 |
| 1263507 | 0.0 |
| 1263508 | 0.0 |
| 1263509 | 0.0 |
| 1263510 | 2.0 |

TABLE 88

Tolerability scores in mice at 700 μg dose

| Compound ID | 3 hr FOB |
|---|---|
| PBS | 0.0 |
| 1165878 | 4.0 |
| 1263511 | 4.0 |
| 1263512 | 6.0 |
| 1263513 | 6.0 |
| 1263514 | 6.5 |
| 1263515 | 4.0 |
| 1263516 | 4.0 |
| 1263517 | 1.0 |

TABLE 88-continued

Tolerability scores in mice at 700 μg dose

| Compound ID | 3 hr FOB |
|---|---|
| 1263518 | 0.0 |
| 1263519 | 1.0 |
| 1263520 | 1.0 |
| 1263521 | 0.0 |
| 1263522 | 0.0 |
| 1263523 | 1.0 |
| 1263524 | 5.2 |
| 1263525 | 4.8 |
| 1263526 | 4.0 |
| 1263527 | 4.0 |
| 1263528 | 4.0 |
| 1263529 | 3.0 |
| 1263530 | 4.0 |
| 1263531 | 5.2 |
| 1263532 | 1.0 |
| 1263533 | 1.0 |
| 1263534 | 1.0 |
| 1263535 | 4.0 |
| 1263536 | 2.0 |
| 1263537 | 1.0 |
| 1263538 | 3.0 |
| 1263539 | 1.0 |
| 1263540 | 0.0 |

TABLE 89

Tolerability scores in mice at 700 μg dose

| Compound ID | 3 hr FOB |
|---|---|
| PBS | 0.0 |
| 1263541 | 1.8 |
| 1263542 | 3.5 |
| 1263543 | 1.0 |
| 1263544 | 1.0 |
| 1263545 | 2.0 |
| 1263546 | 0.0 |
| 1263547 | 1.0 |
| 1263548 | 1.0 |
| 1263549 | 0.0 |
| 1263550 | 1.0 |
| 1263551 | 2.0 |
| 1263552 | 1.0 |
| 1263553 | 5.5 |
| 1263554 | 1.0 |
| 1263555 | 4.0 |
| 1263556 | 1.0 |
| 1263557 | 1.0 |

TABLE 90

Tolerability scores in mice at 700 μg dose

| Compound ID | 3 hr FOB |
|---|---|
| PBS | 0.0 |
| 1263403 | 5.3 |
| 1263404 | 4.3 |
| 1263405 | 6.3 |
| 1263406 | 4.7 |
| 1263407 | 2.3 |
| 1263408 | 0.3 |
| 1263409 | 0.0 |
| 1263410 | 0.0 |
| 1263411 | 0.0 |
| 1263412 | 2.0 |
| 1263413 | 2.3 |
| 1263414 | 5.3 |
| 1263415 | 4.0 |
| 1263416 | 7.0 |
| 1263417 | 3.3 |

TABLE 90-continued

Tolerability scores in mice at 700 µg dose

| Compound ID | 3 hr FOB |
|---|---|
| 1263418 | 3.0 |
| 1263419 | 1.7 |
| 1263420 | 1.0 |
| 1263421 | 3.0 |
| 1263422 | 4.3 |
| 1263423 | 6.0 |
| 1263424 | 6.3 |
| 1263425 | 5.0 |

TABLE 91

Tolerability scores in mice at 700 µg dose

| Compound ID | 3 hr FOB |
|---|---|
| PBS | 0.0 |
| 749952 | 6.0 |
| 749953 | 3.3 |
| 1165583 | 5.7 |
| 1165584 | 3.3 |
| 1263426 | 2.0 |
| 1263427 | 4.0 |
| 1263428 | 4.3 |
| 1263429 | 1.3 |
| 1263430 | 2.3 |
| 1263431 | 6.3 |
| 1263432 | 6.0 |
| 1263433 | 4.7 |
| 1263434 | 1.0 |
| 1263435 | 1.3 |
| 1263436 | 2.3 |
| 1263437 | 4.7 |
| 1263438 | 6.0 |
| 1263439 | 4.7 |
| 1263440 | 6.7 |
| 1263441 | 0.3 |
| 1263442 | 3.7 |
| 1263443 | 3.0 |
| 1263444 | 6.3 |
| 1263445 | 5.0 |
| 1263446 | 5.7 |
| 1263447 | 4.7 |
| 1263448 | 5.0 |
| 1263449 | 4.7 |
| 1263450 | 2.0 |
| 1263451 | 1.3 |
| 1263452 | 0 |
| 1263453 | 0 |

TABLE 92

Tolerability scores in mice at 700 µg dose

| Compound ID | 3 hr FOB |
|---|---|
| PBS | 0 |
| 1065786 | 2.0 |
| 1165526 | 0.7 |
| 1165577 | 3.7 |
| 1263454 | 0.0 |
| 1263455 | 0.0 |
| 1263456 | 3.3 |
| 1263457 | 5.3 |
| 1263458 | 1.3 |
| 1263459 | 1.0 |
| 1263460 | 1.0 |
| 1263461 | 1.0 |
| 1263462 | 1.0 |
| 1263463 | 1.0 |
| 1263464 | 1.3 |
| 1263465 | 1.7 |

TABLE 92-continued

Tolerability scores in mice at 700 µg dose

| Compound ID | 3 hr FOB |
|---|---|
| 1263466 | 5.0 |
| 1263467 | 6.0 |
| 1263468 | 4.3 |
| 1263469 | 7.0 |
| 1263470 | 6.7 |
| 1272943 | 2.0 |
| 1272944 | 2.3 |
| 1272945 | 2.7 |
| 1272946 | 0.0 |
| 1272947 | 0.0 |
| 1272948 | 3.3 |
| 1272949 | 4.0 |
| 1272950 | 3.7 |
| 1272951 | 0.7 |
| 1272952 | 2.0 |
| 1272953 | 0.3 |
| 1272954 | 1.0 |

TABLE 93

Tolerability scores in mice at 700 µg dose

| Compound ID | 3 hr FOB |
|---|---|
| PBS | 0.0 |
| 1272955 | 3.7 |
| 1272956 | 5.3 |
| 1272957 | 4.0 |
| 1272958 | 5.0 |
| 1272959 | 3.3 |
| 1272960 | 1.0 |
| 1272961 | 4.7 |
| 1272962 | 2.0 |
| 1272963 | 4.0 |
| 1272964 | 2.3 |
| 1272965 | 1.0 |
| 1272966 | 2.3 |
| 1272967 | 1.0 |
| 1272968 | 1.0 |
| 1272969 | 0.0 |
| 1272970 | 0.0 |
| 1272971 | 0.0 |
| 1272972 | 0.0 |
| 1272973 | 4.0 |
| 1272974 | 1.0 |
| 1272975 | 1.0 |
| 1272976 | 2.0 |
| 1272977 | 1.0 |
| 1272978 | 2.3 |
| 1272979 | 1.0 |

TABLE 94

Tolerability scores in mice at 700 µg dose

| Compound ID | 3 hr FOB |
|---|---|
| PBS | 0.0 |
| 1272980 | 3.3 |
| 1272981 | 3.3 |
| 1272982 | 1.0 |
| 1272983 | 1.0 |
| 1272984 | 4.0 |
| 1272985 | 1.0 |
| 1272986 | 4.7 |
| 1272987 | 1.0 |
| 1272988 | 1.0 |
| 1272989 | 1.0 |
| 1272990 | 4.0 |
| 1272991 | 4.0 |
| 1272992 | 0.0 |

TABLE 94-continued

Tolerability scores in mice at 700 μg dose

| Compound ID | 3 hr FOB |
|---|---|
| 1272993 | 0.0 |
| 1272994 | 1.0 |
| 1272995 | 1.0 |
| 1272996 | 0.7 |
| 1272997 | 1.0 |
| 1272998 | 0.0 |
| 1272999 | 5.0 |
| 1273000 | 0.0 |
| 1273001 | 3.0 |
| 1273002 | 3.7 |
| 1273003 | 2.7 |
| 1273004 | 3.0 |
| 1273005 | 4.0 |
| 1273006 | 3.3 |
| 1273007 | 3.0 |
| 1273008 | 3.3 |
| 1273009 | 1.0 |
| 1273010 | 4.7 |
| 1273011 | 1.0 |

TABLE 95

Tolerability scores in mice at 700 μg dose

| Compound ID | 3 hr FOB |
|---|---|
| PBS | 0.0 |
| 699781 | 0.0 |
| 1065707 | 2.0 |
| 1065711 | 4.0 |
| 1065921 | 5.7 |
| 1165585 | 3.7 |
| 1165621 | 1.0 |
| 1273012 | 0.0 |
| 1273013 | 4.0 |
| 1273014 | 2.0 |
| 1273015 | 2.0 |
| 1273016 | 0.0 |
| 1273017 | 1.0 |
| 1273018 | 0.0 |
| 1273019 | 0.0 |
| 1273020 | 0.0 |
| 1273021 | 0.0 |
| 1273022 | 0.0 |
| 1273023 | 0.0 |
| 1273024 | 0.0 |
| 1273025 | 5.0 |
| 1273026 | 5.3 |
| 1273027 | 5.0 |
| 1273028 | 0.0 |
| 1273029 | 4.7 |
| 1273030 | 3.0 |
| 1273031 | 0.0 |
| 1273032 | 0.0 |
| 1273033 | 0.0 |

TABLE 96

Tolerability scores in mice at 700 μg dose

| Compound ID | 3 hr FOB |
|---|---|
| PBS | 0.0 |
| 1273034 | 0.0 |
| 1273035 | 1.0 |
| 1273036 | 1.0 |
| 1273037 | 1.0 |
| 1273038 | 1.0 |
| 1273039 | 1.0 |
| 1273040 | 0.0 |
| 1273041 | 0.0 |

TABLE 96-continued

Tolerability scores in mice at 700 μg dose

| Compound ID | 3 hr FOB |
|---|---|
| 1273042 | 0.0 |
| 1273043 | 6.0 |
| 1273044 | 0.0 |
| 1273045 | 0.0 |
| 1273046 | 3.0 |
| 1273047 | 3.0 |
| 1273048 | 0.0 |
| 1273049 | 0.0 |
| 1273050 | 0.0 |
| 1273051 | 0.0 |
| 1273052 | 0.0 |
| 1273053 | 6.0 |
| 1273054 | 3.0 |
| 1273055 | 2.0 |
| 1273056 | 2.3 |
| 1273057 | 2.0 |
| 1273058 | 1.0 |
| 1273059 | 1.0 |
| 1273060 | 0.7 |
| 1273061 | 1.0 |
| 1273062 | 0.0 |
| 1273063 | 0.0 |
| 1273064 | 0.0 |
| 1273065 | 0.0 |
| 1273066 | 0.0 |
| 1273067 | 1.0 |
| 1273068 | 6.0 |
| 1273069 | 6.0 |
| 1273070 | 1.0 |
| 1273071 | 0.0 |
| 1273072 | 0.0 |
| 1273073 | 4.0 |
| 1273084 | 0.0 |
| 1273085 | 3.0 |
| 1273086 | 2.0 |
| 1273087 | 1.0 |
| 1273088 | 0.0 |
| 1273089 | 5.3 |
| 1273090 | 0.0 |
| 1273091 | 0.0 |
| 1273092 | 0.0 |
| 1273093 | 1.0 |
| 1273094 | 6.0 |
| 1273095 | 4.3 |
| 1273096 | 4.7 |
| 1273097 | 5.0 |
| 1273098 | 1.0 |
| 1273099 | 1.0 |
| 1273101 | 0.7 |
| 1273102 | 1.0 |
| 1273103 | 0.0 |
| 1273104 | 0.0 |
| 1273105 | 0.0 |
| 1273106 | 0.0 |
| 1273107 | 0.0 |
| 1273108 | 0.0 |
| 1273109 | 1.0 |
| 1273110 | 0.0 |
| 1273111 | 0.0 |
| 1273112 | 2.3 |
| 1273113 | 0.0 |
| 1273114 | 0.0 |
| 1273115 | 2.3 |

TABLE 97

Tolerability scores in mice at 700 μg dose

| Compound ID | 3 hr FOB |
|---|---|
| PBS | 0.0 |
| 1165523 | 2.0 |
| 1165533 | 2.3 |

TABLE 97-continued

Tolerability scores in mice at 700 µg dose

| Compound ID | 3 hr FOB |
|---|---|
| 1165538 | 3.0 |
| 1165550 | 1.3 |
| 1165563 | 1.3 |
| 1165586 | 2.3 |
| 1165596 | 2.3 |
| 1165608 | 4.0 |
| 1165616 | 3.0 |
| 1165694 | 3.3 |
| 1165737 | 3.7 |
| 1165827 | 3.3 |
| 1165855 | 3.0 |
| 1165897 | 0.3 |
| 1179808 | 2.3 |
| 1179839 | 6.7 |
| 1179841 | 2.0 |
| 1179843 | 2.0 |
| 1273100 | 7.0 |

TABLE 98

Tolerability scores in mice at 700 µg dose

| Compound Number | 3 hr FOB |
|---|---|
| PBS | 0.0 |
| 1165521 | 3.3 |
| 1165524 | 4.7 |
| 1165536 | 4.0 |
| 1165545 | 6.0 |
| 1165552 | 5.7 |
| 1165553 | 6.0 |
| 1165554 | 7.0 |
| 1165555 | 6.0 |
| 1165562 | 5.7 |
| 1165588 | 4.7 |
| 1165590 | 5.7 |
| 1165611 | 6.0 |

Example 11: Tolerability of Modified Oligonucleotides Complementary to Human UBE3A-ATS in Rats, 3 Hour Study Modified oligonucleotides described above were tested in rats to assess the tolerability of the oligonucleotides. Sprague Dawley rats each received a single intrathecal (IT) dose of 3 mg of oligonucleotide listed in the table below. Each treatment group consisted of 4 rats. A group of four rats received PBS as a negative control. At 3 hours post-injection, movement in 7 different parts of the body were evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; (7) the rat's head. For each of the 7 different body parts, each rat was given a sub-score of 0 if the body part was moving or 1 if the body part was paralyzed (the functional observational battery score or FOB). After each of the 7 body parts were evaluated, the sub-scores were summed for each rat and then averaged for each group. For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Results are presented as the average score for each treatment group.

TABLE 99

Tolerability scores in rats at 3 mg dose

| Compound No. | FOB 3 hr |
|---|---|
| PBS | 0.0 |
| 749860 | 0.0 |
| 749861 | 4.0 |
| 749869 | 4.8 |
| 749885 | 0.8 |
| 749893 | 0.5 |
| 749931 | 0.5 |
| 750006 | 4.5 |

TABLE 100

Tolerability scores in rats at 3 mg dose

| Compound No. | FOB 3 hr |
|---|---|
| PBS | 0.0 |
| 750030 | 4.0 |
| 750051 | 4.0 |
| 750092 | 2.5 |
| 750100 | 4.0 |
| 750139 | 5.3 |
| 750140 | 3.5 |
| 750270 | 3.0 |
| 750292 | 0.0 |
| 750325 | 1.8 |
| 750386 | 0.8 |

TABLE 101

Tolerability scores in rats at 3 mg dose

| Compound No. | FOB 3 hr |
|---|---|
| PBS | 0.0 |
| 1065578 | 4.0 |
| 1065586 | 3.0 |
| 1065609 | 2.0 |
| 1065613 | 3.8 |
| 1065635 | 1.8 |
| 1065641 | 3.3 |
| 1065645 | 3.0 |
| 1065646 | 2.5 |

TABLE 102

Tolerability scores in rats at 3 mg dose

| Compound No. | FOB 3 hr |
|---|---|
| PBS | 0.0 |
| 750413 | 0.3 |
| 1065669 | 2.8 |
| 1065680 | 4.0 |
| 1065710 | 5.5 |
| 1065754 | 5.3 |
| 1065785 | 6.0 |
| 1065795 | 3.3 |
| 1065799 | 2.0 |
| 1065812 | 4.0 |
| 1065826 | 2.0 |

TABLE 103

Tolerability scores in rats at 3 mg dose

| Compound No. | FOB 3 hr |
|---|---|
| PBS | 0.0 |
| 1065920 | 3.5 |
| 1065937 | 3.8 |
| 1066092 | 3.3 |
| 1066221 | 4.0 |
| 1066350 | 2.3 |

TABLE 104

Tolerability scores in rats at 3 mg dose

| Compound No. | FOB 3 hr |
|---|---|
| PBS | 0.3 |
| 1263408 | 2.0 |
| 1263409 | 2.5 |
| 1263410 | 2.5 |
| 1263411 | 1.3 |
| 1263412 | 3.0 |
| 1263419 | 1.8 |
| 1263420 | 1.8 |
| 1263429 | 2.5 |
| 1263434 | 2.0 |

TABLE 105

Tolerability scores in rats at 3 mg dose

| Compound No. | FOB 3 hr |
|---|---|
| PBS | 0.3 |
| 1263435 | 3.0 |
| 1263441 | 2.3* |
| 1263450 | 2.0 |
| 1263451 | 4.0 |
| 1263452 | 2.0 |
| 1263453 | 1.8 |
| 1263454 | 1.5 |
| 1263455 | 3.3 |
| 1263458 | 0.3 |

*One of the four rats in this group died during surgery, and so is excluded from this value.

TABLE 106

Tolerability scores in rats at 3 mg dose

| Compound No. | FOB 3 hr |
|---|---|
| PBS | 0.5 |
| 1263476 | 0.3 |
| 1263478 | 1.0 |
| 1263488 | 3.0 |
| 1263489 | 2.3 |
| 1263507 | 2.0 |
| 1263517 | 1.3 |
| 1263518 | 1.8 |
| 1263519 | 1.0 |
| 1263521 | 2.0 |
| 1263533 | 1.3 |

TABLE 107

Tolerability scores in rats at 3 mg dose

| Compound No. | FOB 3 hr |
|---|---|
| PBS | 0.0 |
| 1165563 | 3.0 |
| 1179841 | 3.0 |
| 1179843 | 3.3 |
| 1263407 | 3.8 |
| 1263413 | 4.0 |
| 1263430 | 4.3 |
| 1263436 | 2.8 |
| 1263540 | 2.5 |
| 1272944 | 2.0 |
| 1272994 | 1.0 |
| 1272996 | 1.0 |

TABLE 108

Tolerability scores in rats at 3 mg dose

| Compound No. | FOB 3 hr |
|---|---|
| PBS | 0.0 |
| 1272998 | 0.3 |
| 1273034 | 0.0 |
| 1273035 | 0.8 |
| 1273036 | 0.0 |
| 1273049 | 0.3 |
| 1273051 | 0.0. |
| 1273055 | 2.0 |
| 1273056 | 3.7 |
| 1273057 | 1.0 |
| 1273058 | 0.8 |
| 1273062 | 2.5 |
| 1273065 | 2.3 |
| 1273087 | 2.0 |
| 1273099 | 2.5 |
| 1273102 | 4.5 |
| 1273106 | 2.0 |
| 1273107 | 2.0 |
| 1273108 | 2.0 |
| 1273113 | 1.0 |
| 1273115 | 3.3 |
| 1165523 | 5.0 |
| 1165550 | 3.0 |

TABLE 109

Tolerability scores in rats at 3 mg dose

| Compound No. | FOB 3 hr |
|---|---|
| PBS | 0.0 |
| 1263426 | 2.3 |
| 1263462 | 2.8 |
| 1272974 | 3.8 |
| 1272997 | 0.8 |
| 1273020 | 0.5 |
| 1273033 | 1.8 |
| 1273038 | 3.0 |
| 1273039 | 3.3 |
| 1273042 | 2.0 |
| 1273048 | 3.0 |
| 1273104 | 3.0 |
| 1273105 | 3.0 |
| 1273109 | 3.8 |
| 1273110 | 1.0 |
| 1273111 | 2.7 |
| 1065593 | 1.5 |
| 1263547 | 4.0 |
| 1165586 | 0.0 |

TABLE 109-continued

Tolerability scores in rats at 3 mg dose

| Compound No. | FOB 3 hr |
|---|---|
| 1263537 | 1.5 |

TABLE 110

Tolerability scores in rats at 3 mg dose

| Compound No. | FOB 3 hr |
|---|---|
| PBS | 0.0 |
| 749953 | 4.5 |
| 1065711 | 3.5 |
| 1263417 | 6.3 |
| 1263418 | 3.3 |
| 1263421 | 5.8 |
| 1263443 | 5.0 |
| 1263456 | 5.0 |
| 1263529 | 2.5 |
| 1263538 | 4.7 |
| 1273030 | 0.0 |
| 1273047 | 4.0 |
| 1273085 | 4.0 |

TABLE 111

Tolerability scores in rats at 3 mg dose

| Compound No. | FOB 3 hr |
|---|---|
| PBS | 0.0 |
| 749991 | 1.3 |
| 1263460 | 3.0 |
| 1263461 | 2.0 |
| 1263486 | 3.0 |
| 1263532 | 1.5 |
| 1263551 | 4.0 |
| 1273050 | 1.0 |
| 1273090 | 1.0 |
| 1273091 | 2.0 |
| 1273101 | 3.5 |
| 1263522 | 1.7 |

Example 12: Tolerability of Modified Oligonucleotides Complementary to Human UBE3A-ATS in Wild-Type Mice, Two Week Study Modified oligonucleotides described above were tested in wild-type female C57/Bl6 mice to assess the tolerability of the oligonucleotides. Wild-type female C57/Bl6 mice each received a single ICV dose of 700 µg of modified oligonucleotide listed in the table below. Each treatment group consisted of 4 mice. A group of 4 mice received PBS as a negative control for each experiment (identified in separate tables below). At 2 weeks post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse and averaged within each treatment group. The results are presented in the table below.

TABLE 112

Tolerability scores in mice at 700 µg dose

| Compound Number | 2-week FOB |
|---|---|
| PBS | 0.0 |
| 1065645 | 0.0 |
| 1263517 | 0.0 |
| 1263518 | 0.0 |
| 1263533 | 0.0 |
| 1273039 | 0.0 |
| 1273062 | 0.0 |

Example 13: Activity of Modified Oligonucleotides Complementary to Human UBE3A-ATS in Transgenic Mice Modified oligonucleotides described above were tested in a UBE3A-ATS BAC transgenic mouse model. The transgenic mouse model was developed at the University of Michigan Bacterial Artificial Chromosome Recombineering Core and contains region 25163935-25348867 from human chromosome 15 (GRCh38/hg38 assembly) (from BAC clone RP11-664B13). UBE3A-ATS expression is driven by the ENO2 promoter and terminated with the BGH poly(A) signal. The gene fragment was introduced into fertilized eggs from C57BL/6 mice by pronuclear injection to produce line RP11-748 that is used in the experiments described below.

Treatment

The UBE3A-ATS transgenic mice were divided into groups of 2-4 mice each. Each mouse received a single ICV bolus of 350 µg of modified oligonucleotide. A group of 4 mice received PBS as a negative control.

RNA Analysis

After two weeks, mice were sacrificed and RNA was extracted from cortical brain tissue, hippocampal brain tissue, and spinal cord for real-time PCR analysis of measurement of RNA expression of UBE3A-ATS using primer probe set RTS4796 (described herein above) and/or primer probe set RTS40595 (forward sequence TCCTTCCC-TACCTTAGTCTTGA, designated herein as SEQ ID NO: 14; reverse sequence CCCTCTTGAACCAGGAAACA, designated herein as SEQ ID NO: 15; probe sequence AGATGGCAGCCCACATTTCTACTGT, designated herein as SEQ ID NO: 16). Primer probe set RTS4796 is less reliable when the oligonucleotide binds at a site far from the primer probe binding site. Results are presented as percent change of RNA, relative to PBS control, normalized to mouse GAPDH. Mouse GAPDH was amplified using primer probe set RTS108 (forward sequence GGCAAATT-CAACGGCACAGT, designated herein as SEQ ID NO: 11; reverse sequence GGGTCTCGCTCCTGGAAGAT, designated herein as SEQ ID NO: 12; probe sequence AAGGCCGAGAATGGGAAGCTTGTCATC, designated herein as SEQ ID NO: 13). In some cases, RTPCR value is not defined for a certain sample, and is labeled N.D. (Not Defined).

As shown in the table below, treatment with modified oligonucleotides resulted in reduction of UBE3A-ATS RNA in comparison to the PBS control.

TABLE 113

Reduction of human UBE3A-ATS RNA in transgenic mice

| | UBE3A-ATS RNA (% control) RTS4796 | | | UBE3A-ATS RNA (% control) RTS40595 | | |
|---|---|---|---|---|---|---|
| Compound ID | SPINAL CORD | HIPPOCAMPUS | CORTEX | SPINAL CORD | HIPPOCAMPUS | CORTEX |
| PBS | 100 | 100 | 100 | 100 | 100 | 100 |
| 749860 | 14 | N.D. | 26 | 12 | 24 | 23 |
| 749861 | 27 | N.D. | 51 | 26 | 48 | 49 |
| 749863 | 39 | N.D. | 57 | 36 | 45 | 54 |
| 749865 | 61 | N.D. | 92 | 66 | 97 | 85 |
| 749869 | 31 | 37 | 51 | 29 | 38 | 47 |
| 749882 | 31 | 28 | 35 | 30 | 30 | 32 |
| 749885 | 59 | 65 | 85 | 61 | 68 | 83 |
| 749893 | 28 | 35 | 44 | 27 | 35 | 40 |
| 749894 | 5 | 7 | 9 | 3 | 6 | 7 |
| 749907 | 53 | 48 | 70 | 51 | 47 | 63 |
| 749931 | 35 | 24 | 33 | 15 | 22 | 28 |
| 749969 | 17 | 14 | 14 | 11 | 13 | 10 |
| 749991 | 27 | 26 | 38 | 22 | 24 | 31 |
| 750006 | 24 | 21 | 24 | 19 | 19 | 18 |
| 750028 | 26 | 22 | 34 | 17 | 19 | 26 |
| 750030 | 40 | 30 | 44 | 32 | 26 | 34 |
| 750032 | 17 | 9 | 12 | 10 | 6 | 6 |
| 750040 | 55 | 42 | 65 | 50 | 44 | 59 |
| 750051 | 35 | 27 | 35 | 27 | 26 | 29 |
| 750092 | 55 | 43 | 63 | 47 | 40 | 53 |
| 750139 | 24 | 22 | 30 | 17 | 20 | 23 |
| 750140 | 22 | 16 | 22 | 15 | 13 | 15 |
| 750214 | 48 | 46 | 60 | 45 | 41 | 55 |
| 750292 | 27 | 35 | 40 | 21 | 31 | 34 |
| 750312 | 59 | 48 | 47 | 53 | 43 | 42 |
| 750359 | 30 | 23 | 25 | 25 | 19 | 20 |
| 750360 | 44 | 40 | 54 | 39 | 37 | 47 |
| 750365 | 58 | 69 | 88 | 56 | 65 | 82 |
| 750386 | 34 | 24 | 27 | 26 | 19 | 19 |
| 750413 | 45 | 37 | 38 | 36 | 34 | 30 |
| 750430 | 48 | 42 | 41 | 41 | 42 | 33 |
| 750439 | 53 | 46 | 52 | 34 | 44 | 46 |
| 1065296 | 34 | 34 | 39 | 31 | 34 | 34 |
| 1065578 | 35 | 42 | 49 | 34 | 42 | 42 |
| 1065579 | 19 | 18 | 19 | 17 | 18 | 14 |
| 1065586 | 45 | 55 | 74 | 43 | 55 | 68 |
| 1065590 | 43 | 53 | 67 | 42 | 51 | 63 |
| 1065591 | 21 | 24 | 29 | 19 | 21 | 25 |
| 1065595 | 25 | 34 | 49 | 13 | 30 | 41 |
| 1065599 | 19 | 22 | 27 | 18 | 22 | 24 |
| 1065600 | 31 | 35 | 42 | 32 | 35 | 39 |
| 1065605 | 44 | 64 | 67 | 44 | 62 | 63 |
| 1065607 | 28 | 36 | 39 | 29 | 33 | 34 |
| 1065608 | 18 | 42 | 53 | 18 | 38 | 49 |
| 1065623 | 16 | 28 | 34 | 15 | 29 | 30 |
| 1065635 | 32 | 39 | 41 | 30 | 38 | 36 |
| 1065641 | 32 | 55 | 50 | 30 | 49 | 44 |
| 1065642 | 43 | 58 | 65 | 42 | 52 | 59 |
| 1065645 | 18 | 30 | 24 | 15 | 24 | 18 |
| 1065646 | 39 | 60 | 50 | 39 | 54 | 45 |
| 1065651 | 29 | 47 | 38 | 28 | 43 | 34 |
| 1065667 | 23 | 30 | 26 | 19 | 24 | 22 |
| 1065671 | 21 | 29 | 30 | 18 | 25 | 26 |
| 1065685 | 71 | 76 | 82 | 40 | 68 | 71 |
| 1065690 | 12 | 16 | 20 | 9 | 12 | 15 |
| 1065708 | 28 | 38 | 33 | 24 | 31 | 27 |
| 1065710 | 29 | 34 | 32 | 27 | 29 | 26 |
| 1065713 | 31 | 34 | 40 | 29 | 29 | 34 |
| 1065765 | 25 | 27 | 33 | 21 | 22 | 28 |
| 1065813 | 38 | 49 | 67 | 34 | 41 | 62 |
| 1065823 | 37 | 33 | 36 | 30 | 24 | 28 |
| 1065858 | 23 | 25 | 21 | 15 | 14 | 13 |
| 1065859 | 29 | 20 | 22 | 19 | 11 | 13 |

TABLE 113-continued

Reduction of human UBE3A-ATS RNA in transgenic mice

| | UBE3A-ATS RNA (% control) RTS4796 | | | UBE3A-ATS RNA (% control) RTS40595 | | |
|---|---|---|---|---|---|---|
| Compound ID | SPINAL CORD | HIPPOCAMPUS | CORTEX | SPINAL CORD | HIPPOCAMPUS | CORTEX |
| 1065863 | 52 | 45 | 39 | 39 | 34 | 29 |
| 1065868 | 22 | 19 | 19 | 14 | 13 | 12 |
| 1065920 | 47 | 60 | 56 | 45 | 51 | 44 |
| 1065932 | 28 | 33 | 35 | 23 | 25 | 26 |
| 1065947 | 34 | 35 | 40 | 28 | 25 | 30 |
| 1066221 | 44 | 74 | 76 | 43 | 69 | 69 |
| 1066420 | 55 | 74 | 71 | 52 | 71 | 61 |
| 1066423 | 43 | 42 | 39 | 37 | 35 | 32 |
| 1066429 | 75 | 74 | 83 | 70 | 65 | 72 |

TABLE 114

Reduction of human UBE3A-ATS RNA in transgenic mice

| | UBE3A-ATS RNA (% control) RTS4796 | | | UBE3A-ATS RNA (% control) RTS40595 | | |
|---|---|---|---|---|---|---|
| Compound ID | SPINAL CORD | HIPPOCAMPUS | CORTEX | SPINAL CORD | HIPPOCAMPUS | CORTEX |
| PBS | 100 | 100 | 100 | 100 | 100 | 100 |
| 1065272 | 40 | 29 | 39 | 37 | 31 | 39 |
| 1065582 | 45 | 28 | 52 | 43 | 31 | 51 |
| 1065616 | 38 | 25 | 45 | 36 | 25 | 42 |
| 1065619 | 33 | 23 | 54 | 31 | 27 | 55 |
| 1065621 | 42 | 33 | 57 | 43 | 41 | 54 |
| 1065624 | 20 | 40 | 62 | 20 | 42 | 61 |
| 1065631 | 24 | 32 | 71 | 24 | 34 | 65 |
| 1065669 | 38 | 33 | 89 | 34 | 30 | 72 |
| 1065674 | 37 | 36 | 111 | 35 | 34 | 101 |
| 1065678 | 33 | 36 | 105 | 32 | 35 | 96 |
| 1065680 | 43 | 61 | 134 | 40 | 59 | 121 |
| 1065686 | 21 | 25 | 63 | 19 | 22 | 55 |
| 1065696 | 44 | 36 | 117 | 40 | 32 | 108 |
| 1065719 | 63 | 36 | 122 | 56 | 32 | 109 |
| 1065728 | 20 | 11 | 53 | 14 | 9 | 42 |
| 1065754 | 47 | 25 | 112 | 41 | 24 | 105 |
| 1065766 | 29 | 41 | 110 | 24 | 41 | 98 |
| 1065768 | 40 | 41 | 99 | 32 | 38 | 84 |
| 1065799 | 44 | 43 | 104 | 38 | 40 | 99 |
| 1065812 | 19 | 15 | 35 | 12 | 12 | 26 |
| 1065817 | 29 | 23 | 60 | 22 | 20 | 52 |
| 1065821 | 23 | 19 | 42 | 16 | 17 | 34 |
| 1065829 | 36 | 19 | 80 | 27 | 18 | 58 |
| 1065840 | 27 | 15 | 61 | 21 | 14 | 45 |
| 1065856 | 22 | 19 | 44 | 14 | 13 | 30 |
| 1065857 | 35 | 28 | 58 | 26 | 21 | 38 |
| 1065899 | 37 | 30 | 77 | 30 | 24 | 58 |
| 1065902 | 21 | 17 | 55 | 17 | 14 | 41 |
| 1065937 | 22 | 12 | 91 | 17 | 11 | 65 |
| 1065953 | 19 | 13 | 58 | 13 | 10 | 41 |
| 1065955 | 34 | 19 | 69 | 26 | 16 | 53 |
| 1066046 | 58 | 35 | 122 | 50 | 32 | 106 |
| 1066076 | 46 | 27 | 76 | 41 | 25 | N.D. |
| 1066092 | 27 | 15 | 56 | 21 | 13 | 47 |
| 1066217 | 37 | 26 | 68 | 32 | 26 | 62 |
| 1066253 | 27 | 15 | 50 | 22 | 14 | 39 |
| 1066377 | 50 | 30 | 79 | 40 | 28 | 73 |

TABLE 115

Reduction of human UBE3A-ATS RNA in transgenic mice

| | UBE3A-ATS RNA (% control) RTS4796 | | |
|---|---|---|---|
| Compound ID | SPINAL CORD | HIPPOCAMPUS | CORTEX |
| PBS | 100 | 100 | 100 |
| 1263473 | 43 | 71 | 66 |
| 1263474 | 8 | 15 | 10 |
| 1263475 | 6 | 10 | 8 |
| 1263476 | 6 | 12 | 14 |
| 1263477 | 4 | 10 | 11 |
| 1263478 | 13 | 18 | 17 |
| 1263486 | 27 | 27 | 32 |
| 1263487 | 31 | 43 | 43 |
| 1263488 | 23 | 24 | 14 |
| 1263489 | 16 | 17 | 16 |
| 1263490 | 24 | 28 | 23 |
| 1263491 | 22 | 25 | 21 |
| 1263492 | 29 | 50 | 58 |
| 1263504 | 9 | 11 | 12 |
| 1263505 | 6 | 11 | 7 |
| 1263506 | 5 | 10 | 6 |
| 1263507 | 5 | 14 | 6 |
| 1263508 | 7 | 15 | 9 |
| 1263509 | 6 | 17 | 7 |
| 1263510 | 37 | 70 | 72 |
| 1263517 | 13 | 22 | 17 |
| 1263518 | 19 | 36 | 30 |
| 1263519 | 20 | 25 | 15 |
| 1263520 | 15 | 19 | 11 |
| 1263521 | 20 | 44 | 20 |
| 1263522 | 22 | 29 | 35 |
| 1263523 | 21 | 30 | 32 |
| 1263532 | 29 | 49 | 40 |
| 1263533 | 18 | 24 | 17 |
| 1263534 | 27 | 52 | 37 |
| 1263536 | 30 | 45 | 36 |
| 1263537 | 29 | 43 | 34 |
| 1263539 | 51 | 59 | 88 |
| 1263540 | 22* | 21* | 29* |
| 1263541 | 52 | 66 | 80 |
| 1263543 | 49 | 362 | 84 |
| 1263544 | 53 | 100 | 104 |
| 1263545 | 36 | 54 | 57 |
| 1263546 | 45 | 45 | 88 |
| 1263547 | 26 | 28 | 30 |
| 1263548 | 36 | 45 | 47 |
| 1263549 | 66 | 87 | 84 |
| 1263550 | 47 | 75 | 76 |
| 1263551 | 30 | 45 | 39 |
| 1263552 | 66 | 65 | 93 |
| 1263554 | 72 | 75 | 88 |
| 1263556 | 60 | 59 | 83 |
| 1263557 | 86 | 91 | 109 |
| 1263408 | 45 | 70 | 46 |
| 1263409 | 29 | 44 | 33 |
| 1263410 | 29 | 64 | 42 |
| 1263411 | 42 | 72 | 58 |
| 1263419 | 47 | 126 | 65 |
| 1263420 | 73 | 130 | 72 |
| 1263429 | 27 | 33 | 36 |
| 1263434 | 44 | 50 | 42 |
| 1263435 | 47 | 42 | 61 |
| 1263441 | 22 | 17 | 29 |
| 1263451 | 21 | 16 | 28 |
| 1263452 | 14 | 8 | 15 |
| 1263453 | 13 | 9 | 9 |

*Only 1 animal in group

TABLE 116

Reduction of human UBE3A-ATS RNA in transgenic mice

| | UBE3A-ATS RNA (% control) | | |
|---|---|---|---|
| Compound ID | SPINAL CORD | HIPPOCAMPUS | CORTEX |
| PBS | 100 | 100 | 100 |
| 1263454 | 6 | 8 | 13 |
| 1263455 | 5 | 19 | 35 |
| 1263458 | 39 | 62 | 88 |
| 1263459 | 28 | 45 | 52 |
| 1263460 | 11 | 28 | 34 |
| 1263461 | 24 | 30 | 35 |
| 1263462 | 25 | 24 | 25 |
| 1263463 | 36 | 40 | 66 |
| 1263464 | 25 | 22 | 38 |
| 1263465 | 32 | 35 | 39 |
| 1065786 | 121 | 75 | 32 |
| 1165526 | 116 | 78 | 46 |
| 1272943 | 41 | 73 | 32 |
| 1272946 | 37 | 69 | 33 |
| 1272947 | 55 | 94 | 54 |
| 1272951 | 70 | 89 | 75 |
| 1272952 | 125 | 85 | 109 |
| 1272953 | 86 | 78 | 51 |
| 1272954 | 110 | 89 | 70 |
| 1272955 | 137 | 136 | 70 |
| 1272960 | 59 | 77 | 40 |
| 1272962 | 45 | 52 | 26 |
| 1272964 | 74 | 58 | 62 |
| 1272965 | 43 | 39 | 25 |
| 1272966 | 52 | 68 | 67 |
| 1272967 | 65 | 69 | 62 |
| 1272968 | 76 | 62 | 66 |
| 1272969 | 83 | 60 | 147 |
| 1272970 | 143 | 57 | 60 |
| 1272971 | 81 | 58 | 48 |
| 1272972 | 74 | 69 | 38 |
| 1272974 | 40 | 29 | 18 |
| 1272975 | 124 | 86 | 96 |
| 1272976 | 93 | 62 | 50 |
| 1272977 | 58 | 59 | 47 |
| 1272978 | 39 | 46 | 40 |
| 1272979 | 61 | 69 | 46 |
| 1272982 | 60 | 58 | 42 |
| 1272983 | 84 | 83 | 70 |
| 1272985 | 72 | 56 | 38 |
| 1272987 | 181 | 37 | 28 |
| 1272988 | 66 | 34 | 31 |
| 1272989 | 87 | 60 | 68 |
| 1272992 | 77 | 45 | 42 |
| 1272993 | 57 | 36 | 60 |
| 1272994 | 16 | 12 | 10 |
| 1272995 | 182 | 35 | 93 |
| 1272996 | 26 | 9 | 18 |
| 1272997 | 24 | 12 | 27 |
| 1272998 | 26 | 14 | 17 |
| 1273000 | 104 | 45 | 56 |
| 1273003 | 93 | 28 | 60 |
| 1273009 | 39 | 8 | 19 |
| 1273011 | 145 | 78 | 80 |
| 1273012 | 110 | 36 | 71 |
| 1273014 | 46 | 19 | 37 |
| 1273015 | 79 | 35 | 68 |
| 1273016 | 58 | 34 | 37 |
| 1273017 | 46 | 39 | 56 |
| 1273018 | 41 | 24 | 60 |
| 1273019 | 98 | 39 | 80 |
| 1273020 | 44 | 10 | 19 |
| 1273021 | 59 | 27 | 47 |
| 1273022 | 73 | 23 | 45 |
| 1273023 | 54 | 23 | 31 |

TABLE 116-continued

Reduction of human UBE3A-ATS RNA in transgenic mice

| Compound ID | UBE3A-ATS RNA (% control) | | |
|---|---|---|---|
| | SPINAL CORD | HIPPOCAMPUS | CORTEX |
| 1273024 | 29 | 21 | 25 |
| 1273028 | 46 | 50 | 28 |
| 1273031 | 45 | 17 | 28 |
| 1273032 | 40 | 21 | 35 |
| 1273033 | 36 | 12 | 26 |
| 699781 | 66 | 25 | 37 |
| 1065707 | 78 | 44 | 70 |
| 1165621 | 107 | 41 | 71 |

TABLE 117

Reduction of human UBE3A-ATS RNA in transgenic mice

| Compound ID | UBE3A-ATS RNA (% control) | |
|---|---|---|
| | SPINAL CORD | HIPPOCAMPUS |
| PBS | 100 | 100 |
| 1273034 | 25 | 23 |
| 1273035 | 16 | 20 |
| 1273036 | 24 | 26 |
| 1273061 | 33 | 22 |
| 1273062 | 28 | 10 |
| 1273063 | 32 | 29 |
| 1273064 | 38 | 25 |
| 1273065 | 27 | 16 |
| 1273066 | 34 | 36 |
| 1273067 | 44 | 42 |
| 1273070 | 25 | 23 |
| 1273071 | 57 | 71 |
| 1273072 | 38 | 48 |
| 1273037 | 12 | 25 |
| 1273038 | 16 | 29 |
| 1273039 | 15 | 29 |
| 1273040 | 39 | 33 |
| 1273041 | 48 | 29 |
| 1273042 | 51 | 17 |
| 1273044 | 45 | 27 |
| 1273045 | 48 | 24 |
| 1273048 | 30 | 18 |
| 1273049 | 19 | 15 |
| 1273050 | 30 | 31 |
| 1273051 | 17 | 21 |
| 1273052 | 14 | 15 |
| 1273055 | 14 | 20 |
| 1273056 | 16 | 22 |
| 1273057 | 16 | 18 |
| 1273058 | 20 | 22 |
| 1273059 | 16 | 17 |
| 1273060 | 36 | 35 |
| 1273084 | 41 | 35 |
| 1273087 | 12 | 14 |
| 1273088 | 33 | 28 |
| 1273090 | 24 | 41 |
| 1273091 | 26 | 31 |
| 1273092 | 37 | 38 |
| 1273093 | 28 | 23 |
| 1273098 | 17 | 23 |
| 1273099 | 14 | 10 |
| 1273101 | 29 | 32 |
| 1273102 | 20 | 18 |
| 1273103 | 12 | 5 |
| 1273104 | 57 | 16 |
| 1273105 | 34 | 9 |
| 1273106 | 30 | 11 |
| 1273107 | 24 | 8 |
| 1273108 | 31 | 13 |
| 1273109 | 30 | 13 |
| 1273110 | 37 | 8 |
| 1273111 | 46 | 12 |
| 1273113 | 25 | 10 |
| 1273114 | 46 | 26 |
| 1273115 | 15 | 7 |
| 1165523 | 38 | 17 |
| 1165533 | 31 | 19 |
| 1165538 | 64 | 25 |
| 1165550 | 47 | 11 |
| 1165563 | 30 | 12 |
| 1165586 | 35 | 19 |
| 1165596 | 69 | 49 |
| 1165616 | 109 | 25 |
| 1165855 | 49 | 16 |
| 1165897 | 39 | 28 |
| 1179808 | 83 | 36 |
| 1179841 | 22 | 9 |
| 1179843 | 22 | 11 |

Example 14: Activity of Modified Oligonucleotides Complementary to Human UBE3A-ATS in Transgenic Mice, Multiple Doses Modified oligonucleotides described above were tested in the UBE3A-ATS BAC transgenic mouse model RP11-748 line.

Treatment

The UBE3A-ATS transgenic mice were divided into groups of 3 mice each. Each mouse received a single ICV bolus of 10, 30, 100, 300, or 700 μg of modified oligonucleotide. and sacrificed two weeks later. A group of 8 mice received PBS as a negative control.

RNA Analysis

After two weeks, mice were sacrificed, and RNA was extracted from cortical brain tissue, hippocampal brain tissue, and spinal cords for real-time PCR analysis of measurement of RNA expression of UBE3A-ATS using primer probe set RTS40595 (forward sequence TCCTTCCC-TACCTTAGTCTTGA, designated herein as SEQ ID NO: 14; reverse sequence CCCTCTTGAACCAGGAAACA, designated herein as SEQ ID NO: 15; probe sequence AGATGGCAGCCCACATTTCTACTGT, designated herein as SEQ ID NO: 16). Results are presented as percent change of RNA, relative to PBS control, normalized to mouse GAPDH (measured by primer-probe set RTS108).

As shown in the table below, treatment with modified oligonucleotides resulted in dose-dependent reduction of UBE3A-ATS RNA in comparison to the PBS control.

TABLE 118

Dose-dependent percent reduction of human UBE3A-ATS RNA in transgenic mice

| Compound ID | Dose (μg) | Cortex UBE3A-ATS RNA (% control) | ED50 (μg) | Hippocampus UBE3A-ATS RNA (% control) | ED50 (μg) | Spinal Cord UBE3A-ATS RNA (% control) | ED50 (μg) |
|---|---|---|---|---|---|---|---|
| PBS | 0 | 100 | — | 100 | — | 100 | — |
| 749860 | 10 | 98.16531 | 138 | 81.99485 | 109 | 59.65406 | 17 |
|  | 30 | 84.95562 |  | 91.16468 |  | 45.18495 |  |
|  | 100 | 67.32992 |  | 52.07824 |  | 25.79271 |  |
|  | 300 | 26.23195 |  | 33.3197 |  | 10.36557 |  |
|  | 700 | 11.97921 |  | 16.72183 |  | 9.517061 |  |
| 1065645 | 10 | 90.14288 | 74 | 88.23692 | 71 | 37.14751 | 6 |
|  | 30 | 72.43123 |  | 66.81222 |  | 16.11173 |  |
|  | 100 | 49.12943 |  | 51.83015 |  | 10.87515 |  |
|  | 300 | 16.34235 |  | 25.55912 |  | 7.843655 |  |
| 1263461 | 10 | 88.27412 | 94 | 86.23292 | 126 | 60.06681 | 14 |
|  | 30 | 81.19946 |  | 84.36883 |  | 33.7366 |  |
|  | 100 | 55.94376 |  | 68.69458 |  | 21.85816 |  |
|  | 300 | 16.25568 |  | 23.08811 |  | 28.43356 |  |
|  | 700 | 11.55421 |  | 20.98394 |  | 18.26012 |  |
| 1263486 | 10 | 84.88829 | 91 | 88.16814 | 110 | 80.05438 | 49 |
|  | 30 | 73.65319 |  | 88.23227 |  | 67.24883 |  |
|  | 100 | 53.51549 |  | 46.18175 |  | 35.76668 |  |
|  | 300 | 29.17494 |  | 39.41106 |  | 25.80888 |  |
|  | 700 | 13.16333 |  | 21.58236 |  | 14.67831 |  |
| 1263517 | 10 | 61.99356 | 27 | 78.62965 | 38 | 28.43223 | 5 |
|  | 30 | 57.35782 |  | 64.77742 |  | 4.093424 |  |
|  | 100 | 28.22543 |  | 31.27599 |  | 3.855931 |  |
|  | 300 | 13.48909 |  | 11.49965 |  | 2.253222 |  |
|  | 700 | 6.218008 |  | 9.114471 |  | 0.845911 |  |
| 1263518 | 10 | 83.49507 | 47 | 74.9207 | 36 | 7.813722 | N.C. |
|  | 30 | 63.00462 |  | 58.90944 |  | 6.925703 |  |
|  | 100 | 36.83505 |  | 35.79351 |  | 9.984906 |  |
|  | 300 | 10.60636 |  | 16.33499 |  | 22.15675 |  |
| 1263532 | 10 | 87.76102 | 437 | 104.2908 | 508 | 85.92361 | 126 |
|  | 30 | 93.21178 |  | 107.4279 |  | 86.97925 |  |
|  | 100 | 82.08274 |  | 79.80543 |  | 56.10128 |  |
|  | 300 | 63.11973 |  | 71.02516 |  | 37.9068 |  |
| 1263533 | 10 | 85.64712 | 62 | 91.08657 | 93 | 79.33594 | 35 |
|  | 30 | 74.82061 |  | 92.99996 |  | 56.07265 |  |
|  | 100 | 37.83251 |  | 50.48182 |  | 32.95345 |  |
|  | 300 | 17.85169 |  | 15.11169 |  | 16.13775 |  |
|  | 700 | 13.22447 |  | 16.26845 |  | 14.77717 |  |
| 1263537 | 10 | 99.27557 | 167 | 101.6452 | 149 | 58.69295 | 32 |
|  | 30 | 61.11154 |  | 67.12889 |  | 57.56289 |  |
|  | 100 | 70.65222 |  | 60.23925 |  | 35.5374 |  |
|  | 300 | 35.35647 |  | 38.67746 |  | 31.30235 |  |
|  | 700 | 37.55784 |  | 42.24916 |  | 26.47357 |  |
| 1272944 | 10 | 85.26636 | 171 | 98.97738 | 241 | 86.06921 | 66 |
|  | 30 | 83.3624 |  | 91.08809 |  | 60.22092 |  |
|  | 100 | 64.40395 |  | 69.68625 |  | 45.39798 |  |
|  | 300 | 47.00232 |  | 54.90247 |  | 34.02307 |  |
|  | 700 | 18.19851 |  | 26.34956 |  | 26.27892 |  |
| 1273033 | 10 | 92.81903 | 159 | 104.9703 | 202 | 71.92708 | 27 |
|  | 30 | 86.45458 |  | 92.23621 |  | 47.44761 |  |
|  | 100 | 71.94214 |  | 74.17289 |  | 34.27954 |  |
|  | 300 | 28.94805 |  | 34.12991 |  | 17.19729 |  |
|  | 700 | 19.14991 |  | 35.15452 |  | 16.60517 |  |
| 1273039 | 10 | 84.62214 | 63 | 93.89685 | 77 | 52.24285 | 33 |
|  | 30 | 70.19074 |  | 70.45983 |  | 45.93645 |  |
|  | 100 | 40.06878 |  | 45.44749 |  | 30.60229 |  |
|  | 300 | 22.18407 |  | 28.77613 |  | 27.68067 |  |
|  | 700 | 16.46246 |  | 23.35814 |  | 20.2156 |  |

TABLE 118-continued

Dose-dependent percent reduction of human UBE3A-ATS RNA in transgenic mice

| Compound ID | Dose (µg) | Cortex UBE3A-ATS RNA (% control) | ED50 (µg) | Hippocampus UBE3A-ATS RNA (% control) | ED50 (µg) | Spinal Cord UBE3A-ATS RNA (% control) | ED50 (µg) |
|---|---|---|---|---|---|---|---|
| 1273050 | 10 | 60.65157 | 34 | 76.1426 | 178 | 108.4293 | 45 |
|  | 30 | 46.72804 |  | 76.65907 |  | 59.53868 |  |
|  | 100 | 42.13233 |  | 63.21802 |  | 30.24442 |  |
|  | 300 | 35.42049 |  | 42.84989 |  | 16.76795 |  |
|  | 700 | 27.88596 |  | 44.42969 |  | 16.65603 |  |
| 1273055 | 10 | 54.09476 | 104 | 101.4753 | 139 | 95.64317 | 46 |
|  | 30 | 75.60993 |  | 80.40454 |  | 46.396 |  |
|  | 100 | 62.55598 |  | 61.10855 |  | 43.64926 |  |
|  | 300 | 37.44794 |  | 36.83808 |  | 26.42752 |  |
|  | 700 | 18.68964 |  | 24.28962 |  | 17.02671 |  |
| 1273062 | 10 | 83.90397 | 65 | 91.25815 | 65 | 96.79799 | 85 |
|  | 30 | 71.94265 |  | 68.4521 |  | 78.51707 |  |
|  | 100 | 41.74674 |  | 43.10219 |  | 45.07505 |  |
|  | 300 | 23.62598 |  | 26.78065 |  | 25.9929 |  |
|  | 700 | 8.048482 |  | 17.65158 |  | 20.9903 |  |
| 1273090 | 10 | 51.37967 | 25 | 83.05922 | 143 | 94.48769 | 120 |
|  | 30 | 53.46583 |  | 70.46917 |  | 79.90936 |  |
|  | 100 | 41.09529 |  | 69.46586 |  | 53.85753 |  |
|  | 300 | 25.47022 |  | 49.33954 |  | 51.06804 |  |
| 1273091 | 10 | 48.66948 | 28 | 86.34518 | 195 | 126.1334 | 240 |
|  | 30 | 49.31716 |  | 78.33165 |  | 118.9585 |  |
|  | 100 | 48.19272 |  | 67.14459 |  | 75.20145 |  |
|  | 300 | 31.19941 |  | 48.97407 |  | 42.91308 |  |
|  | 700 | 28.63277 |  | 34.46767 |  | 43.51426 |  |

Example 15: Tolerability of Modified Oligonucleotides Complementary to Human UBE3A-ATS in Wild-Type Mice. 3 Hour and 2 Week Study Modified oligonucleotides closely matched to LNA/DNA oligonucleotides described in WO2017/081223 were tested in female wild-type C57/Bl6 mice to assess the tolerability of the oligonucleotides. See, Certain Comparator Compounds, hereinabove. Wild-type female C57/Bl6 mice each received a single ICV dose of 700 µg of modified oligonucleotide listed in the table below. Each treatment group consisted of 4 mice. A group of 4 mice received PBS as a negative control for the experiment. At 3 hours post-injection and 2 weeks post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse and averaged within each treatment group. The results are presented in the table below.

TABLE 119

Tolerability scores in mice at 700 µg dose

| Compound ID | 3 hr FOB | 2 week FOB | SEQ ID NO: 1 Start Site | SEQ ID NO: 1 Stop Site | Chemistry Notation (5' to 3') | SEQ ID NO |
|---|---|---|---|---|---|---|
| PBS | 0.0 | 0.0 |  |  |  |  |
| 1219022 | 7.0 | n.d. | 468275 | 468294 | $A_{ls}A_{ls}A_{ds}T_{d}ST_{ls}A_{ds}T_{ls}T_{ds}T_{ds}A_{ds}S T_{ds}A_{ds}{}^{m}C_{ds}A_{ds}{}^{m}C_{ds}{}^{m}C_{ds}A_{ls}T_{ls}{}^{m}C_{ls}A_{l}$ | 2905 |
| 1219023 | 1.0 | 3.5 | 462549 | 462566 | $T_{ls}T_{ls}T_{ls}A_{ds}T_{ds}{}^{m}C_{ls}A_{ds}A_{ds}T_{ds}A_{ds}T_{ds}{}^{m}C_{ds}T_{ds}T_{ds}{}^{m}C_{ds}T_{ls}{}^{m}C_{ls}A_{l}$ | 2906 |
| 1219024 | 5.3 | 6.5 | 471876 | 471894 | $G_{ls}{}^{m}C_{ds}A_{ls}{}^{m}C_{ds}A_{ls}T_{d}ST_{ds}{}^{m}C_{ds}T_{ds}T_{ds}T_{ds}{}^{m}C_{ds}T_{ds}A_{ds}T_{ds}A_{ds}{}^{m}C_{ds}{}^{m}C_{ls}T_{l}$ | 2907 |
| 1219025 | 4.0 | 6.0 | 461987 | 462003 | $T_{ls}T_{ls}A_{ds}T_{ls}A_{ls}G_{ds}{}^{m}C_{ds}{}^{m}C_{ds}A_{ds}T_{ds}T_{ds}{}^{m}C_{ds}T_{ds}A_{ds}T_{ds}{}^{m}C_{ls}T_{l}$ | 2908 |
| 1219026 | 1.0 | 6.0 | 487371 | 487387 | $^{m}C_{ls}T_{ds}{}^{m}C_{ls}A_{ls}A_{ls}A_{ds}G_{ds}A_{d}ST_{d}S {}^{m}C_{ds}A_{ds}T_{ds}T_{ds}{}^{m}C_{ls}T_{ls}{}^{m}C_{ls}A_{l}$ | 2909 |

TABLE 119-continued

Tolerability scores in mice at 700 μg dose

| Compound ID | 3 hr FOB | 2 week FOB | SEQ ID NO: 1 Start Site | SEQ ID NO: 1 Stop Site | Chemistry Notation (5' to 3') | SEQ ID NO |
|---|---|---|---|---|---|---|
| 1219027 | 1.0 | 0.0 | 487430 | 487449 | $T_{ls}T_{ds}A_{ls}{}^mC_{ds}A_{ls}$ $^mC_{ds}T_{ls}T_{ds}A_{ds}A_{ds}$ $T_{ds}T_{ds}A_{ds}T_{ds}A_{ds}$ $^mC_{ds}T1ST_{ds}{}^mC_{ls}{}^mC_l$ | 2910 |
| 1219028 | 6.0 | 6.0 | 496570 | 496587 | $G_{ls}T_{ds}T_{ds}T_{ds}{}^mC_{ds}$ $^mC_{ds}A_{ds}T_{ds}{}^mC_{ds}T_{ds}$ $A_{ds}{}^mC_{ds}T_{ls}A_{ls}T_{ds}$ $T_{ls}A_{ls}A_l$ | 2911 |
| 1219029 | 6.3 | 6.0 | 503154 | 503170 | $^mC_{ls}T_{ls}G_dST_{ds}A_{ls}$ $T_{ds}A_{ds}{}^mC_{ds}A_{ds}{}^mC_{ds}$ $^mC_{ds}A_{ds}T_{ds}{}^mC_{ds}{}^mC_d$ $_s{}^mC_{ls}A_l$ | 2912 |
| 1219030 | 5.0 | 5.0 | 487478 | 487494 | $A_{ls}G_{ds}T_{ds}T_{ls}{}^mC_{ls}$ $T_{ds}A_{ds}{}^mC_{ds}T_{ds}A_{ds}$ $T_{ds}A_{ds}{}^mC_{ds}T_{ls}T_{ls}$ $T_{ls}{}^mC_l$ | 2913 |
| 1219031 | 5.3 | 6.0 | 464879 | 464898 | $T_{ls}A_{ls}T_{ds}A_{ds}{}^mC_{ls}$ $^mC_{ds}T_{ls}T_{ds}T_{ds}{}^mC_{ds}$ $T_{ds}T_{ds}T_{ds}A_{ds}A_{ds}$ $^mC_{ds}{}^mC_{ds}{}^mC_{ds}T_{ls}T_l$ | 2914 |

A subscript "l" indicates a 4'-2' LNA modified sugar moiety, a subscript "d" indicates a 2'-β-D-deoxyribosyl sugar moiety, a subscript "s" indicates a phosphorothioate internucleoside linkage, and a superscript "m" before a C indicates 5-methyl cytosine.
n.d. means no data; not tested.

Example 16: Tolerability of Modified Oligonucleotides Complementary to Human UBE3A-ATS in Rats, 8 Week Study Modified oligonucleotides described above were tested in rats to assess the tolerability of the oligonucleotides. Groups of male, 6-8 week old Sprague Dawley rats each received a single intrathecal (IT) dose of 3 mg of oligonucleotide as listed in the table below. Each treatment group consisted of 4 rats, approximately matched for starting weights. A group of four rats received PBS as a negative control. The rats were weighed before dosing, and were weighed again at 8 weeks post-dose. Rats are expected to gain weight over the course of the study due to growth; too little weight gain is a sign of compound toxicity. Absolute values of body weight change were normalized to the body weight change observed in PBS-treated groups to allow comparison between two studies with different average starting weights for the rats, with the body weight change of the PBS group set to 100%. Statistical significance (p-value) of the change in body weight compared to the PBS-treated group was calculated by a two-tailed Welch's T-test in Excel (two sample, unequal variance). A p-value of <0.05 indicates that there is less than a 5% chance that the observed differences are due to random sampling errors.

TABLE 120

| Body Weight Change in Rats at 8 weeks post-dose | | |
|---|---|---|
| Compound ID | B.W. change as % PBS | p-value |
| PBS | 100 | n/a |
| 1219027 | 87 | 0.03 |
| 1065645 | 101 | 0.83 |
| 1263517 | 100 | 0.91 |
| 1263518 | 103 | 0.50 |
| 1263533 | 100 | 0.99 |
| 1273039 | 105 | 0.26 |
| 1273062 | 100 | 0.98 |

SEQUENCE LISTING

The patent contains a lengthy sequence listing. A copy of the sequence listing is available in electronic form from the USPTO web site (https://seqdata.uspto.gov/?pageRequest=docDetail&DocID=US12129466B2). An electronic copy of the sequence listing will also be available from the USPTO upon request and payment of the fee set forth in 37 CFR 1.19(b)(3).

The invention claimed is:
1. A modified oligonucleotide according to the following chemical structure:
(SEQ ID NO: 2752)
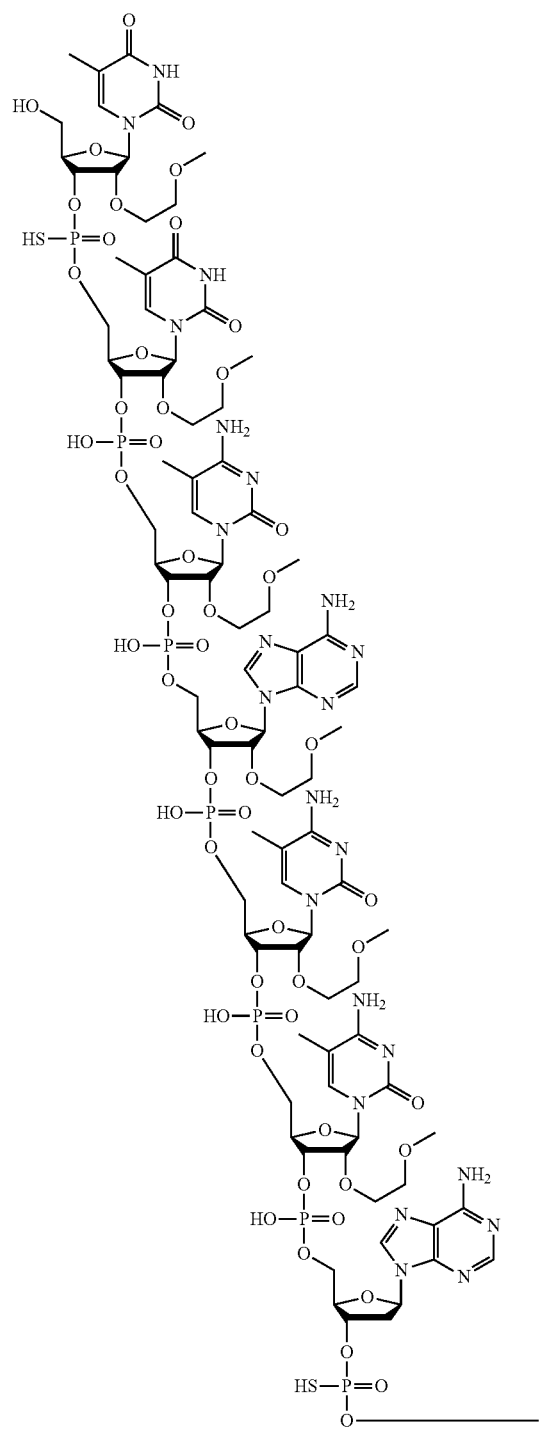
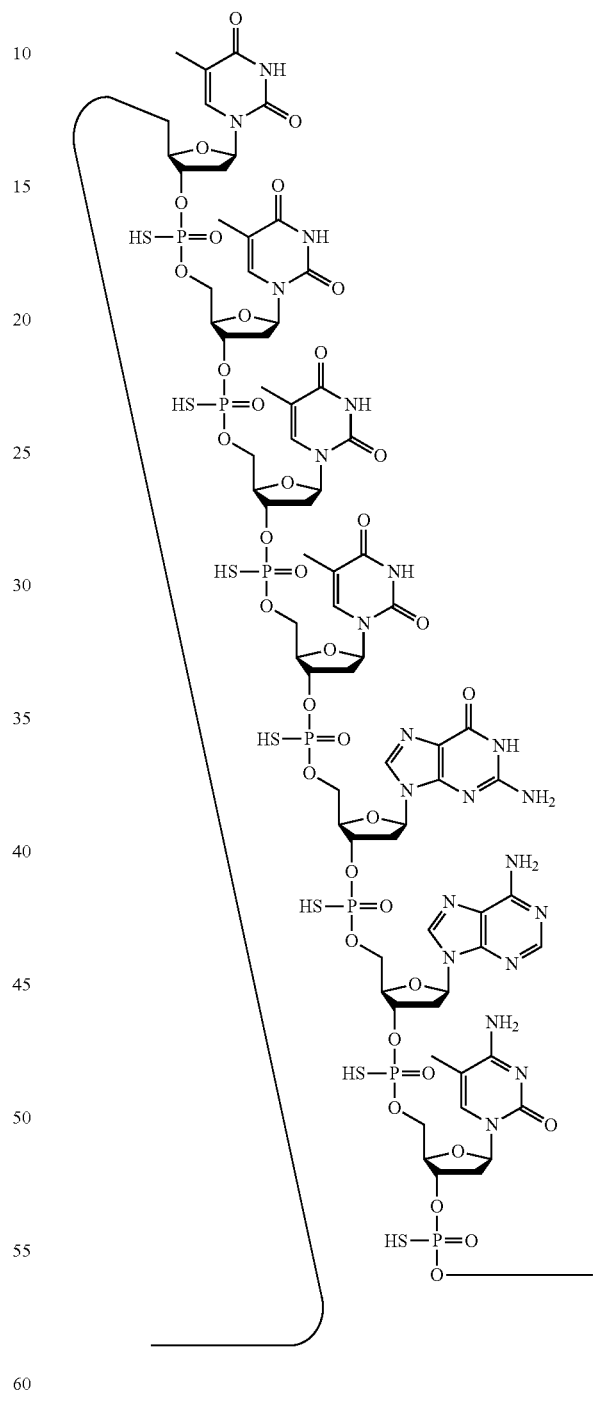

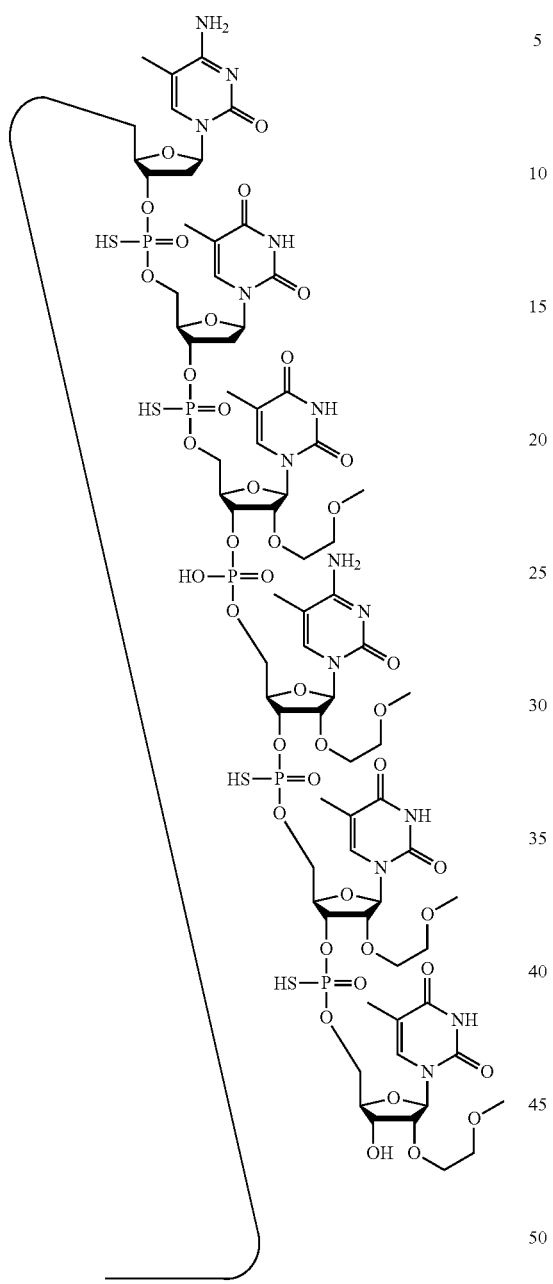
or a salt thereof.
2. A modified oligonucleotide corresponding to the following chemical structure:

(SEQ ID NO: 2752)

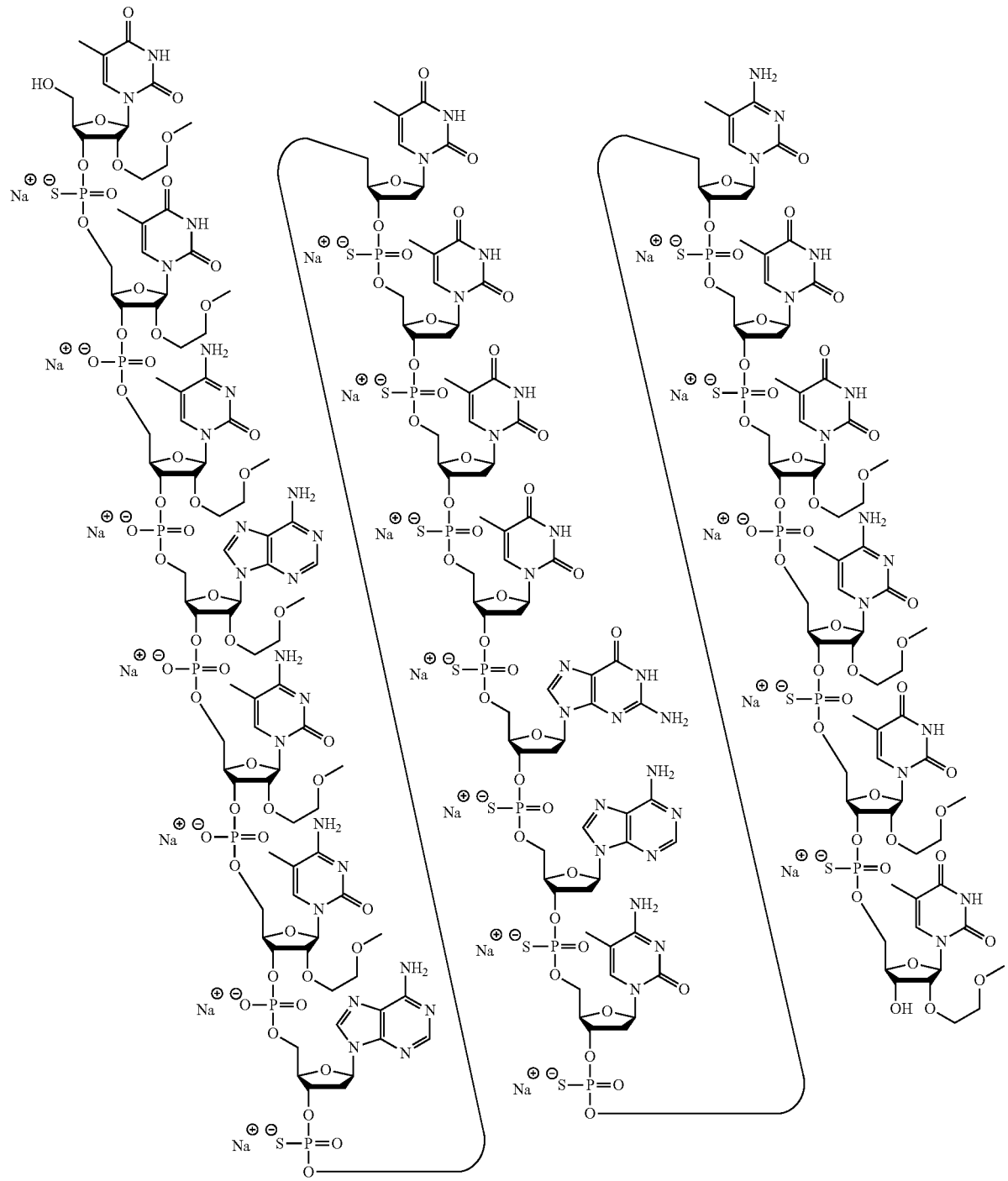

3. The modified oligonucleotide of claim 1 which is the sodium salt or the potassium salt.

4. A pharmaceutical composition comprising the modified oligonucleotide of claim 1 and a pharmaceutically acceptable carrier or diluent.

5. The pharmaceutical composition of claim 4, wherein the pharmaceutically acceptable diluent is artificial cerebrospinal fluid.

6. The pharmaceutical composition of claim 5, wherein the pharmaceutical composition consists essentially of the modified oligonucleotide and artificial cerebrospinal fluid.

7. A compound comprising a modified oligonucleotide according to the following chemical notation:

$T_{es}T_{eo}{}^mC_{eo}A_{eo}{}^mC_{eo}{}^mC_{eo}A_{ds}T_{ds}T_{ds}T_{ds}T_{ds}G_{ds}$
$A_{ds}{}^mC_{ds}{}^mC_{ds}T_{ds}T_{eo}{}^mC_{es}T_{es}T_e$ (SEQ ID NO: 2752), wherein:

A=an adenine nucleobase,
mC=a 5-methyl cytosine nucleobase,
G=a guanine nucleobase,
T=a thymine nucleobase,
e=a 2'-MOE sugar moiety,
d=a 2'-β-D-deoxyribosyl sugar moiety,
s=a phosphorothioate internucleoside linkage, and
o=a phosphodiester internucleoside linkage.

8. The compound of claim 7, comprising the modified oligonucleotide covalently linked to a conjugate group.

9. A pharmaceutical composition comprising the compound of claim 7 and a pharmaceutically acceptable diluent or carrier.

10. The pharmaceutical composition of claim 9, wherein the pharmaceutically acceptable diluent is artificial cerebrospinal fluid.

11. The pharmaceutical composition of claim 10, wherein the pharmaceutical composition consists essentially of the compound and artificial cerebrospinal fluid.

12. A pharmaceutical composition comprising the modified oligonucleotide of claim 2 and a pharmaceutically acceptable carrier or diluent.

13. The pharmaceutical composition of claim 12, wherein the pharmaceutically acceptable diluent is artificial cerebrospinal fluid.

14. The pharmaceutical composition of claim 13, wherein the pharmaceutical composition consists essentially of the modified oligonucleotide and artificial cerebrospinal fluid.

15. A pharmaceutical composition comprising the compound of claim 8 and a pharmaceutically acceptable diluent or carrier.

16. The pharmaceutical composition of claim 15, wherein the pharmaceutically acceptable diluent is artificial cerebrospinal fluid.

17. The pharmaceutical composition of claim 16, wherein the pharmaceutical composition consists essentially of the compound and artificial cerebrospinal fluid.

18. A method comprising administering to a subject the pharmaceutical composition of claim 4.

19. A method of treating Angelman Syndrome, comprising administering to an individual having or at risk for developing Angelman Syndrome a therapeutically effective amount of the pharmaceutical composition of claim 4.

* * * * *